(12) United States Patent
D'Andrea et al.

(10) Patent No.: US 8,343,477 B2
(45) Date of Patent: *Jan. 1, 2013

(54) INHIBITORS OF HEPATITIS C VIRUS

(75) Inventors: Stanley D'Andrea, Wallingford, CT (US); Zhizhen Barbara Zheng, Cheshire, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 836 days.

This patent is subject to a terminal disclaimer.

(21) Appl. No.: 11/923,918

(22) Filed: Oct. 25, 2007

(65) Prior Publication Data

US 2008/0107624 A1    May 8, 2008

Related U.S. Application Data

(60) Provisional application No. 60/863,837, filed on Nov. 1, 2006.

(51) Int. Cl.
| | |
|---|---|
| A61K 38/12 | (2006.01) |
| A61K 38/21 | (2006.01) |
| A61K 38/20 | (2006.01) |
| C07K 7/00 | (2006.01) |
| A61P 31/12 | (2006.01) |

(52) U.S. Cl. .............. 424/85.4; 424/85.2; 424/85.7; 514/4.3; 514/9; 530/317

(58) Field of Classification Search .................. None
See application file for complete search history.

(56) References Cited

U.S. PATENT DOCUMENTS

| | | | |
|---|---|---|---|
| 2005/0153877 | A1 | 7/2005 | Miao et al. |
| 2006/0172950 | A1 | 8/2006 | Wang et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0032936 | A1 | 2/2008 | Gai et al. |
| 2008/0039375 | A1 | 2/2008 | Moore et al. |
| 2008/0039470 | A1 | 2/2008 | Niu et al. |
| 2008/0107625 | A1* | 5/2008 | D'Andrea et al. ........... 424/85.4 |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 6/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |

(Continued)

OTHER PUBLICATIONS

U.S. Appl. No. 11/923,948, filed Oct. 25, 2007, D'Andrea et al.

(Continued)

*Primary Examiner* — Sun Jae Loewe
(74) *Attorney, Agent, or Firm* — Samuel J. DuBoff; Pamela A. Mingo

(57) ABSTRACT

Macrocyclic peptides are disclosed having the general formula:

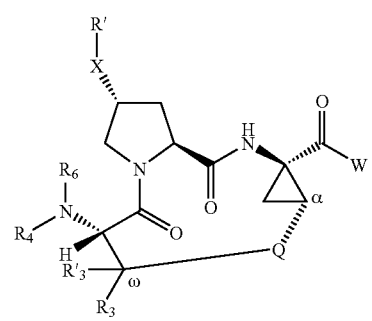

I wherein $R_3$, $R'_3$, $R_4$, $R_6$, $R'$, X, Q and W are described. Compositions comprising the compounds and methods for using the compounds to inhibit HCV are also disclosed.

13 Claims, No Drawings

FOREIGN PATENT DOCUMENTS

| | | |
|---|---|---|
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |

OTHER PUBLICATIONS

U.S. Appl. No. 11/923,977, filed Oct. 25, 2007, D'Andrea et al.
U.S. Appl. No. 11/934,840, filed Nov. 5, 2007, Sin et al.
U.S. Appl. No. 11/939,753, filed Nov. 14, 2007, Wang et al.
U.S. Appl. No. 11/939,768, filed Nov. 14, 2007, Wang et al.
U.S. Appl. No. 11/937,780, filed Nov. 14, 2007, Wang et al.
Lauer G. M. et al., "Hepatitis C Virus Infection," New England Journal of Medicine, vol. 345 No. 1, pp. 41-52, (2001).
Poupart, M.-A. et al., "Solid-Phase Synthesis of Peptidomimetic Inhibitors for the Hepatitis C Virus NS3 Protease," The Journal of Organic Chemistry, vol. 66 No. 14, pp. 4743-4751, (2001).
Llinas-Brunet et al. (2004) Journal of Medicinal Chemistry, vol. 47 pp. 6584-6594.

* cited by examiner

INHIBITORS OF HEPATITIS C VIRUS

CROSS-REFERENCE TO RELATED APPLICATIONS

This application claims the benefit of U.S. Provisional Application Ser. No. 60/863,837 filed Nov. 1, 2006.

FIELD OF THE INVENTION

The present disclosure is generally directed to antiviral compounds, and more specifically directed to compounds which inhibit the functioning of the NS3 protease (also referred to herein as "serine protease") encoded by Hepatitis C virus (HCV), compositions comprising such compounds and methods for inhibiting the functioning of the NS3 protease.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to cleave at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

SUMMARY OF THE INVENTION

The present disclosure provides macrocyclic compounds of the following formula:

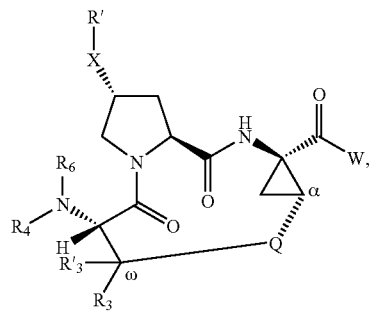

I or a pharmaceutically acceptable salt thereof, wherein:

(a) $R_4$ is hydrogen; $C_{1-6}$ alkyl; $C_{3-7}$ cycloalkyl; alkoxy; —C(O)—$R_5$; C(O)—N($R_5$)$_2$; C(O)—O$R_5$; $C_{7-14}$ alkylaryl; or $C_{3-7}$ cycloalkyl, wherein the alkyl and the cycloalkyl are optionally substituted with halo; and wherein each $R_5$ is independently selected from $C_{1-9}$ alkyl, wherein the alkyl is optionally substituted with $C_{1-6}$ alkoxy, $C_{3-7}$ cycloalkoxy, halo-$C_{1-6}$ alkoxy, cyano, halo, hydroxy, amino, $C_{1-6}$ alkylamino, di ($C_{1-6}$) alkylamino, di ($C_{1-6}$) alkylamide, carboxyl, or ($C_{1-6}$) carboxyester;

(b) $R_6$ is hydrogen, $C_{1-6}$ alkyl, or $C_{3-7}$ cycloalkyl;

(c) $R_3$ and $R_{13}$ are each independently hydrogen or methyl;

(d) Q is a $C_{3-9}$ saturated or unsaturated chain wherein from 1 to 3 carbon atoms are independently replaced with an $NR_8$ group, wherein each $NR_8$ group is separated from another $NR_8$ group by at least one carbon atom in the chain; wherein $R_8$ is hydrogen; $C_{1-6}$ alkyl; $C_{1-6}$ cycloalkyl; —C(O)—$R_9$, C(O)—O$R_{10}$, C(O)—N$R_{11}R_{12}$ or —SO$_2R_{13}$; wherein the alkyl and the cycloalkyl are optionally substituted with halo, $C_{1-6}$ alkoxy, cyano or $C_{1-6}$ haloalkoxy; and wherein $R_9$, $R_{11}$, and $R_{12}$ are each independently hydrogen; $C_{1-6}$ alkyl or $C_{1-6}$ cycloalkyl, wherein the alkyl and the cycloalkyl are optionally substituted with halo, $C_{1-6}$ alkoxy, cyano or $C_{1-6}$ haloalkoxy; and wherein $R_{10}$ is $C_{1-6}$ alkyl or $C_{1-6}$ cycloalkyl, wherein the alkyl and the cycloalkyl are optionally substituted with halo, $C_{1-6}$ alkoxy, cyano or $C_{1-6}$ haloalkoxy; and wherein $R_{13}$ is aryl, $C_{1-6}$ alkyl or $C_{1-6}$ cycloalkyl, wherein the aryl, the alkyl, and the cycloalkyl are optionally substituted with halo, $C_{1-6}$ alkoxy, cyano or $C_{1-6}$ haloalkoxy;

(e) W is OH, —O—$R_1$, or —NH—SO$_2$—$R_2$; wherein $R_1$ is $C_{1-6}$ alkyl, unsaturated $C_{3-7}$ cycloalkyl, $C_{6-14}$ aryl, or $C_{7-16}$ alkylaryl; and $R_2$ is $C_{1-8}$ alkyl, $C_{4-10}$ alkylcycloalkyl, or unsubstituted $C_{3-7}$ cycloalkyl; or $R_2$ is cyclopropyl or cyclobutyl optionally substituted with $C_{1-4}$ alkyl, $C_{2-5}$ alkenyl, $C_{7-16}$ alkylaryl, alkoxy, alkoxyalkyl, $C_{5-7}$ cycloalkyl, $C_{5-7}$ cycloalkenyl, $C_{6-10}$-alkylcycloalkyl, halo, haloalkyl, cyano, alkylcyano, haloalkoxy, or C(O)—X; wherein the $C_{5-7}$ cycloalkyl, the $C_{5-7}$ cycloalkenyl, and the $C_{6-10}$ alkylcycloalkyl are further optionally substituted with $C_{1-4}$ alkyl or hydroxy; and wherein X is selected from phenyl and —$NHR^x$; wherein $R^x$ is selected from $C_{1-6}$ alkyl, Het, and $C_{6-10}$ aryl;

(f) X is O, S, SO, $SO_2$, $OCH_2$, $CH_2O$ or NH;

(g) R' is Het, $C_{6-10}$ aryl or $C_{7-14}$ alkylaryl, each optionally substituted with from one to five of the same or different $R^a$ groups; or $C_{3-9}$ cycloalkyl or $C_{1-7}$ alkyl, wherein the cycloalkyl and the alkyl are optionally substituted with from one to five of the same or different members of the group consisting of halo, cyano, alkoxy, and dialkylamino;

provided that —XR' is other than:

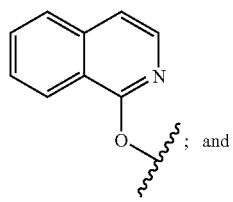

and (h) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, di ($C_{1-6}$) alkyl(alkoxy)amine, $C_{6-10}$ aryl, $C_{7-14}$ alkylaryl, or a 5-7 membered monocyclic heterocycle.

The present disclosure also provides compositions comprising the compounds or pharmaceutically acceptable salts thereof and a pharmaceutically acceptable carrier. In particular, the present disclosure provides pharmaceutical compositions useful for inhibiting HCV NS3 protease comprising a therapeutically effective amount of a compound of the present disclosure, or a pharmaceutically acceptable salt thereof, and a pharmaceutically acceptable carrier.

The present disclosure further provides methods for treating patients infected with HCV, comprising administering to the patient a therapeutically effective amount of a compound of the present disclosure, or a pharmaceutically acceptable salt thereof. Additionally, the present disclosure provides methods of inhibiting HCV NS3 protease by contacting the NS3 protease with a compound of the present disclosure.

By virute of the present disclosure, it is now possible to provide drugs comprising the compounds of the disclosure which can be effective in the treatment of patients infected with HCV. Specifically, the present disclosure provides peptide compounds that can inhibit the functioning of the NS3 protease, e.g., in combination with the NS4A protease. Further, the present disclosure makes it possible to administer combination therapy to a patient whereby a compound in accordance with the present disclosure, which is effective to inhibit the HCV NS3 protease, can be administered with another compound having anti-HCV activity, e.g., a compound which is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

DETAILED DESCRIPTION

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture. With reference to the instances where (R) or (S) is used, it is to designate the absolute configuration of a substituent in context to the whole compound and not in context to the substituent alone.

Unless otherwise specifically noted herein, the terms set forth below will have the following definitions.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445. The compounds of the present disclosure are useful in the form of the free base or acid or in the form of a pharmaceutically acceptable salt thereof. All forms are within the scope of the disclosure.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the disclosure", and equivalent expressions, are meant to embrace compounds of formula I, and pharmaceutically acceptable enantiomers, diastereomers, and salts thereof. Similarly, references to intermediates, are meant to embrace their salts where the context so permits. References to the compound of the disclosure also include the preferred compounds, e.g. formula II.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18th ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The term "substituted" as used herein includes substitution at from one to the maximum number of possible binding sites on the core, e.g., organic radical, to which the substitutent is bonded, e.g., mono-, di-, tri- or tetra-substituted, unless otherwise specifically stated.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine or arylalkyl, include all possible stable configurations, unless otherwise specifically stated. Certain radicals and combinations are defined below for purposes of illustration.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents having the specified number of carbon atoms and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specifically stated. Thus a $C_{4-10}$ alkylcycloalkyl may contain from 1-7 carbon atoms in the alkyl group and from 3-9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralalkyl" mean an aryl group substituted with one or more alkyl groups. Unless the carbon range of each group is specified, the stated range applies to the entire substituent. Thus, a $C_{7-14}$ alkylaryl group many have from 1-8 carbon atoms in the alkyl group for a monocyclic aromatic and from 1-4 carbon atoms in the alkyl group for a fused aromatic. The attachment of the group to bonding site on the molecule can be either at the aryl group or the alkyl group. Unless a specific aryl radical is specified, e.g., fluoro-phenyl, or the radical is stated to be unsubstituted, the aryl radicals include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl(alkoxy)amine. Examples of alkylaryl groups include benzyl, butylphenyl and 1-naphthylmethyl.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "alkylamide" as used herein means an amide mono-substituted with an alkyl, such as

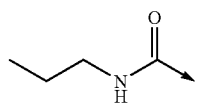

The term "heterocycle", also referred to as "Het", as used herein means 7-12 membered bicyclic heterocycles and 5-7 membered monocyclic heterocycles.

Preferred bicyclic heterocycles are 7-12 membered fused bicyclic ring systems (both rings share an adjacent pair of atoms) containing from one to four heteroatoms selected from nitrogen, oxygen and sulfur, wherein both rings of the heterocycle are fully unsaturated. The nitrogen and sulfur heteroatoms may be optionally oxidized. The bicyclic heterocycle may contain the heteroatoms in one or both rings. Unless a specific heterocycle is specified, e.g., a fluorinated 7-12 membered bicyclic heterocycle, or the heterocycle is stated to be unsubstituted, the heterocycles include those substituted with typical substituents known to those skilled in the art. For example, the bicyclic heterocycle may also contain substituents on any of the ring carbon atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, $C_{1-6}$ alkylsulfoxide, di ($C_{1-6}$) alkyl(alkoxy)amine, $C_{6-10}$ aryl, $C_{7-14}$ alkylaryl, and a 5-7 membered monocyclic heterocycle. When two substituents are attached to vicinal carbon atoms of the bicyclic heterocycle, they can join to form a ring, e.g., a five, six or seven membered ring system containing up to two heteroatoms selecting from oxygen and nitrogen. The bicyclic heterocycle may be attached to the molecule, e.g. R' in formula I, at any atom in the ring and preferably carbon.

Examples of bicyclic heterocycles include, but are not limited to, the following ring systems:

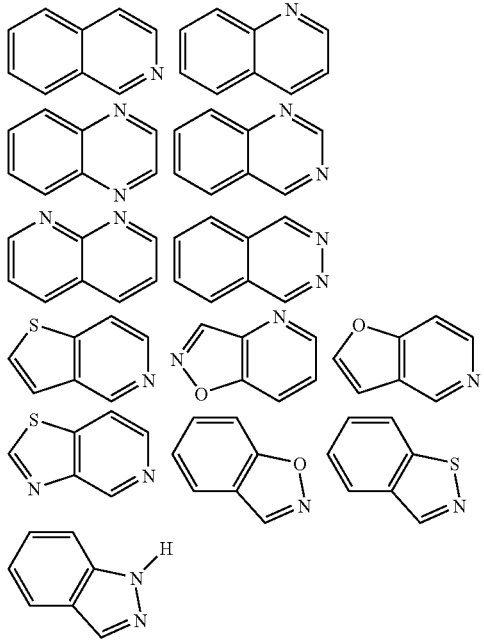

Preferred monocyclic heterocycles are 5-7 membered saturated, partially saturated or fully unsaturated ring system (this latter subset also herein referred to as unsaturated heteroaromatic) containing in the ring from one to four heteroatoms selected from nitrogen, oxygen and sulfur, wherein the sulfur and nitrogen heteroatoms may be optionally oxidized. Unless a specific heterocycle is specified, e.g., a $C_{1-6}$ alkoxy substituted 5-7 membered monocyclic heterocycle, or the heterocycle is stated to be unsubstituted, the heterocycles include those substituted with typical substituents known to those skilled in the art. For example, the monocyclic heterocycle may also contain substituents on any of the ring atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfoxide, $C_{1-6}$ alkylsulfonamide, di ($C_{1-6}$) alkyl (alkoxy)amine, $C_{6-10}$ aryl, $C_{7-14}$ alkylaryl and an additional 5-7 membered monocyclic heterocycle. The monocyclic heterocycle may be attached to the molecule, e.g. R' in formula I, at any atom in the ring.

Examples of monocyclic heterocycles include, but are not limited to, the following (and their tautomers):

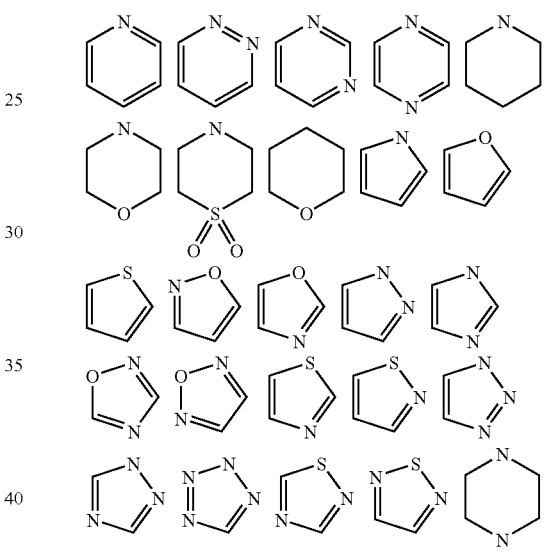

Those skilled in the art will recognize that the heterocycles used in the compounds of the present disclosure should be stable. Generally, stable compounds are those which can be synthesized, isolated and formulated using techniques known the those skilled in the art without degradation of the compound.

The term "substituent" with reference to an amino acid or amino acid derivative means a radical derived from the corresponding α-amino acid. For instance, the substituents methyl, iso-propyl, and phenyl represent the amino acids alanine, valine, and phenyl glycine, respectively.

Where used in naming compounds of the present disclosure, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.)(see Berger A. & Schechter I., Transactions of the Royal Society London series (1970), B257, 249-264].

In one aspect of the disclosure X is selected from O, OCH$_2$, CH$_2$O, S, and NH. In another embodiment X is O.

In another aspect of the disclosure R' is selected from the following heterocycles:

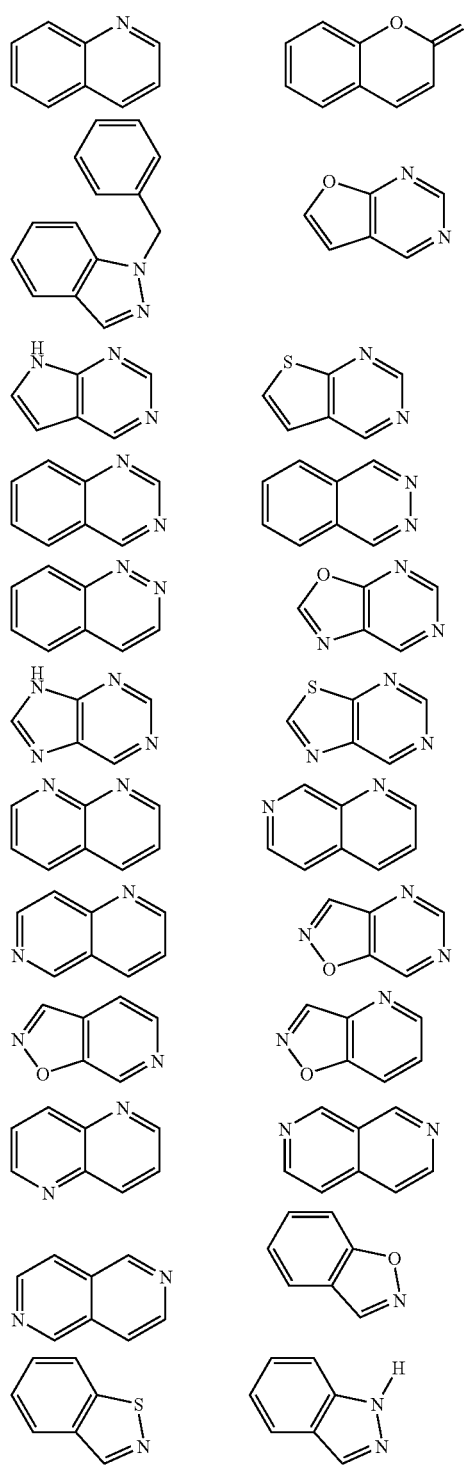
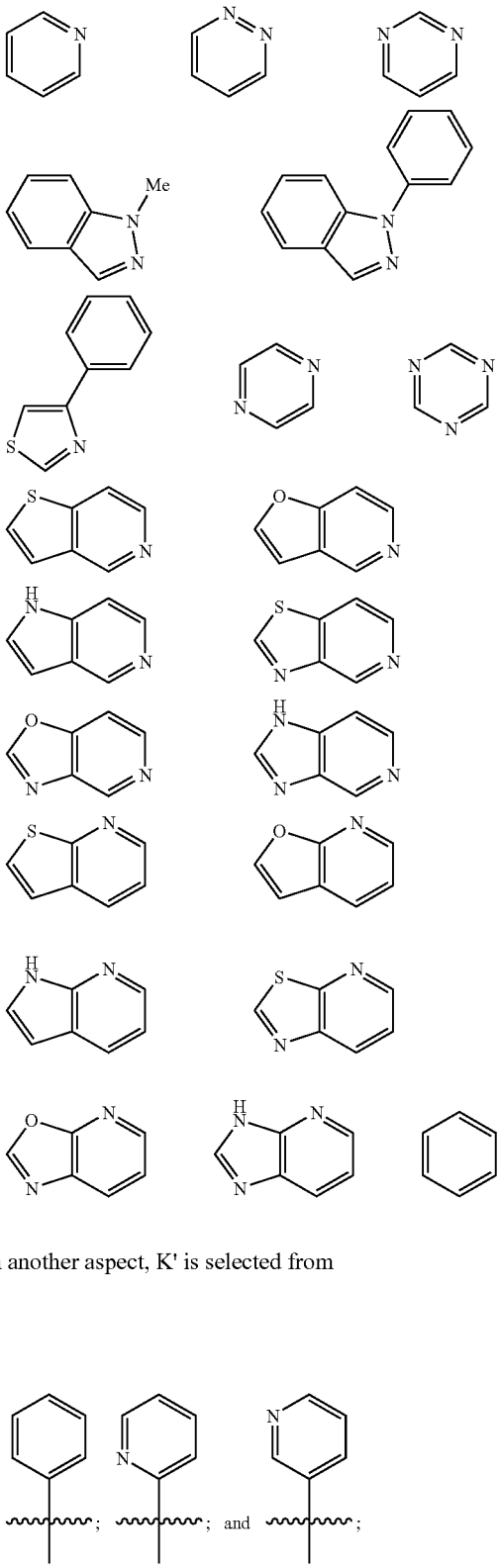

In another aspect, K' is selected from each optionally substituted with from one to five of the same or different R$^a$ groups.

In another aspect of the disclosure X—R' is selected from the following:

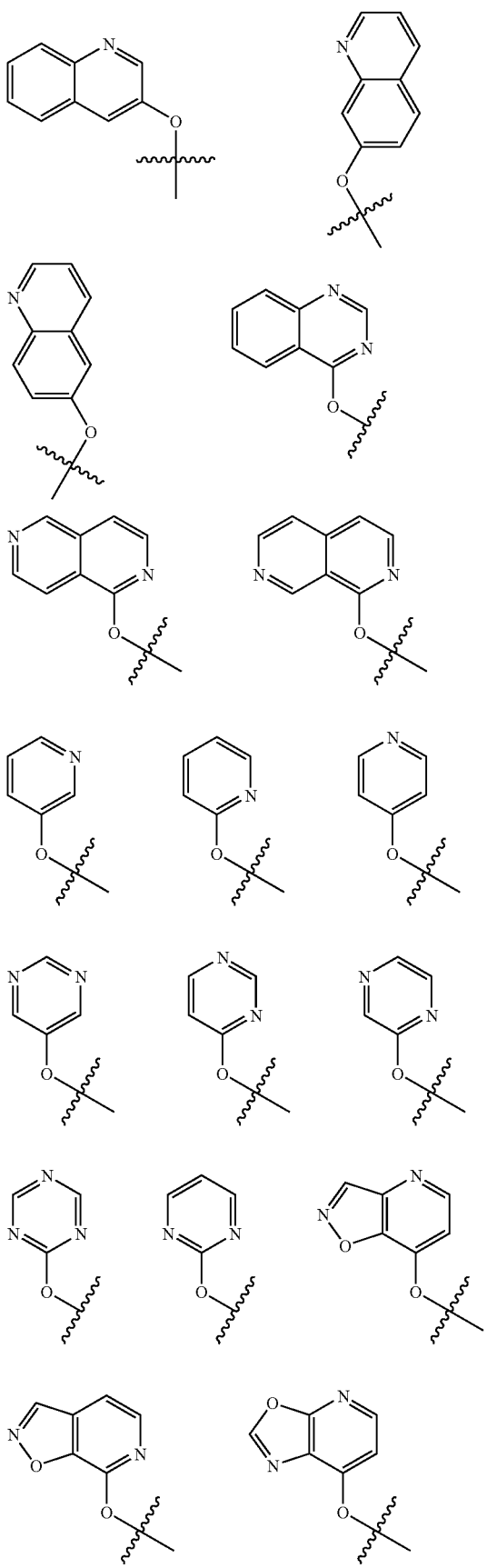
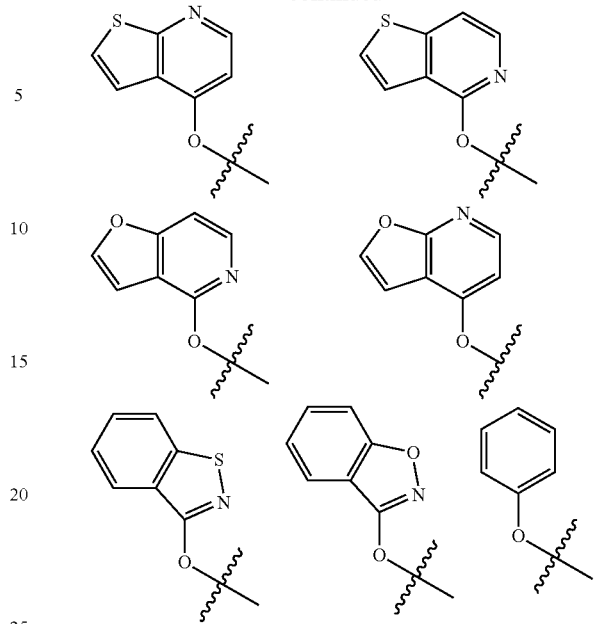

In another aspect, W is —NH—SO$_2$—R$_2$: wherein R$_2$ is C$_{1-8}$ alkyl, C$_{4-10}$ alkylcycloalkyl, or unsubstituted C$_{3-7}$ cycloalkyl; or R$_2$ is cyclopropyl or cyclobutyl optionally substituted with C$_{1-4}$ alkyl or C$_{7-16}$ alkylaryl. In another aspect, R$_2$ is unsubstituted C$_{3-7}$ cycloalkyl. In another aspect R$_2$ is unsubstituted cyclopropyl.

In another aspect, Q is a C$_{5-7}$ saturated or unsaturated chain optionally containing one to three NR$_8$ groups. In another aspect, Q is unsaturated. In another aspect, Q has the following structure:

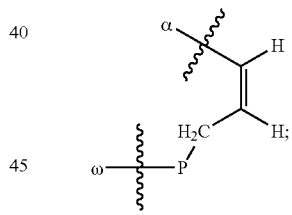

wherein P is a C$_3$ saturated chain containing one NR$_8$ group, wherein R$_8$ is hydrogen; C$_{1-6}$ alkyl; or C$_{1-6}$ cycloalkyl, wherein the alkyl and the cycloalkyl are optionally substituted with halo, C$_{1-6}$ alkoxy, cyano or C$_{1-6}$ haloalkoxy; —C(O)—R$_9$, C(O)—OR$_{10}$, C(O)—NR$_{11}$R$_{12}$ or —SO$_2$R$_{13}$; R$_9$, R$_1$, and R$_{12}$ are each independently hydrogen; C$_{1-6}$ alkyl or C$_{1-6}$ cycloalkyl, wherein the alkyl and the cycloalkyl are optionally substituted with halo, C$_{1-6}$ alkoxy, cyano or C$_{1-6}$ haloalkoxy; R$_{10}$ is C$_{1-6}$ alkyl or C$_{1-6}$ cycloalkyl, wherein the alkyl and the cycloalkyl are optionally substituted with halo, C$_{1-6}$ alkoxy, cyano or C$_{1-6}$ haloalkoxy; R$_{13}$ is aryl, C$_{1-6}$ alkyl or C$_{1-6}$ cycloalkyl, wherein the aryl, the alkyl, and the alkyl are optionally substituted with halo, C$_{1-6}$ alkoxy, cyano or C$_{1-6}$ haloalkoxy.

In another aspect, R$_4$ is C(O)—OR$_5$; wherein R$_5$ is C$_{1-6}$ alkyl optionally substituted with halo, alkoxy, or cyano. In another aspect, R$_5$ is C$_{1-6}$ alkyl optionally substituted with halo and R$_6$ is hydrogen.

In another aspect, R$_3$ and R$_{13}$ are each hydrogen.

In another aspect of the disclosure, the compounds of the present disclosure have the structure of Formula II:

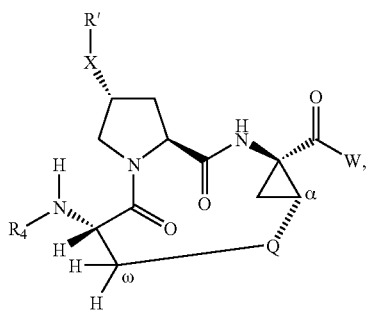

or a pharmaceutically acceptable salt thereof, wherein:

$R_4$ is C(O)—$OR_5$; wherein $R_5$ is $C_{1-9}$ alkyl optionally substituted with $C_{1-6}$ alkoxy, cyano, or halo;

Q is a $C_{5-7}$ saturated or unsaturated chain wherein one carbon atom is replaced with an $NR_8$ group; $R_8$ is $C_{1-6}$ cycloalkyl, optionally substituted with halo, $C_{1-6}$ alkoxy, cyano or $C_{1-6}$ haloalkoxy;

W is NH—$SO_2$—$R_2$; wherein $R_2$ is $C_{3-7}$ cycloalkyl;

X is O;

R' is Het, $C_{6-10}$ aryl or $C_{7-14}$ alkylaryl, each optionally substituted with from one to five of the same or different $R^a$ groups; or $C_{3-9}$ cycloalkyl or $C_{1-7}$ alkyl, each optionally substituted with from one to five of the same or different members of the group consisting of halo, cyano, alkoxy and dialkylamino;

provided that —XR' is other than:

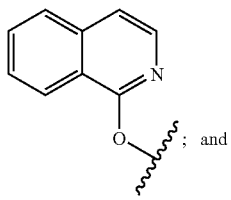 [SMILES: *Oc1nccc2ccccc12 ; ";" ; "and"]

$R^a$ is selected from the group consisting of $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, halo-$C_{1-6}$ alkoxy, cyano, halo, thioalkyl, hydroxy, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, di ($C_{1-6}$) alkyl(alkoxy)amine, $C_{6-10}$ aryl, $C_{7-14}$ alkylaryl and a 5-7 membered monocyclic heterocycle.

The compounds of the present disclosure, which contain a basic moiety, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present disclosure, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Asymmetric centers exist in the compounds of the present disclosure. For example, the compounds may include P1 cyclopropyl element of formula

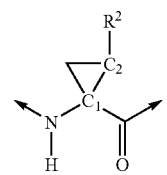

wherein $C_1$ and $C_2$ each represent an asymmetric carbon atom at positions 1 and 2 of the cyclopropyl ring. Not withstanding other possible asymmetric centers at other segments of the compounds, the presence of these two asymmetric centers means that the compounds can exist as racemic mixtures of diastereomers, such as the diastereomers wherein $R^2$ is configured either syn to the amide or syn to the carbonyl as shown below.

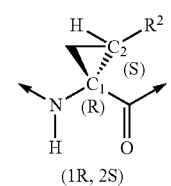

(1R, 2S)
$R^2$ is syn to carbonyl

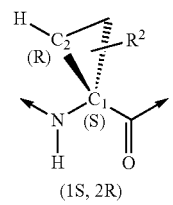

(1S, 2R)
$R^2$ is syn to carbonyl

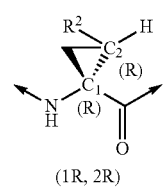

(1R, 2R)
$R^2$ is syn to amide

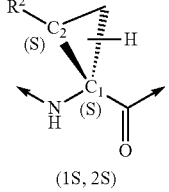

(1S, 2S)
$R^2$ is syn to amide

It should be understood that the disclosure encompasses all stereochemical isomeric forms, or mixtures thereof, which possess the ability to inhibit HCV protease.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

The starting materials useful to synthesize the compounds of the present disclosure are known to those skilled in the art and can be readily manufactured or are commercially available.

The compounds of the present disclosure can be manufactured by methods known to those skilled in the art. The following methods set forth below are provided for illustrative purposes and are not intended to limit the scope of the claimed disclosure. For example, compounds of the present disclosure having the structure of Formula I can be synthesized, as shown in scheme 1. It will be recognized that it may be preferred or necessary to prepare such a compound in which a functional group is protected using a conventional protecting group then to remove the protecting group to provide a compound of the present disclosure. The details concerning the use of protecting groups in accordance with the present disclosure are known to those skilled in the art.

As shown in scheme 1, intermediates of the present disclosure such as dipeptide 1, can be used for the preparation of compounds of Formula I. In the first step of this process the Boc protected nitrogen of 1 is deprotected using an acid such as HCl in a solvent such as ether, to provide the corresponding free amine 2. Amine 2 can be subsequently coupled to amino acid 3 using a coupling agent such as HATU in a solvent such as dichloromethane to provide the tripeptide intermediate 4. It should be noted that in some cases intermediates like 3 are commercially available, and alternatively such compounds can be readily prepared in racemic or chiral fashion by methods known in the art. A key transformation in the construction of compounds of Formula I is the macrocyclization process wherein intermediates of general structure 4 are converted into intermediates of general structure 5. In the general example cited, the conversion of intermediate 4 into 5 can be affected by an intramolecular olefin metathesis reaction. This class of reactions is well established in the art and as such, a number of olefin-metathesis-catalysts have been developed and are commercially available. For example the conversion of diene 4 to macrocycle 5 could be affected by the treatment of 4 with a sufficient quantity of Grubb's first-generation olefin metathesis catalyst, in a solvent such as dichloromethane or dichloroethane. In some examples for the conversion of 4 to 5, it may be necessary to heat the reaction mixture in order to effect this cyclization process. Intermediate 5 is then coverted to compounds of Formula I such as 7 by a two step process. In the first step of this process, the ester functionality of intermediate 5 is hydrolyzed to the corresponding carboxylic 6. This transformation can be accomplished by a saponification reaction wherein 5 is treated with a base such as lithium hydroxide in a mixture of THF, methanol and water. The resulting acid 6 can be converted to a compound of Formula I by a simple coupling reaction with a sulfonamide derivative as shown. For example, it is well established in the art that treatment of a carboxylic acid like 6, with CDI in a solvent such as methylene chloride, generates in situ a reactive intermediate which when treated with a sulfonamide provides for 7, a compound of Formula 1.

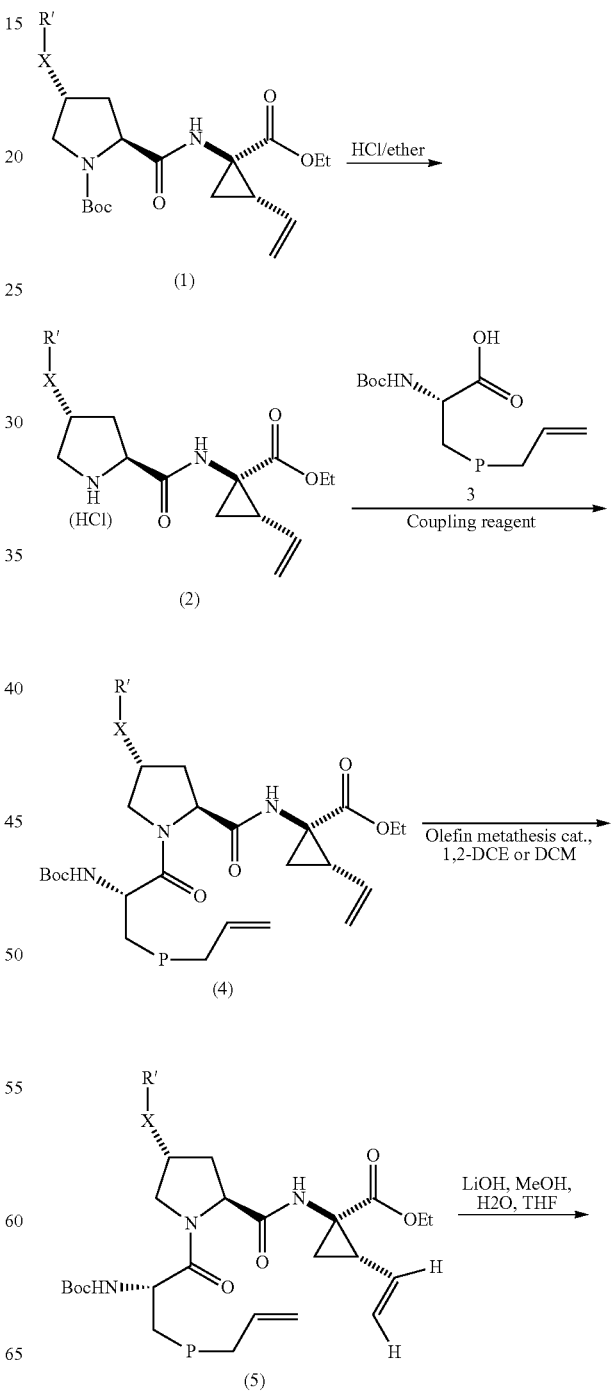

Scheme 1

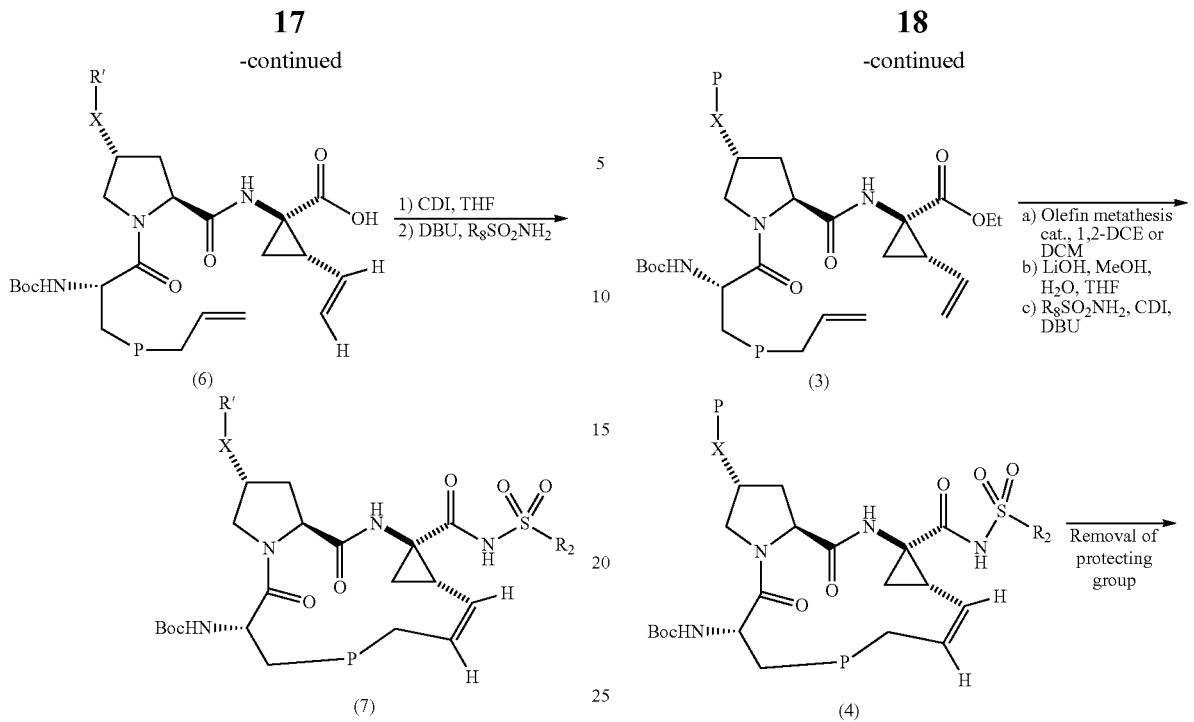

An additional process wherein compounds of Formula I can be prepared is outlined below (Scheme 2). Therein, the P2* functionality, defined herein as the functional group attached to the proline C4-moiety (XR'), is incorporated after the P1-P3 macrocyclization step. However, it should be noted that the process of incorporating of P2* into the molecule can be executed at any suitable stage of the synthesis. In the present, nonlimiting scheme, (Scheme 2) the proline substituent X is protected using a suitable protecting group. This group is then carried through several steps in the synthesis as shown, and removed after the cyclization process to provide an intermediate like 5, which is then converted into a compound of Formula I

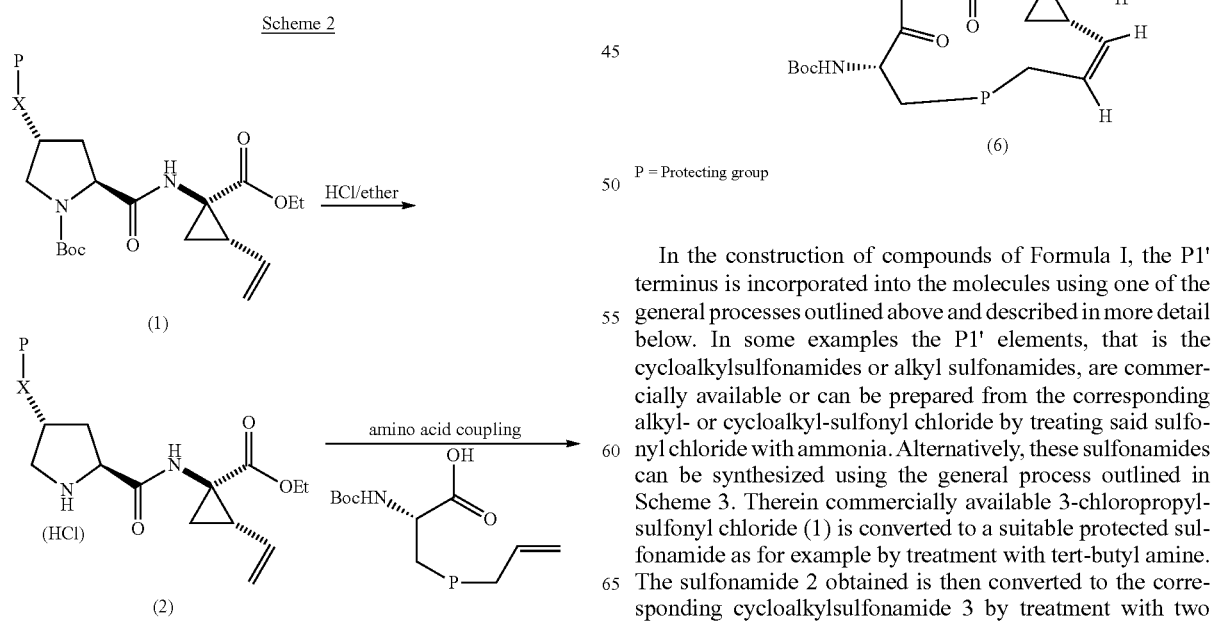

P = Protecting group

In the construction of compounds of Formula I, the P1' terminus is incorporated into the molecules using one of the general processes outlined above and described in more detail below. In some examples the P1' elements, that is the cycloalkylsulfonamides or alkyl sulfonamides, are commercially available or can be prepared from the corresponding alkyl- or cycloalkyl-sulfonyl chloride by treating said sulfonyl chloride with ammonia. Alternatively, these sulfonamides can be synthesized using the general process outlined in Scheme 3. Therein commercially available 3-chloropropyl-sulfonyl chloride (1) is converted to a suitable protected sulfonamide as for example by treatment with tert-butyl amine. The sulfonamide 2 obtained is then converted to the corresponding cycloalkylsulfonamide 3 by treatment with two equivalents of a base such as butyl lithium in a solvent such as THF at low temperature. The resulting cycloalkylsulfonamide can be deprotected by treatment with an acid to provide the desired unprotected cycloalkylsulfonamide 4. Said P1' fragment 4 can be incorporated into compounds of Formula I. Additionally, the cycloalkyl ring of intermediates like 4 can be further functionalized. For example, treatment of intermediate 3 with a base such as butyl lithium followed by the addition of an electrophile such as an alkyl halide should provide intermediates like 5, wherein the C1 position of the cycloalkyl ring is functionalized. Reactions of this type can be conducted in solvents such as THF. In such a reaction it may be necessary to add two or more equivalents of base to intermediate 3. Moreover, the temperature of such a reaction will likely need to be carefully monitored wherein the THF solution of 3 is cooled to −78C prior to the addition of base and this is described in detail herein.

-continued

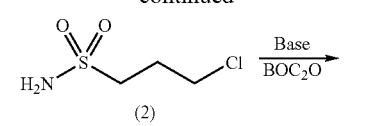

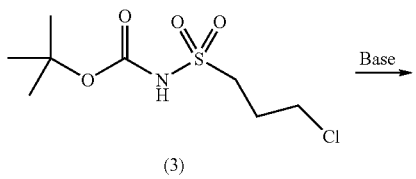

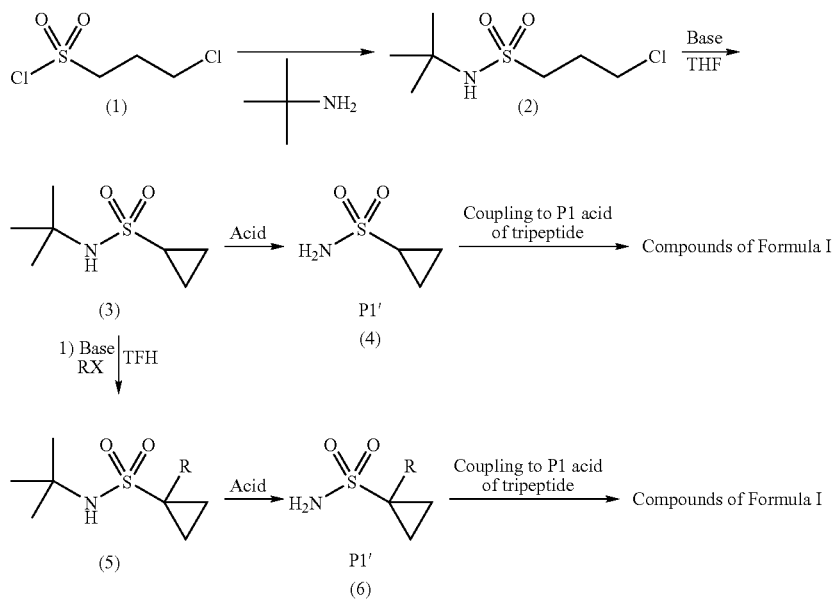

Scheme 3

As an alternative to the t-butyl protecting group used in the above scheme (eg. intermediate 2 of scheme 3) a Boc group can be employed as shown below (Scheme 4). Said Boc group can be incorporated by treatment of an intermediate like 2 with Boc anhydride in the presence of a base such as triethylamine in conjunction with catalytic DMAP. The acylsulfonamide 3 obtained is then converted to the corresponding cycloalkylacylsulfonamide 4 by treatment with two equivalents of a base such as butyl lithium in a solvent such as THF at low temperature. The resulting cycloalkylacylsulfonamide 4 can be deprotected by treatment with an acid to provide the desired unprotected cycloalkylsulfoamide. Said P1' fragment can be incorporated into compounds of Formula I.

-continued

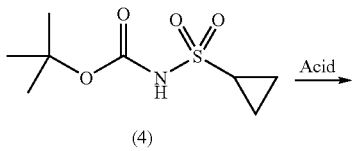

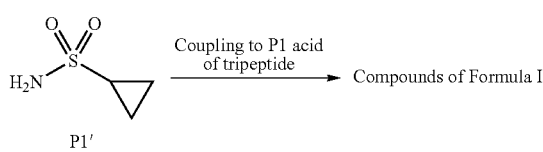

In the preparation of compounds of Formula I, dipeptide intermediates like 2 shown below can be prepared by the coupling of hydroxyproline derivative 1 with cyclopropyl amino acid B as shown. This coupling reaction can be carried out using reagents such as HATU or HBTU and in solvents such as methylene chloride or DMF or THF.

Scheme 4

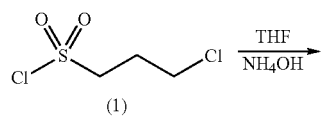

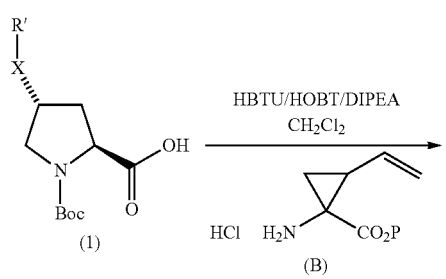

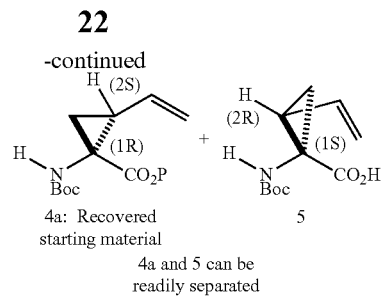

4a: Recovered starting material

5

4a and 5 can be readily separated

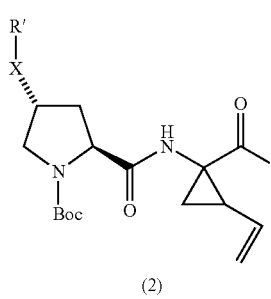

Intermediate B can be synthesized as shown in scheme 5.

Treatment of commercially available, or readily synthesized imine 1 with 1,4-dihalobutene 2 in presence of a base provides the imine 3. Acid hydrolysis of 3 then provides B as a mixture of diastereoisomers. It is preferred that for compounds 3 and B that the vinyl group is syn to the ester. The amine moiety of B can protected using a Boc group to provide the fully protected amino acid 4a/4b. This intermediate is a racemate, a 1:1 mixture of enantiomers, and each enantiomer is shown in the above scheme. Racemate 4a/4b can be resolved by an enzymatic process wherein the ester moiety of 4 is cleaved to provide the corresponding carboxylic acid. Without being bound to any particular theory, it is believed that this reaction is selective in that one of the enantiomers, that is 4b, with the absolute stereochemistry designated (1S, 2R) undergoes the reaction at a much greater rate than its mirror image, 4a, providing for a kinetic resolution of racemate 4a/4b. Hence, in the course of this enzyme catalyzed ester cleavage, 4b will be readily converted to the corresponding acid 5, whereas 4a will remain as unreacted starting material. Once the reaction is terminated, the carboxylic acid 5 and recovered starting material 4a, can be separated by routine methods such as aqueous extraction methods or chromatography. As shown below, intermediate 4a can be readily converted into compounds of Formula I by the methods described herein. For example, removal of the Boc group from intermediate 4a can be accomplished by subjecting 4a to an acid such as HCl in a solvent such as ether, to provide the corresponding amine hydrochloride 6. Intermediate 6 can then be coupled to a functionalized proline moiety 1 to provide the P1-P2 dipeptide 2. Intermediates like 2 can be converted to compounds of Formula I by the methods described herein.

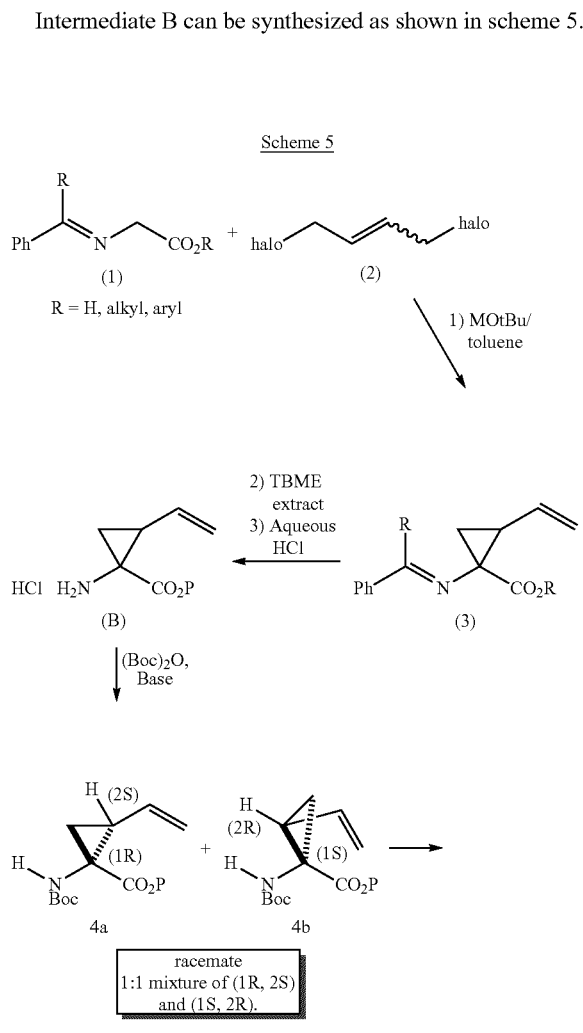

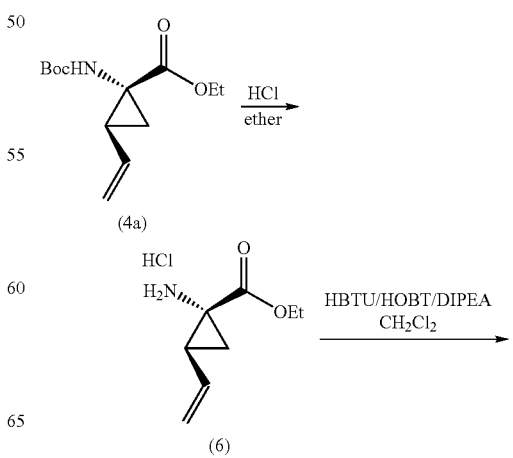

-continued

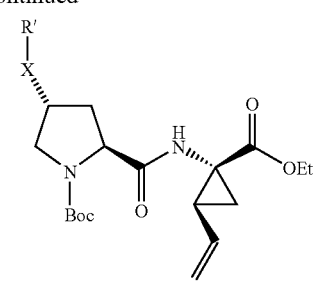

(2)

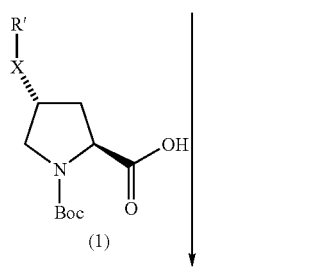

(1)

Compounds of Formula 1

-continued

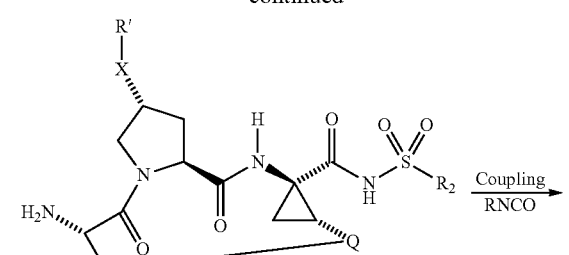

(2)

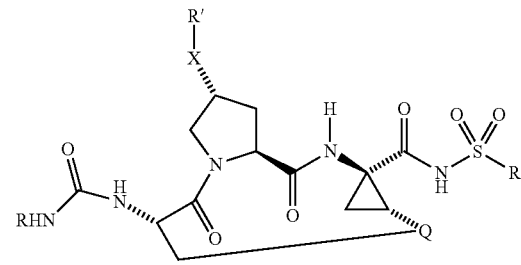

(3)

Compounds of Formula I

Compounds of Formula I can also be converted into other compounds of Formula I as described herein. An example of such a process is shown in Scheme 6, wherein a compound of Formula I (1) which bears a Boc group at the P4 position is converted into a compound of Formula I (3) wherein said compound bears a urea group at the P4 position. The conversion of 1 to 3 can be carried out in a two step process the first of which is the conversion of 1 to amine 2 by treatment of 1 with an acid such as TFA in a solvent such as methylene chloride. The resulting amine TFA salt can be treated with an isocyanate in the presence of one equivalent of base to provide a compound of Formula I (3) wherein the P3 moiety is capped with a urea. As previously noted one skilled in the art will recognize that intermediate 2 can be used as starting material for the preparation of compounds of Formula I wherein the P3 group is capped with an amide or a carbamate. The construction of said compounds of Formula I can be achieved using standard conditions for the formation of said P4 functionalities from amines.

Scheme 6

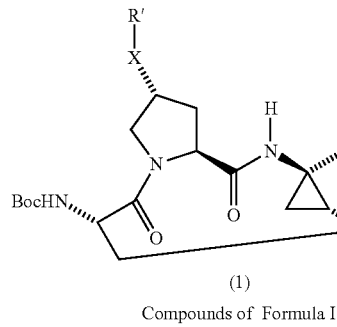

(1)
Compounds of Formula I

One skilled in the art would recognize that the incorporation of P2* into the molecule can be carried out at any stage in the assembly of the peptide backbone. This is illustrated below (Scheme 7) for the conversion of intermediates like 1, 3 or 5 into compounds of Formula 1.

Scheme 7

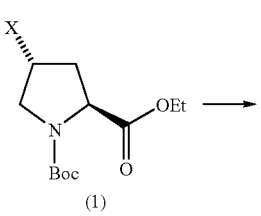

(1)

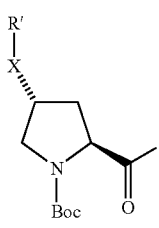 → Compounds of Formula 1

(2)

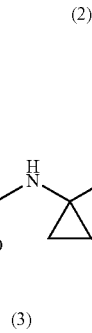 →

(3)

25

-continued

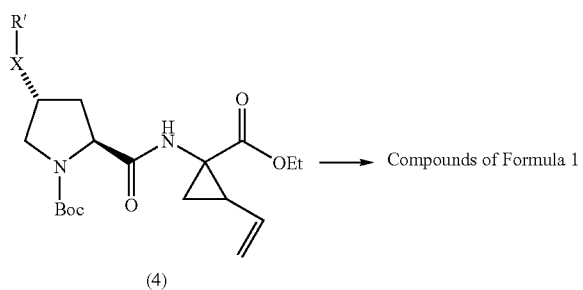

(4)

→ Compounds of Formula 1

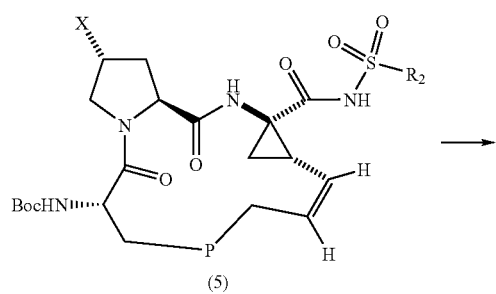

(5)

26

-continued

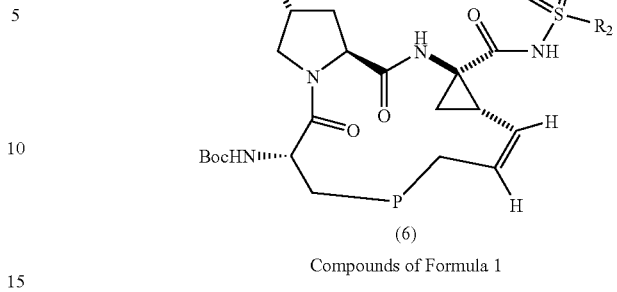

(6)

Compounds of Formula 1

Aza macrocycles can be prepared by the process outline in Scheme 8. Therein, amino acid 1 is coupled with P2-P1 dipeptide 2, using agents such as HATU in conjunction with an amine bases such as morpholine, and in a solvent such as DMF. The resulting tripeptide 3, is then converted to the macrocycle 4 using a ring closing metathesis reaction. There are a number of reagents developed for this process as for example the ruthenium species shown, which is commonly referred to as the "Grubbs Second Generation catalyst". Subjecting 3 to such a ring closing metathesis reagent should provide the desired macrocycle 4. This reaction can be conducted in solvents such as methylene chloride, dichloroethane, or benzene. Moreover, in some examples it may be necessary to heat the reaction vessel to affect cyclization or to drive the reaction to completion.

Scheme 8

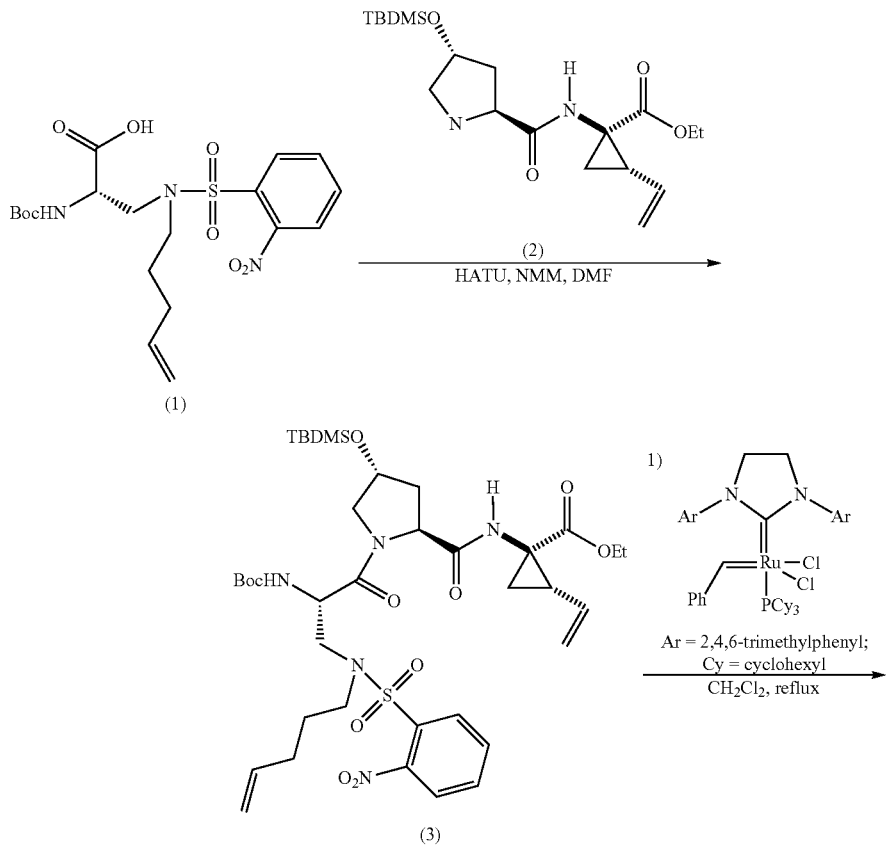

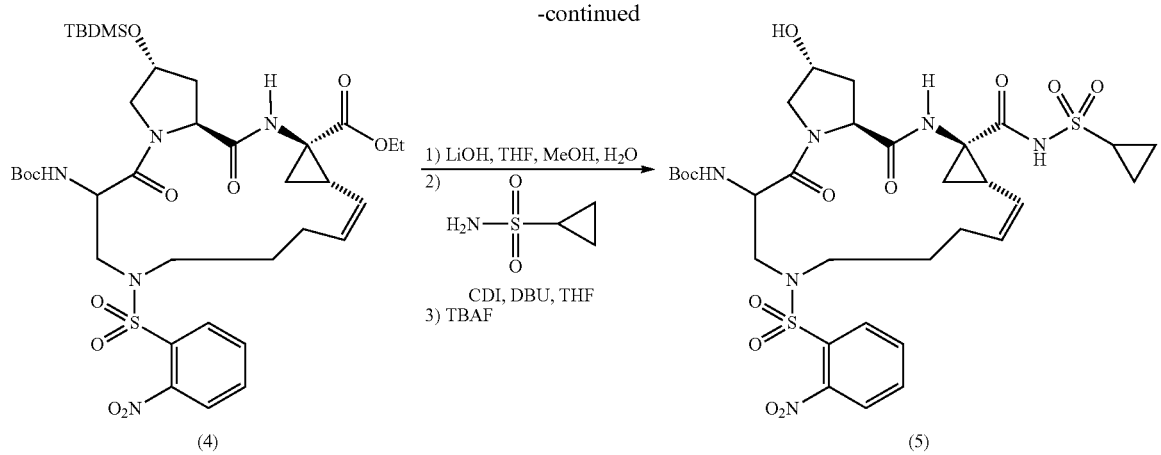

The present disclosure also provides compositions comprising a compound of the present disclosure, or a pharmaceutically acceptable enantiomer, diastereomer, or salt thereof, and a pharmaceutically acceptable carrier. Pharmaceutical compositions of the present disclosure comprise a therapeutically effective amount of a compound of the disclosure, or a pharmaceutically acceptable enantiomer, diastereomer, or salt thereof, and a pharmaceutically acceptable carrier, with a pharmaceutically acceptable carrier, e.g. excipient, or vehicle diluent.

The active ingredient, i.e., compound, in such compositions typically comprises from 0.1 weight percent to 99.9 percent by weight of the composition, and often comprises from about 5 to 95 weight percent.

Thus, in one aspect of the disclosure, there is provided a composition comprising the compound of formula I and a pharmaceutically acceptable carrier. Preferably, the composition further comprises a compound having anti-HCV activity. As used herein, the term "anti-HCV activity" means the compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection. Often, the other compound having anti-HCV activity is effective to inhibit the function of target in the HCV life cycle other than the HCV NS3 protease protein.

In one preferred aspect, the compound having anti-HCV activity is an interferon. Preferably, the interferon is selected from the group consisting of interferon alpha 2B, pegylated interferon alpha, consensus interferon, interferon alpha 2A, lymphoblastiod interferon tau.

In another aspect of the disclosure, the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In one preferred aspect of the disclosure, the composition comprises a compound of the disclosure, an interferon and ribavirin.

In another aspect the disclosure provides a composition comprising the compound of formula I, or a pharmaceutically acceptable salt thereof, and a pharmaceutically acceptable carrier. In one embodiment of this aspect the composition further comprises at least one additional compound having anti-HCV activity. In another embodiment at least one of the additional compounds is an interferon or a ribavirin. In another embodiment the interferon is selected from interferon alpha 2B, pegylated interferon alpha, consensus interferon, interferon alpha 2A, and lymphoblastiod interferon tau.

In another aspect the disclosure provides a composition comprising the compound of formula I, or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In another aspect the disclosure provides a composition comprising the compound of formula I, or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In another aspect the disclosure provides a method of treating an HCV infection in a patient, comprising administering to the patient a therapeutically effective amount of a compound of formula I, or a pharmaceutically acceptable salt thereof. In one embodiment the method further comprises administering at least one additional compound having anti-HCV activity prior to, after, or simultaneously with the compound of formula I, or a pharmaceutically acceptable salt thereof. In another embodiment at least one of the additional compounds is an interferon or a ribavirin. the interferon is selected from interferon alpha 2B, pegylated interferon alpha, consensus interferon, interferon alpha 2A, and lymphoblastiod interferon tau.

In another aspect the disclosure provides a method of treating an HCV infection in a patient, comprising administering to the patient a therapeutically effective amount of a compound of formula I, or a pharmaceutically acceptable salt thereof and at least one additional compound having anti-HCV activity prior to, after, or simultaneously with the compound of formula I, or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In another aspect the disclosure provides a method of treating an HCV infection in a patient, comprising administering to the patient a therapeutically effective amount of a compound of formula I, or a pharmaceutically acceptable salt thereof and at least one additional compound having anti-HCV activity prior to, after, or simultaneously with the compound of formula I, or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In another aspect the present disclosure provides a composition comprising a compound of formula (I), or a pharmaceutically acceptable salt thereof, one, two, three, four, or five additional compounds having anti-HCV activity, and a pharmaceutically acceptable carrier. In a first embodiment of this aspect the composition comprises three or four additional compounds having anti-HCV activity. In a second embodiment the composition comprises one or two additional compounds having anti-HCV activity.

In another aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of this aspect the method comprises administering three or four additional compounds having anti-HCV activity. In a second embodiment the method comprises administering one or two additional compounds having anti-HCV activity.

Other aspects of the present disclosure may include suitable combinations of embodiments disclosed herein.

Yet other aspects and embodiments may be found in the description provided herein.

Certain illustrative HCV inhibitor compounds which can be administered with the compounds of the present disclosure include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc, New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288; 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/ Eli Lilly and Co. Inc., Indianapolis, IN |
| HCV-796 | Antiviral | NS5B Replicase Inhibitor | Wyeth/ Viropharma |
| NM-283 | Antiviral | NS5B Replicase Inhibitor | Idenix/ Novartis |
| GL-59728 | Antiviral | NS5B Replicase Inhibitor | Gene Labs/ Novartis |

TABLE 1-continued

| Brand Name | Physiological Class | Type of Inhibitor or Target | Source Company |
|---|---|---|---|
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |

TABLE 1-continued

| Brand Name | Physiological Class | Type of Inhibitor or Target | Source Company |
|---|---|---|---|
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| TMC-465350 | Antiviral | serine protease inhibitor | Medivir/Tibotec |

The pharmaceutical compositions of this disclosure may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

When orally administered, the pharmaceutical compositions of this disclosure may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Other suitable carriers for the above noted compositions can be found in standard pharmaceutical texts, e.g. in "Remington's Pharmaceutical Sciences", 19th ed., Mack Publishing Company, Easton, Pa., 1995.

The pharmaceutical compositions can be prepared by known procedures using well-known and readily available ingredients. The compositions of this disclosure may be formulated so as to provide quick, sustained or delayed release of the active ingredient after administration to the patient by employing procedures well known in the art. In making the compositions of the present disclosure, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like. Further details concerning the design and preparation of suitable delivery forms of the pharmaceutical compositions of the disclosure are known to those skilled in the art.

Dosage levels of between about 0.01 and about 1000 milligram per kilogram ("mg/kg") body weight per day, preferably between about 0.5 and about 250 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable enantiomers, diastereomers, or salts are formulated together with a pharmaceutically acceptable carrier, the resulting composition may be administered in vivo to mammals, such as man, to inhibit HCV NS3 protease or to treat or prevent HCV virus infection.

Accordingly, another aspect of this disclosure provides methods of inhibiting HCV NS3 protease activity in patients by administering a compound of the present disclosure or a pharmaceutically acceptable enantiomer, diastereomer, salt or solvate thereof.

In one aspect of the disclosure, there is provided a method of treating an HCV infection in a patient, comprising administering to the patient a therapeutically effective amount of the compound of the disclosure, or a pharmaceutically acceptable enantiomer, diastereomer, or salt thereof.

Preferably, the method of administering the compound is effective to inhibit the function of the HCV NS3 protease protein. In a preferred aspect, the method further comprises administering another compound having anti-HCV activity (as described above) prior to, after or concurrently with a compound of the disclosure.

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the disclosure can be used for the manufacture of a medicament for treating HCV infection in a patient.

EXAMPLES

The specific examples that follow illustrate the syntheses of the compounds of the present disclosure, and are not to be construed as limiting the scope of the claims which follow. The methods may be adapted to variations in order to produce compounds embraced by this disclosure but not specifically disclosed. Further, variations of the methods to produce the same compounds in somewhat different manner will also be evident to one skilled in the art.

Chemical abbreviations commonly used to identify chemical compounds disclosed herein include Bn: benzyl; Boc: tert-butyloxycarbonyl {Me3COC(O)}; BSA: bovine serum albumin; CDI: carbonyldiimidazole; DBU: 1,8-diazabicy-clo[5.4.0]-undec-7-ene; CH2Cl2=DCM: methylene chloride; TBME: tert-butyl methyl ether; DEAD: diethylazodicarboxylate; DIAD: diisopropylazodicarboxylate; DIEA: diisopropylethylamine; DIPEA: diisopropylethylamine; 4-DMAP: 4-dimethylaminopyridine; DCC: 1,3-dicyclohexylcarbodiimide; DMF: dimethylformamide; DMSO: dimethylsulfoxide; DPPA: diphenylphosphoryl azide; Et: ethyl; EtOH: ethanol; EtOAc: ethyl acetate; Et2O: diethyl ether; Grubb's Catalyst: bis(tricyclohexylphosphine)benzylidene ruthenium (IV) dichloride; Grubb's 2nd Generation Catalyst: tricyclohexylphosphine[1,3-bis(2,4,6-trimethylphenyl)-4,5-dihydroimidazol-2-ylidene][benzylidene]ruthenium (IV) dichloride; HATU: [O-(7-azabenzotriazol-1-yl)-N,N,N',N'-tetramethyluronium hexafluorophosphate; HBTU: [O-(1H-benzotriazol-1-yl)-N,N,N',N'-tetramethyluronium hexafluorophosphate; HOBT, 1-hydroxybenzotriazole; HOAT, 1-hydroxy-7-azabenzotriazole; HPLC: high performance liquid chromatography; MS: mass spectrometry; Me: methyl; MeOH: methanol; NMM: N-methylmorpholine; NMP: N-methylpyrrolidine; Pr: propyl; PPA: polyphosphoric acid; TBAF: tetra-n-butylammonium fluoride; 1,2-DCE or DCE: 1,2-dichloroethane; TFA: trifluoroacetic acid; THF: tetrahydrofuran.

Solution percentages express a weight to volume relationship, and solution ratios express a volume to volume relationship, unless stated otherwise. Nuclear magnetic resonance (NMR) spectra were recorded either on a Bruker 300, 400 or 500 megahertz (MHz) spectrometer; the chemical shifts ($\delta$) are reported in parts per million. Flash chromatography was carried out on silica gel (SiO2) according to Still's flash chromatography technique (J. Org. Chem. 1978, 43, 2923). Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+). Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts ($\delta$) are reported in parts per million.

The examples, compounds and chemical intermediates of the present disclosure, described in the following examples, were prepared according to the following methods.

Example 1

Preparation of racemic (1R,2S)/(1S,2R)-1-amino-2-vinylcyclopropane carboxylic acid ethyl ester hydrochloride (Method A and Method B)

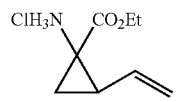

The named compound was made racemic by each of the following methods A and B.

Method A

Preparation of N-Benzyl Imine of Glycine Ethyl Ester

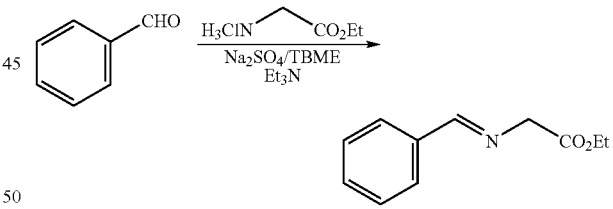

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous NaHCO3 (1 L) and brine (1 L). The solution was dried over MgSO4, concentrated in vacuo to afford 392.4 g of the N-benzyl imine product as a thick yellow oil that was used directly in the next step. $^1$H NMR (CDCl$_3$, 300 MHz) $\delta$ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Preparation of racemic
N-Boc-(1R,2S)/(1S,2R)-1-amino-2-vinylcyclopropane carboxylic acid ethyl ester

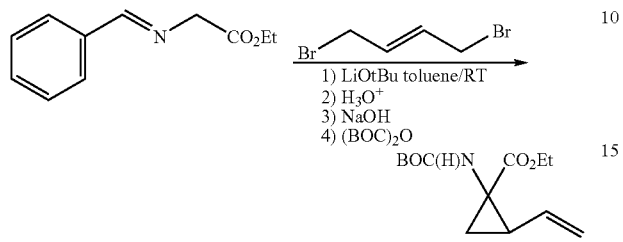

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO4) and concentrated to a volume of 1 L. To this solution of free amine, was added BOC2O or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over MgSO4 and concentrated in vacuo to afford 80 g of crude material. This residue was purified by flash chromatography (2.5 Kg of SiO2, eluted with 1% to 2% MeOH/CH$_2$Cl$_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1).

Preparation of Racemic (1R,2S)/(1S,2R) 1-amino-2-vinylcyclopropane carboxylic acid ethyl ester hydrochloride

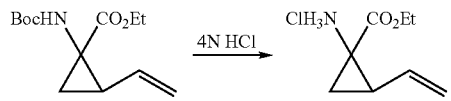

N-Boc-(1R,2 S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quanitative yield (7 g, 100%). $^1$H NMR (methanol-d4) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26-4.34 (m, 2H), 5.24 (dd, 10.3, 1.3 Hz, 1H) 5.40 (d, J=17.2 Hz, 1H), 5.69-5.81 (m, 1H).

Method B

Preparation of Racemic
N-Boc-1-amino-2-vinylcyclopropane carboxylic acid ethyl ester hydrochloride

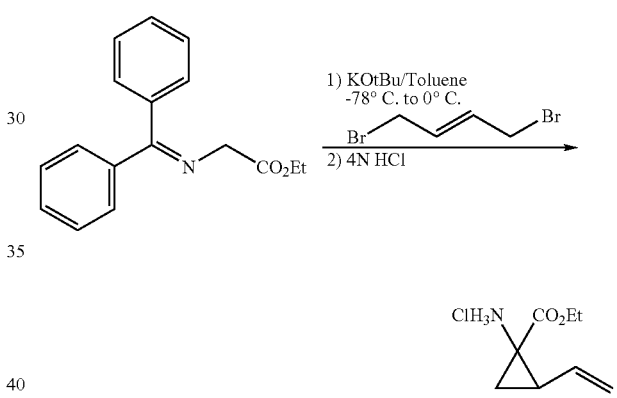

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et2O (530 mL), 1N aq. HCl solution (106 mL, 106 mmol) added and the resulting biphasic mixture stirred for 3.5 h at rt. The layers were separated and the aqueous layer was washed with Et2O (2×) and basified with a saturated aq. NaHCO3 solution. The desired amine was extracted with Et2O (3×) and the combined organic extract was washed with brine, dried (MgSO4), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Example 2

Resolution of N-Boc-(1R,2S)/(1S2R)-1-amino-2-vinylcyclopropane carboxylic acid ethyl ester racemate: 1:1 mixture of (1R, 2S) and (1S, 2R)

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO3 (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% (210 nm, containing no acid; 100% enantiomeric excess ("ee").

The aqueous layer from the extraction process was then acidified to pH 2 with 50% H2SO4 and extracted with MTBE (2×2 L). The MTBE extract was washed with water (3×100 mL) and evaporated to give the acid as light yellow solid (42.74 g; purity: 99% @210 nm, containing no ester).

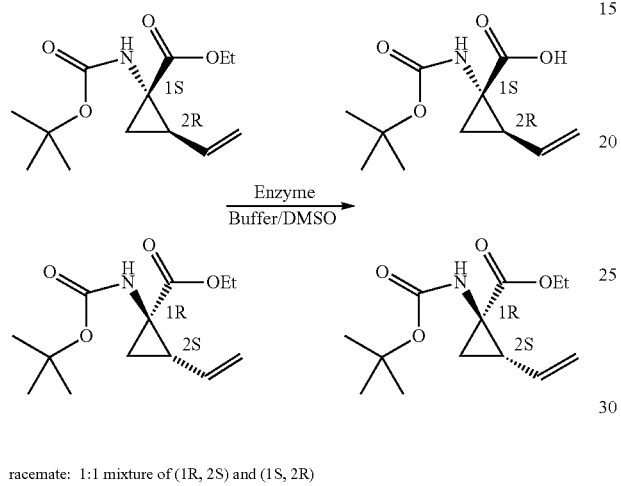

1R, 2S-ester 1S, 2R-acid

| | ester | acid |
|---|---|---|
| High Resolution Mass Spec | (+) ESI, C13H22NO4, $[M + H]^+$, cal. 256.1549, found 256.1542 | (−) ESI, C11H16NO4, $[M − H]^−$, cal. 226.1079, found 226.1089 |

NMR observed chemical shift
Solvent: CDCl$_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | 118.1 |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution B

To 0.5 mL 100 mM Heps•Na buffer (pH 8.5) in a well of a 24 well plate (capacity: 10 ml/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("µl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µl of the supernatant was analyzed with the chiral HPLC and enantio-excess of the ester was determined to be 100%.

Resolution C

To 0.5 ml 100 mM Heps•Na buffer (pH 8.5) in a well of a 24 well plate (capacity: 10 mL/well), 0.1 ml of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after centrifugation, 10 µl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µl of the supernatant was analyzed with the chiral HPLC and enantio-excess of the ester was determined to be 100%.

Samples analysis was carried out in the following manner:

1) Sample preparation: About 0.5 ml of the reaction mixture was mixed well with 10 volume of EtOH. After centrifugation, 10 µl of the supernatant was injected onto HPLC column.

2) Conversion determination:

Column: YMC ODS A, 4.6×50 mm, S-5 µm

Solvent: A, 1 mM HCl in water; B, MeCN

Gradient: 30% B for 1 min; 30% to 45% B over 0.5 min; 45% B for 1.5 min; 45% to 30% B over 0.5 min.

Flow rate: 2 ml/min

UV Detection: 210 nm

Retention time: acid, 1.2 min; ester, 2.8 min.

3) Enantio-excess determination for the ester:

Column: CHIRACEL OD-RH, 4.6×150 mm, S-5 µm

Mobile phase: MeCN/50 mM $HClO_4$ in water (67/33)

Flow rate: 0.75 ml/min.

UV Detection: 210 nm.

Retention Time:

(1S,2R)-1-amino-2-vinylcyclopropane carboxylic acid 5.2 min;

Racemate (1R,2S)/(1S,2R)-1-amino-2-vinylcyclopropane carboxylic acid ethyl ester 18.5 min and 20.0 min;

(1R,2S)-1-amino-2-vinylcyclopropane carboxylic acid ethyl ester 18.5 min.

Resolution D

5 L of 0.3 M sodium phosphate buffer (pH 8) was maintained at 38° C. in a 20 Liter jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funel. The reaction temperature was then adjusted to 48° C. After 21 hours, enantio-excess of the ester reached 99.3%. Heating was stopped at 24 hour and the reaction was slowly cooled down to room temperature (about 25° C.) and stirred overnight. pH of the reaction mixture was adjusted to 8.5 with 10 N NaOH and the mixture was extracted with MTBE (2×4 L). The combined MTBE extract was washed with 5% NaHCO3 (3×400 ml) and water (3×400 ml), and evaporated to give enantiomerically pure N-Boc-(1R,2S)/-1-amino-2-vinylcyclopropane carboxylic acid ethyl ester as light yellow crystal (259 g; purity: 96.9% @210 nm, containing no acid; 100% ee).

Resolution E

10 L of 0.1 M sodium phosphate buffer (pH 8) was maintained at 40° C. in a 20 Liter jacked reactor, stirred at 360 rpm. 1.5 liters of Alcalase 2.4 L (Novozymes North America Inc.) was added to the reactor. When temperature of the mixture closed to 38° C., pH was adjusted to 8.0 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 1 hour via an addition funel. The reaction temperature was then adjusted to 40° C. After 3 hours, pH was adjusted to 8.0 with 10 N NaOH. After 21 hours, the reaction was cooled down to 25° C. pH of the reaction mixture was adjusted to 8.5 with 10 N NaOH and the mixture was extracted with MTBE (2×5 L). The combined MTBE extract was washed with 5% NaHCO3 (3×500 ml) and water (3×200 ml), and evaporated to give 110 gram of yellow oil. The oil was set at room temperature under house vacuum and gave enantiomerically pure N-Boc-(1R, 2S)/-1-amino-2-vinylcyclopropane carboxylic acid ethyl ester as colorless long rod crystal (101 g; purity: 97.9% @210 nm, containing no acid; 100% ee).

The crystal structure enantiomerically pure N-Boc-(1R, 2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N, O 3.159 Å).

Structure of N-Boc-(1R,2S)-1-amino-2-vinylcyclopropane carboxylic acid ethyl ester:

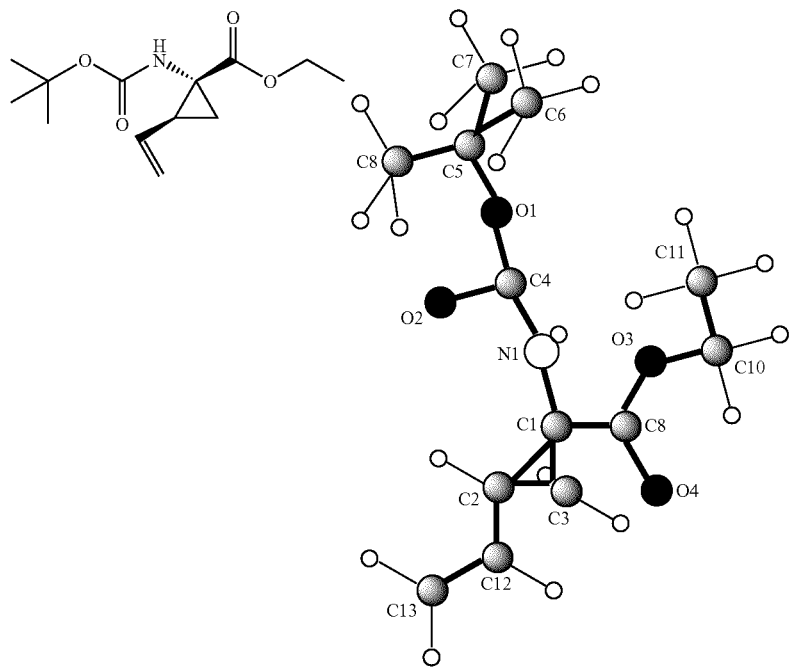

| Crystal Data: | Experimental: |
| --- | --- |
| Chemical formula: $C_{13}H_{21}N_1O_4$ | Crystallization |
| Crystal system: Orthorhombic | Crystal source: MTBE |
| Space Group: $P2_12_12_1$ | Crystal description: Colorless rod |
| a = 5.2902(1) Å   α = 90° | Crystal size (mm): 0.12 × 0.26 × 0.30 |
| b = 13.8946(2) Å   β = 90° | Data Collection |
| c = 19.9768(3) Å   γ = 90° | Temperature (K): 293 |
| V = 1468.40(4) Å$^3$ | $θ_{max}$ (°): 65.2 (Cu Kα) |
| Z = 4   $d_x$ = 1.155 g cm$^{-3}$ | No. of reflections measured: 7518 |
| No. of reflections for lattice parameters: 6817 | No. of independent reflections: 2390 ($R_{int}$ = 0.0776) |
| θ range for lattice parameters (s): 2.2-65.2 | No. of observed reflections (1 ≧ 2 σ): 2284 |
| Absorption coefficient (mm$^{-1}$): 0.700 | Absorption correction ($T_{min}$-$T_{max}$): 0.688-1.000 |

Resolution F

5 L of 0.2 M sodium borate buffer (pH 9) was maintained at 45° C. in a 20 liter jacked reactor, stirred at 400 rpm. Three liter of DI water and four liters of Savinase 16L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 min, via an addition funel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hour, temperature was lowered to 35° C. At 42 hour, temperature was raised to 48° C. and pH was adjusted to 9.0 with 10 N NaOH. Heating was stopped at 48 hour and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% NaHCO3 (6×300 ml) and water (3×300 ml), and evaporated to give enantiomerically pure N-Boc-(1R,2 S)/-1-amino-2-vinylcyclopropane carboxylic acid ethyl ester as light yellow crystal (101A g; purity: 95.9% @210 nm, containing no acid; 98.6% ee).

Example 3

Step 1: Preparation of ethyl 1(R)-amino-2(S)-vinylcyclopropane carboxylate hydrochloride

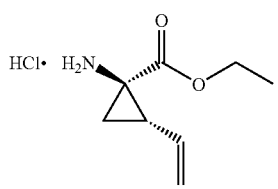

Ethyl 1(R)-tert-butoxycarbonylamino-2(S)-vinylcyclopropanecarboxylate (8.5 g, 33.3 mmol) was stirred under an N2 atmosphere with 200 mL of 4N HCl/dioxane (Aldrich) at rt for 3 h. The solvent was removed under reduced pressure keeping the temperature below 40° C. This gave 6.57 g (~100%) of ethyl 1(R)-amino-2(S)-vinylcyclopropanecarboxylate hydrochloride as a light tan solid. $^1$H NMR (300

MHz, CD$_3$OD) δ 1.31 (t, J=7.0 Hz, 3 H), 1.69-1.82 (m, 2 H), 2.38 (q, J=8.8 Hz, 1 H), 4.29 (q, J=7.0 Hz, 2 H), 5.22 (d, J=10.3 Hz, 1 H), 5.40 (d, J=17.2 Hz, 1 H), 5.69-5.81 (m, 1 H). MS m/z 156 (M++1).

Step 2: Preparation of ethyl 1(R)-[1-tert-butoxycarbonyl-4(R)-hydroxypyrrolidine-2(S)-carboxamido]-2(S)-vinylcyclopropanecarboxylate

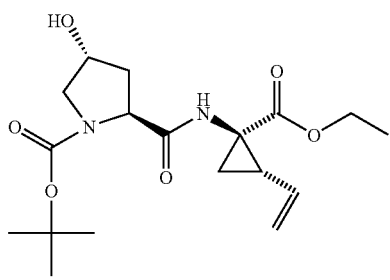 [SMILES: C=C[C@@H]1C[C@]1(NC(=O)[C@@H]1C[C@@H](O)CN1C(=O)OC(C)(C)C)C(=O)OCC]

A stirred slurry of Boc-L-4-hydroxyproline (N-Boc (2S, 4R)-hydroxyproline) (10 g, 43.3 mmol) in 400 mL of methylene chloride was treated sequentially with N-methyl morpholine (9.3 mL, 84.7 mmol), HATU (19.5 g, 51.3 mmol), and ethyl 1(R)-amino-2(S)-vinylcyclopropanecarboxylate hydrochloride (9.1 g, 47.5 mmol). The gold homogeneous solution was stirred at rt under N2 for 18 h, and then concentrated in vacuo to give a brown oil. This was partitioned between ethyl acetate and sat. aq. NaHCO3. The organic phase was washed with brine, dried (MgSO4), and concentrated in vacuo to give 15 g (94%) of ethyl 1(R)-[1-tert-butoxycarbonyl-4(R)-hydroxypyrrolidine-2(S)-carboxamido]-2(S)-vinylcyclopropanecarboxylate as a off-white solid: LC-MS (Xterra HPLC column: 3.0×50 mm length. Gradient: 100% Solvent A/0% Solvent B to 0% Solvent A/100% Solvent B. Gradient time: 3 min. Hold time: 1 min. Flow rate: 5 mL/min. Detector Wavelength: 220 nm. Solvent A: 10% MeOH/90% H$_2$O/0.1% TFA. Solvent B: 10% H$_2$O/90% MeOH/0.1% TFA.) (Retention time: 2.09 min), MS m/z 369 (M++1).

Step 3: Preparation of ethyl 1(R)-[4(R)-hydroxypyrrolidine-2(S)-carboxamido]-2(S)-vinylcyclopropanecarboxylate hydrochloride

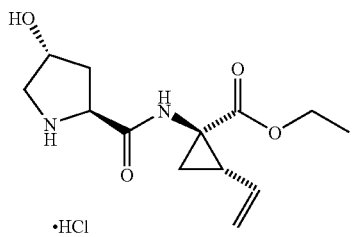 [SMILES: C=C[C@@H]1C[C@]1(NC(=O)[C@@H]1C[C@@H](O)CN1)C(=O)OCC ; Cl]

A stirred slurry of ethyl 1(R)-[1-tert-butoxycarbonyl-4(R)-hydroxypyrrolidine-2(S)-carboxamido]-2(S)-vinylcyclopropanecarboxylate (5.0 g, 13.6 mmol) was treated with 4N HCl/dioxane (20 mL) for 3 h. The reaction mixture was concentrated in vacuo to give 4.5 g (97%) of ethyl 1(R)-[4(R)-hydroxypyrrolidine-2(S)-carboxamido]-2(S)-vinylcyclopropanecarboxylate hydrochloride as a white solid: $^1$H NMR (300 MHz, CD$_3$OD) δ 1.26 (t, J=7.14 Hz, 3 H), 1.46 (dd, J=9.70, 5.31 Hz, 1 H), 1.80 (dd, J=8.23, 5.31 Hz, 1 H), 2.00-2.15 (m, 1 H), 2.18-2.30 (m, 1 H), 2.45 (dd, J=13.36, 7.50 Hz, 1 H), 3.36-3.48 (m, 1 H), 4.11-4.24 (m, 2 H), 4.44 (dd, J=10.25, 7.68 Hz, 1 H), 4.58-4.65 (m, 1 H), 4.84-4.94 (m, 1 H), 5.17 (d, J=1.83 Hz, 1 H), 5.27-5.42 (m, 1 H), 5.67-5.89 (m, 1 H).

Example 4

Preparation of Cyclopropylsulfonamide Methods A and B

Method A:

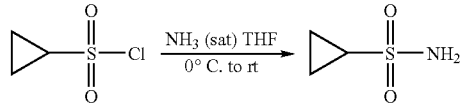

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1-2 mL of solvent remained, applied on to 30 g plug of SiO2 (eluted with 30% to 60% EtOAc/Hexanes) to afford 3.45 g (100%) of cyclopropyl sulfonamide as a white solid. $^1$H NMR (Methanol-d4) δ 0.94-1.07 (m, 4H), 2.52-2.60 (m, 1H); $^{13}$C NMR (methanol-d4) δ 5.92, 33.01.

Method B:

Step 1: Preparation of N-tert-Butyl-(3-chloro)propylsulfonamide

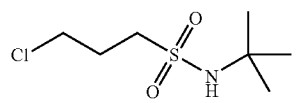

tert-Butylamine (3.0 mol, 315.3 mL) was dissolved in THF (2.5 L). The solution was cooled to −200C. 3-Chloropropanesulfonyl chloride (1.5 mol, 182.4 mL) was added slowly. The reaction mixture was allowed to warm to rt and stirred for 24 h. The mixture was filtered, and the filtrate was concentrated in vacuo. The residue was dissolved in CH2Cl2 (2.0 L). The resulting solution was washed with 1 N HCl (1.0 L), water (1.0 L), brine (1.0 L) and dried over Na2SO4. It was filtered and concentrated in vacuo to give a slightly yellow solid, which was crystallized from hexane to afford the product as a white solid (316.0 g, 99%).

$^1$H NMR (CDCl$_3$) δ 1.38 (s, 9H), 2.30-2.27 (m, 2H), 3.22 (t, J=7.35 Hz, 2H), 3.68 (t, J=6.2 Hz, 2H), 4.35 (b, 1H).

Step 2: Preparation of Cyclopropanesulfonic Acid tert-Butylamide

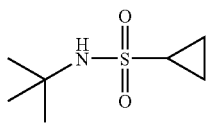

To a solution of N-tert-butyl-(3-chloro)propylsulfonamide (2.14 g, 10.0 mmol) in THF (100 mL) was added n-BuLi (2.5 M in hexane, 8.0 mL, 20.0 mmol) at −78° C. The reaction mixture was allowed to warm up to room temperature over period of 1 h. The volatiles were removed in vacuo. The residue was partitioned between EtOAC and water (200 mL, 200 mL). The separated organic phase was washed with brine, dried over Na2SO4, filtered and concentrated in vacuo. The residue was recrystallized from hexane to yield the desired product as a white solid (1.0 g, 56%).
$^1$H NMR (CDCl$_3$) δ 0.98-1.00 (m, 2H), 1.18-1.19 (m, 2H), 1.39 (s, 9H), 2.48-2.51 (m, 1H), 4.19 (b, 1H).

Step 3: Preparation of Cyclopropylsulfonamide

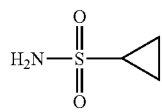

A solution of cyclopropanesulfonic acid tert-butylamide (110.0 g, 0.62 mol) in TFA (500 mL) was stirred at room temperature for 16 h. The volatile was removed in vacuo. The residue was recrystallized from EtOAC/hexane (60 mL/240 mL) to yield the desired product as a white solid (68.5 g, 91%).
$^1$H NMR (DMSO-d$_6$) δ 0.84-0.88 (m, 2H), 0.95-0.98 (m, 2H), 2.41-2.58 (m, 1H), 6.56 (b, 2H).

Example 5

Preparation of N-tert-butyl-(1-methyl)cyclopropylsulfonamide

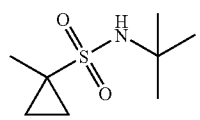

Step 1a Preparation of N-tert-butyl-(3-chloro)propylsulfonamide

As shown above.

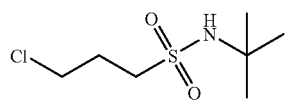

Step 1b. Preparation of N-tert-Butyl-(1-methyl)cyclopropylsulfonamide

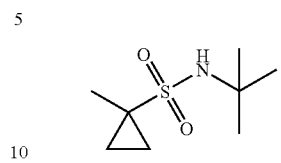

A solution of N-tert-butyl-(3-chloro)propylsulfonamide (4.3 g, 20 mmol) was dissolved in dry THF (100 mL) and cooled to −78° C. To this solution was added n-BuLi (17.6 mL, 44 mmol, 2.5 M in hexane) slowly. The dry ice bath was removed and the reaction mixture was allowed to warm to rt over a period of 1.5 h. This mixture was then cooled to −78° C., and a solution of n-BuLi (20 mmol, 8 mL, 2.5 M in hexane) was added. The reaction mixture was warmed to rt, recooled to −78° C. over a period of 2 h and a neat solution of methyl iodide (5.68 g, 40 mmol) added. The reaction mixture was allowed to warm to rt overnight, quenched with saturated NH4Cl (100 mL) at rt. It was extracted with EtOAc (100 mL). The organic phase was washed with brine (100 mL), dried (MgSO4), and concentrated in vacuo to give a yellow oil which was crystallized from hexane to afford the product as a slightly yellow solid (3.1 g, 81%): $^1$H NMR (CDCl$_3$) δ 0.79 (m, 2H), 1.36 (s, 9H), 1.52 (m, 2H), 1.62 (s, 3H), 4.10 (bs, 1H).

Step 1c: Preparation of 1-methylcyclopropylsulfonamide

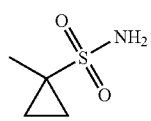

A solution of N-tert-butyl-(1-methyl)cyclopropylsulfonamide (1.91 g, 10 mmol) was dissolved in TFA (30 mL), and the reaction mixture stirred at rt for 16 h. The solvent was removed in vacuo to give a yellow oil which was crystallized from EtOAc/hexane (1:4, 40 mL) to yield 1-methylcyclopropylsulfonamide, as a white solid (1.25 g, 96%): $^1$H NMR (CDCl$_3$) δ 0.84 (m, 2H), 1.41 (m, 2H), 1.58 (s, 3H), 4.65 (bs, 2H). Anal. Calcd. For C$_4$H$_9$NO$_2$S: C, 35.54; H, 6.71; N, 10.36. Found: C, 35.67; H, 6.80; N, 10.40.

Example 6

Preparation of 1-Benzylcyclopropylsulfonamide

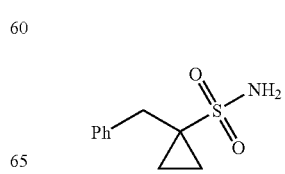

Steps 1b: Preparation of
N-tert-Butyl-(1-benzyl)cyclopropyl-sulfonamide

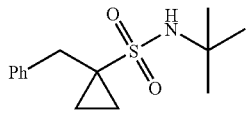

This compound was obtained in 60% yield using the procedure described for the synthesis of N-tert-butyl-(1-methyl)cyclopropylsulfonamide except 1.05 equivalents of benzyl bromide were used, followed by trituration with 10% EtOAc in hexane: $^1$H NMR (CDCl$_3$) δ 0.92 (m, 2H), 1.36 (m, 2H), 1.43 (s, 9H), 3.25 (s, 2H), 4.62 (bs, 1H), 7.29-7.36 (m, 5H).

Steps 1c: Preparation of
1-Benzylcyclo-propylsulfonamide

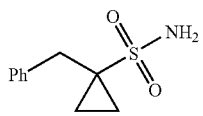

This compound 1-benzylcyclopropylsulfonamide, was obtained in 66% yield from N-tert-butyl(1-benzyl)cyclopropylsulfonamide using the procedure described for the synthesis of 1-methylcyclopropylsulfonamide, followed by recrystallization from the minimum amount of 10% EtOAc in hexane: $^1$H NMR (CDCl$_3$) δ 0.90 (m, 2H), 1.42 (m, 2 H), 3.25 (s, 2 H), 4.05 (s, 2 H), 7.29 (m, 3 H), 7.34 (m, 2 H); $^{13}$C NMR (CDCl$_3$) δ 11.1, 36.8, 41.9, 127.4, 128.8, 129.9, 136.5.

Example 7

Preparation of 1-Propylcyclopropylsulfonamide

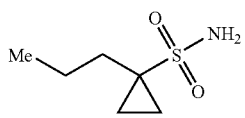

Steps 1b: Preparation of
N-tert-Butyl-(1-benzyl)cyclopropyl-sulfonamide

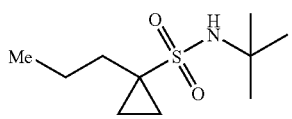

This compound was prepared using the process described for the preparation of 1-methylcyclopropylsulfonamide except propyl halide was utilized in place of methyl iodide in the second step of this process.

Example 8

Preparation of
N-tert-Butyl-(1-allyl)cyclopropylsulfonamide

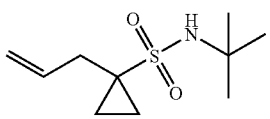

This compound, N-tert-Butyl-(1-allyl)cyclopropylsulfonamide, was obtained in 97% yield according to the procedure described in the synthesis of N-tert-Butyl-(1-methyl)cyclopropylsul-fonamide except 1.25 equivalents of allyl bromide were used as electrophile. The compound was taken directly into the next reaction without purification: $^1$H NMR (CDCl$_3$) δ 0.83 (m, 2H), 1.34 (s, 9H), 1.37 (m, 2H), 2.64 (d, J=7.3 Hz, 2H), 4.25 (bs, 1H), 5.07-5.10 (m, 2H), 6.70-6.85 (m, 1H).

Preparation of 1-allylcyclopropylsulfonamide

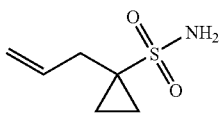

This compound, 1-allylcyclopropylsulfonamide, was obtained in 40% yield from N-tert-butyl-(1-allyl)cyclopropylsulfonamide according to the procedure described in the synthesis of 1-Methylcyclopropylsulfonamide. The compound was purified by column chromotography over SiO2 using 2% MeOH in CH2Cl2 as the eluent: $^1$H NMR (CDCl$_3$) δ 0.88 (m, 2 H), 1.37 (m, 2 H), 2.66 (d, J=7.0 Hz, 2 H), 4.80 (s, 2 H), 5.16 (m, 2 H), 5.82 (m, 1 H); $^{13}$C NMR (CDCl$_3$) δ 11.2, 35.6, 40.7, 119.0, 133.6.

Example 9

Preparation of N-tert-Butyl-[1-(1-hydroxy)cyclohexyl]-cyclopropylsulfonamide

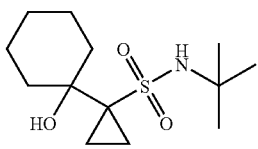 [SMILES: CC(C)(C)NS(=O)(=O)C1(C2(O)CCCCC2)CC1]

This compound was obtained in 84% yield using the procedure described for the synthesis of N-tert-Butyl-(1-methyl)cyclopropylsul-fonamide except 1.30 equivalents of cyclohexanone were used, followed by recrystallization from the minimum amount of 20% EtOAc in hexane: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (bs, 1H), 4.55 (bs, 1H).

Example 10

Preparation of 1-(1-cyclohexenyl)cyclopropyl-sulfonamide

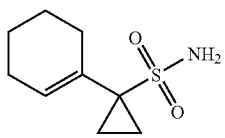 [SMILES: NS(=O)(=O)C1(C2=CCCCC2)CC1]

This compound, 1-(1-cyclohexenyl)-cyclopropylsulfonamide was obtained in 85% yield from N-tert-butyl-[1-(1-hydroxy)cyclohexyl]-cyclopropylsulfonamide $^1$H NMR (DMSO-d6) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d6) δ 11.6, 21.5, 22.3, 25.0, 27.2, 46.9, 131.6, 132.2; LR-MS (ESI): 200 (M+−1).

Example 11

Preparation of N-tert-Butyl-(1-benzoyl)cyclopropyl-sulfonamide

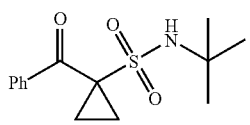

This compound was obtained in 66% yield using the procedure described for the synthesis of N-tert-Butyl-(1-methyl) cyclopropylsulfonamide except 1.2 equivalents of methyl benzoate was used as the electrophile. The compound was purified by column chromatography over SiO2 using 30% to 100% CH2Cl2 in hexane: $^1$H NMR (CDCl$_3$) δ 1.31 (s, 9H), 1.52 (m, 2H), 1.81 (m, 2H), 4.16 (bs, 1H), 7.46 (m, 2H), 7.57 (m, 1H), 8.05 (d, J=8.5 Hz, 2H).

Preparation of 1-benzoylcyclo-propylsulfonamide

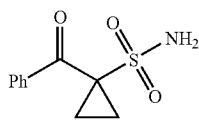

This compound 1-benzoylcyclopropyl-sulfonamide, was obtained in 87% yield from N-tert-butyl(1-benzoyl)cyclopropylsul-fonamide using the procedure described for the synthesis of 1-Methylcyclopropylsulfonamide, followed by recrystallization from the minimum amount of EtOAc in hexane: $^1$H NMR (DMSO-d6) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-d6) δ 12.3, 48.4, 128.1, 130.0, 133.4, 135.3, 192.0.

Example 12

Preparation of N-tert-Butyl-(1-phenylaminocarboxy)-cyclopropylsulfonamide

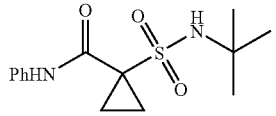

This compound was obtained in 42% yield using the procedure described for the synthesis of N-tert-Butyl-(1-methyl) cyclopropylsulfonamide using 1 equivalent of phenylisocyanate, followed by recrystallization from the minimum amount of EtOAc in hexane $^1$H NMR (CDCl$_3$) δ 1.38 (s, 9H), 1.67-1.71 (m, 4H), 4.30 (bs, 1H), 7.10 (t, J=7.5 Hz, 1H), 7.34 (t, J=7.5 Hz, 2H), 7.53 (t, J=7.5 Hz, 2H).

Example 13

Preparation of Cyclopropylsulfonylamine Tert-Butyl Carbamate, a Key Intermediate in the Preparation of C$_1$-Substituted Cyclopropylsulfonamides

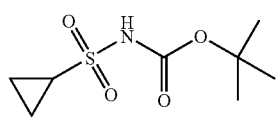

Step 1: Preparation of 3-chloropropylsulfonamide

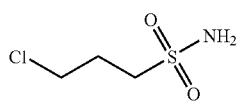

A solution of 3-chloropropanesulfonyl chloride (55 g, 310.7 mmol) was dissolved in THF (200 mL) and added dropwise over 30 minutes to a solution of NH4OH (200 mL) cooled to 0° C. The reaction mixture was warmed to room temperature, stirred 1 hour, and the aqueous layer partioned multiple time with dichloromethane (4×500 mL). The combined dichloromethane layer was washed with 1N HCl (150 mL), water (150 mL), dried over MgSO4, filtered, and concentrated in vacuo. The crude solid was recrystallized from the minimum amount of dichloromethane in hexanes to afford 3-chloropropylsulfonamide as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step 2: Preparation of 3-Chloropropylsulfonylamine tert-Butylcarbamate

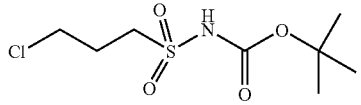

To a solution of 3-chloropropylsulfonamide (30.2 g, 191.5 mmol), triethylamine (30.2 mL, 217.0 mmol), and 4-DMAP (2.40 g, 19.6 mmol) in dichloromethane (350 mL) cooled to 0° C. was added slowly dropwise a solution of di-tert-butyl-dicarbonate (47.2 g, 216.9 mmol) in dichloromethane (250 mL) over 30 minutes. The reaction mixture was allowed to warm to room temperature, stirred an additional 3 hours and was partioned with 1N HCl (300 mL), water (300 mL), brine (300 mL), dried over MgSO4, filtered, and concentrated in vacuo to afford the crude product. This material was triturated with 70 mL of 5% dichloromethane in hexanes to afford 3-chloropropylsulfonylamine tert-butylcarbamate as an off-white solid (47.2 g, 96%): $^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

Step 3: Preparation of Cyclopropylsulfonylamine tert-Butyl Carbamate

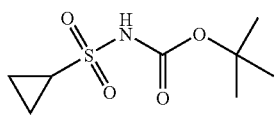

A solution of n-butyl lithium (74.7 mL, 119.5 mmol, 1.6M in hexane) was dissolved in dry THF (105 mL) and cooled to −78° C. under a Argon atmosphere. To this solution was added a solution of 3-chloropropylsulfonylamine tert-butyl-carbamate (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried (MgSO4), filtered, and concentrated in vacuo to afford the cyclopropylsulfonylamine tert-butyl carbamate as a waxy off-white solid (12.08 g, 100%): $^1$H NMR (CDCl$_3$) δ 1.10 (m, 2H), 1.34 (m, 2H), 1.50 (s, 9H), 2.88 (m, 1H), 7.43 (s, 1H). $^{13}$C NMR (CDCl$_3$) δ 6.21, 28.00, 31.13, 84.07, 149.82.

Example 14

Preparation of 1-methoxy-methylcyclopropyl-sulfonamide

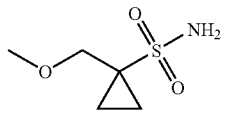

Step 1: Preparation of 1-methoxymethylcyclopropylsulfonylamine tert-butylcarbamate

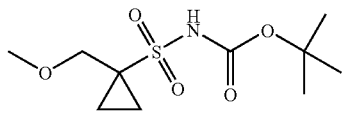 [SMILES: COCC1(S(=O)(=O)NC(=O)OC(C)(C)C)CC1]

To a solution of cyclopropylsulfonylamine tert-butyl carbamate (1.0 g, 4.5 mmol) dissolved in THF (30 mL) cooled to −78° C., was added n-butyl lithium (6.4 mL, 10.2 mmol, 1.6M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried (MgSO$_4$), filtered, and concentrated to afford 1-methoxymethylcyclopropylsulfonylamine tert-butylcarbamate, as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

Step 2: Preparation of 1-methoxymethylcyclopropysulfonamide

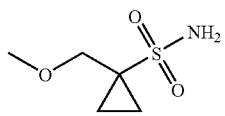

A solution of 1-methoxymethylcyclopropylsulfonylamine tert-butylcarbamate (1.14 g, 4.30 mmol) was dissolved in a solution of 50% TFA/dichloromethane (30 mL) and was stirred stirred at room temperature for 16 hours. The solvent was removed in vacuo and the residue chromatographed over 80 g of SiO$_2$ (eluting with 0% to 60% ethyl acetate/hexanes to 1-methoxymethylcyclopropylsulfonamide as a white solid (0.55 g, 77% overall over two steps): $^1$H NMR (CDCl$_3$) δ 0.95

(m, 2H), 1.44 (m, 2H), 3.36 (s, 3H), 3.65 (s, 2H), 4.85 (s, 2H); $^{13}$C NMR (CDCl$_3$) δ 11.17, 40.87, 59.23, 74.80; LRMS m/z 183 (M$^+$+NH$_4$)—

Example 15

Preparation of 1-cyclopropylmethylcyclopropylsulfonamide

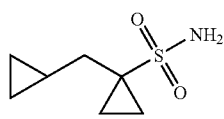

Step 1: Preparation of 1-cyclopropylmethylcyclopropylsulfonylamine tert-butylcarbamate

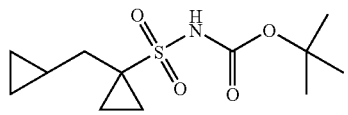 [SMILES: CC(C)(C)OC(=O)NS(=O)(=O)C1(CC2CC2)CC1]

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate, except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-cyclopropylmethylcyclopropylsulfonamide

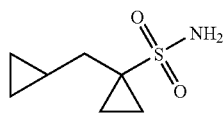 [SMILES: NS(=O)(=O)C1(CC2CC2)CC1]

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromatography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$)—

Example 16

Preparation of 1-propylcarbamoylcyclopropanesulfonamide

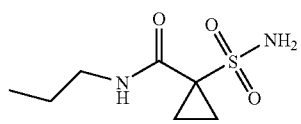

Step 1: Preparation of 1-propylcarbamoylcyclopropanesulfonamide tert-butylcarbamate

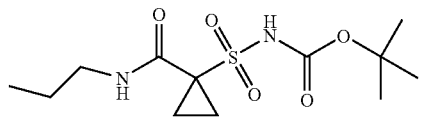 [SMILES: CCCNC(=O)C1(S(=O)(=O)NC(=O)OC(C)(C)C)CC1]

This compound was obtained in a crude 100% yield according to the procedure described for the synthesis of 1-methoxymethylcyclopropylsulfonylamine tert-butyl-carbamate except that 1.10 equivalents of n-propyl isocyanate was used as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-propylcarbamoylcyclopropanesulfonamide

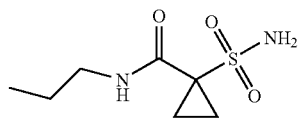

This compound was obtained in an optimized 50% yield from 1-propylcarbamoylcyclopropanesulfonamide tert-butylcarbamate according to the procedure described for the synthesis of 1-methoxymethylcyclopropylsulfonamide, except that no chromatography was used as the material was recrystallized from the minimum amount of dichloromethane/hexanes: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

Example 17

Preparation of 1-(3,5-dimethylisoxazol-4-yl)carbamoylcyclopropanesulfonamide

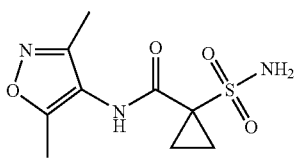 [SMILES: Cc1noc(C)c1NC(=O)C1(S(N)(=O)=O)CC1]

Step 1: Preparation of 1-(3,5-dimethylisoxazol-4-yl)carbamoylcyclopropanesulfonamide tert-butylcarbamate

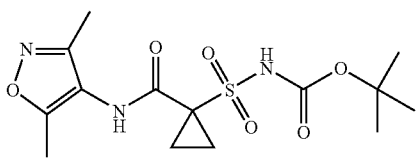 [SMILES: Cc1noc(C)c1NC(=O)C1(S(=O)(=O)NC(=O)OC(C)(C)C)CC1]

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

Step 2: Preparation of 1-(3,5-dimethylisoxazol-4-yl)carbamoylcyclopropanesulfonamide

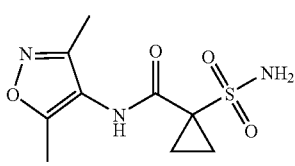 [SMILES: Cc1noc(C)c1NC(=O)C1(S(N)(=O)=O)CC1]

This compound was obtained in 50% yield (580 mg) from 1.62 g (4.52 mmol) of 1-(3,5-dimethylisoxazol-4-yl)carbamoylcyclo-propanesulfonamide tert-butylcarbamate using 30 mL (120 mmol) of 4N HCl/dioxanes, stirring overnight, concentration and chromatography over a Biotage 40M column (eluting with 0% to 5% methanol/dichloromethane: $^1$H NMR (methanol-d$_4$) δ 1.57 (m, 2H), 1.61 (m 2H), 2.15 (s, 3H), 2.30 (s, 3H), 4.84 (s, 3H); $^{13}$C NMR (methanol-d$_4$) δ 9.65, 10.94, 15.01, 46.11, 114.82, 159.45, 165.55, 168.15; LRMS m/z 260(M$^+$+H).

Example 18

Preparation of Cyclobutylsulfonamide from Cylobutylbromide

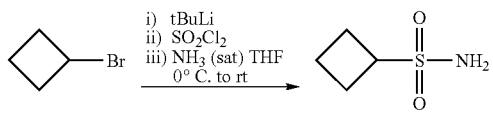

To a solution of 5.0 g (37.0 mmol) of cyclobutyl bromide in 30 mL of anhydrous diethyl ether (Et2O) cooled to −78° C. was added 44 mL (74.8 mmol) of 1.7M tert-butyl lithium in pentanes and the solution slowly warmed to −35° C. over 1.5 h. This mixture was cannulated slowly into a solution of 5.0 g (37.0 mmol) of freshly distilled sulfuryl chloride in 100 mL of hexanes cooled to −40° C., warmed to 0° C. over 1 h and carefully concentrated in vacuo. This mixture was redissolved in Et2O, washed once with some ice-cold water, dried (MgSO4) and concentrated carefully. This mixture was redissolved in 20 mL of THF, added dropwise to 500 mL of saturated NH3 in THF and was allowed to stir overnite. The mixture was concentrated in vacuo to a crude yellow solid and was recrystallized from the minimum amount of CH$_2$Cl$_2$ in hexanes with 1-2 drops of MeOH to afford 1.90 g (38%) of cyclobutylsulfonamide as a white solid. $^1$H NMR (CDCl$_3$) δ 1.95-2.06 (m, 2H), 2.30-2.54 (m, 4H), 3.86 (p, J=8 Hz, 1H), 4.75 (brs, 2H); $^{13}$C NMR (CDCl3) δ 16.43, 23.93, 56.29. HRMS m/z (M−H)$^−$ calcd for C4H8NSO2: 134.0276, found 134.0282.

Example 19

Preparation of Cyclopentyl Sulfonamide

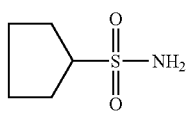

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 h and was then carefully concentrated in vacuo. This mixture was redissolved in Et2O (200 mL), washed once with some ice-cold water (200 mL), dried (MgSO4) and concentrated carefully. This mixture was redissolved in 35 mL of THF, added dropwise to 500 mL of saturated NH3 in THF and was allowed to stir overnite. The mixture was concentrated in vacuo to a crude yellow solid, the residue filtered through 50 g of silica gel using 70% EtOAc-hexanes as the eluent and the solution was then concentrated. The residue was recrystallized from the minimum amount of CH2Cl2 in hexanes with 1-2 drops of MeOH to afford 2.49 g (41%) of cyclopentylsulfonamide as a white solid. $^1$H NMR (CDCl$_3$) δ 1.58-1.72 (m, 2H), 1.74-1.88

(m, 2H), 1.94-2.14 (m, 4H), 3.48-3.59 (m, 1H), 4.80 (bs, 2H); $^{13}$C NMR (CDCl$_3$) δ 25.90, 28.33, 63.54; MS m/e 148 (M–H)–.

Example 20

Preparation of Cyclohexyl Sulfonamide

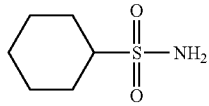

A solution of 18.5 mL (37.0 mmol) of 2M cyclohexylmagnesium chloride (TCI Americas) in ether was added dropwise to a solution of 3.0 mL (37.0 mmol) freshly distilled sulfuryl chloride in 100 mL of hexanes cooled to –78° C. The mixture was warmed to 0° C. over 1 h and was then carefully concentrated in vacuo. This mixture was redissolved in Et2O (200 mL), washed once with some ice-cold water (200 mL), dried (MgSO4) and concentrated carefully This mixture was redissolved in 35 mL of THF, added dropwise to 500 mL of saturated NH3 in THF and was allowed to stir overnite. The mixture was concentrated in vacuo to a crude yellow solid, the residue filtered through 50 g of silica gel using 70% EtOAc-hexanes as the eluent and was concentrated. The residue was recrystallized from the minimum amount of CH2Cl2 in hexanes with 1-2 drops of MeOH to afford 1.66 g (30%) of cyclohexyl-sulfonamide as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (bs, 2H); $^{13}$C NMR (CDCl$_3$) δ 25.04, 25.04, 26.56, 62.74; MS m/e 162 (M–1)–.

Example 21

Preparation of Neopentylsulfonamide

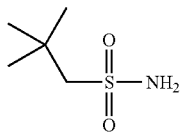

Following the procedure for the preparation of cyclohexylsulfonamide, 49 mL (37 mmol) of 0.75M neopentylmagnesium chloride (Alfa) in diethyl ether was converted to 1.52 g (27%) of neopentylsulfonamide as a white solid. $^1$H NMR (CDCl$_3$) δ 1.17 (s, 9H), 3.12 (s, 2H), 4.74 (brs, 2H); $^{13}$C NMR (CDCl$_3$) δ 29.46, 31.51, 67.38; MS m/e 150 (M–1)–.

Example 22

Preparation of Cyclobutylcarbinylsulfonamide

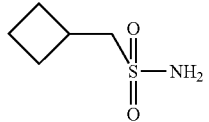

A solution of 12.3 g (83 mmol) of cyclobutylcarbonyl bromide (Aldrich) and 13.7 g (91 mmol) of sodium iodide in 150 mL of acetone was refluxed overnight and then cooled to room temperature. The inorganic solids were filtered off and the acetone and cyclopropylcarbonyl iodide (8.41 g, 46%) distilled off at ambient and 150 torr at 80° C., respectively.

A solution of 4.0 g (21.98 mmol) of cyclobutyl carbinyl iodide in 30 mL of anhydrous diethyl ether (diethyl ether) cooled to –78° C. was cannulated into a solution of 17 mL (21.98 mmol) of 1.3M sec-butyl lithium in cyclohexanes and the solution was stirred for 5 minutes. To this mixture was cannulated a solution of 3.0 g (21.98 mmol) of freshly distilled sulfuryl chloride in 110 mL of hexanes cooled to –78° C., the mixture warmed to room temperature over 1 hour and was then carefully concentrated in vacuo. This mixture was redissolved in diethyl ether, washed once with some ice-cold water, dried (MgSO4), filtered, and concentrated carefully. This mixture was redissolved in 30 mL of THF, added dropwise to 500 mL of saturated NH3 in THF and was allowed to stir overnight. The mixture was concentrated in vacuo to a crude yellow solid and was recrystallized from the minimum amount of dichloromethane in hexanes with 1-2 drops of methanol to afford 1.39 g (42%) of cyclobutyl carbonylsulfonamide as a white solid. $^1$H NMR (CDCl$_3$) δ 1.81-2.03 (m, 4H), 2.14-2.28 (m, 2H), 2.81-2.92 (m, 1H), 3.22 (d, J=7 Hz, 2H), 4.74 (brs, 2H); $^{13}$C NMR (CDCl$_3$) δ 19.10, 28.21, 30.64, 60.93; MS m/e 148 (M–1)–.

Example 23

Preparation of Cyclopropylcarbonylsulfonamide

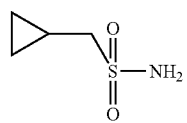

Using the procedure employed for the preparation of cyclobutylcarbonylsulfonamide, cyclopropylcarbonylsulfonamide was prepared from cyclopropylcarbonyl bromide (Aldrich) (see also JACS 1981, p. 442-445). $^1$H NMR (CDCl$_3$) δ 0.39-0.44 (m, 2H), 0.67-0.76 (m, 2H), 1.13-1.27 (m, 1H), 3.03 (d, J=7.3 Hz, 2H), 4.74 (brs, 2H); $^{13}$C NMR (CDCl$_3$) δ 4.33, 5.61, 59.93; MS m/e 134 (M–1).

Example 24

Preparation of cyclopropanesulfonic acid (1-(R)-amino-2-(S)-vinyl-cyclopropanecarbonyl)amide HCl salt

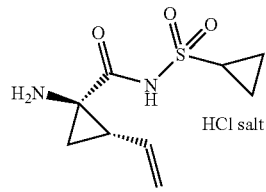

Step 1: Preparation of 1(R)-tert-butoxycarbonylamino-2(S)-vinyl-cyclopropanecarboxylic acid

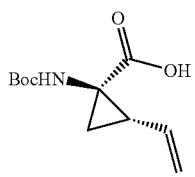

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature and quenched with 1N NaOH (15 mL) and water (20 mL). The resulting mixture was washed with ethyl acetate (20 mL), and the organic phase was extracted with 20 mL 0.5N NaOH. The combined aqueous phases were acidified with 1N HCl until pH 4 and extracted with ethyl acetate (3×40 mL). The combined organic extracts were washed with brine, dried (MgSO4), filtered and concentrated to yield the title compound as a white solid (2.62 g, 87%). $^1$H NMR: (DMSO-d6) δ 1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); MS m/z 228 (M++H).

Step 2: Preparation of cyclopropanesulfonic acid (1-(R)-tert-butoxycarbonylamino-2-(S)-vinylcyclopropanecarbonyl)-amide

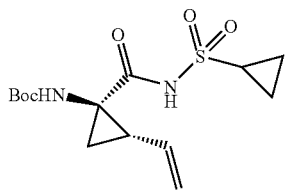 [SMILES: C=C[C@@H]1C[C@]1(NC(=O)OC(C)(C)C)C(=O)NS(=O)(=O)C1CC1]

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1N HCl to pH 1 and THF was concentrated in vacuo. The suspension was extracted with ethyl acetate (2×50 mL) and the combined organic extracts were dried (Na2SO4), filtered, and concentrated. Purification by recrystallization from hexanes-ethyl acetate (1:1) afforded the title compound (2.4 g) as a white solid. The mother liquor was purified by a Biotage 40S column (eluted 9% acetone in dichloromethane) to give a second batch of the title compound (1.1 g). Both batches were combined (total yield 92%). $^1$H NMR (DMSO-d6) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers); MS m/z 331 (M++H).

Step 3: Preparation of cyclopropanesulfonic acid (1-(R)-amino-2-(S)-vinyl-cyclopropanecarbonyl) amide HCl salt

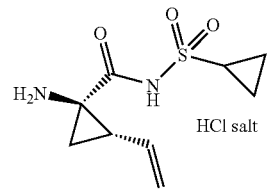

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1N HCl in diethyl ether (20 mL) and concentrated in vacuo. This procedure was repeated once. The resulting mixture was triturated from pentane and filtered to give the title compound as a hygroscopic, off-white solid (2.60 g, 92%). $^1$H NMR: (DMSO-d6) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); MS m/z 231 (M++H).

Example 25

Preparation of (1S,4R,6S,14S,18R)-7-cis-14-tert-butoxycarbonylamino-18-hydroxy-2,15-dioxo-3,16-diazatricyclo[14.3.0.0$^{4,6}$]nonadec-7-ene-4-carboxylic acid Example 25

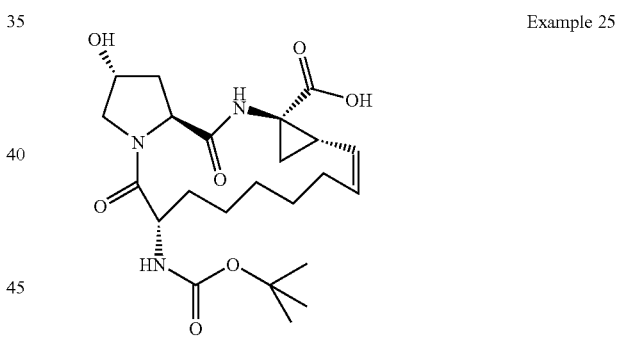

Step 1: Preparation of 1-(2(S)-tert-Butoxycarbonylamino-non-8-enoyl)-4(R)-hydroxy-pyrrolidine-2(S)-carboxylic acid methyl ester

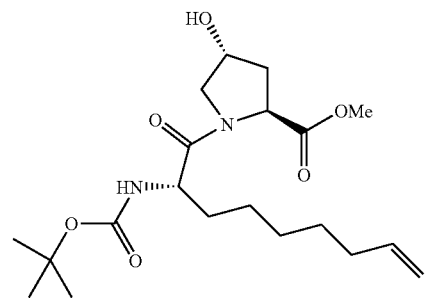 [SMILES: C=CCCCCC[C@H](NC(=O)OC(C)(C)C)C(=O)N1C[C@H](O)C[C@H]1C(=O)OC]

A solution of 2(S)-tert-butoxycarbonylamino-8-nonenoic acid (purchased from RSP Amino Acids)(3.5 g, 12.9 mmol) in 200 mL of DCM was treated sequentially with 4(R)-hydroxy-pyrrolidine-2(S)-carboxylic acid methyl ester hydrochloride (2.15 g, 11.8 mmol), N-methyl morpholine (4.25 mL, 38.6 mmol), and HATU (5.37 g, 14.1 mmol). The reaction mixture was stirred at rt under $N_2$ for 3 days, and then concentrated in vacuo. The residue was partitioned between ethyl acetate and pH 4 buffer (biphthalate). The organic phase was washed with sat. aq. $NaHCO_3$, dried ($MgSO_4$), and concentrated in vacuo to give the crude product. Flash chromatography (50% ethyl acetate/hexane to 100% ethyl acetate) gave 4.7 g (~100%) of 1-(2(S)-tert-Butoxycarbonylamino-non-8-enoyl)-4(R)-hydroxy-pyrrolidine-2(S)-carboxylic acid methyl ester as a colorless oil: $^1$H NMR (500 MHz, $CD_3OD$) δ 1.33-1.50 (m, 8 H), 1.46 (s, 9 H), 1.57 (m, 1 H), 1.72 (m, 1 H) 2.08 (m, 2 H), 2.28 (m, 1 H), 3.72 (s, 3 H,) 3.75-3.87 (m, 2 H), 4.36 (m, 1 H), 4.51 (bs, 1 H), 4.57 (t, J=8.2 Hz, 1 H), 4.95 (d, J=10.4 Hz, 1 H), 5.01 (m, 1 H), 5.83 (m, 1 H); MS m/z 399 ($M^+$+1).

Step 2: Preparation of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester

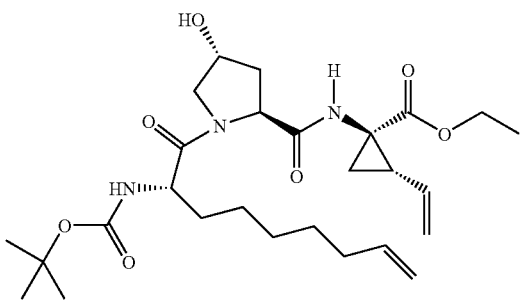 [SMILES: C=CCCCCC[C@H](NC(=O)OC(C)(C)C)C(=O)N1C[C@H](O)C[C@H]1C(=O)N[C@]1(C(=O)OCC)C[C@H]1C=C]

1-(2(S)-tert-Butoxycarbonylamino-non-8-enoyl)-4(R)-hydroxy-pyrrolidine-2(S)-carboxylic acid methyl ester (4.7 g, 11.8 mmol) was dissolved in THF (80 mL), methanol (20 mL), and water (40 mL). Powdered lithium hydroxide (5.6 g, 233 mmol) was added. The light yellow slurry was stirred at rt under $N_2$ for 16 h, and then concentrated in vacuo. The residue was partioned between ether and water. The ether phase was discarded, and the aqueous phase was treated with 1N HCl until the pH was 4. This acidic solution was extracted with EtOAc (3×). The combined EtOAc extracts were dried ($MgSO_4$) and concentrated in vacuo to give 4.36 g (96%) of 1-(2(S)-tert-butoxycarbonylamino-8-nonenoyl)-4(R)-hydroxy-pyrrolidine-2(S)-carboxylic acid as a white solid. This acid was then dissolved in 150 mL of DMF and (1R,2S)-1-amino-2-vinylcyclopropane carboxylic acid ethyl ester hydrochloride (2.61 g, 13.6 mmol), N-methyl morpholine (2.5 mL, 22.6 mmol), and HATU (5.2 g, 13.7 mmol) was added. The reaction mixture was stirred at rt under $N_2$ for 16 h, and then concentrated in vacuo. The residue was partitioned between ethyl acetate and pH 4 buffer (biphthalate). The organic phase was washed with sat. aq. $NaHCO_3$, dried ($MgSO_4$), and concentrated in vacuo to give the crude product. Flash chromatography (60%-80% ethyl acetate/hexane) gave 6.0 g (98%) of 1-{[1-(2(S)-tert-Butoxycarbonylamino-non-8-enoyl)-4(R)-hydroxy-pyrrolidine-2(carbonyl)-(1R)-amino}-2(S)-vinyl-cyclopropanecarboxylic acid ethyl ester as a white solid: $^1$H NMR (500 MHz, $CD_3OD$) δ 1.25 (t, J=7.2 Hz, 3 H), 1.33-1.80 (m, 10 H), 1.46 (s, 9 H), 2.09 (m, 3 H), 2.25 (m, 2 H), 3.76 (m, 2 H), 4.14 (m, 2 H), 4.27 (dd, J=8.5, 5.2 Hz, 1 H), 4.50 (m, 2 H), 4.94 (d, J=10.1 Hz, 1 H), 5.01 (dd, J=17.1, 1.8 Hz, 1 H), 5.11 (dd, J=10.4, 1.8 Hz, 1 H), 5.30 (d, J=15.6 Hz, 1 H), 5.80 (m, 2 H), 8.57 (s, 1 H); MS m/z 522 ($M^+$+1).

Step 3: Preparation of (1S,4R,6S,14S,18R)-7-cis-14-tert-butoxycarbonylamino-18-hydroxy-2,15-dioxo-3,16-diazatricyclo[14.3.0.0$^{4,6}$]nonadec-7-ene-4-carboxylic acid ethyl ester

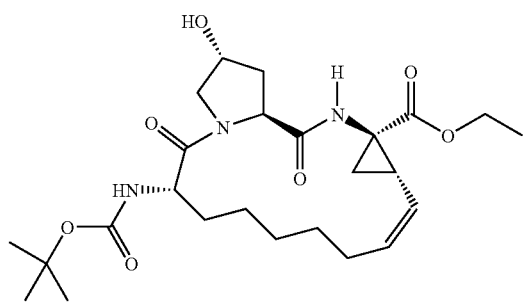 [SMILES: CCOC(=O)[C@@]12C[C@H]1/C=C\CCCCC[C@H](NC(=O)OC(C)(C)C)C(=O)N1C[C@H](O)C[C@H]1C(=O)N2]

A solution of 1-{[1-(2(S)-tert-Butoxycarbonyl-amino-non-8-enoyl)-4(R)-hydroxy-pyrrolidine-2(S)carbonyl]-(1R)-amino}-2(S)-vinylcyclopropane-carboxylic acid ethyl ester (800 mg, 1.53 mmol) in 2 L of methylene chloride was flushed with N2 for 0.5 h. Then tricyclohexylphosphine[1,3-bis(2,4,6-trimethyl-phenyl)-4,5-dihydroimidazol-2-ylidene][benzylidene]-ruthenium (IV) dichloride (Strem) (64 mg, 0.075 mmol) was added, and the mixture was flushed with N2 for another 10 min. The light orange homogeneous solution was refluxed for 2 h to give a dark orange solution. The reaction mixture was cooled to rt and concentrated in vacuo to give an orange oil. Flash chromatography (ethyl acetate) gave 460 mg (61%) of (1S,4R,6S,14S,18R)-7-cis-14-tert-butoxycarbonylamino-18-hydroxy-2,15-dioxo-3,16-diazatricyclo[14.3.0.04,6]-nonadec-7-ene-4-carboxylic acid ethyl ester as a gray solid. $^1$H NMR (500 MHz, $CDCl_3$) δ 1.19 (t, J=7.2 Hz, 3 H), 1.42 (s, 9 H), 1.22-1.8 (m, 8 H), 1.87 (m, 2 H), 2.03-2.22 (m, 4 H), 2.63 (m, 1 H), 3.65 (m, 1 H), 4.09 (m, 3 H), 4.45 (m, 1 H), 4.56 (s, 1 H), 4.82 (m, 1 H), 5.23 (m, 1 H), 5.51 (s, 1 H), 7.16 (s, 1 H); MS m/z 494 (M++1).

Step 4: (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid

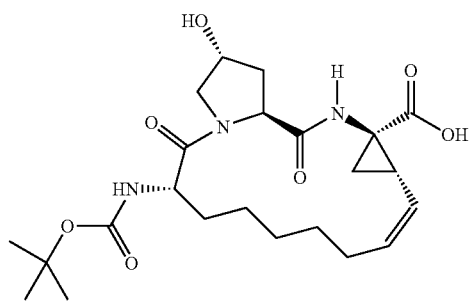 [SMILES: CC(C)(C)OC(=O)N[C@H]1CCCCC/C=C\[C@@H]2C[C@@]2(C(=O)O)NC(=O)[C@@H]2C[C@@H](O)CN2C1=O]

To a solution of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid ethyl ester (493 mg, 1.0 mmol) in THF (4 mL), methanol (1 mL), and water (2 mL), was added powdered lithium hydroxide (480 mg, 20 mmol), and the light yellow slurry stirred at rt under N$_2$ for 16 h. The mixture was then concentrated in vacuo and the residue partioned between ether and water. The ether phase was discarded, and the aqueous phase was treated with 1 N HCl until pH 4. This acidic solution was extracted with EtOAc three times. The combined EtOAc extracts were dried (MgSO$_4$) and concentrated in vacuo to give 460 mg (98%) of Example 18, (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid as a gray solid. $^1$H NMR (500 MHz, CD$_3$OD) δ ppm 1.26 (t, J=7.2 Hz, 3 H), 1.35-1.52 (m, 15 H), 1.57-1.68 (m, 3 H), 1.79 (m, 1 H), 2.04 (m, 1 H), 2.16-2.41 (m, 3 H), 3.80 (dd, J=10.7, 4.3 Hz, 1 H), 3.88 (m, 1 H), 4.38 (dd, J=8.9, 3.1 Hz, 1 H), 4.55 (m, 2 H), 5.39 (t, J=9.8 Hz, 1 H), 5.58 (m, 1 H); MS m/z 466 (M$^+$+1).

Example 26

Preparation of (4-Cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester Example 26

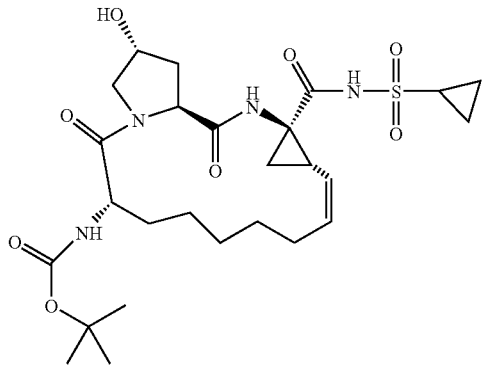

Step 1: Preparation of 1-{[1-(2-tert-Butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester

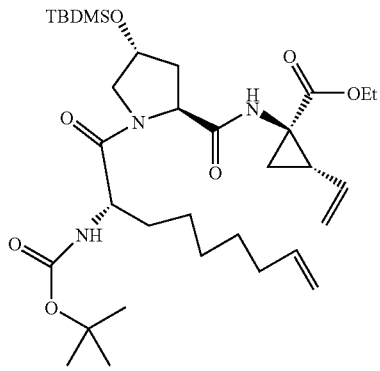 [SMILES: C=CCCCCC[C@H](NC(=O)OC(C)(C)C)C(=O)N1C[C@H](O[Si](C)(C)C(C)(C)C)C[C@H]1C(=O)N[C@]1(C(=O)OCC)C[C@H]1C=C]

To a mixture of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester (1.5 g, 2.87 mmoL) in 10 mL of DMF was added imidazole (0.25 g, 3.67 mmoL) and tert-butyl-dimethylsilyl chloride (516 mg, 3.44 mmoL). The mixture was stirred at rt for two days. The reaction mixture was then concentrated in vacuo, and the residue was dissolved in ethyl acetate. This solution was washed with water, dried over magnesium sulfate, and concentrated in vacuo to obtain a crude solid. Purification by flash chromatography (eluting with 20% ethyl acetate in hexane) gave 1.43 g (78%) of 1-{[1-(2-tert-butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester as a white solid.

$^1$H NMR (300 MHz, CD$_3$OD) δ 0.10 (s, 6 H), 0.89 (s, 9 H), 1.22 (m, 3 H), 1.31-1.48 (m, 16 H), 1.50-1.75 (m, 3 H), 2.06 (m, 3 H), 2.11-2.33 (m, 2 H), 3.70 (m, 2 H), 4.03-4.19 (m, 2 H), 4.21 (m, 1 H), 4.45 (t, J=7.87 Hz, 1 H), 4.59 (m, 1 H), 4.91 (d, J=9.15 Hz, 1 H), 4.98 (d, J=17.20 Hz, 1 H), 5.08 (dd, J=10.25, 1.83 Hz, 1 H), 5.27 (dd, J=17.38, 1.65 Hz, 1 H), 5.65-5.87 (m, 2 H); MS m/z 636 (M++1).

Step 2: Preparation of 14-tert-Butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid, ethyl ester

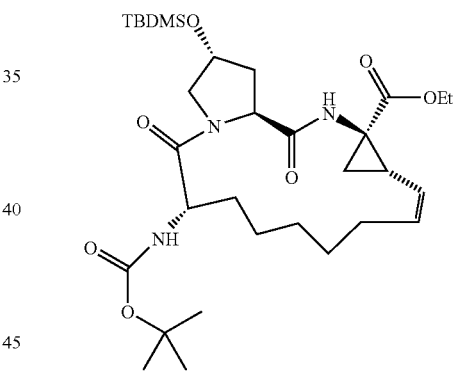

To a solution of 1-{[1-(2-tert-butoxycarbonylamino-non-8-enoyl)-4-(tert-butyl-dimethyl-silanyloxy)-pyrrolidine-2-carbonyl]-amino}-2-vinyl-cyclopropanecarboxylic acid ethyl ester (1.63 g, 2.56 mmoL) in 640 mL of methylene chloride was added 215 mg (0.26 mmoL) of tricyclohexylphosphine[1,3-bis(2,4,6-tri[benzylidene]ruthenium(IV) dichloride. The mixture was heated at reflux for 15 min. The residue was concentrated in vacuo, and then purified by flash chromatography eluting with 30% ethyl acetate/hexane. To further decolorize the sample, the crude product was chromatographed a second time eluting with 50% ether in hexane to give 1.5 g (96%) of 14-tert-butoxycarbonylamino-18-(tert-butyl-dimethyl-silanyloxy)-2,15-dioxo-3,16-diaza-tricyclo[14.3.0.04,6]nonadec-7-ene-4-carboxylic acid ethyl ester as a white solid. $^1$H NMR (500 MHz, CD$_3$Cl) δ 0.06 (s, 3 H), 0.07 (s, 3 H), 0.86 (s, 9 H), 1.18-1.24 (m, 6 H), 1.34-1.64 (m, 14 H), 1.86-1.96 (m, 3 H), 2.02-2.09 (m, 1 H), 2.11-2.17 (m, 1 H), 2.19-2.28 (m, 1 H), 2.57-2.63 (m, 1 H), 3.50-3.54 (m, 1 H), 3.71 (dd, J=10.22, 6.26 Hz, 1 H), 4.06-4.17 (m, 2 H), 4.52-4.58 (m, 2 H), 4.75 (d, J=8.55 Hz, 1 H), 5.21 (t, J=9.92 Hz, 1 H), 5.35 (d, J=7.63 Hz, 1 H), 5.45-5.50 (m, 1 H), 6.94 (s, 1 H); MS m/z 608 (M++1).

Step 3: Preparation of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid

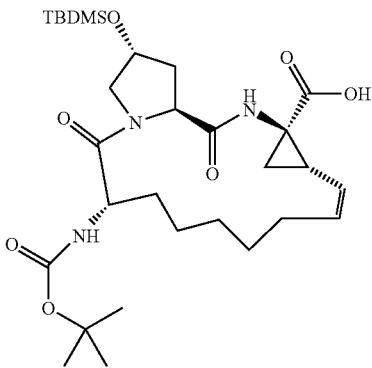 [SMILES: CC(C)(C)OC(=O)N[C@H]1CCCCC/C=C\[C@@H]2C[C@@]2(C(=O)O)NC(=O)[C@@H]2C[C@@H](O[Si](C)(C)C(C)(C)C)CN2C1=O]

To a solution of 14-tert-butoxycarbonylamino-18-(tert-butyl-dimethyl-silanyloxy)-2,15-dioxo-3,16-diaza-tricyclo[14.3.0.04,6]nonadec-7-ene-4-carboxylic acid ethyl ester (1.5 g, 2.47 mmoL) in a mixed solvent system of THF (4 mL), methanol (1 mL), and water (2 mL), was added powdered lithium hydroxide monohydrate (1.0 g, 50 mmoL). The light yellow slurry was stirred at rt under N2 for 4 h. The mixture was then concentrated in vacuo, and the residue partioned between ether and water. The ether phase was discarded, and the aqueous phase was treated with 1 N HCl until reaching pH 4. This acidic solution was extracted with EtOAc (3×). The combined EtOAc extracts were dried (MgSO4), and concentrated in vacuo to give 1.2 g (84%) of 14-tert-butoxycarbonylamino-18-(tert-butyl-dimethyl-silanyloxy)-2,15-dioxo-3,16-diaza-tricyclo[14.3.0.04,6]nonadec-7-ene-4-carboxylic acid as an off-white solid. $^1$H NMR (300 MHz, CD$_3$OD) 0.12 (s, 6 H), 0.89 (s, 9 H), 1.23-1.64 (m, 17 H), 1.70-1.87 (m, 1 H), 1.90-2.49 (m, 6 H), 3.70-3.80 (m, 1 H), 3.83-3.90 (m, 1 H), 4.28-4.36 (m, 1 H), 4.47-4.55 (m, 1 H), 4.65 (s, 1 H), 5.30-5.39 (m, 1 H), 5.53-5.62 (m, 1 H); MS m/z 580 (M++1).

Step 4: Preparation of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester

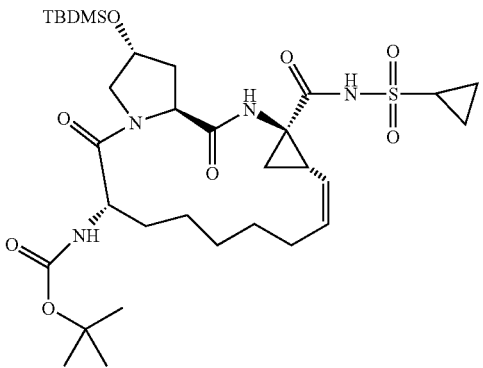 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](O[Si](C)(C)C(C)(C)C)CN2C1=O]

14-tert-Butoxycarbonylamino-18-(tert-butyl-dimethyl-silanyloxy)-2,15-dioxo-3,16-diaza-tricyclo[14.3.0.04,6]nonadec-7-ene-4-carboxylic acid (500 mg, 0.86 mmoL) was dissolved in 25 mL of THF and treated with CDI (180 mg, 1.12 mmoL). (Care was taken to avoid moisture by using oven dried glassware and maintaining a dry N2 atmosphere). After refluxing the reaction mixture for 2 h, it was cooled to rt and treated sequentially with cyclopropylsulfonamide (135 mg, 1.12 mmoL) and DBU (170 mg, 1.12 mmoL). The reaction mixture was stirred for 4 h at rt, and the THF was removed by rotary evaporation. The residue was partitioned between ethyl acetate and pH 4 buffer. The organic phase was dried (MgSO4) and concentrated in vacuo to give the crude product. It was then purified by flash chromatography (eluting with 33% ethyl acetate in hexane) to give 300 mg (51%) of [18-(tert-butyl-dimethyl-silanyloxy)-4-cyclopropanesulfonylaminocarbonyl-2,15-dioxo-3,16-diaza-tricyclo[14.3.0.04,6]nonadec-7-en-14-yl]-carbamic acid tert-butyl ester as a white solid. $^1$H NMR (300 MHz, CD$_3$OD) δ 1H 0.07 (s, 3 H), 0.08 (s, 3 H), 0.85 (s, 9 H), 0.87-1.49 (m, 21 H), 1.73-1.95 (m, 3 H), 2.08-2.16 (m, 1 H), 2.25-2.36 (m, 2 H), 2.42-2.56 (m, 1 H), 2.85-2.93 (m, 1 H), 3.65-3.74 (dd, J=10.61, 3.66 Hz, 1 H), 3.89 (d, J=10.25 Hz, 1 H), 4.34 (m, J=9.70, 9.70 Hz, 1 H), 4.43 (t, J=7.87 Hz, 1 H), 4.57 (s, 1 H), 4.94-5.01 (m, 1 H), 5.10 (d, J=8.78 Hz, 1 H), 5.66-5.75 (m, 1 H), 6.55 (s, 1 H), 10.13 (s, 1 H); MS m/z 683 (M++1).

Step 5: Preparation of (4-Cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester Example 26

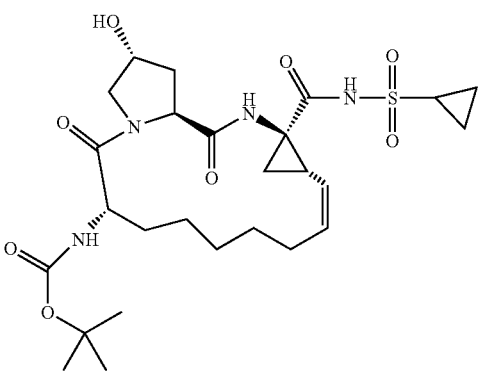

To a mixture of [18-(tert-butyl-dimethylsilanyloxy)-4-cyclopropanesulfonylaminocarbonyl-2,15-dioxo-3,16-diaza-tricyclo[14.3.0.04,6]nonadec-7-en-14-yl]-carbamic acid tert-butyl ester (330 mg, 0.48 mmoL) in 25 mL of THF was added tetrabutylammonium fluoride (150 mg, 0.54 mmoL). The reaction mixture was stirred at rt for 18 h, and then the THF was removed by rotary evaporation. The residue was partitioned between ethyl acetate and water. The organic phase was dried (MgSO4) and concentrated in vacuo to give the crude product. It was then purified by triturating with hexane to yield 200 mg (73%) of (4-cyclopropanesulfonylaminocarbonyl-18-hydroxy-2,15-dioxo-3,16-diaza-tricyclo[14.3.0.04,6]nonadec-7-en-14-yl)-carbamic acid tert-butyl ester, Example 19, as a white solid. $^1$H NMR (500 MHz, CD3Cl) δ 1.87-1.64 (m, 21 H), 1.70-1.98 (m, 3 H), 2.15-2.56 (m, 5 H), 2.85-2.94 (m, 1 H), 3.71 (d, J=13.91 Hz, 1 H), 4.10-4.26 (m, 2 H), 4.51 (t, J=7.87 Hz, 1 H), 4.62 (s, 1 H), 4.98 (m, 1 H), 5.06 (d, J=8.78 Hz, 1 H), 5.64-5.71 (m, 1 H), 6.72 (s, 1 H), 10.24 (s, 1 H); MS m/z 569 (M++1).

The following macrocyclic alcohol intermediates A and B were prepared employing the procedures described in examples 25 and 26:

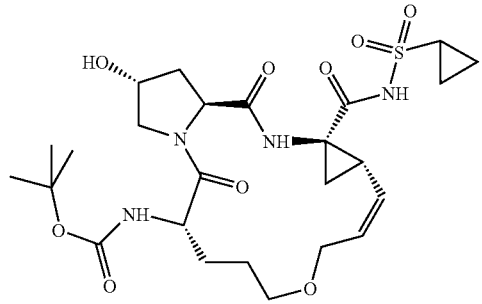

A

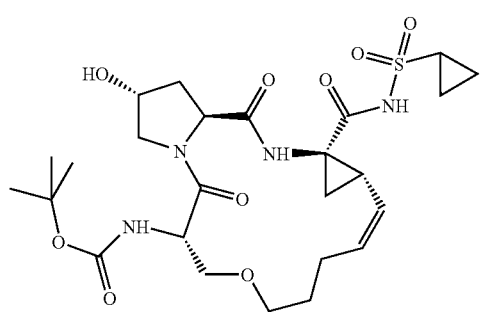

B

The following macrocyclic alcohol intermediates C, D, E, F could be prepared employing the chemistry described and referenced herein as for example in Examples 25 and 26:

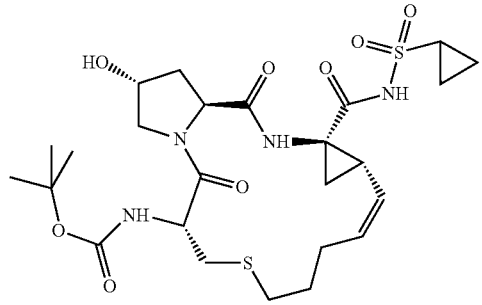

C

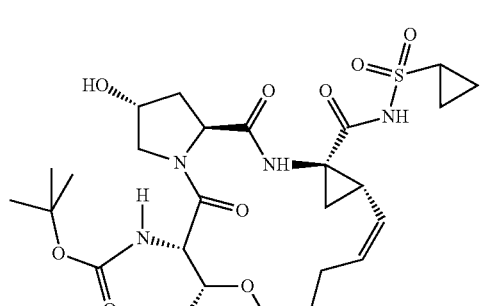

D

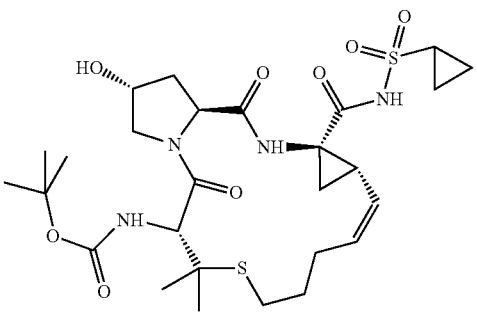

E

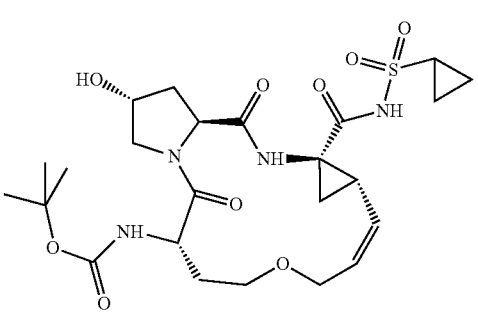

F

Example 27

Preparation of Example 27, 2(S)-tert-butoxycarbony-lamino-3-pent-4-enylsulfanylpropionic acid

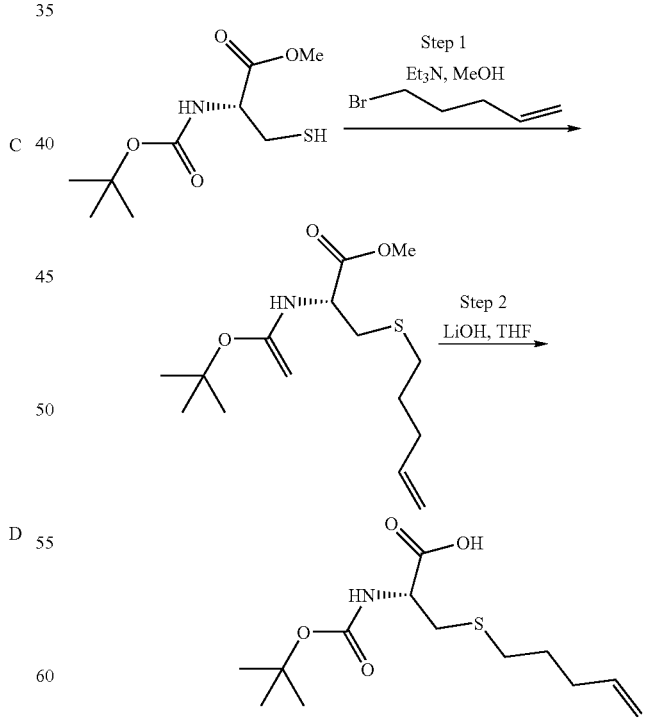

Example 27

Step 1: To a solution of N-Boc-cysteine methyl ester (3.36 g, 0.014 mol) in methanol (166 mL) at RT was added triethylamine (10.8 mL) and 1-bromopent-4-ene (3.19 g, 21 mmol, 1.5 equivalents) and the resulting solution was stirred at room temperature overnight. The mixture was then concentrated in vacuo and the resulting residual mixture was purified using flash chromatography (hexane, ethyl acetate gradient) to provide 1.76 g (41%) of the desired thioether. $^1$H NMR (500 MHz, CDCl$_3$) δ 1.43 (s, 9H), 1.64 (m, 2H), 2.11 (m, 2H), 2.51 (m, 2H), 2.95 (m, 2H), 3.75 (s, 3H), 4.51 (m, 1H), 4.95-5.03 (m, 2H), 5.34 (m, 1H), 5.80 (1H, m); MS m/z 304(M++1).

Step 2: The thioether product of step 1 (9.51 g, 31.4 mmol) was added to a mixture of 1M LiOH in water (200 mL) and THF (200 mL) and the resulting mixture was stirred at room temperature overnight. The reaction mixture was then acidified using 1N hydrochloric acid and the resulting mixture was extracted several times with ethyl acetate. The extracts were combined, dried over magnesium sulfate, and concentrated in vacuo to provide the desired acid, Example 27, which was used as is in the next reaction.

Example 28

Preparation of Example 28,
N-tert-Butoxycarbonyl-3-(4-pentenylthio)-L-valine

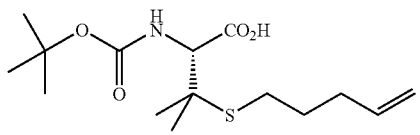

Example 28

Step 1: Preparation of N-tert-butoxycarbonyl-3-(4-pentenylthio)-L-valine, methyl ester

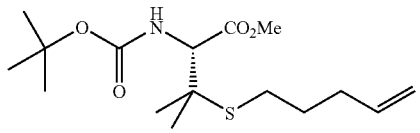 [SMILES: C=CCCCSC(C)(C)[C@H](NC(=O)OC(C)(C)C)C(=O)OC]

To a solution of 7.12 g (48 mmol, 1.0 eq) of L-penicillamine in 100 mL of 1,4-dioxane and 25 mL of water at room temperature was added 9.60 mL (96 mmol, 2.0 eq) of 10N aqueous sodium hydroxide solution, followed by the dropwise addition of 12.00 mL (101 mmol, 2.1 eq) of 5-bromo-1-pentene over several minutes. The resulting mixture was stirred at room temperature for 68 hours. At this point 12.50 g (57 mmol, 1.2 eq) of di-tert-butyl dicarbonate was added, and the mixture was stirred at room temperature for another 6 hours. The mixture was concentrated under vacuum, and the residue was dissolved in water. The aqueous mixture was washed with diethyl ether, adjusted to pH 3 employing 1N hydrochloric acid, and then extracted with ethyl acetate. The combined extracts were washed with brine, dried over anhydrous magnesium sulfate, filtered, and concentrated under vacuum.

The crude product (12.20 g) was dissolved in 120 mL of anhydrous dimethylsulfoxide. To this solution was added 10.50 g (76 mmol) of potassium carbonate and 4.70 mL (76 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2-10% ethyl acetate/hexane) provided 8.54 g of N-tert-butoxycarbonyl-3-(4-pentenylthio)-L-valine, methyl ester as a colorless oil. NMR (300 MHz, CDCl$_3$): δ 5.76 (d of d of t, 1 H, J=17.2, 10.3, 6.6 Hz), 5.35 (br d, 1 H, J=9.0 Hz), 5.05-4.94 (m, 2 H), 4.27 (br d, 1 H, J=9.0 Hz), 3.73 (s, 3 H), 2.52 (m, 2 H), 2.13 (quart., 2 H, J=7.3 Hz), 1.61 (quint., 2 H, J=7.3 Hz), 1.43 (s, 9 H), 1.35 (s, 3 H), 1.33 (s, 3 H).

Step 2: Preparation of Example 28,
N-tert-Butoxycarbonyl-3-(4-pentenylthio)-L-valine

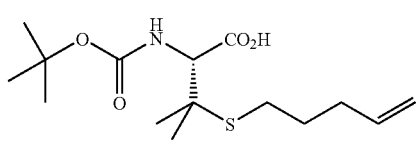

Example 28

To a solution of 8.52 g (25.7 mmol) of N-tert-butoxycarbonyl-3-(4-pentenylthio)-L-valine, methyl ester in 200 mL of tetrahydrofuran at room temperature was added a solution of 1. Og (26.2 mmol) of lithium hydroxide monohydrate in 50 mL of water. The resulting mixture was stirred at room temperature for 65 hours. To the reaction mixture then was added 28 mL of 1.00N hydrochloric acid. The mixture was diluted with diethyl ether, washed with water (3×) and brine, dried over anhydrous sodium sulfate, filtered, and concentrated under vacuum to afford 8.10 g of N-tert-butoxycarbonyl-3-(4-pentenylthio)-L-valine as a colorless oil. NMR (300 MHz, CDCl$_3$): δ 5.75 (d of d of t, 1 H, J=17.2, 10.3, 6.6 Hz), 5.40 (br s, 1 H), 5.05-4.94 (m, 2 H), 4.28 (br s, 1 H), 2.56 (m, 2 H), 2.13 (quart., 2 H, J=7.3 Hz), 1.63 (quint., 2 H, J=7.3 Hz), 1.44 (s, 9 H), 1.39 (s, 3 H), 1.37 (s, 3 H).

Example 29

Preparation of Example 29, 5-Allyloxy-2(S)-(tert-butoxycarbonylamino)pentanoic acid

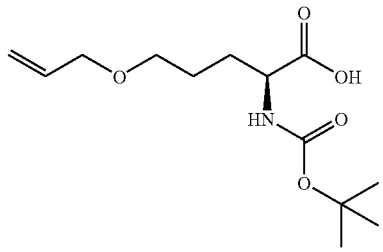

Example 29

Step 1: Preparation of Isopropyl pyrrolidin-5-one-2(S)-carboxylate

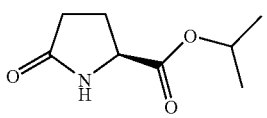

A solution of L-pyroglutamic acid (Aldrich, 25.0 g, 195 mmol) and para-toluenesulfonic acid mono hydrate (3.71 g, 19.5 mmol) was refluxed in isopropanol (40 mL) under nitrogen for 6 hours using a Dean-Stark trap variation (condensate returned through a Soxhlet extractor filled with 4 Å molecular sieves). After cooling to room temperature, the reaction was diluted with ether, washed with saturated aqueous sodium bicarbonate and then saturated aqueous NaCl, dried (MgSO4) and evaporated to give a colorless syrup. It crystallized upon setting. Triturating the crystalline residue in hexane provided 31.9 g (96%) of isopropyl pyrrolidin-5-one-2 (S)-carboxylate as white prisms: $^1$H NMR (300 MHz, Chloroform-D) δ 6.35 (br s, 1 H), 5.04 (sept. 1 H, J=6.2 Hz), 4.18 (dd, 1 H, J=8.4, 5.3 Hz), 2.51-2.28 (m, 3 H), 2.27-2.12 (m, 1 H), 1.24 (d, 6 H, J=6.2 Hz). LCMS m/z 172 (M+H)+.

Step 2: Preparation of Isopropyl 1-(tert-butoxycarbonyl)-pyrrolidin-5-one-2(S)-carboxylate

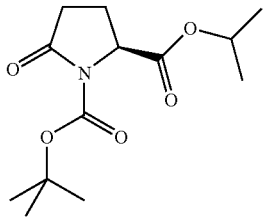 [SMILES: CC(C)OC(=O)[C@@H]1CCC(=O)N1C(=O)OC(C)(C)C]

A solution of isopropyl pyrrolidin-5-one-2(S)-carboxylate (product of step 26A, 31.9 g, 188 mmol), di-tert-butyl dicarbonate (48.6 g, 225 mmol) and DMAP (2.30 g, 8.8 mmol) in acetonitrile (300 mL) was stirred at room temperature under $N_2$ for 30 minutes. The reaction was evaporated to about 100 mL, diluted with ether, washed with 1N HCl then saturated aqueous NaCl, dried (MgSO$_4$) and evaporated to give isopropyl 1-(tert-butoxycarbonyl)pyrrolidin-5-one-2(S) carboxylate as a light yellow oil, 50.1 g (99%): $^1$H NMR (300 MHz, Chloroform-D) δ 5.06 (sept. 1 H, J=6.2 Hz), 4.53 (dd, 1 H, J=9.5, 2.9 Hz), 2.66-2.40 (m, 2 H), 2.36-2.22 (m, 1 H), 2.03-1.93 (m, 1 H), 1.47 (s, 9 H), 1.26 (d, 3 H, J=6.2 Hz), 1.24 (d, 3 H, J=6.2 Hz). LCMS m/z 272 (M+H)$^+$.

Step 3: Preparation of Isopropyl 2(S)-(tert-butoxycarbonylamino)-5-hydroxypentanoate

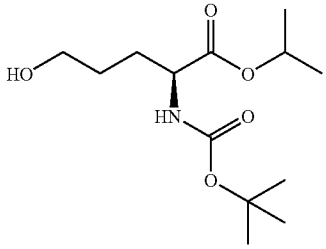 [SMILES: CC(C)OC(=O)[C@H](CCCO)NC(=O)OC(C)(C)C]

To a solution of isopropyl 1-(tert-butoxycarbonyl)pyrrolidin-5-one-2(S)-carboxylate (product of step 26B, 49.5 g, 183 mmol) in methanol (300 mL) was added sodium borohydride (10.0 g, 263 mmol) in ~1 g portions over 1.5 hours. The reaction was stirred under nitrogen for another 10 minutes. It was diluted with water, extracted with ether, combined organic fractions washed with saturated aqueous NaCl, dried (MgSO$_4$) and evaporated to give a light yellow oil. Flash chromatography (silica gel, 20-30% ethyl acetate/hexane) gave 31.8 g (64%) of isopropyl 2(S)-(tert-butoxycarbonylamino)-5-hydroxypentanoate as a colorless syrup: $^1$H NMR (300 MHz, Chloroform-D) δ 5.16 (br d, 1 H, J=7.3 Hz), 5.03 (sept., 1 H, J=6.2 Hz), 4.28 (br d, 1 H, J=6.2 Hz), 3.67 (br dd, J=10.2, 5.5 Hz), 1.94-1.79 (m, 2 H), 1.76-1.67 (m, 1 H), 1.66-1.56 (m, 2 H), 1.43 (s, 9 H), 1.25 (d, 3 H, J=6.2 Hz), 1.23 (d, 3 H, J=6.2 Hz). LCMS m/z 276 (M+H)$^+$.

Step 4: Preparation of Isopropyl-5-allyloxy-2(S)-(tert-butoxycarbonylamino)pentanoate

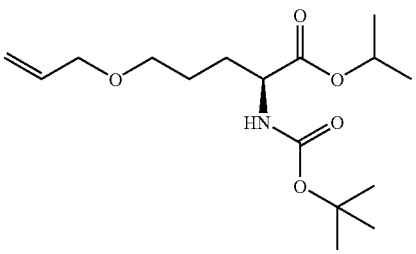 [SMILES: C=CCOCCC[C@H](NC(=O)OC(C)(C)C)C(=O)OC(C)C]

A degassed mixture of isopropyl 2(S)-(tert-butoxycarbonylamino)-5-hydroxypentanoate (product of step 26C, 17.6 g, 63.9 mmol), allyl methyl carbonate (24.0 ml, 213 mmol), Pd2(dba)$_3$ (1.62 g, 1.78 mmol) and BINAP (4.42 g, 7.10 mmol) in THF (150 mL) was refluxed under nitrogen for 3 hours. After cooling to room temperature, the reaction was diluted with ether, filtered through celite and evaporated giving a dark brown syrup. Flash chromatography of the residue (silica gel, 30% ether/hexane) gave isopropyl 5-allyloxy-2 (S)-(tert-butoxycarbonylamino)pentanoate as a viscous colorless oil, 16.3 g (81%): $^1$H NMR (300 MHz, Chloroform-D) δ 5.88 (ddt, 1 H, 17.4, 10.4, 5.5), 5.28 (m, 1 H), 5.22-5.11 (m, 1 H), 5.02 (sept., 1 H, J=6.2 Hz), 4.21 (br t, 1 H, J=6.7 Hz), 3.94 (dt, 2 H, J=5.9, 1.5 Hz), 3.42 (t, 2 H, J=5.9 Hz), 1.90-1.82 (m, 1 H), 1.75-1.57 (m, 3 H), 1.42 (s, 9 H), 1.21 (d, 3 H, J=6.2 Hz), 1.19 (d, 3 H, J=6.2 Hz). LCMS m/z 316 (M+H)+.

Step 5: Preparation of 5-Allyloxy-2(S)-(tert-butoxycarbonylamino)pentanoic acid Example 29

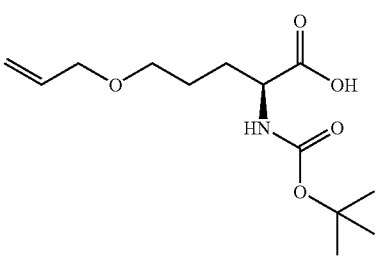

A mixture of isopropyl 5-allyloxy-2(S)-(tert-butoxycarbonylamino)pentanoate (product of step 26D, 16.1 g, 51.1 mmol) and lithium hydroxide hydrate (4.19 g, 102 mmol) in THF/water (100 mL/20 mL) was stirred at room temperature under nitrogen for 16 hours. The reaction was diluted with water, washed with ether, pH of aqueous fraction adjusted to ~4, extracted with ether, combined organic fractions washed with saturated NaCl, dried (MgSO4) and evaporated giving 5-allyloxy-2(S)-(tert-butoxycarbonylamino)pentanoic acid as a light yellow syrup: ¹H NMR (300 MHz, Chloroform-D) δ 5.89 (ddt, 1 H, J=17.4, 10.4, 5.5), 5.25 (dd, 1 H, J=17.4, 1.6 Hz), 5.17 (dd, 1 H, J=10.4, 1.6 Hz), 4.30 (br d, 1 H, J=6.2), 3.96 (dt, 2 H, J=5.9, 1.5 Hz), 3.46 (t, 2 H, J=5.9 Hz), 1.96-1.86 (m, 1 H), 1.85-1.77 (m, 1 H), 1.75-1.64 (m, 2 H), 1.43 (s, 9 H). LCMS m/z 274 (M+H)+.

Example 30

General Procedure for the Preparation of Example 30

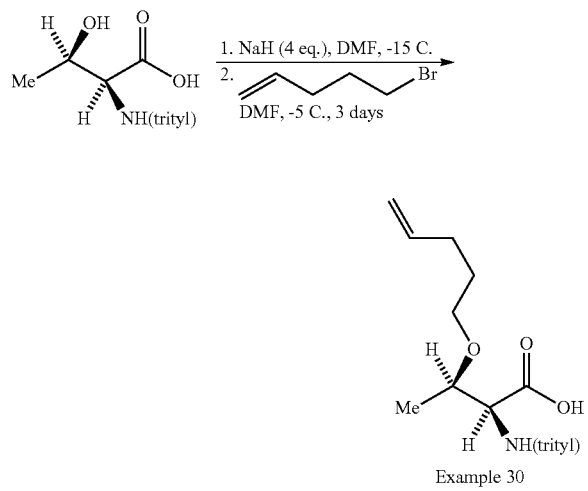

Example 30

Example 23 was prepared by adding a DMF solution of N-trityl protected threonine to a DMF solution of sodium hydride cooled to −15° C. The reaction mixture was stirred for 30 minutes at −15° C. after which 5-bromo-1-pentene was added and the resulting mixture was warmed to −5° C. The reaction mixture was maintained at −5° C. for 3 days after which time the reaction was quenched by the addition of 1N aqueous HCl and worked up using standard extraction procedures as described above. Example 23 was obtained in pure form by standard chromatography procedures.

Example 31

Preparation of Example 31, N-tert-Butoxycarbonyl-O-(4-pentenyl)-L-serine

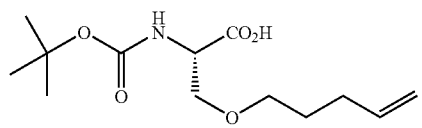

Example 31

Step 1: Preparation of N-tert-Butoxycarbonyl-O-(4-pentenyl)-L-serine, methyl ester

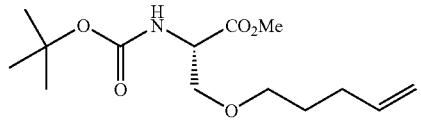 [SMILES: C=CCCCOC[C@H](NC(=O)OC(C)(C)C)C(=O)OC]

To a solution of 10.26 g (50 mmol, 1.0 eq) of N-tert-butoxycarbonyl-L-serine in 500 mL of anhydrous dimethylsulfoxide at room temperature was added 2.00 g (50 mmol, 1.0 eq) of 60% sodium hydride in mineral oil. This mixture was stirred at room temperature for 0.5 hour until the evolution of gas had ceased. To the resulting solution was added 6.00 mL (50 mmol, 1.0 eq) of 5-bromo-1-pentene followed immediately by another 2.00 g (50 mmol, 1.0 eq) of 60% sodium hydride in mineral oil. The reaction mixture then was stirred at room temperature for 16 hours. The mixture was diluted with 200 mL of water, adjusted to pH 3-4 by the addition of 50 mL of 1.00N hydrochloric acid, and extracted with ethyl acetate. The organic phase was washed with water (2×) and brine, dried over anhydrous sodium sulfate, filtered, and concentrated under vacuum. To remove the residual mineral oil the resulting material was dissolved in a dilute aqueous sodium hydroxide solution. This aqueous solution was washed with hexane and then adjusted to pH 4 employing hydrochloric acid, and extracted with ethyl acetate. The extract was washed with water (2×) and brine, dried over anhydrous sodium sulfate, filtered, and concentrated under vacuum.

The crude product (7.70 g) was dissolved in 100 mL of anhydrous dimethylsulfoxide. To this solution was added 7.80 g (56 mmol) of potassium carbonate and 3.50 mL (56 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2-10% ethyl acetate/hexane) provided 6.70 g of N-tert-butoxycarbonyl-O-(4-pentenyl)-L-serine, methyl ester as a colorless oil. NMR (300 MHz, CDCl₃): δ 5.78 (d of d of t, 1 H, J=17.2, 10.2, 6.6 Hz), 5.34 (br d, 1 H, J=8.0 Hz), 5.03-4.92 (m, 2 H), 4.40 (m, 1 H), 3.81 (d of d, 1 H, J=9.5, 2.9 Hz), 3.74 (s, 3 H), 3.61 (d of d, 1 H, J=9.5, 3.5 Hz), 3.42 (m, 2 H), 2.06 (quart., 2 H, J=7.3 Hz), 1.61 (quint., 2 H, J=7.3 Hz), 1.44 (s, 9 H).

Step 2: Preparation of Example 31, N-tert-Butoxycarbonyl-O-(4-pentenyl)-L-serine

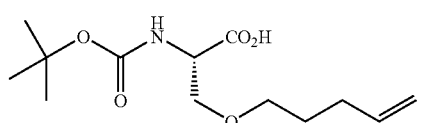

Example 31

To a solution of 6.65 g (23 mmol) of N-tert-butoxycarbonyl-O-(4-pentenyl)-L-serine, methyl ester in 500 mL of tetrahydrofuran at room temperature was added a solution of 1.95 g (46 mmol) of lithium hydroxide monohydrate in 100 mL of water. The resulting mixture was stirred at room temperature for 40 hours. To the reaction mixture then was added 46 mL of 1.00N hydrochloric acid. The mixture was diluted with ethyl acetate, washed with water (3×) and brine, dried over anhydrous sodium sulfate, filtered, and concentrated under vacuum to afford 6.30 g of N-tert-butoxycarbonyl-O-(4-pentenyl)-L-serine as a colorless oil. NMR (300 MHz, CDCl$_3$): δ 5.77 (d of d of t, 1 H, J=17.2, 10.2, 6.6 Hz), 5.37 (br d, 1 H, J=8.0 Hz), 5.03-4.92 (m, 2 H), 4.42 (m, 1 H), 3.87 (d of d, 1 H, J=9.5, 2.6 Hz), 3.63 (d of d, 1 H, J=9.5, 4.0 Hz), 3.45 (t, 2 H, J=6.6 Hz), 2.07 (quart., 2 H, J=7.3 Hz), 1.64 (quint., 2 H, J=7.3 Hz), 1.44 (s, 9 H).

Example 32

Preparation of (S)-4-allyloxy-2-(tert-butoxycarbonylamino)butyric acid

Example 32

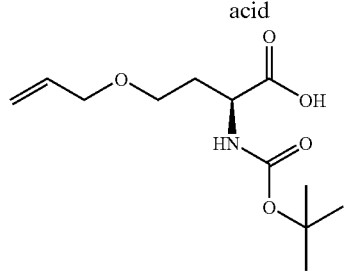

To a mixture of sodium hydride (913 mg, 22.8 mmoL) in DMF at 0° C. was added N-t-Boc-L-homoserine (2 g, 9.13 mmoL). This reaction mixture was stirred at 0° C. for 15 min, and then allyl bromide (1.38 g, 11.4 mmoL) was added. The mixture was warmed up to rt, and stirred for 2 h. It was then concentrated in vacuo. The residue was diluted with water, and sequentially washed with hexane and ether. The organic layers were discarded, and the aqueous layer was carefully adjusted to pH 3 with 1 N HCl. This acidic aqueous solution was extracted with ethyl acetate. The organic phase was dried (MgSO4), and concentrated in vacuo to yield 2.2 g (93%) of (S)-4-allyloxy-2-(tert-butoxycarbonylamino)butyric acid as a colorless oil. $^1$H NMR (300 MHz, CD$_3$OD) δ 1.42 (s, 9 H), 1.80-1.90 (m, 1 H), 2.04-2.16 (m, 1 H), 3.50-3.54 (m, 2 H), 3.97 (d, J=4.39 Hz, 2 H), 4.23 (dd, J=8.78, 4.39 Hz, 1 H), 5.15 (d, J=10.25 Hz, 1 H), 5.26 (dd, J=17.38, 1.65 Hz, 1 H), 5.84-5.97 (m, 1 H).

Example 33

Preparation of Compound 1

Compound 1

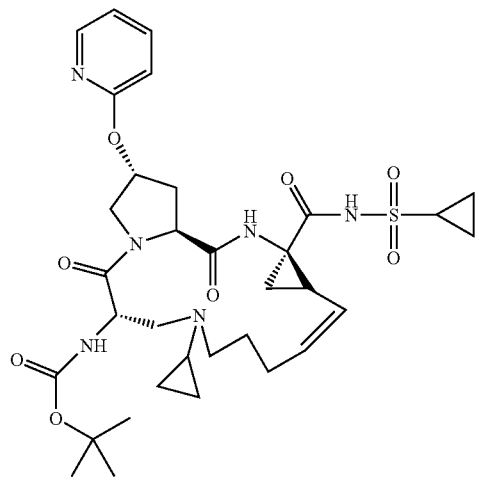

Step A: Synthesis of N-(pent-4-enyl)cyclopropanamine 1a

Using an addition funnel, a solution of 5-bromopentene (15.8 g, 106 mmol) in 50 mL of methanol was added over the course of 5 min to a solution of cyclopropylamine (20.6 g, 361 mmol) in 200 mL of methanol. The resultant mixture was allowed to stir at rt for 72 h at which time it was refluxed for 1 h. The methanol and excess cyclopropylamine were removed by distillation. The residue, hydrobromide salt of 1a, was partitioned between ether and 4 N NaOH. The aqueous phase was washed with ether (2×). The combined ether extracts were dried (MgSO4), filtered, and concentrated to give 8 g (60%) of 1a as a yellow oil: $^1$H NMR (500 MHz, CDCl$_3$) δ 0.31-0.36 (m, 2 H) 0.40-0.46 (m, 2 H) 1.53-1.63 (m, 2 H) 1.87 (brs, 1 H) 2.05-2.10 (m, 2 H) 2.10-2.14 (m, 1 H) 2.69 (t, J=7.32 Hz, 2 H) 4.91-5.07 (m, 2 H) 5.72-5.88 (m, 1 H).

Step B: Synthesis of (S)-2-(tert-butoxycarbonyl)-3-(cyclopropyl(pent-4-enyl)amino)propanoic acid 1b 1b

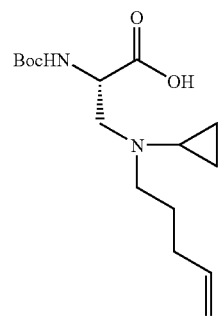

N-(Pent-4-enyl)cyclopropanamine 1a (668 mg, 5.30 mmol) in 20 mL of acetonitrile was added to a slurry of N-t-butoxycarbonyl-L-serine-beta-lactone (1.0 g, 5.30 mmol) in 40 mL of acetonitrile. The mixture was stirred under N2 at rt for 5 days, and then concentrated in vacuo to give ~1.7 g of the crude product (S)-2-(tert-butoxycarbonyl)-3-(cyclopropyl(pent-4-enyl)amino)propanoic acid 1b as a yellow oil. It was used directly in Step C without purification. LC-MS (Phenomenex 10 µm C18 HPLC column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nm. Solvent A: 10% MeOH/90% H2O/0.1% TFA. Solvent B: 10% H2O/90% MeOH/0.1% TFA. (Retention time: 2.50 min), MS m/z 313 (M30 +1).

Step C: Synthesis of (1R,2S)-ethyl 1-((3R,5S)-1-((S)-2-(tert-butoxycarbonyl)-3-(cyclopropyl(pent-4-enyl)amino)propanoyl)-3-hydroxypyrrolidine-5-carboxamido)-2-vinylcyclopropanecarboxylate 1c Compound 1c

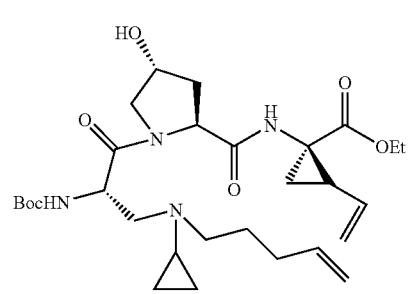

A solution of crude (S)-2-(tert-butoxycarbonyl)-3-(cyclopropyl(pent-4-enyl)amino)propanoic acid 1b (1.47 g, 4.71 mmoL) in 20 mL of DCM was treated sequentially with (1R,2S)-ethyl 1-((3R,5S)-3-hydroxypyrrolidine-5-carboxamido)-2-vinylcyclopropanecarboxylate hydrochloride (1.44 g, 4.71 mmoL), N-methyl morpholine (1.80 mL, 16.3 mmoL), and HATU (2.14 g, 5.53 mmoL). The reaction mixture was stirred at rt under N2 for 3 h, and then concentrated in vacuo. The residue was dissolved in water, and 1N HCl was added until the pH=5. This aqueous solution was extracted with EtOAc (3×). The combined organic phases were washed with sat. aq. NaHCO3, dried (MgSO4), and concentrated in vacuo to give the crude product. Flash chromatography (50% ethyl acetate/hexane to 100% ethyl acetate) gave 1.55 g (58%) of (1R,2S)-ethyl 1-((3R,5S)-1-((S)-2-(tert-butoxycarbonyl)-3-(cyclopropyl(pent-4-enyl)amino)propanoyl)-3-hydroxypyrrolidine-5-carboxamido)-2-vinylcyclopropanecarboxylate 1c as a white foam: LC-MS (Phenomenex-Luna S10 HPLC column: 3.0×50 mm length. Gradient: 100% Solvent A/0% Solvent B to 0% Solvent A/100% Solvent B. Gradient time: 2 min. Hold time: 1 min. Flow rate: 4 mL/min. Detector Wavelength: 220 nm. Solvent A: 10% MeOH/90% H2O/0.1% TFA. Solvent B: 10% H2O/90% MeOH/0.1% TFA.) (Retention time: 1.38 min), MS m/z 564 (M++1).

Step D: Synthesis of (1R,2S)-ethyl 1-((3R,5S)-1-((S)-2-(tert-butoxycarbonyl)-3-(cyclopropyl(pent-4-enyl)amino)propanoyl)-3-(tert-butyldimethylsilyloxy)pyrrolidine-5-carboxamido)-2-vipylcyclopropanecarboxylate 1d

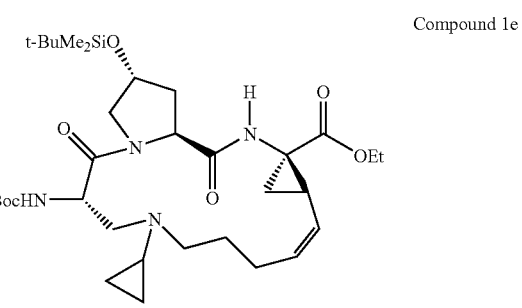

Compound 1d

To a mixture of compound 1c (1.55 g, 2.75 mmoL) in 10 mL of DMF was added imidazole (0.47 g, 6.88 mmoL) and tert-butyldimethylsilyl chloride (826 mg, 5.50 mmoL). The mixture was stirred at rt for 18 h, concentrated in vacuo, and partitioned between ethyl acetate and water. The organic phase was dried over magnesium sulfate, and concentrated in vacuo to obtain an off-white solid. Flash chromatography (eluting with methylene chloride and then ethyl acetate) gave (1R,2S)-ethyl 1-((3R,5S)-1-((S)-2-(tert-butoxycarbonyl)-3-(cyclopropyl(pent-4-enyl)amino)propanoyl)-3-(tert-butyldimethylsilyloxy)pyrrolidine-5-carboxamido)-2-vinylcyclopropanecarboxylate 1d as a white solid (1.75 g, 94%): LC-MS (Phenomenex 10 µm C18 HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nm. Solvent A: 10% MeOH/90% H2O/0.1% TFA. Solvent B: 10% H2O/90% MeOH/0.1% TFA.) (Retention time: 2.51 min), MS m/z 677 (M++1).

Step E: Synthesis of Compound 1e

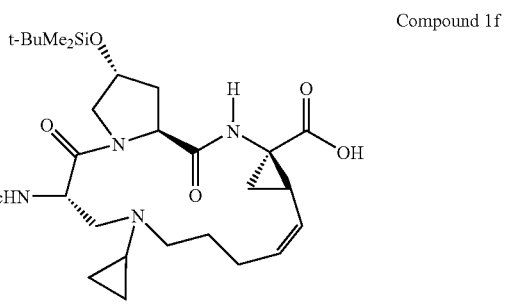

Compound 1e

To a solution of compound 1d (1.45 g, 2.14 mmoL) in 1 L of methylene chloride was added 181 mg (0.21 mmoL) of Grubb's 2nd generation catalyst: (1,3-Bis-(2,4,6-trimethylphenyl)-2-imidazolidinylidene)dichloro(phenylmethylene)-(tricyclohexylphosphine)ruthenium. The mixture was heated at reflux for 1 h. A second fraction of the catalyst (50 mg, 0.058 mmol) was added, and the mixture was stirred at rt overnight. The residue was concentrated in vacuo, and then purified by flash chromatography eluting with 50% ether/hexane to give 0.84 g (62%) of the product 1e as a white solid: LC-MS (Phenomenex 10 µm C18 HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nm. Solvent A: 10% MeOH/90% H2O/0.1% TFA. Solvent B: 10% H2O/90% MeOH/0.1% TFA.) (Retention time: 2.43 min), MS m/z 649 (M++1).

Step F: Synthesis of compound 1f

Compound 1f

To a solution of compound 1e (0.84 g, 1.30 mmoL) in a mixture of THF (30 mL), methanol (15 mL), and water (4 mL), was added powdered lithium hydroxide hydrate (0.31 g, 12.90 mmoL). The resultant light yellow slurry was stirred at rt under N2 overnight. The mixture was then concentrated in vacuo, and partitioned between hexane/ether (1:1) and water. The organic phase was discarded, and the aqueous phase was treated with 1 N HCl until the pH=5. This acidic solution was extracted with EtOAc (3×). The combined EtOAc extracts were dried (MgSO4) and concentrated in vacuo to give 0.495 g (61%) of if as an off-white solid: LC-MS (Phenomenex 10 µm C18 HPLC column: 3.0×50 mm length. Gradient: 100%

Solvent A/0% Solvent B to 0% Solvent A/100% Solvent B. Gradient time: 2 min. Hold time: 1 min. Flow rate: 5 mL/min. Detector Wavelength: 220 nm. Solvent A: 10% MeOH/90% H2O/0.1% TFA. Solvent B: 10% H2O/90% MeOH/0.1% TFA.) (Retention time: 2.36 min), MS m/z 621 (M++1).

Step G: Synthesis of Compound 1g

Compound 1g

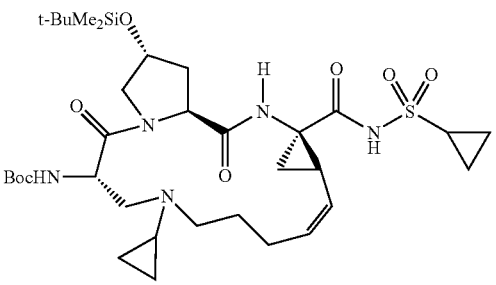

Compound 1f (490 mg, 0.79 mmol) was dissolved in 15 mL of THF and treated with CDI (179 mg, 1.10 mmoL). (Care was taken to exclude moisture by using oven dried glassware and maintaining a dry N2 atmosphere.) After refluxing the reaction mixture for two hours, it was cooled to rt and treated sequentially with cyclopropylsulfonamide (134 mg, 1.10 mmoL) and DBU (168 mg, 1.10 mmoL). After stirring overnight at rt, the THF was removed by rotary evaporation. The residue was dissolved in water and 1N HCl was added until the pH=5. This aqueous solution was extracted with EtOAc (3×). The combined EtOAc extracts were dried (MgSO4) and concentrated in vacuo to give the crude product. Purification by flash column, eluting with 3% methanol in methylene chloride, gave 300 mg (53%) of 1 g as a white solid: LC-MS (Phenomenex 10 μm C18 HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nm. Solvent A: 10% MeOH/90% H2O/0.1% TFA. Solvent B: 10% H2O/90% MeOH/0.1% TFA.) (Retention time: 2.40 min), MS m/z 724 (M++1).

Step H: Synthesis of Compound 1h

Compound 1h

To a mixture of compound 1g (250 mg, 0.35 mmoL) in 15 mL of THF was added tetrabutylammonium fluoride (129 mg, 0.46 mmoL). The mixture was stirred at rt for 18 h. THF was removed by rotary evaporation, and the residue was partitioned between ethyl acetate and water. The organic phase was dried (MgSO4) and concentrated in vacuo to give the crude product. Purification by triturating with hexane provided 200 mg (94%) of 1h as a white solid: LC-MS (Phenomenex 10 μm C18 HPLC column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nm. Solvent A: 10% MeOH/90% H2O/0.1% TFA. Solvent B: 10% H2O/90% MeOH/0.1% TFA.) (Retention time: 2.32 min), MS m/z 610 (M++1).

Step I: Synthesis of Compound 1

To a mixture of compound 1h (10 mg, 0.016 mmoL) in 0.5 mL of DMSO was added t-BuOK (1M in THF)(82μ/M, 0.082 mmol) and 2-fluoropyridine (3 mg, 0.031 mmol). The reaction was stirred for 5 h at rt. The reaction mixture then was partitioned between hexane (5 mL) and water (3 mL). The aqueous phase was acidified to pH 4 using 1 N HCl. The resulting solution was extracted with EtOAc (3×20 mL). The combined EtOAc extracts were dried (MgSO4), filtered, and concentrated in vacuo to give a white solid. Purification by flash column eluting with 2% MeOH/CH$_2$Cl$_2$ gave 9 mg (82%) of the product 1 as a white powder. $^1$H NMR (500 MHz, MeOD) δ ppm 0.42 (d, J=46.69 Hz, 2 H), 0.74 (d, J=34.79 Hz, 2 H), 1.02 (brs, 1 H), 1.08-1.15 (m, 2 H), 1.26 (s, 9 H), 1.29-1.38 (m, 3 H), 1.51-1.64 (m, 2 H), 1.74 (dd, J=8.24, 5.49 Hz, 1 H), 1.79 (s, 1 H), 2.32-2.43 (m, 2 H), 2.50-2.59 (m, 2 H), 2.68 (s, 3 H), 2.88-2.96 (m, 1 H), 3.23-3.31 (m, 1 H), 4.06-4.12 (m, 1 H), 4.35 (d, J=11.60 Hz, 1 H), 4.47 (dd, J=10.38, 6.71 Hz, 1 H), 4.84-4.87 (m, 1 H), 5.08 (s, 1 H), 5.68-5.73 (m, 1 H), 5.73-5.80 (m, 1 H), 6.76 (d, J=8.24 Hz, 1 H), 6.93-7.01 (m, 1 H), 7.65-7.72 (m, 1 H), 8.14-8.20 (m, 1 H). LC-MS (Phenomenex 10 μm C18 HPLC column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nm. Solvent A: 10% MeOH/90% H2O/0.1% TFA. Solvent B: 10% H2O/90% MeOH/0.1% TFA. (Retention time: 2.71 min), MS m/z 687 (M++1).

Example 34

Compound 2

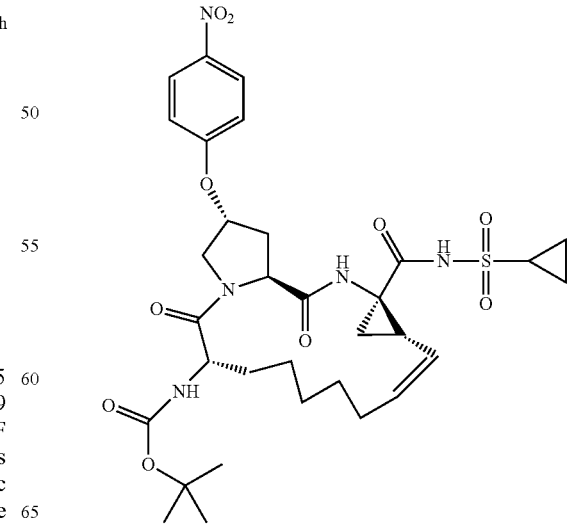

Step 1: Preparation of 14-tert-Butoxycarbonylamino-18-(4-nitrophenoxy)-2,15-dioxo-3,16-diazatricyclo[14.3.0.0$^{4,6}$]nonadec-7-ene-4-carboxylic acid

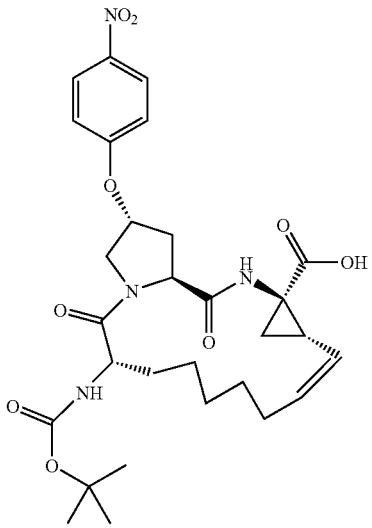 [SMILES: CC(C)(C)OC(=O)N[C@H]1CCCCC/C=C\[C@@H]2C[C@@]2(C(=O)O)NC(=O)[C@@H]2C[C@@H](Oc3ccc([N+](=O)[O-])cc3)CN2C1=O]

To a mixture of (14-tert-butoxycarbonylamino-18-hydroxy-2,15-dioxo-3,16-diaza-tricyclo[14.3.0.04,6]nonadec-7-ene-4-carboxylic acid, ethyl ester (192 mg, 0.39 mmol; prepared in Ex. 25, step 3) in 3 mL of THF was added sodium hydride (50 mg, 60% in oil, 1.25 mmol). The mixture was stirred at rt for 5 min. then 1-fluoro-4-nitrobenzene (60 mg, 0.42 mmol) was added and stirring was continued at rt overnight. The reaction was quenched by adding 10 mL of water, and then 0.1 N hydrochloric acid was used bring the pH to 4. This acidic solution was then extracted with ethyl acetate. The organic phase was dried over magnesium sulfate and concentrated in vacuo to obtain 14-tert-butoxycarbonylamino-18-(4-nitrophenoxy)-2,15-dioxo-3,16-diaza-tricyclo[14.3.0.04, 6]nonadec-7-ene-4-carboxylic acid as a white solid (100 mg, 44%). LC-MS (YMC Xterra MS C18 S7 column: 3.0×50 mm length. Gradient: 100% Solvent A/0% Solvent B to 0% Solvent A/100% Solvent B. Gradient time: 4 min. Hold time: 1 min. Flow rate: 4 mL/min. Detector Wavelength: 220 nm. Solvent A: 10% MeOH/90% H2O/0.1% TFA. Solvent B: 10% H2O/90% MeOH/0.1% TFA.)(Retention time: 3. 17 min), MS m/z 587(M++1).

Step 2: Preparation of Compound 2

14-tert-Butoxycarbonylamino-18-(4-nitro-phenoxy)-2,15-dioxo-3,16-diaza-tricyclo[14.3.0.04,6]nonadec-7-ene-4-carboxylic acid (100 mg, 0.17 mmol) was dissolved in 5 mL of THF and treated with carbonyl diimidazole (38 mg, 0.23 mmol). (Care was taken to exclude moisture by using oven dried glassware and maintaining a dry N2 atmosphere.) After refluxing the reaction mixture for one hour, it was cooled to rt and treated sequentially with cyclopropylsulfonamide (29 mg, 0.24 mmol) and DBU (36 mg, 0.24 mmoL). After stirring for 24 h at rt, the THF was removed by rotary evaporation. The residue was partitioned between ethyl acetate and pH 4 buffer. The organic phase was dried (MgSO4) and concentrated in vacuo to give the crude product. Flash chromatography (50% ethyl acetate in hexane) gave 30 mg (26%) of compound 2. LC-MS (YMC Xterra MS C18 S7 column: 3.0×50 mm length. Gradient: 100% Solvent A/0% Solvent B to 0% Solvent A/100% Solvent B. Gradient time: 4 min. Hold time: 1 min. Flow rate: 4 mL/min. Detector Wavelength: 220 nm. Solvent A: 10% MeOH/90% H2O/0.1% TFA. Solvent B: 10% H2O/90% MeOH/0.1% TFA.)(Retention time: 3. 21 min), MS m/z 690(M++1).

Example 35

Compound 3

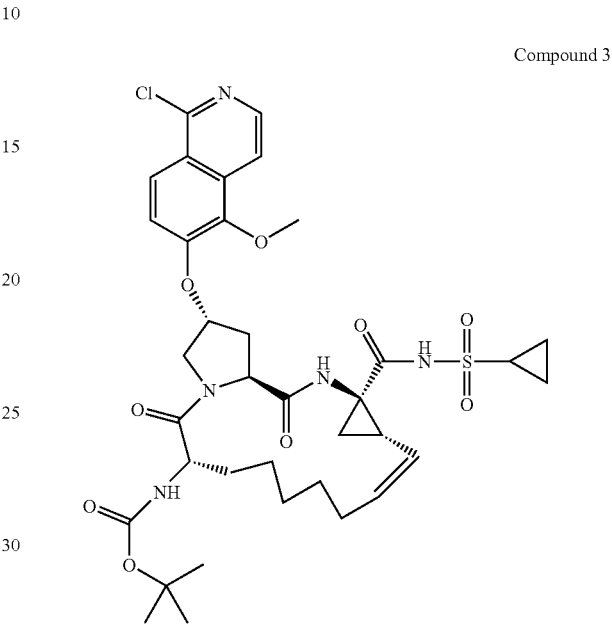

Preparation of Compound 3

To a mixture of (4-cyclopropanesulfonylaminocarbonyl-18-hydroxy-2,15-dioxo-3,16-diaza-tricyclo[14.3.0.04,6] nonadec-7-en-14-yl)carbamic acid tert-butyl ester (20 mg, 0.035 mmol; prepared in Ex. 26, step 5) in DMF (2 mL) was added t-BuOK (20 mg, 0.15 mmol) and 1-chloro-6-fluoro-5-methoxyisoquinoline (15 mg, 0.07 mmol). The reaction was stirred for 16 h at rt. The reaction mixture then was partitioned between ether (10 mL) and water (5 mL). The aqueous phase was acidified to pH 4 using 1 N HCl. The resulting solution was extracted with EtOAc (3×20 mL). The combined EtOAc extracts were dried (MgSO4), filtered, and concentrated in vacuo to give a white solid. This crude product was purified by preparative HPLC (YMC Xterra, S5, 19×50 mm, 60% to 100% B, gradient 15 min, hold 2 min, flow rate 25 mL/min) to give 10 mg (38%) of the compound 3 as a white powder: LC-MS (YMC Xterra S7 column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nm. Solvent A: 10% MeOH/90% H2O/0.1% TFA. Solvent B: 10% H2O/90% MeOH/0.1% TFA.)(Retention time: 2.53 min), MS m/z 760 (M++1). $^1$H NMR (500 MHz, CDCl$_3$) δ ppm 0.89-0.97 (m, 1 H), 1.04-1.16 (m, 3 H), 1.20-1.51 (m, 7 H), 1.30 (s, 9 H), 1.54-1.64 (m, 1 H), 1.73-1.96 (m, 3 H), 2.22-2.31 (m, 1 H), 2.47-2.57 (m, 1 H), 2.60-2.67 (m, 2 H), 2.86-2.94 (m, 1 H), 3.97 (s, 3 H), 3.99-4.10 (m, 1 H), 4.31 (t, J=7.63 Hz, 1 H), 4.45 (d, J=11.29 Hz, 1 H), 4.65 (t, J=7.48 Hz, 1 H), 4.97 (t, J=9.46 Hz, 1 H), 5.16 (d, J=7.93 Hz, 1 H), 5.32 (s, 1 H), 5.71 (q, J=8.95 Hz, 1 H), 6.84 (s, 1 H), 7.10 (s, 1 H), 7.53 (d, J=5.80 Hz, 1 H), 7.55 (s, 1 H), 8.22 (d, J=5.49 Hz, 1 H), 10.18 (s, 1 H).

Example 36

Compound 4

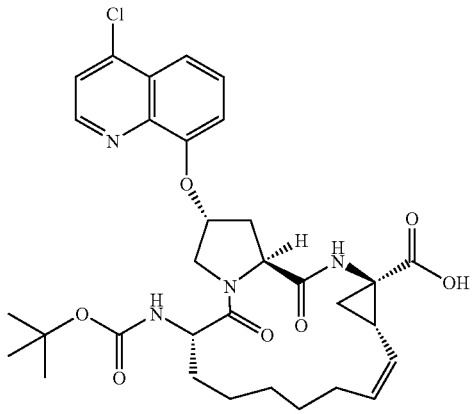

Preparation of Compound 4

To a suspension of 49 mg (0.105 mmol) of (1S,4R,6S,14S, 18R)-7-cis-14-tert-butoxycarbonylamino-18-hydroxy-2,15-dioxo-3,16-diazatricyclo[14.3.0.04,6]nonadec-7-ene-4-carboxylic acid (prepared in Ex. 25, step 4) and 26 mg (0.106 mmol) of LaCl3 in 1.0 mL of DMF cooled to −78° C. was added 0.53 mL (0.53 mmol) of 1M KOtBu in THF, followed by the addition of 4-chloro-8-fluoroquinoline (19 mg, 0.105 mmol). The mixture was stirred for an hour and warmed to rt. Analytical reversed phase HPLC (Method G) showed no starting material but two new products consistent with the displacement at the 4-Cl (MS m/z, [M++1]=611, retention time 2.78 min, major component), and at the 8-F (MS m/z, [M++1]=627, retention time 3.20 min, minor component) of the quinoline ring. It was quenched with a half-saturated NH4Cl aq. solution and organic residues extracted into EtOAc (10 mL×3). The combined EtOAc extracts were dried (MgSO4), concentrated in vacuo and dissolved in 2 mL of MeOH. This solution was separated by preparative HPLC using the following conditions: Column Xterra 30×100 mm S5, 30% to 100% Solvent B/A for 14 min gradient, hold time 5 min; where Solvent A is 10% MeOH/90% H2O with 0.1% TFA, Solvent B is 90% Me0H/10% H2O with 0.1% TFA and flow rate is 40 mL/min). The major component was not recovered from the preparative HPLC while the minor component, (1S,4R,6S,14S,18R)-7-cis-14-tert-butoxycarbonylamino-18-(4-chloroquinolin-8-yloxy)-2,15-dioxo-3,16-diazatricyclo[14.3.0.04,6]nona-dec-7-ene-4-carboxylic acid, was collected and concentrated into a white foam (1.9 mg, 3%). $^1$H NMR (400 MHz, CD$_3$OD) δ 1.02 (s, 9 H), 1.18-1.47 (m, 6 H), 1.48-1.77 (m, 3 H), 1.93 (m, 1 H), 2.22-2.34 (m, 2 H), 2.44 (m, 1 H), 2.56-2.64 (m, 1 H), 2.70-2.78 (m, 1 H), 4.02 (m, 1 H), 4.14 (m, 1 H), 4.54 (m, 1 H), 5.38 (m, 1 H), 5.52-5.62 (m, 2 H), 7.6 (d, J=9 Hz, 1 H), 7.86 (t, J=8 Hz, 1 H), 7.94-8.03 (m, 2 H), 8.9 (d, J=8 Hz, 1 H). LC-MS m/z 627 [M++1].

Analytical LCMS conditions: 3×50 mm YMC Xterra, gradient 3 min, flow 4 mL/min.

Example 37

Compound 5

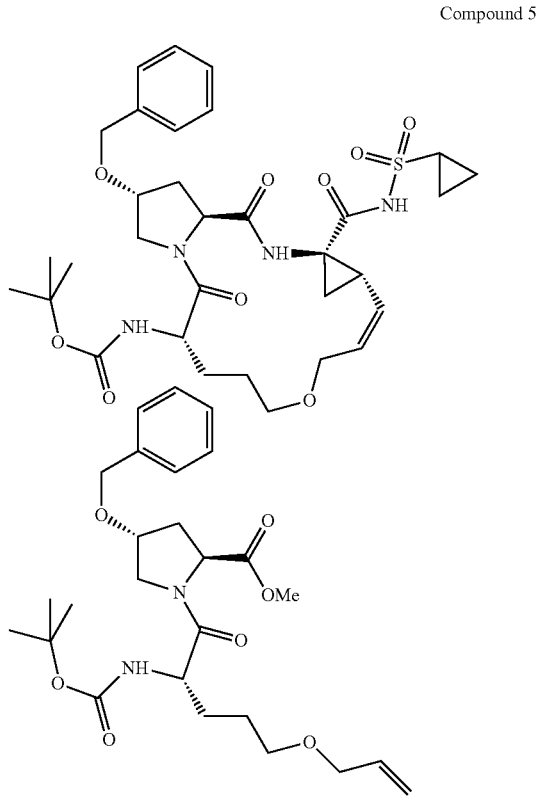

Step 1: Prepared 1-(2(S)-tert-butoxycarbonylamino-non-8-enoyl)-4(R)-benzyloxy-pyrrolidine-2(S)-carboxylic acid, methyl ester by way of example 25, step 1 using 5-Allyloxy-2(S)-(tert-butoxycarbonylamino)pentanoic acid (2.77 g, 10.1 mmol; prepared in Ex. 29, step 5) and methyl 4(R)-benzyloxy-pyrrolidine-2(S)-carboxylate hydrochloride (2.50 g, 9.22 mmol) to give 1-(2(S)-tert-butoxycarbonylamino-non-8-enoyl)-4(R)-benzyloxy-pyrrolidine-2(S)-carboxylic acid methyl ester as a colorless oil, 4.53 g (100%), MS 491 (ES+, M+H+).

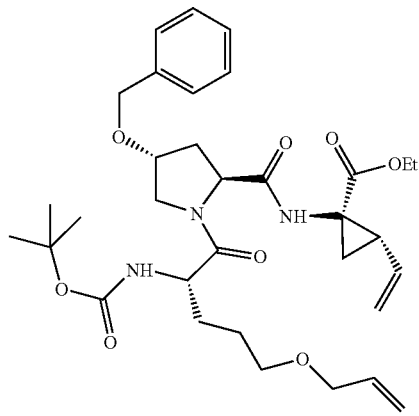

Step 2: Prepared 1-{[1-(2(S)-tert-Butoxycarbonylamino-non-8-enoyl)-4(R)-benzyloxypyrrolidine-2(S)carbonyl]-(1R)-amino}-2(S)-vinyl-cyclopropanecarboxylic acid ethyl by way of example 25, step 2 using 1-(2(S)-tert-butoxycarbonylamino-non-8-enoyl)-4(R)-benzyloxy-pyrrolidine-2(S)-carboxylic acid methyl ester (2.78 g 5.80 mmol), saponifying and then coupling with (1R,2S)-1-amino-2-vinylcyclopropane carboxylic acid ethyl ester hydrochloride (0.989 g, 6.38 mmol) to give 1-{[1-(2(S)-tert-Butoxycarbonylamino-non-8-enoyl)-4(R)-benzyloxypyrrolidine-2(S)carbonyl]-(1R)-amino}-2(S)-vinyl-cyclopropanecarboxylic acid ethyl ester as a light yellow thick oil, 3.21 g (90%), MS 614 (M+1).

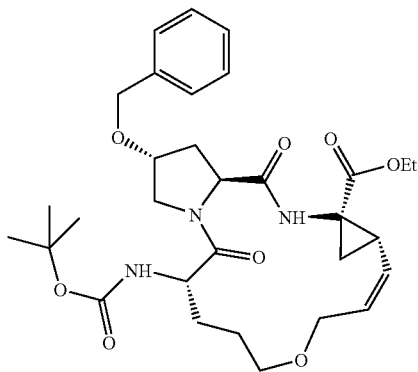

Step 3: Prepared (1S,4R,6S,14S,18R, 7-cis)-14-tert-butoxycarbonylamino-18-benzyloxy-2,15-dioxo-3,16-diazatricyclo[14.3.0.04,6]-nonadec-7-ene-4-carboxylic acid, ethyl ester by way of example 25, step 3 using 1-{[1-(2(S)-tert-butoxycarbonylamino-non-8-enoyl)-4(R)-benzyloxy-pyrrolidine-2(S)carbonyl]-(R)-amino}-2(S)-vinyl-cyclopropanecarboxylic acid ethyl ester (2.71 g, 4.42 mmol) to give (1S,4R,6S,14S,18R, 7-cis)-14-tert-butoxycarbonylamino-18-benzyloxy-2,15-dioxo-3,16-diazatricyclo[14.3.0.04,6]-nonadec-7-ene-4-carboxylic acid ethyl ester as a tan foam, 1.44 g (56%), MS 586 (ES+, M+H+).

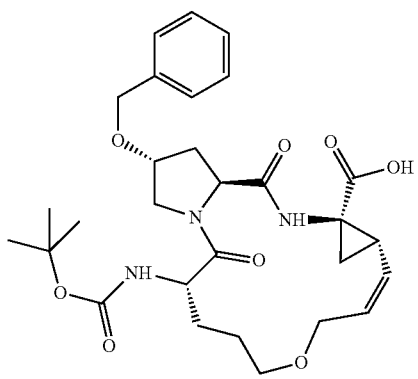 [SMILES: CC(C)(C)OC(=O)N[C@H]1CCCOC/C=C\[C@@H]2C[C@@]2(C(=O)O)NC(=O)[C@@H]2C[C@@H](OCc3ccccc3)CN2C1=O]

Step 4: Prepared (1S,4R,6S,14S,18R, 7-cis)-14-tert-butoxycarbonylamino-18-benzyloxy-2,15-dioxo-3,16-diazatricyclo[14.3.0.04,6]-nonadec-7-ene-4-carboxylic acid by way of example 25, step 4 using (1S,4R,6S,14S,18R, 7-cis)-14-tert-butoxycarbonylamino-18-benzyloxy-2,15-dioxo-3,16-diazatricyclo[14.3.0.04,6]-nonadec-7-ene-4-carboxylic acid ethyl ester (1.30 g, 2.22 mmol) to give (1S,4R,6S,14S,18R, 7-cis)-14-tert-butoxycarbonylamino-18-benzyloxy-2,15-dioxo-3,16-diazatricyclo[14.3.0.04,6]-nonadec-7-ene-4-carboxylic acid as a white powder, 0.862 g (70%), MS 558 (ES+, M+1).

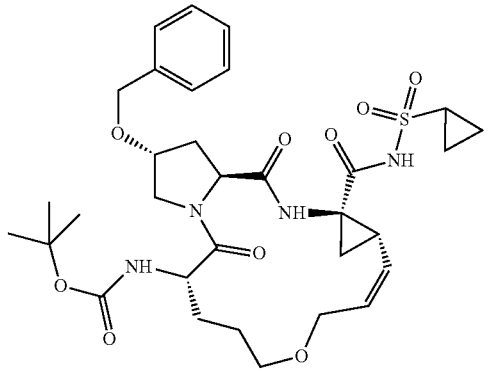 [SMILES: CC(C)(C)OC(=O)N[C@H]1CCCOC/C=C\[C@@H]2C[C@@]2(C(=O)NS(=O)(=O)C2CC2)NC(=O)[C@@H]2C[C@@H](OCc3ccccc3)CN2C1=O]

Step 5: Prepared (1S,4R,6S,14S,18R, 7-cis)-18-benzyloxy-14-tert-butoxycarbonylamino-4-cyclopropanesulfonylaminocarbonyl-2,15-dioxo-3,16-diaza-10-oxatricyclo[14.3.0.04,6]nonadec-7-ene by way of example 26, step 4 using (1S,4R,6S,14S,18R, 7-cis)-14-tert-butoxycarbonylamino-18-benzyloxy-2,15-dioxo-3,16-diazatricyclo[14.3.0.04,6]-nonadec-7-ene-4-carboxylic acid (860 mg, 1.51 mmol) and cyclopropylsulfonamide (365 mg, 3.02 mmol) to give (1S,4R,6S,14S,18R, 7-cis)-18-benzyloxy-14-tert-butoxycarbonylamino-4-cyclopropanesulfonylaminocarbonyl-2,15-dioxo-3,16-diaza-10-oxatricyclo[14.3.0.04,6]nonadec-7-ene as a white powder, 603 mg (61%). MS 660 (ES+, M+H+), HRMS cal. 661.2907 found 661.2903, mp 147-149° C., $^1$H NMR (300 MHz, CDCl$_3$) δ 0.83-0.95 (m, 3 H), 1.01-1.16 (m, 3 H), 1.21-1.27 (m, 2 H), 1.38 (s, 9 H), 1.42-1.52 (m, 2 H), 1.87-1.93 (m, 1 H), 1.97-2.04 (m, 1 H), 2.30-2.36 (m, 1 H), 2.59-2.68 (q, J=9 Hz 1 H), 2.82-2.91 (m, 1 H), 3.57-3.62 (dd, J=9 Hz & 3 Hz, 1 H), 3.69-3.74 (dd, J=9 Hz & 6 Hz, 1 H), 4.19-4.23 (d, J=12 Hz, 1 H), 4.31-4.39 (m, 2 H), 4.43-4.58 (m, 2 H), 5.18-5.25 (t, J=9 Hz, 2 H), 5.68-5.76 (m, 1H), 6.73 (s, 1 H), 7.25-7.31 (m, 5H), 10.00 (s, 1 H).

Example 38

Compound 6

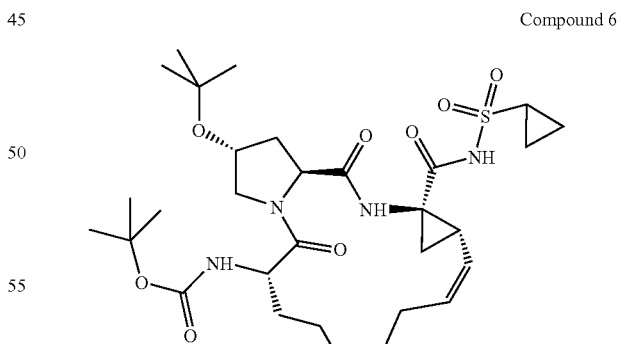

Preparation of Compound 6

Prepared (1S,4R,6S,14S,18R, 7-cis)-18-tert-butoxy-14-tert-butoxycarbonylamino-4-cyclopropanesulfonylaminocarbonyl-2,15-dioxo-3,16-diaza-10-oxatricyclo[14.3.0.04,6]nonadec-7-ene from methyl 4(R)-tert-butoxypyrrolidine-2(S)-carboxylate hydrochloride employing the procedures of example 37, steps 1-5; MS 627 (ES+, M+H+), HRMS cal. 627.3064, found 627.3073, $^1$H-NMR (500 MHz, CD$_3$OD) δ 5.77-5.72 (m, 1H), 5.43-5.39 (m, 1H), 4.58 (br s, 1H), 4.54-4.49 (m, 2H), 4.33 (m, 1H), 3.94 (m, 1H), 3.83 (m, 1H), 3.74 (m, 1H), 3.57-3.48 (m, 2H), 2.93 (m, 1H), 2.63 (m, 1H), 2.25 (m, 1H), 2.15 (m, 1H), 1.99 (m, 1H), 1.76 (m, 2H), 1.70-1.67 (m, 1H), 1.58 (m, 2H), 1.44 (s, 9H), 1.29 (m, 1H), 1.25 (s, 9H), 1.15-1.09 (m, 2H), 1.04 (m, 1H).

Example 39 through Example 86 describe the preparation of intermediates. These intermediates can be used to make compounds of Formula I by using the teachings described, or referenced, in this document.

Example 39

Preparation of Intermediate 39;

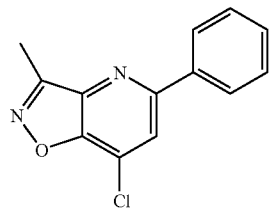

Intermediate 39

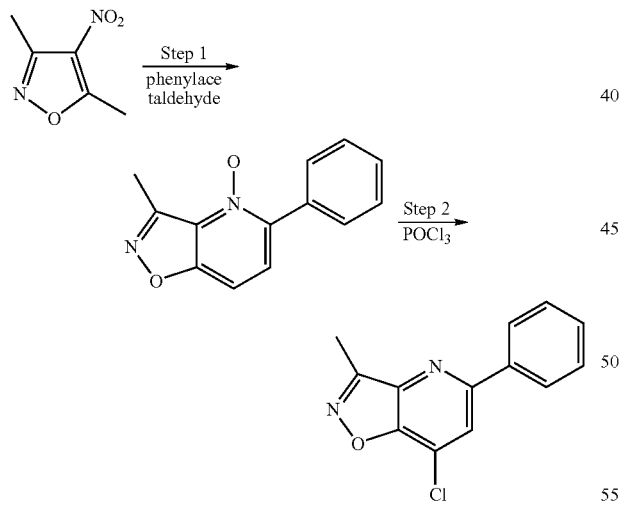

Scheme 1

Step 1: A mixture of 3,5-dimethyl-4-nitro-isoxazole (1.42 g, 10.0 mmol), phenylacetaldehyde (1.32 g, 11.0 mmol) in piperidine (1 mL) and ethanol (10 mL) was heated to reflux for 16 h. After cooling down to the ambient temperature, the product precipitated out was collected by filtration. The cake was washed with cold ethanol thoroughly to afford 1.20 g (53%) of the desired product as a white solid. $^1$H NMR (CDCl$_3$) δ 2.87 (s, 3H), 7.46-7.50 (m, 3H), 7.56 (d, J=8.5 Hz, 1H), 7.7-7.80 (m, 2H); MS m/z 227 (M++H).

Step 2: A solution of 3-methyl-5-phenyl-isoxazolo[4,5-b]pyridine 4-oxide (1.00 g, 4.40 mmol) and POCl3 (2.71 g, 17.7 mmol) in chloroform (10 mL) was heated to reflux for 1 h. After cooling down to the ambient temperature, the final solution was diluted with chloroform (50 mL) and washed with NaHCO3 (aq.) (two 50 mL portions) and brine, dried over MgSO4, filtered, evaporated. The residue was purified by flash chromatography (4:1 hexane-EtOAc) to afford 790 mg (73%) of the desired product as a white solid.

$^1$H NMR (CDCl$_3$) δ 2.72 (s, 3H), 7.46-7.54 (m, 3H), 7.91 (s, 1H), 8.00-8.03 (m, 2H);

MS m/z 245, 247 (M++H).

Intermediate 39 can be used to make compounds of Formula I as follows:

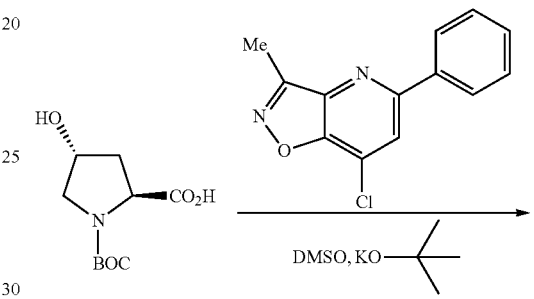

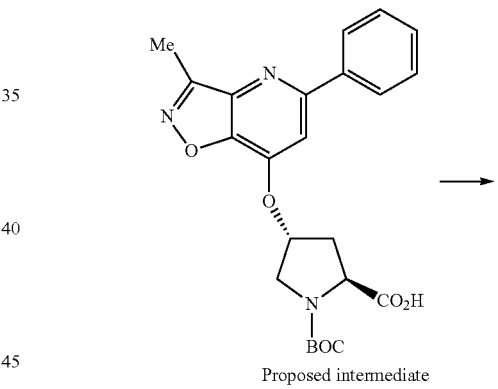

Proposed intermediate

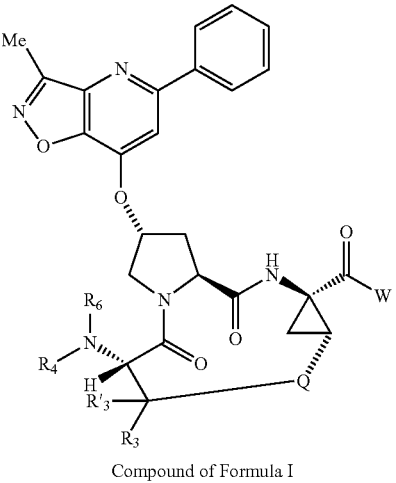

Compound of Formula I

Example 40

Preparation of Intermediate 40

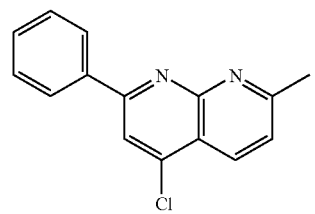

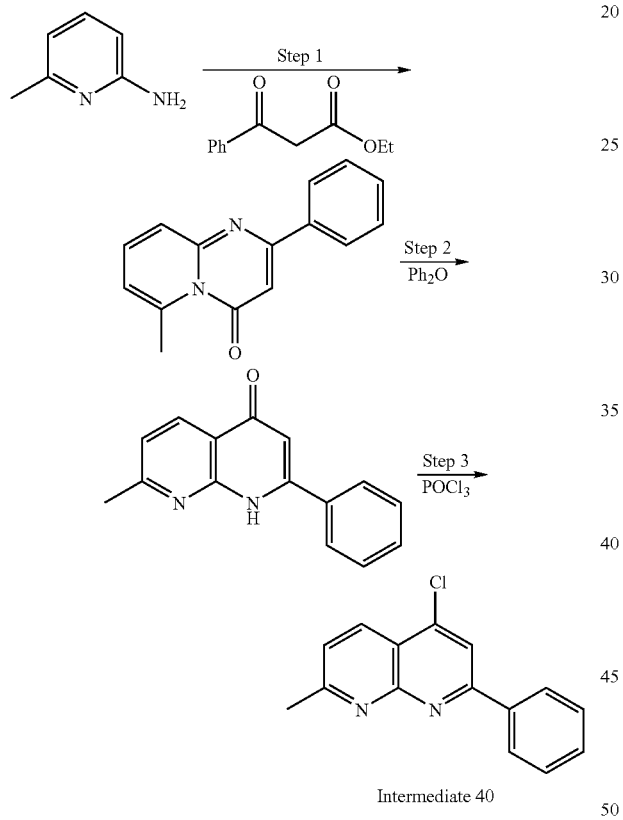

Step 1: A mixture of 2-amino-6-methylpyridine (1.08 g, 10.0 mmol), ethyl benzoylacetate (2.30 g, 12.0 mmol) and polyphosphoric acid (6.00 g, 61.2 mmol) was heated to 1100C. for 5 h. After cooling to the ambient temperature, the mixture was poured into iced water (20 mL) and neutralized to pH 7 with 10 M NaOH. Extracted with CHCl3. The organic layer was washed with brine, dried over MgSO4, filtered, evaporated. The residue was purified by flash chromatography (1:1 hexane-EtOAc) to afford 510 mg (22%) of the desired product as a pale yellow solid. $^1$H NMR (CDCl$_3$) δ 3.08 (s, 3H), 6.64 (d, J=7.0 Hz, 1H), 6.71 (s, 1H), 7.42-7.52 (m, 5H), 8.04-8.06 (m, 2H); MS m/z 237 (M++H).

Step 2: A solution of 6-methyl-2-phenyl-pyrido[1,2a]pyrimidin-4-one (489 mg, 2.07 mmol) in melted diphenyl ether (5 mL) was heated to gentle reflux for 5 h. After cooling to the ambient temperature, the formed suspension was diluted with diethyl ether (10 mL), filtered. The cake was washed with diethyl ether thoroughly to afford 450 mg (92%) of the desired product as a brownish solid. MS m/z 237 (M++H).

Step 3: A suspension of 7-methyl-2-phenyl-1H-[1,8]naphthyridin-4-one (450 mg, 1.91 mmol) in POCl3 (10 mL) was heated to gentle reflux for 3 h. then evaporated in vacuo. The residue was poured into iced water (20 mL) and neutralized to pH 10 with 10 M NaOH. The mixture was then extracted with CHCl3 and the organic layer was washed with brine, dried over MgSO4, filtered and evaporated. The residue was purified by flash chromatography (2:1 hexane-EtOAc) to afford 450 mg (92%) of the desired product as a pink solid. $^1$H NMR (CD$_3$OD) δ 2.80 (s, 3H), 7.54-7.56 (m, 3H), 7.61 (d, J=8.4 Hz, 1H), 8.25-8.30 (m, 3H), 8.58 (d, J=8.4 Hz, 1H); MS m/z 255, 257 (M++H). Intermediate 40 can be used to make of Formula I as follows:

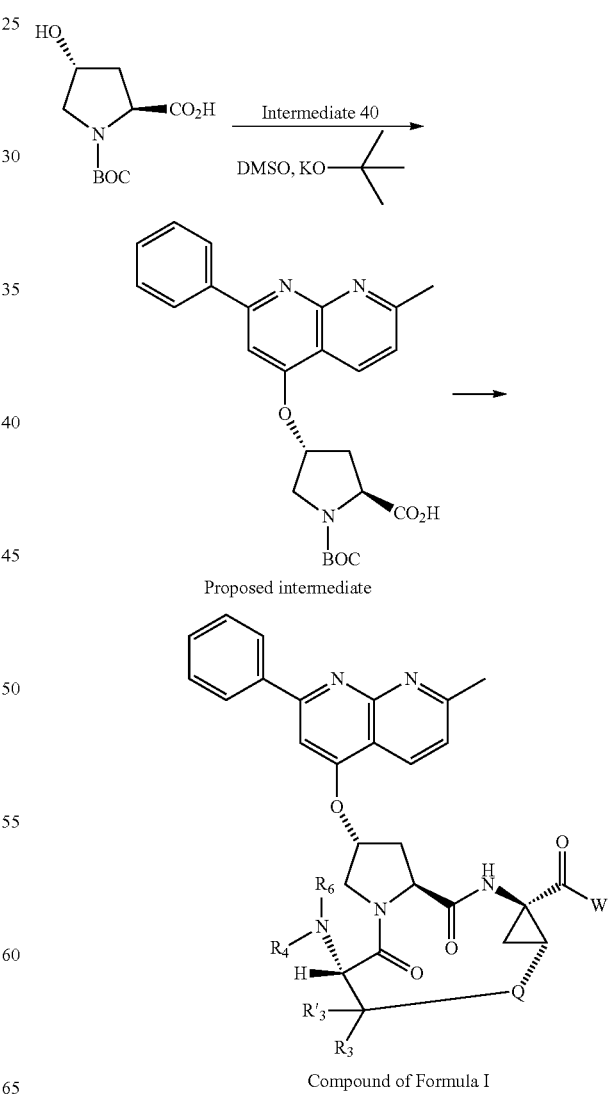

Example 41

Preparation of Intermediate 41

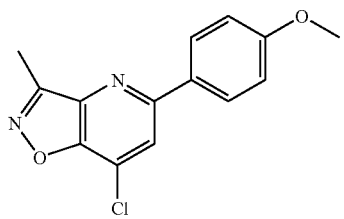

Intermediate 41

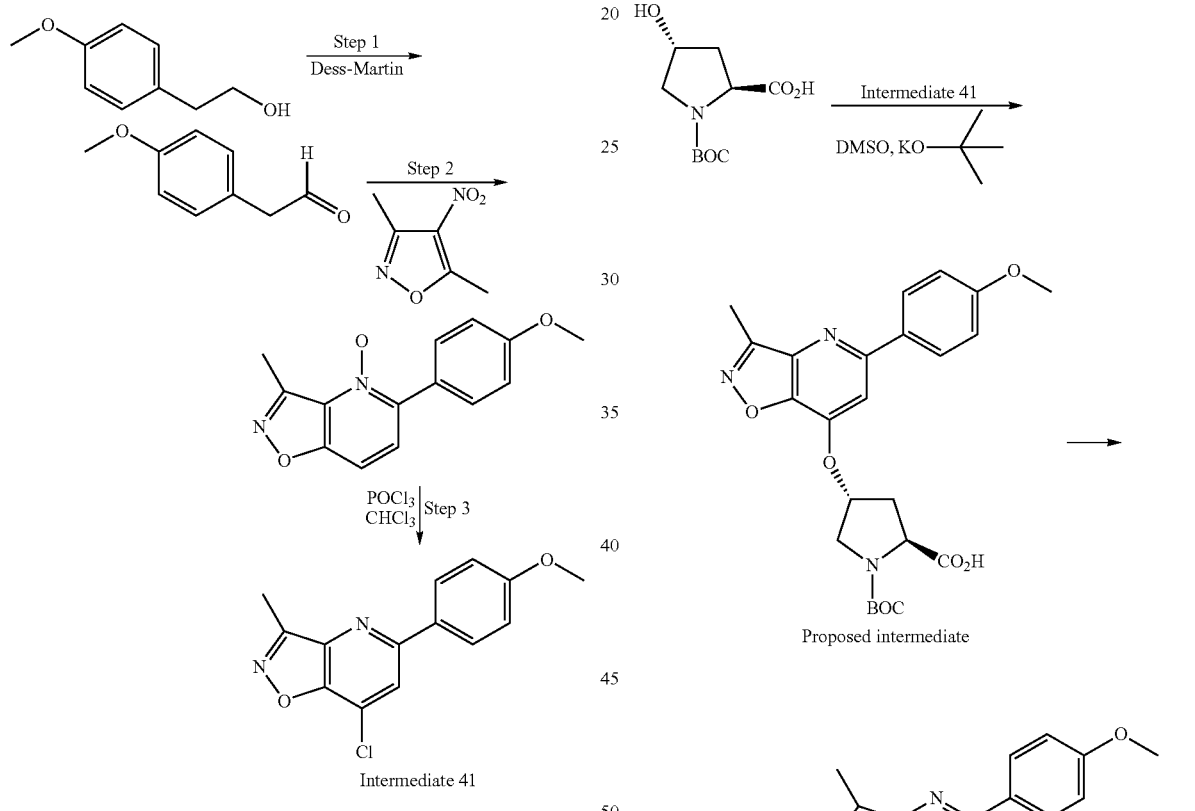

Scheme 1

Proposed intermediate

Step 1: To a solution of 4-methoxyphenethyl alcohol (1.52 g, 10.0 mmol) in $CH_2Cl_2$ (50 mL) at 0° C. was added Dess-Martin reagent (4.45 g, 10.5 mmol) in one portion. The formed mixture was allowed to warm to the ambient temperature for 1 h. Washed with sat. Na2S2O3 (aq) and 1M NaOH, brine respectively. Dried over MgSO4, evaporated in vacuo to give 1.50 g (100%) of the desired aldehyde as a viscous oil. This product was used as crude without any further purification.

Step 2: A solution of 3,5-dimethyl-4-nitro-isoxazole (142 mg, 1.0 mmol), 4-methoxy-phenylacetaldehyde from Example 3, Step 1 (180 mg, 1.1 mmol) in piperidine (0.1 mL) and ethanol (2 mL) was heated to reflux for 12 h. After cooling down to the ambient temperature, the product precipitated out was collected by filtration. The cake was washed with cold ethanol thoroughly to afford 130 mg (51%) of the desired product as a grayish solid.

$^1$H NMR (CDCl$_3$) δ 2.88 (s, 3H), 3.87 (s, 3H), 7.02 (d, J=8.5 Hz, 2H), 7.50 (d, J=9.0 Hz, 1H), 7.57 (d, J=9.0 Hz, 1H), 7.81 (d, J=8.5 Hz, 2H); MS m/z 257 (M++H). Step 3: This product was prepared by the same procedure as described in Example 39, Step 2. $^1$H NMR (CDCl$_3$) δ 2.70 (s, 3H), 3.87 (s, 3H), 7.00-7.03 (m, 2H), 7.84 (s, 1H), 7.96-7.98 (m, 2H); MS m/z 275, 277 (M++H).

Intermediate 41 can be used to make compounds of Formula I as follows:

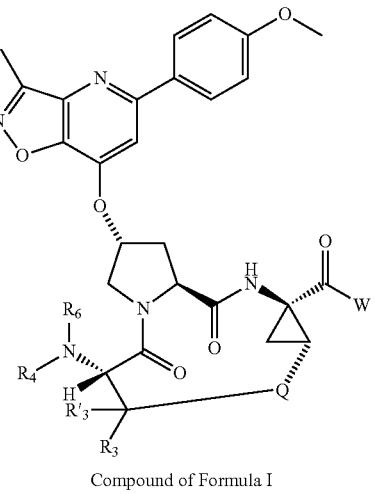

Compound of Formula I

Example 42

Preparation of Intermediate 42

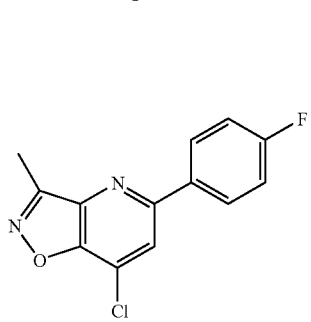

Intermediate 42

Scheme 1

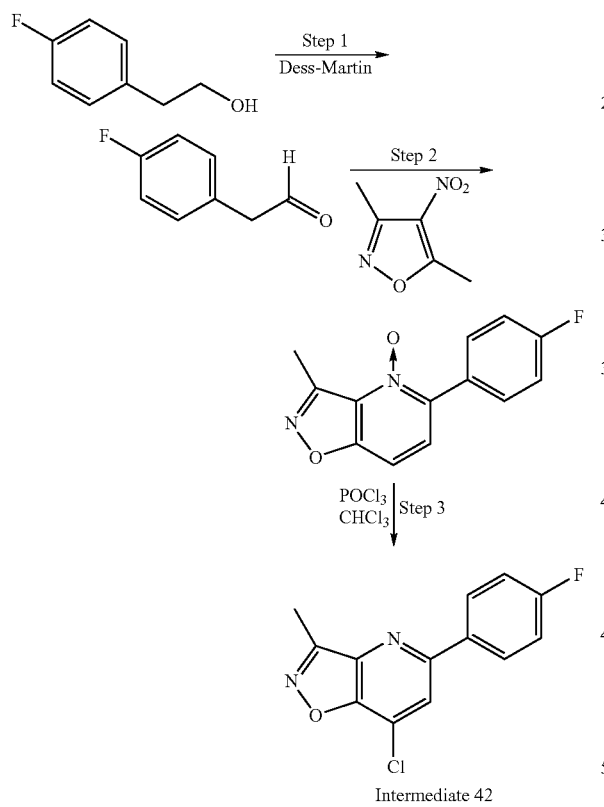

Step 1 & 2:

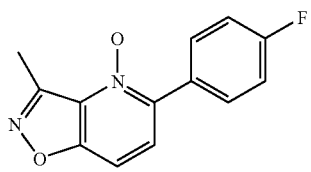

This product was prepared by the same procedure as described in Example 41, Step 1 & 2, except using 4-fluorophenethyl alcohol instead. MS m/z 245 (M++H).

Step 3:

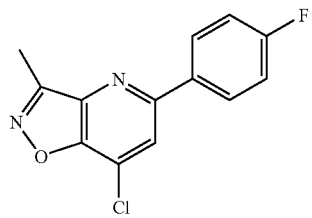 [SMILES: Cc1noc2c(Cl)cc(-c3ccc(F)cc3)nc12]

This product was prepared by the same procedure as described in step 2 of Example 39.

$^1$H NMR (CDCl3) δ 2.71 (s, 3H), 7.17-7.20 (m, 2H), 7.86 (s, 1H), 8.00-8.02 (m, 2H);

MS m/z 263, 265 (M++H).

Intermediate 42 can be used to make compounds of Formula I as follows:

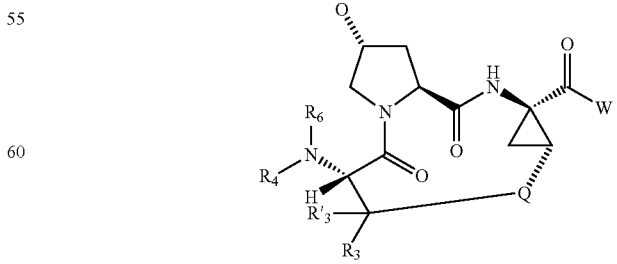

Compound of Formula I

Example 43

Preparation of Intermediate 43

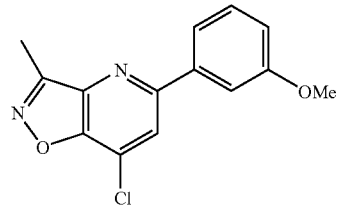

Intermediate 43

Scheme 1

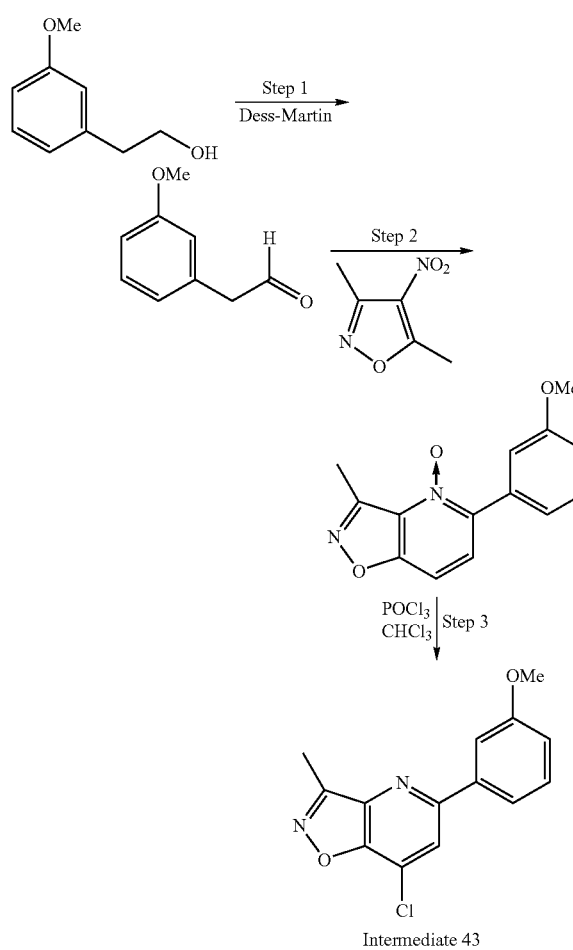

Step 1& 2:

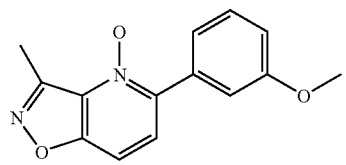

This product was prepared by the same procedure as described in Example 41, Step 1 & 2, except using 3-methoxyphenethyl alcohol as starting material. MS m/z 257 (M++H).

Step 3:

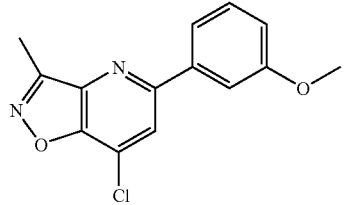 [SMILES: COc1cccc(-c2cc(Cl)c3onc(C)c3n2)c1]

This product was prepared by the same procedure as described in Example 39 step 2. $^1$H NMR (CDCl$_3$) δ 2.72 (s, 3H), 3.90 (s, 3H), 7.00-7.02 (m, 1H), 7.41 (t, J=8.0 Hz, 1H), 7.55 (d, J=7.5 Hz, 1H), 7.59 (d, J=2.0 Hz, 1H), 7.89 (s, 1H); MS m/z 275, 277 (M++H).

Intermediate 43 can be used to make compounds of Formula I as follows:

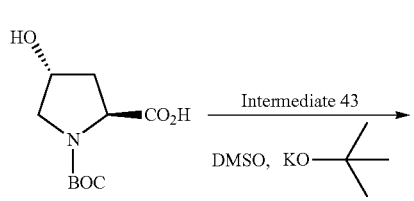

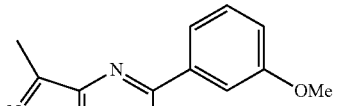

Proposed intermediate

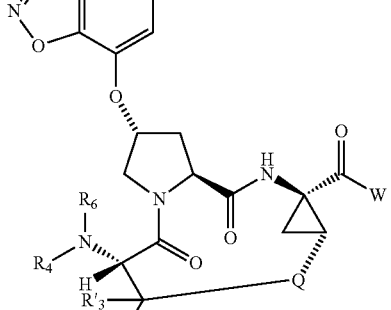

Compound of Formula I

Example 44

Preparation of Intermediate 44

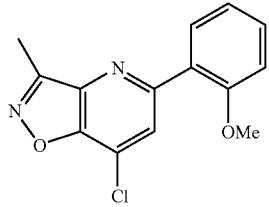

Intermediate 44

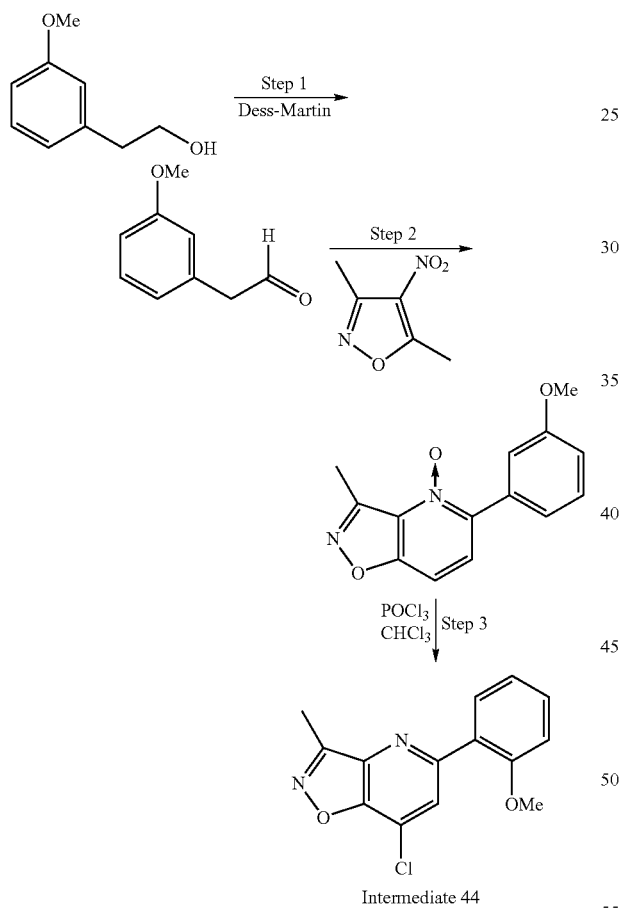

This product was prepared by the same procedure as described in Example 41, Step 1&2, except using 2-methoxyphenethyl alcohol as starting material. MS m/z 257 (M++H).

Step 3:

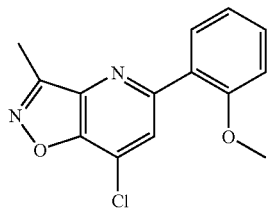

This product was prepared by the same procedure as described in Example 39, Step 2.

$^1$H NMR (CDCl$_3$) δ 2.721 (s, 3H), 3.88 (s, 3H), 7.03 (d, J=8.0 Hz, 1H), 7.11 (t, J=7.5 Hz, 1H), 7.41-7.44 (m, 1H), 7.79-7.81 (m, 1H), 8.04 (s, 1H); MS m/z 275, 277 (M++H).

Intermediate 44 can be used to make compounds of Formula I as follows:

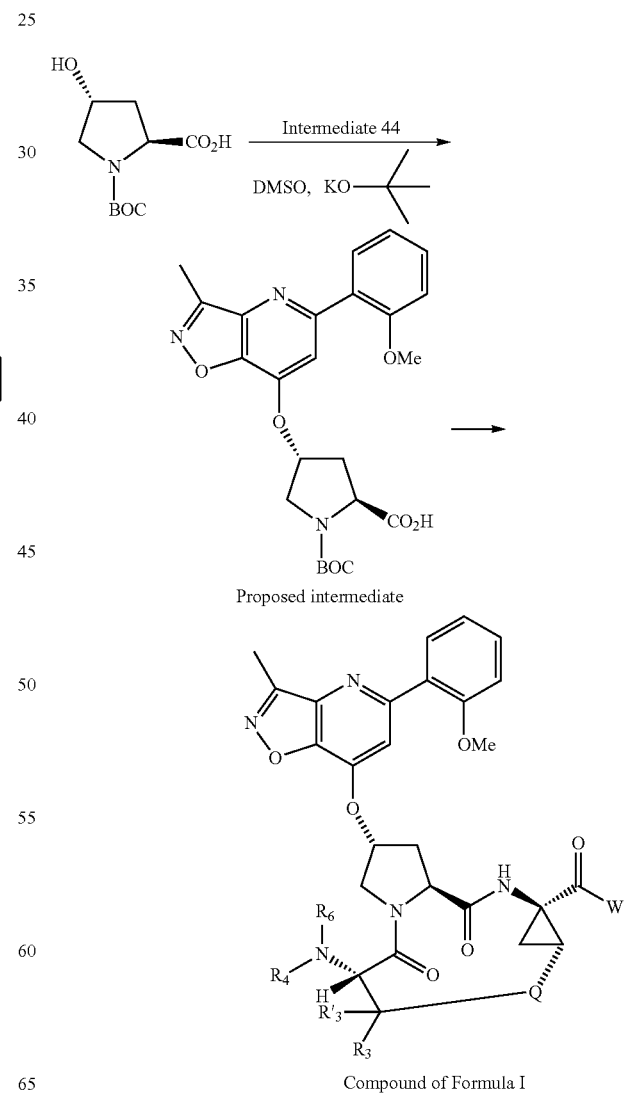

Step 1 & 2:

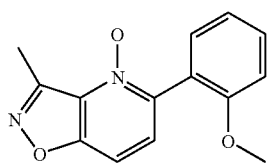

Example 45

Preparation of Intermediate 45

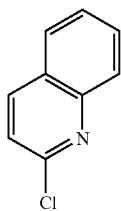

Intermediate 45

Intermediate 45 is commercially available

Intermediate 45 can be used to make compounds of Formula I as follows:

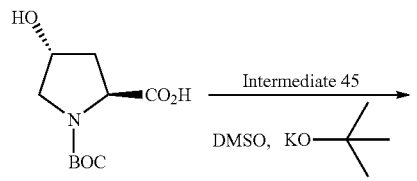

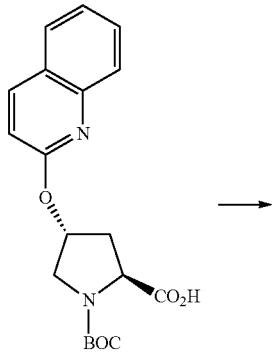

Proposed intermediate

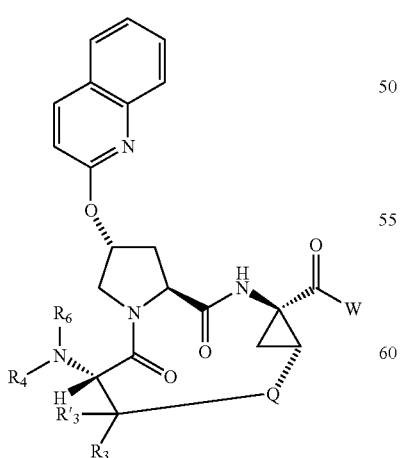

Compound of Formula I

Example 46

Preparation of Intermediate 46

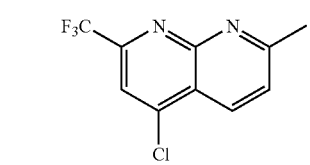

Intermediate 46

Intermediate 46 was prepared as described by P. Ferrarini et al, in J Heterocyclic Chem, 1983, p1053.

Intermediate 46 can be used to make compounds of Formula I as follows:

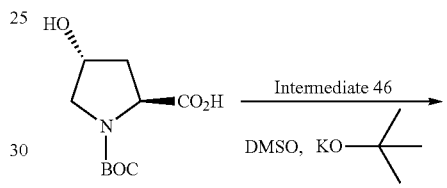

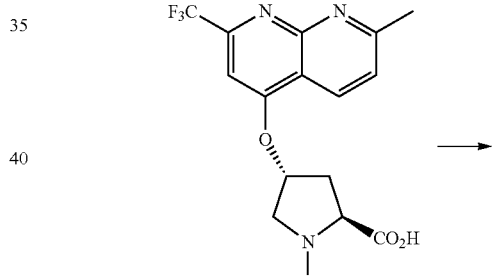

Proposed intermediate

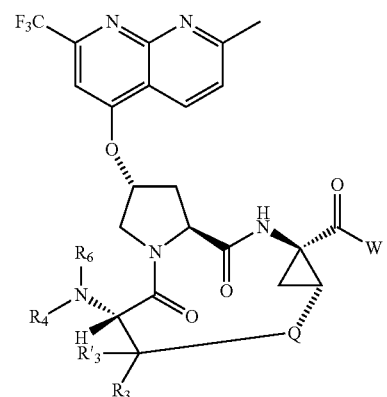

Compound of Formula I

Example 47
Preparation of Intermediate 47
Intermediate 47
Intermediate 47 was prepared as described by R. Nesi et al, Synth Comm. 1992, 22(16), 2349.
Intermediate 47 can be used to make compounds of Formula I as follows:
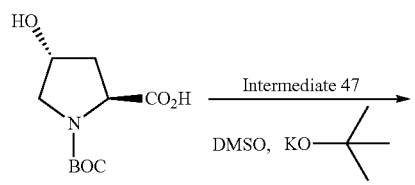
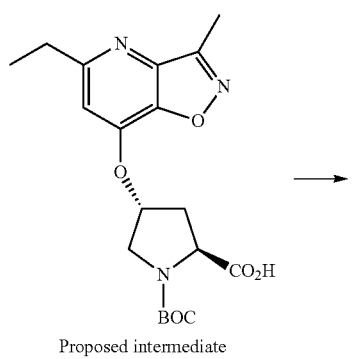
Proposed intermediate
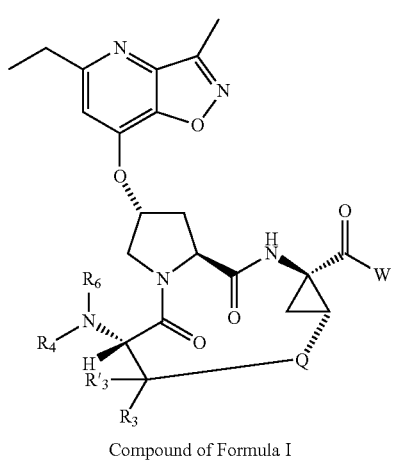
Compound of Formula I
Example 48
Preparation of Intermediate 48
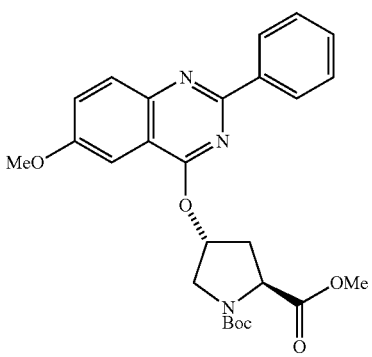
Intermediate 48
Scheme 1
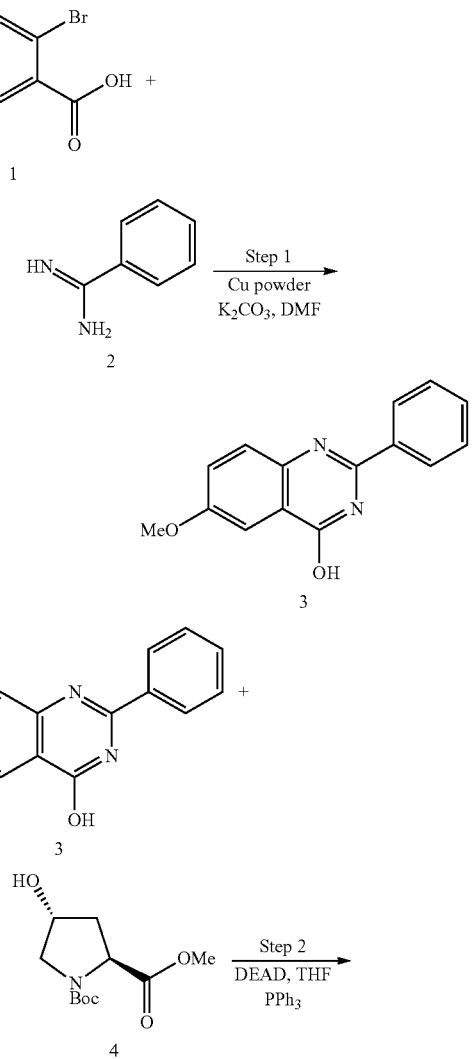

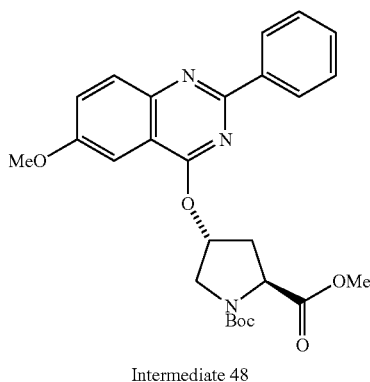

Intermediate 48

Step 1: To a solution of 2-bromo-5-methoxybenzoic acid (1.68 g, 7.27 mmol) in DMF (50 mL) in a medium pressure flask (Chemglass) was added benzamidine (1.25 g, 8.00 mmol), K2CO3 (6.0 g, 43.6 mmol), and copper powder (336 mg, 1.45 mmol). The reaction mixture was heated to 180° C. for 1 h. Copper and excess K2CO3 were removed by vacuum filtration and washed with MeOH. The filtrate was concentrated and the resulting crude was purified by flash column chromatography (SiO2, 5% MeOH in DCM) to give a light green solid (1.55 g, 84% yield): $^1$H NMR (DMSO-d6) δ 3.84 (s, 3H), 7.26 (d, J=7.8 Hz, 1H), 7.46 (br s, 5H), 7.57 (s, 1H), 8.38 (br s, 1 H); MS m/z (MH+) 253.

Step 2: To a 0° C. slurry of Boc-cis-Hydroxyproline-OMe (2.0 g, 8.15 mmol) and 3 (2.26 g, 8.97 mmol) in THF (82 mL) was added Ph3P and diisopropyl azocarboxylate (1.98 g, 8.97 mmol). After stirring at rt for 17 h, the reaction mixture was diluted with EtOAc (100 mL) and washed with H2O (50 mL). The aqueous layer was separated and back-extracted with EtOAc (2×50 mL). The combined organic layer was washed with brine, dried over MgSO4 and concentrated to give a viscous oil which was redissolved in minimal amount of EtOAc and hexanes was added to effect the precipitation of most of the Ph3PO by-product. Ph3PO was removed by vacuum filtration and the liquid filtrate was concentrated. The resulting viscous oil was purified by a flash column chromatography (SiO2, 4:1 hex:EtOAc) to give a white solid product (1.76 g, 45% yield): $^1$H NMR (60/40 rotamers, CDCl$_3$) δ 1.47 (s, 9H), 2.49-2.55 (m, 1H), 2.73-2.83 (m, 1H), 3.80 (s, 1.8H), 3.81 (s, 1.2H), 3.96 (s, 3H), 4.03-4.09 (m, 1H), 4.54 (t, J=8.0 Hz, 0.6H), 4.66 (t, J=7.8 Hz), 4.96-5.06 (m, 1H), 5.97 (br s, 0.6H), 6.04 (br s, 0.4H), 7.33 (dd, J=6.1, 2.7 Hz, 1H), 7.46-7.51 (m, 4H), 7.91 (d, J=9.2 Hz, 1H), 8.49 (t, J=8.5 Hz, 2H); $^{13}$C NMR (rotamers, CDCl$_3$) δ 21.7, 22.0, 28.3, 28.4, 35.8, 36.8, 52.3, 52.4, 52.6, 55.8, 55.9, 57.9, 58.3, 74.5, 74.9, 80.6, 101.2, 101.3, 115.7, 125.8, 126.0, 128.1, 128.5, 129.7, 130.2, 137.9, 147.8, 153.8, 157.7, 158.0, 158.0, 164.8, 173.1, 173.3; MS m/z (MH+) 480.

Intermediate 48 can be used to make compounds of Formula I as follows:

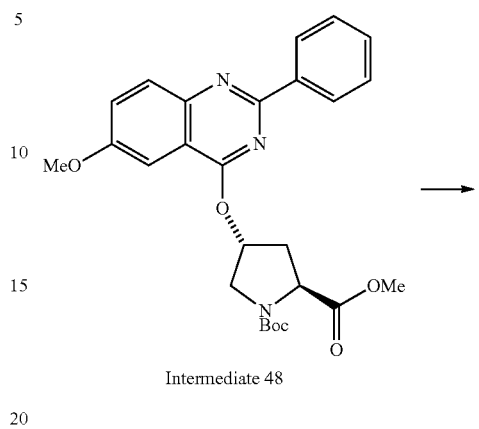

Intermediate 48

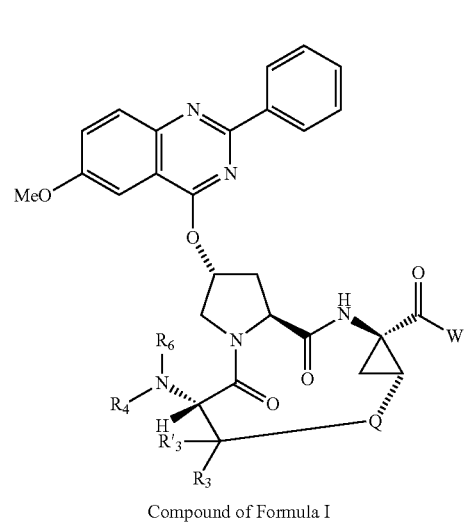

Compound of Formula I

Example 49

Preparation of Intermediate 49

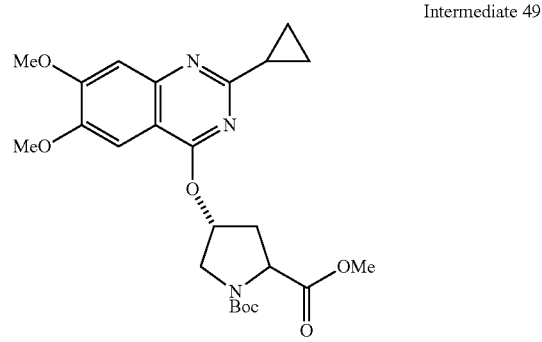 [SMILES: COC(=O)C1C[C@@H](Oc2nc(C3CC3)nc3cc(OC)c(OC)cc23)CN1C(=O)OC(C)(C)C]

Intermediate 49

Step 1:

As described for Example 48

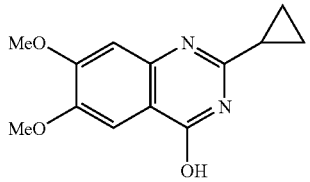 [SMILES: COc1cc2nc(C3CC3)nc(O)c2cc1OC]

Data: ¹H NMR (DMSO-d6) δ 0.97-1.01 (m, 2H), 1.03-1.06 (m, 2H), 1.90-1.94 (m, 1H), 3.84 (s, 3H), 3.87 (s, 3H), 6.93 (s, 1H), 7.37 (s, 3H), 12.28 (s, 1H); ¹³CNMR (DMSO-d6) δ 9.03, 13.17, 55.47, 55.73, 104.81, 107.27, 113.26, 145.16, 147.48, 154.44, 157.21, 160.89; MS m/z (MH+) 247.

Step 2:

As described for Example 48

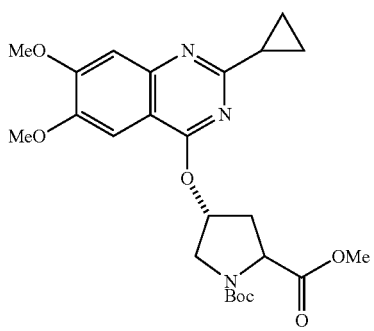 [SMILES: COC(=O)C1C[C@@H](Oc2nc(C3CC3)nc3cc(OC)c(OC)cc23)CN1C(=O)OC(C)(C)C]

Data: ¹H NMR (CDCl₃) δ 1.00-1.04 (m, 2H), 1.07-1.11 (m, 2H), 1.43 (s, 5.4H), 1.46 (s, 3.6H), 2.17-2.21 (m, 1H), 2.37-2.43 (m, 1H), 2.62-2.69 (m, 1H), 3.75 (s, 1.8H), 3.78 (s, 1.2H), 3.92 (d, J=2.8 Hz, 1H), 4.00 (s, 3.6H), 4.01 (s, 2.4H), 4.48 (t, J=8.0 Hz, 0.6H), 4.59 (t, J=7.6 Hz, 0.4H), 5.7 (br s, 0.6H), 5.74 (br s, 0.4H), 7.18 (s, 1H), 7.20 (s, 1H); ¹³C NMR (CDCl₃) δ 9.6, 9.7, 18.1, 28.3, 28.4, 35.8, 36.7, 52.2, 52.4, 56.3, 57.8, 58.2, 74.0, 74.5, 80.5, 80.6, 101.0, 101.1, 106.3, 108.6, 148.8, 149.1, 153.8, 155.4, 164.4, 165.9, 172.9, 173.2; LC-MS m/z (MH+) 474.

Intermediate 49 can be used to make compounds of Formula I as follows:

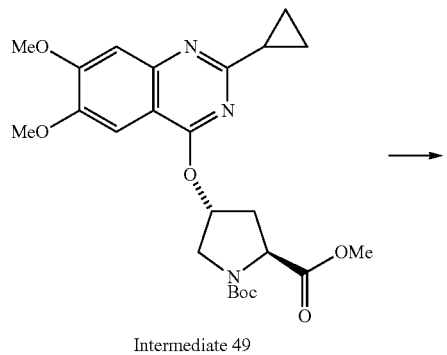

Intermediate 49

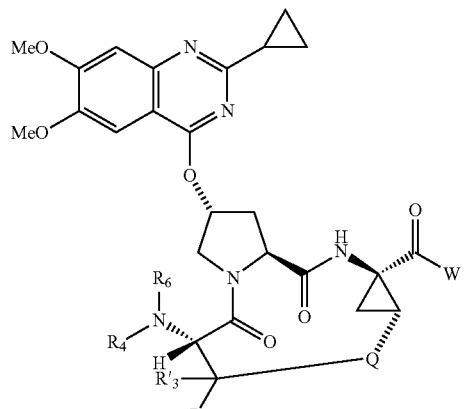

Compound of Formula I

Example 50

Preparation of Intermediate 50

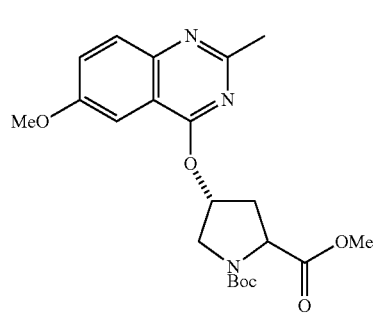

Intermediate 50

Step 1:

As described in Example 48 wherein acetamidine hydrochloride and 2-bromo-5-methoxybenzoic acid were utilized as starting materials.

Product:

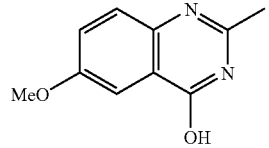

Data: ¹H NMR (DMSO) δ 2.31 (s, 3H), 3.85 (s, 3H), 7.36 (d, J=6.2 Hz, 1H), 7.37 (s, 1H), 7.51 (d, J=7.8 Hz, 1H), 12.15 (s, 1H); ¹³C NMR (DMSO) δ 21.11, 55.41, 105.57, 121.22, 123.59, 128.12, 143.34, 151.68, 157.00, 161.45; LC-MS m/e (MH+) 191.

Step 2: As described in Example 48.

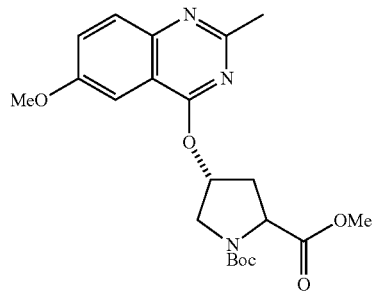
Intermediate 50

Data: $^1$H NMR (CDCl$_3$) δ 1.43 (s, 5.4H), 1.45 (s, 3.6H), 2.38-2.45 (m, 1H), 2.62-2.71 (m, 1H), 2.66 (s, 1.8H), 2.68 (s, 1.2H), 3.77 (1.8H), 3.79 (s, 1.2H), 3.92 (s, 3H), 3.93-3.98 (m, 2H), 4.49 (t, J=8.0 Hz, 0.6H), 4.61 (t, J=7.8 Hz, 0.4H), 5.82 (t, J=2.1 Hz, 0.6H), 5.89 (t, J=2.3 Hz, 0.4H), 7.26 (dd, J=4.7, 3.2 Hz, 1H), 7.42 (dd, J=6.3, 2.8 Hz, 1H), 7.75 (d, J=9.15 Hz, 1H); $^{13}$C NMR (CDCl$_3$) δ 26.1, 28.3, 28.4, 35.8, 36.7, 52.2, 52.2, 52.4, 52.5, 55.755.8, 57.9, 58.2, 74.1, 74.7, 80.6, 101.0, 101.2, 114.9, 125.6, 125.9, 128.6, 147.3, 153.8, 154.5, 157.6, 157.6, 161.2, 164.6, 173.0, 173.3; LC-MS m/e (MH$^+$) 418.

Intermediate 50 can be used to make compounds of Formula I as follows:

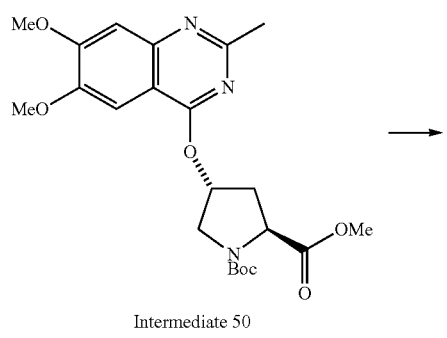
Intermediate 50

→

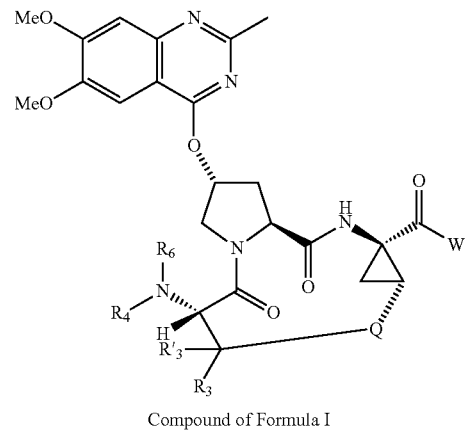
Compound of Formula I

Example 51

Preparation of Intermediate 51

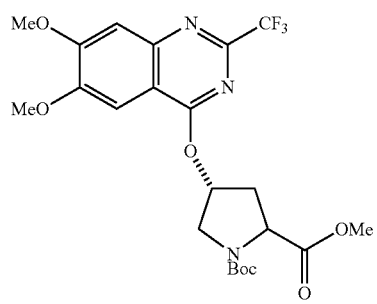
Intermediate 51

Step 1: Prepared as described in Example 48 and using 2-bromo-4,5-dimethoxybenzoic acid and trifluoroamidine as starting materials.

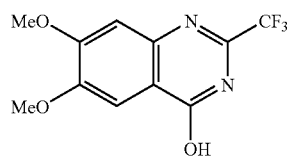 [SMILES: COc1cc2nc(C(F)(F)F)nc(O)c2cc1OC]

Data: $^1$H NMR (DMSO) δ 3.92 (s, 3H), 3.94 (s, 3H), 7.33 (s, 1H), 7.50 (s, 1H), 13.40 (br s, 1H); $^{13}$C NMR (DMSO) δ 55.8, 56.1, 104.9, 108.7, 150.2, 155.0; LC-MS m/e (MH+) 275.

Step 2: As described in Example 48.

Product:

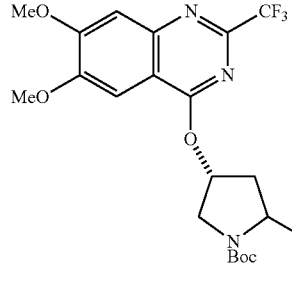
Intermediate 51

Data: $^1$H NMR (CDCl$_3$) δ 1.42 (s, 3.6H), 1.44 (s, 5.4H), 2.42-2.49 (m, 1H), 2.67-2.73 (m, 1H), 3.37 (s, 1.2H), 3.78 (s, 1.8H), 3.97 (t, J=6.5 Hz, 1H), 4.02 (s, 2.4H), 4.04 (s, 3.6H), 4.48 (t, J=7.9 Hz, 0.6H), 4.60 (t, J=7.7 Hz, 0.4H), 5.86 (br s, 0.6H), 5.90 (br s, 0.4H), 7.27-7.29 (m, 1H), 7.38-7.44 (m, 1H); $^{13}$C NMR (CDCl$_3$) δ 8.2, 28.3, 35.7, 36.7, 52.1, 52.2, 52.4, 56.5, 57.8, 58.2, 75.5, 76.0, 80.7, 100.8, 107.6, 111.0, 119.7, 148.2, 150.2, 151.4, 153.8, 154.5, 156.4, 165.1, 172.7, 173.0; LC-MS m/e (MH+) 502.

Intermediate 51 can be used to make compounds of Formula I as follows:

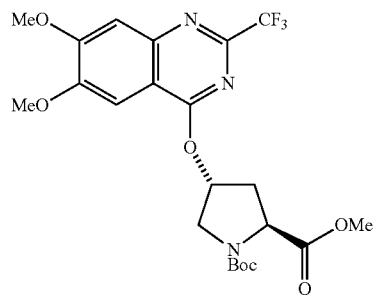

Intermediate 51

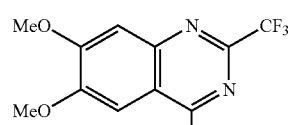

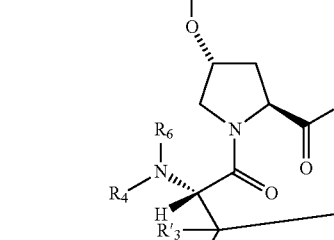

Compound of Formula I

Example 52

Preparation of Intermediate 52

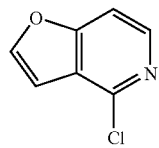

Intermediate 52

Intermediate 52 is commercially available and can be used to make compounds of Formula I.

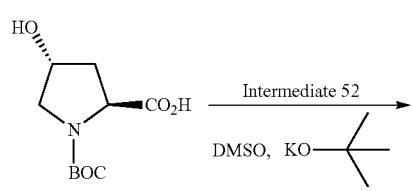

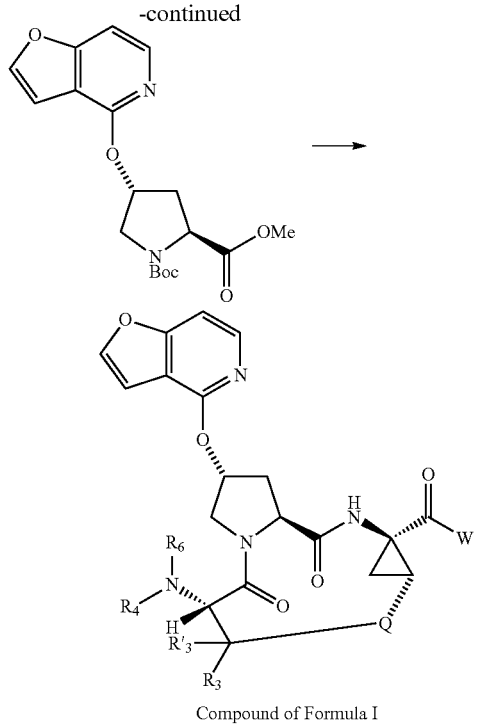

Compound of Formula I

Example 53

Preparation of Intermediate 53

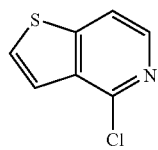

Intermediate 53

Intermediate 53 is commercially available and can be used to make compounds of Formula I.

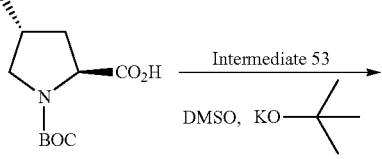

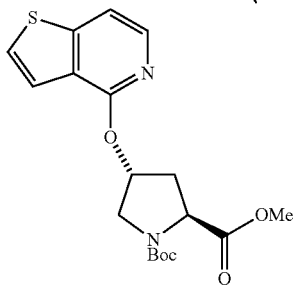

113
-continued

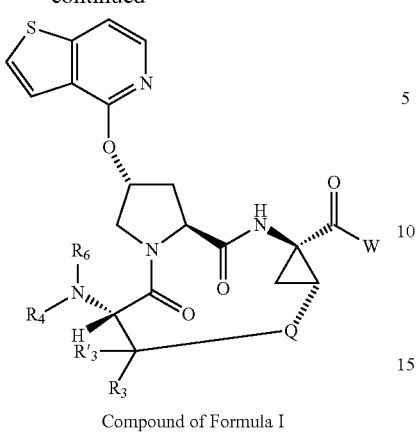

Compound of Formula I

Example 54

Preparation of Intermediate 54

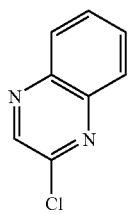

Intermediate 54

Intermediate 54 is commercially available and can be used to make compounds of Formula I.

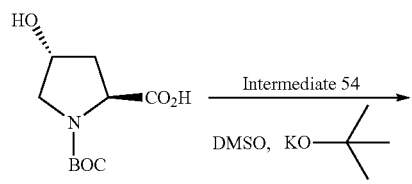

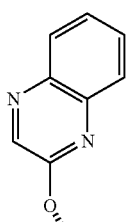

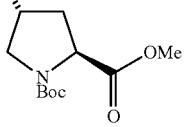

114
-continued

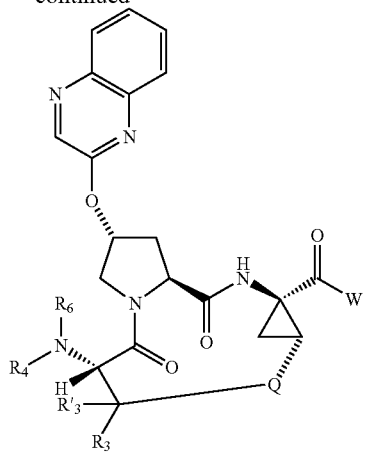

Compound of Formula I

Example 55

Preparation of Intermediate 55

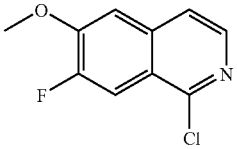

Intermediate 55

Reference scheme for preparation of Intermediate 55.

Scheme 1

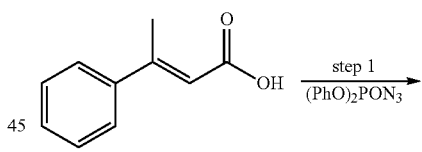

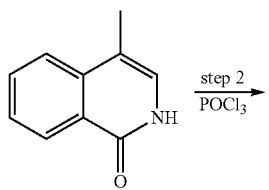

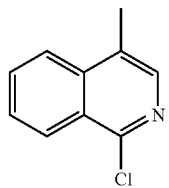

Step 1: A solution of 3-phenyl-but-2-enoic acid (16.2 g), diphenylphosphoryl azide (27.5 g), and triethylamine (10.1 g) in benzene (100 mL) was stirred for 1 h. After filtration through a silica gel plug washing with benzene and concentration, the residue was dissolved in diphenylmethane (80 mL) and refluxed for 3 h. After cooling to rt, solids were collected through a plug washing with benzene and dried to give 10 g (63%) of the desired product as a solid. $^1$H NMR (400 MHz, CD$_3$OD) δ ppm 2.30 (s, 3 H), 7.00 (s, 1 H), 7.54 (m, 1 H), 7.77 (m, 2 H), 8.33 (d, J=7.34 Hz, 1 H).

Step 2: A solution of 4-methyl-2H-isoquinolin-1-one (4.8 g) in POCl3 (50 mL) was refluxed for 3 h. After cooling and concentration, the residue was based with 5 N NaOH and extracted with CH$_2$Cl$_2$. The organic layer was washed with brine and dried over MgSO4. After concentration, purification by flash chromatography of Biotage with 5% ethyl acetate in hexanes gave 4.8 g (90%) of the desired product as a solid. $^1$H NMR (400 MHz, CDCl$_3$) δ ppm 2.59 (s, 3 H), 7.68 (t, J=7.70 Hz, 1 H), 7.78 (m, 1 H), 7.94 (d, J=8.31 Hz, 1 H), 8.11 (s, 1 H), 8.35 (d, J=8.31 Hz, 1 H).

Chemistry for preparation of Intermediate 55

Intermediate 55

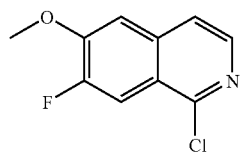

Step 1: Preparation of 7-fluoro-6-methoxy-2H-isoquinolin-1-one. As shown in step 1 of this example using 19.6 g 4-fluoro-3-methoxycinnamic acid as starting material. 9.5 g product obtained (48% yield).

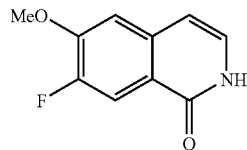 [SMILES: COc1cc2cc[nH]c(=O)c2cc1F]

Data: $^1$H NMR (400 MHz, CD$_3$COCD$_3$) δ ppm 4.00 (s, 1 H), 6.49 (d, J=7.34 Hz, 1 H), 7.19 (d, J=7.09 Hz, 1 H), 7.29 (d, J=8.07 Hz, 1 H), 7.86 (d, J=11.74 Hz, 1 H).

Step 2: Preparation of 1-chloro-7-fluoro-6-methoxyisoquinoline: As shown in step 2 of this example using 7-fluoro-6-methoxy-2H-isoquinolin-1-one (9 g) as starting material. 7 g of desired product obtained (70% yield).

Intermediate 55

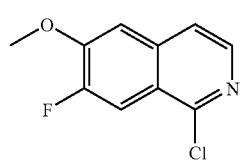

Data: $^1$H NMR (400 MHz, CDCl$_3$) δ ppm 4.04 (s, 3 H), 7.17 (d, J=8.07 Hz, 1H), 7.48 (d, J=5.62 Hz, 1 H), 7.94 (d, J=11.49 Hz, 1 H), 8.20 (d, J=5.62 Hz, 1 H).

Intermediate 55 can be used to make compounds of Formula I.

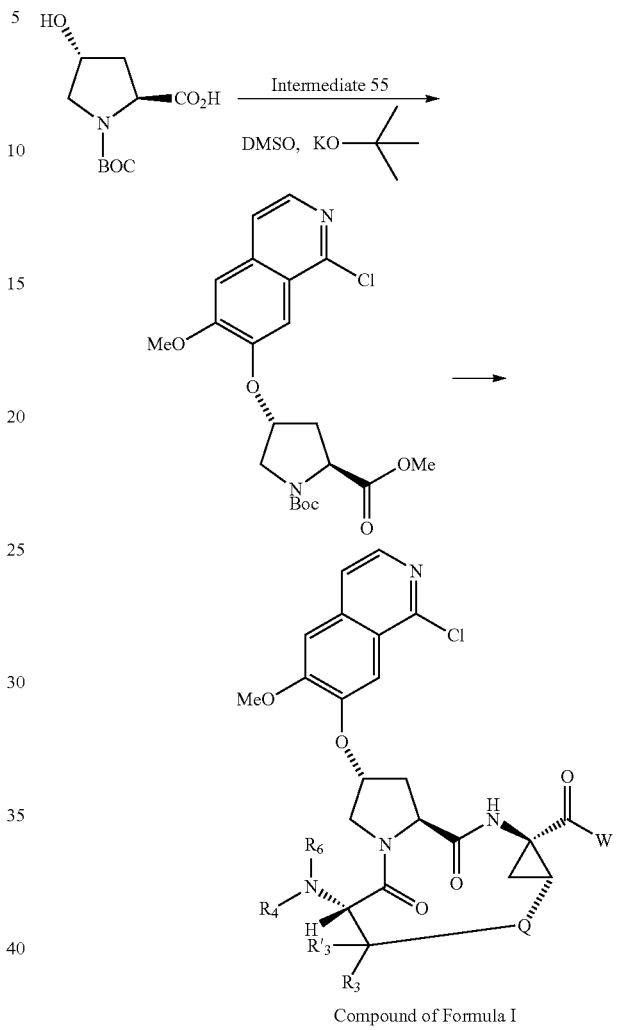

Compound of Formula I

Example 56

Preparation of Intermediate 56

Intermediate 56

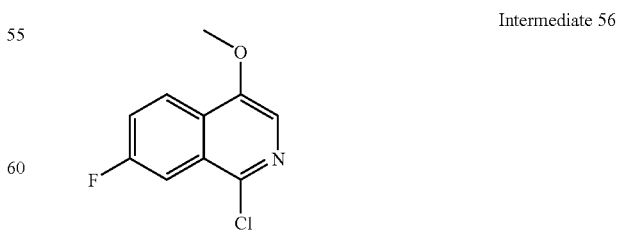

Step 1: As in Example 55 step 1 but with 3.82 g of 3-(4-Fluoro-phenyl)-3-methoxy-acrylic acid as starting material. 198 mg product obtained (5% yield).

Product:

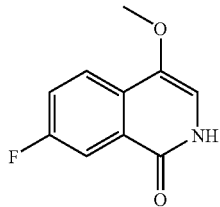

Data: MS: (M+H)⁺ 194.

Step 2: As in Example 55, step 1, but with 193 mg 7-fluoro-4-methoxy-2H-isoquinolin-1-one as starting material. 199 mg product obtained (94% yield).

Product:

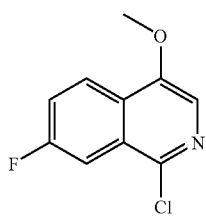

Data: ¹H NMR (400 MHz, CDCl$_3$) δ ppm 4.05 (s, 3 H), 7.49 (m, 1 H), 7.78 (s, 1 H), 7.86 (dd, J=9.66, 2.57 Hz, 1 H), 8.23 (dd, J=9.29, 5.38 Hz, 1 H); MS: (M+H)+ 212.

Intermediate 56 can be used to make compounds of Formula I.

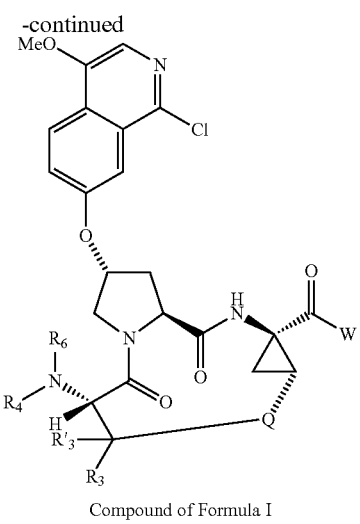

Compound of Formula I

Example 57

Preparation of Intermediate 57

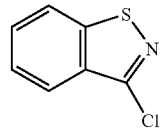

Intermediate 57

Intermediate 57 can be used to make compounds of Formula I.

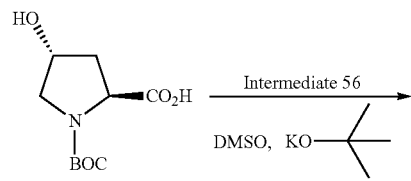

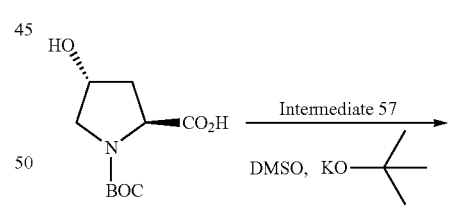

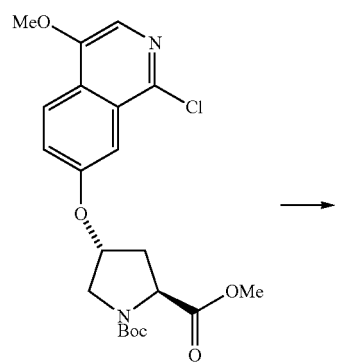

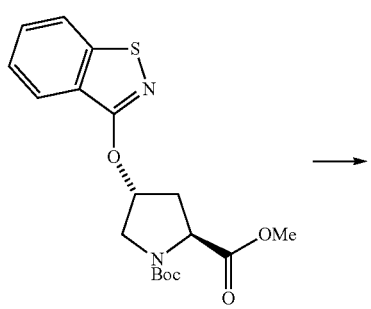

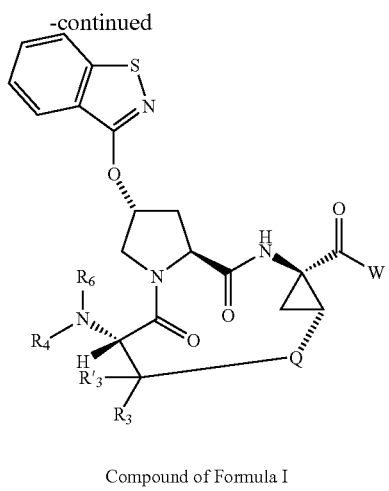

Compound of Formula I

Example 58

Preparation of Intermediate 58

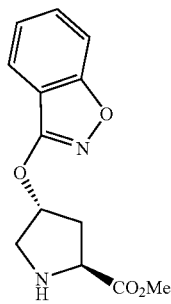

Intermediate 58

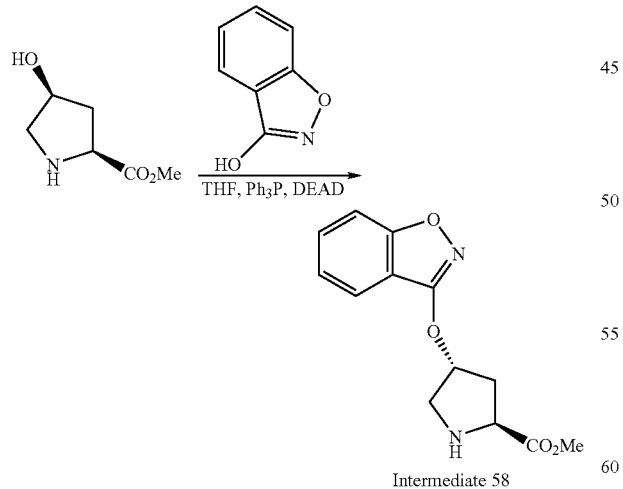

Intermediate 58

To a solution of Boc-cis-HYP-OMe (122.6 mg, 0.5 mmol) in THF (15 mL) at 0° C., triphenylphosphine (196.7 mg, 0.75 mmol) and benzo[d]isoxazol-3-ol (81 mg, 0.6 mmol) were added. Then DEAD (0.118 mL, 0.75 mmol) was added. The reaction mixture was warmed to rt. and stirred for 3 hr. Then solvent was evaporated and the residue was purified by Prep. HPLC to give a colorless thick oil. (117 mg, 54% yield)

$^1$H NMR (400 MHz, CD$_3$OD) δ 1.41 (m, 9 H), 2.38 (m, 1 H), 2.75 (m, 1 H), 3.75 (m, 3 H), 3.81 (m, 1 H), 3.90 (m, 1 H), 4.47 (m, 1 H), 5.44 (m, 1 H), 7.31 (t, J=7.46 Hz, 1 H), 7.47 (d, J=8.56 Hz, 1 H), 7.59 (t, J=7.83 Hz, 1 H), 7.66 (d, J=8.07 Hz, 1 H).

LC-MS (retention time: 2.65 min.), MS m/z 363 (MH+).

Intermediate 58 can be used to make compounds of Formula I.

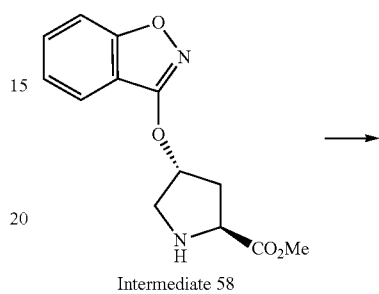

Intermediate 58

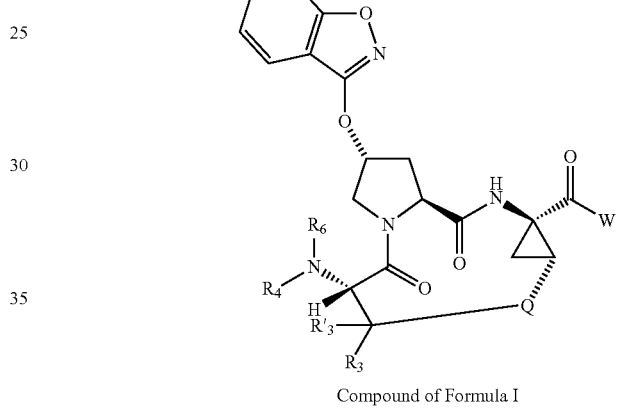

Compound of Formula I

Example 59

Preparation of Intermediate 59

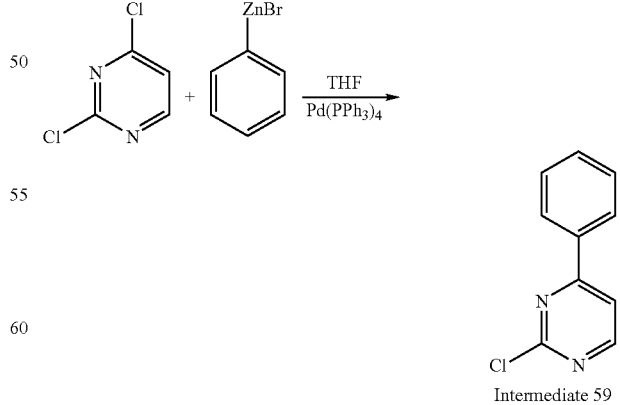

Intermediate 59

To a solution of 2,4-dichloropyrimidine (149 mg, 1 mmol) in THF (5 mL), tetrakis(triphenylphosphine) palladium (23 mg, 2 mol %) and 0.5M solution of phenylzinc bromide (2.1 mL, 1.05 mmol) in THF were added. The reaction mixture was stirred at 50° C. for overnight. Then it was added saturated ammonium chloride solution and extracted with EtOAc twice. The organic layers were combined, washed with water and dried (MgSO4). Evaporation of solvent gave a yellow residue which was purified by Prep. HPLC to afford a yellowish oil as 2-chloro-4-phenyl-pyrimidine.

Intermediate 59 can be used to make compounds of Formula I.

To a solution of 2,4-dichloropyrimidine (149 mg, 1 mmol) in THF (5 mL), tetrakis(triphenylphosphine) palladium (58 mg, 5 mol %) and 0.5M solution of 2-pyridinylzinc bromide (2.4 mL, 1.2 mmol) in THF were added. The reaction mixture was stirred at 50° C. for overnight. Then it was added saturated ammonium chloride solution and extracted with EtOAc twice. The organic layers were combined, washed with water and dried (MgSO4). Evaporation of solvent gave a yellow residue which was purified by Prep. HPLC to afford a yellowish oil as product. (Intermediate 60, 11 mg, 3.6% yield) $^1$H NMR (500 MHz, CD$_3$OD) δ 7.61 (m, 1 H), 8.07 (m, 1 H), 8.36 (d, J=5.19 Hz, 1 H), 8.50 (d, J=7.94 Hz, 1 H), 8.75 (d, J=3.97 Hz, 1 H), 8.82 (d, J=5.19 Hz, 1 H). MS m/z 192 (MH+).

Intermediate 60 can be used to make compounds of Formula I.

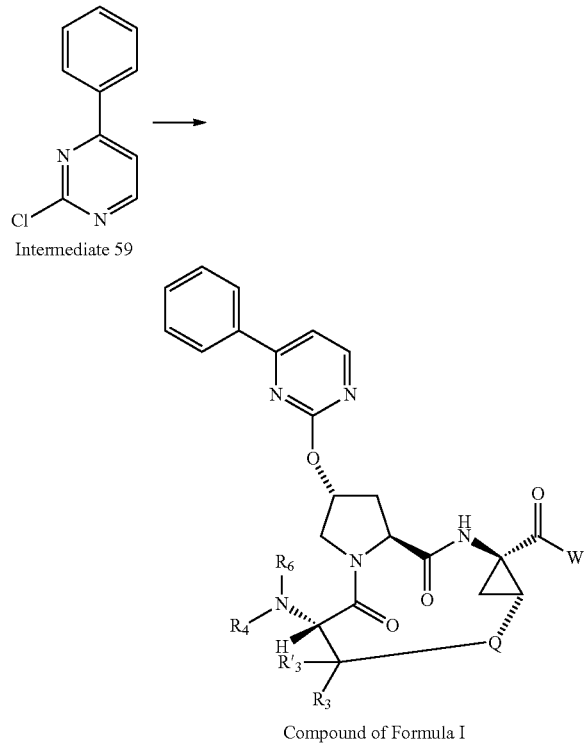

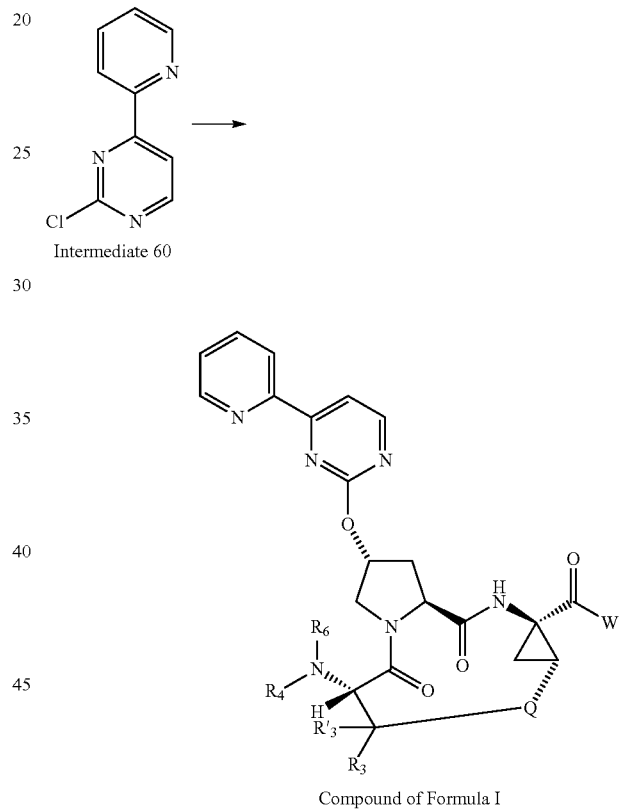

Example 60

Preparation of Intermediate 60

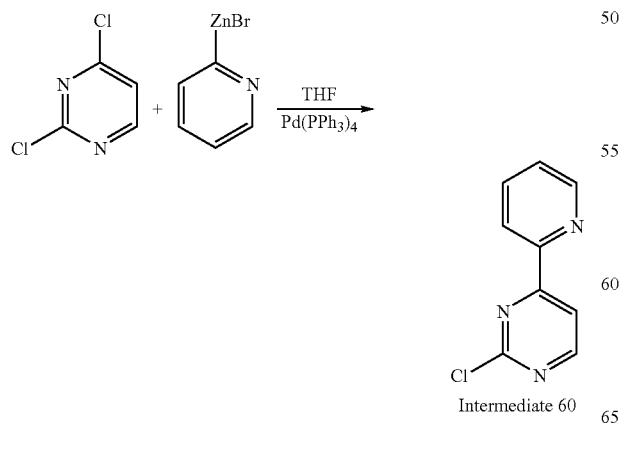

Example 61

Preparation of Intermediate 61

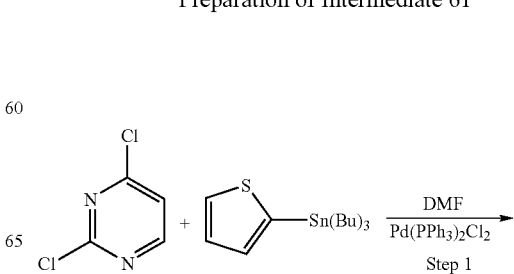

Step 1

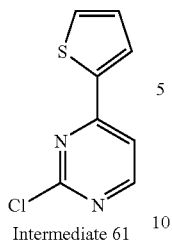

Intermediate 61

To a solution of 2,4-dichloropyrimidine (149 mg, 1 mmol) in DMF (5 mL), dichloro bis(triphenylphosphine) palladium (II) (35 mg, 5 mol %) and 2-(tributylstannyl)thiophene (0.38 mL, 1.2 mmol) were added. The reaction mixture was heated at 70° C. for 3 hr. Then it was added saturated KF solution in methanol (20 mL) and stirred at rt for 4 hr. The reaction mixture was concentrated with a small amount of silica gel and the residue was filtered through filter paper and washed with EtOAc. The filtrate was then concentrated and the residue was purified by Prep. HPLC to afford an off-white solid as product. (110 mg, 35% yield) $^1$H NMR (400 MHz, CD$_3$OD) δ 7.20 (dd, J=5.01, 3.79 Hz, 1 H), 7.74 (dd, J=5.01, 1.10 Hz, 1 H), 7.77 (d, J=5.38 Hz, 1 H), 7.98 (dd, J=3.79, 1.10 Hz, 1 H), 8.55 (d, J=5.38 Hz, 1 H). MS m/z 197 (MH+).

Intermediate 61 can be used to make compounds of Formula I.

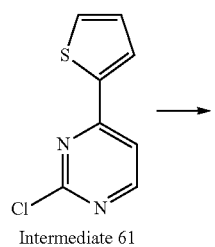

Intermediate 61

→

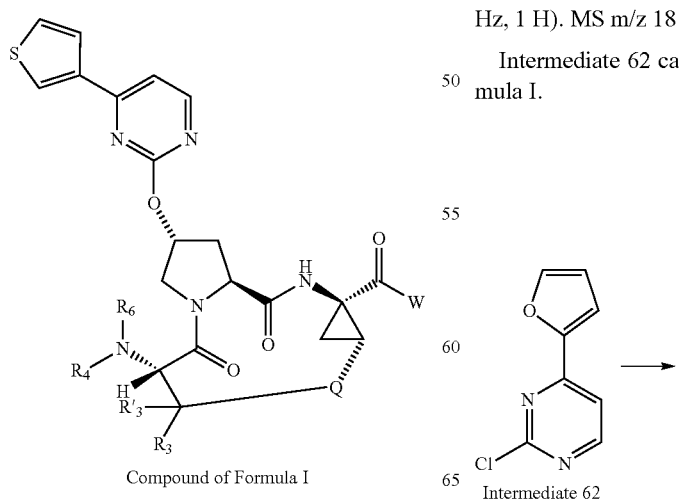

Compound of Formula I

Example 62

Preparation of Intermediate 62

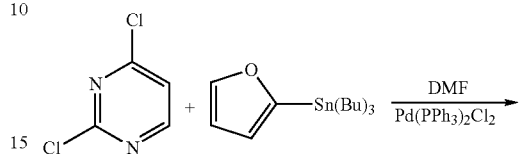

Intermediate 62

To a solution of 2,4-dichloropyrimidine (149 mg, 1 mmol) in DMF (5 mL), dichloro bis(triphenylphosphine) palladium (II) (35 mg, 5 mol %) and 2-(tributylstannyl)furan (0.35 mL, 1.1 mmol) were added. The reaction mixture was heated at 70° C. for 3 hr. Then it was added saturated KF solution in methanol (20 mL) and stirred at rt for 4 hr. The reaction mixture was concentrated with a small amount of silica gel and the residue was filtered through filter paper and washed with EtOAc. The filtrate was then concentrated and the residue was purified by Prep. HPLC to afford a brownish solid as product. (80 mg, 27% yield) $^1$H NMR (400 MHz, CD$_3$OD) δ 6.68 (dd, J=3.67, 1.71 Hz, 1 H), 7.42 (d, J=3.67 Hz, 1 H), 7.67 (d, J=5.13 Hz, 1 H), 7.30 (d, J=1.71 Hz, 1 H), 8.62 (d, J=5.14 Hz, 1 H). MS m/z 181 (MH+).

Intermediate 62 can be used to make compounds of Formula I.

Intermediate 62

→

-continued

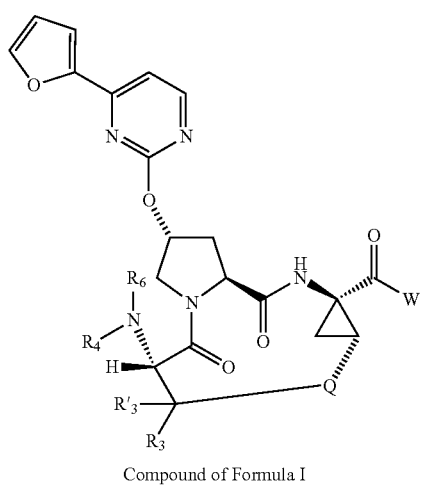

Compound of Formula I

Example 63

Preparation of Intermediate 63

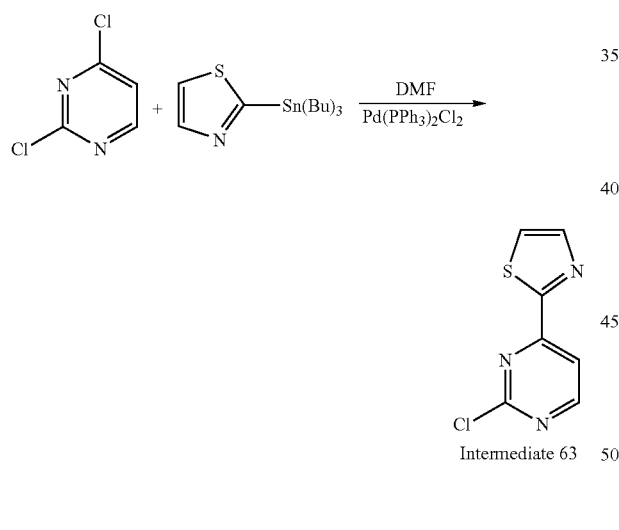

Intermediate 63

To a solution of 2,4-dichloropyrimidine (149 mg, 1 mmol) in DMF (5 mL), dichloro bis(triphenylphosphine) palladium (II) (35 mg, 5 mol %) and 2-(tributylstannyl)thiazole (412 mg, 1.1 mmol) were added. The reaction mixture was heated at 80° C. for 3 hr. Then it was added saturated KF solution in methanol (20 mL) and stirred at rt for 4 hr. The reaction mixture was concentrated with a small amount of silica gel and the residue was filtered through filter paper and washed with EtOAc. The filtrate was then concentrated and the residue was purified by Prep. HPLC to afford a brownish solid as product. (9 mg, 3% yield). MS m/z 198 (MH+).

Intermediate 63 can be used to make compounds of Formula I.

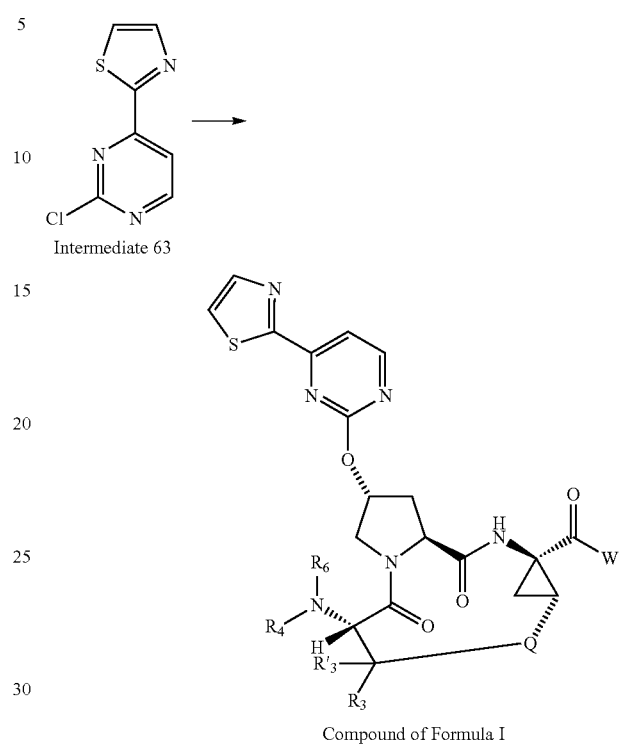

Compound of Formula I

Example 64

Preparation of Intermediate 64

Intermediate 64

Scheme 1

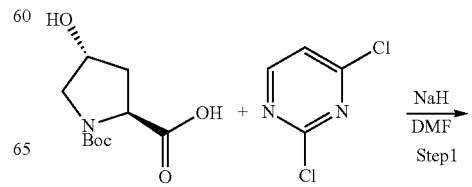

-continued

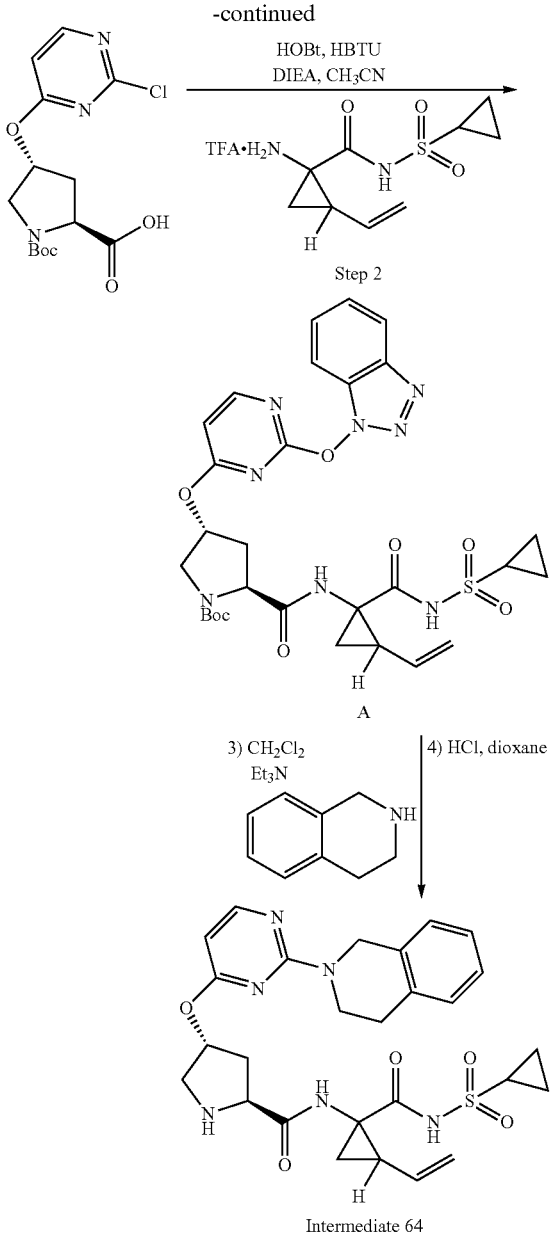

Step 1: To a solution of Boc-HYP-OH (1.0 g, 4.324 mmol) in DMF (20 mL), NaH (0.38 g of 60% dispersion in mineral oil, 9.513 mmol) was added at 0° C. The reaction mixture was stirred for 1 hr. Then 2,4-dichloropyrimidine (0.709 g, 0.0289 mmol) was added. The reaction mixture was warmed to rt and stirred for overnight. It was then quenched with 1N HCl solution and extracted with EtOAc. The organic layer was separated, washed with brine and dried (MgSO4). Evaporation of solvent gave crude product which was then purified by Prep. HPLC to give colorless oil as product. (0.4 g, 27% yield)

$^1$H NMR (CD$_3$OD, 300 MHz) δ 1.13 (m, 9 H), 2.37 (m, 1 H), 2.62 (m, 1 H), 3.70-3.84 (m, 2 H), 4.38 (m, 1 H), 5.65 (m, 1 H), 6.88 (d, J=5.86 Hz, 1 H), 8.37 (d, J=5.86 Hz, 1 H). MS m/z 344 (MH$^+$).

Step 2: To a solution of (2S,4R) 4-(2-Chloro-pyrimidin-4-yloxy)-pyrrolidine-1,2-dicarboxylic acid 1-tert-butyl ester (0.34 g, 0.99 mmol) in CH3CN (20 mL) was added (1R,2S)/(1S,2R) (1-cyclopropanesulfonyl-aminocarbonyl-2-vinyl-cyclo-propyl)-carbamic acid (0.511 g, 1.48 mmol), DIEA (0.86 mL, 4.95 mmol) and the coupling reagent HOBt (0.226 g, 1.48 mmol) and HBTU (0.561 g, 1.48 mmol). The solution was stirred at rt. overnight. Then it was concentrated, washed with water and extracted with ethyl acetate twice. The combined organic layers were washed with brine, dried over MgSO4 and concentrated. It was then purified by Prep. HPLC column to give a yellow solid (A). (0.33 g, 41% yield). MS m/z 655 (MH+).

Step 3: To a solution of intermediate 4 (50 mg, 0.061 mmol) in CH$_2$Cl$_2$ (2.5 mL), 1,2,3,4-tetrahydroisoquinoline (0.011 mL, 0.0915 mmol) and Et3N (0.021 mL, 0.153 mmol) were added. The reaction mixture was stirred at rt for overnight and at 40° C. for 1 day. The solvent was stripped and the residue was purified by Prep. HPLC to give a colorless oil. It was then dissolved in 4N HCl in dioxane (1 mL) and stirred for overnight. Evaporation of solvent gave a colorless oil as hydrochloride salt. (20 mg, 52% yield). MS m/z 553 (MH+).

Step 4: To a solution of 4-[2-(3,4-Dihydro-1H-isoquinolin-2-yl)-pyrimidin-4-yloxy]-pyrrolidine-2-carboxylic acid (1-cyclopropanesulfonylaminocarbonyl-2-vinyl-cyclopropyl)-amide hydrochloride (20 mg, 0.032 mmol) in CH3CN (5 mL) was added 2-methoxycarbonylamino-3,3-dimethyl-butyric acid (9.1 mg, 0.048 mmol), DIEA (0.028 mL, 0.16 mmol) and the coupling reagent HOBt (7.3 mg, 0.048 mmol) and HBTU (18.2 mg, 0.048 mmol). The solution was stirred at rt. overnight. Then it was concentrated, washed with water and extracted with ethyl acetate twice. The combined organic layers were washed with brine, dried over MgSO4 and concentrated to give yellowish oil. It was purified by Prep. HPLC column to give a colorless oil as TFA salt (Intermediate 64). (16 mg, 60% yield)

$^1$H NMR (CD$_3$OD, 500 MHz) δ 0.98-1.06 (m, 13 H), 1.13 (m, 1 H), 1.22-1.32 (m, 1 H), 1.35-1.44 (m, 1 H), 1.82 (dd, J=8.24, 5.19 Hz, 0.5 H), 1.90 (dd, J=8.24, 5.49 Hz, 0.5 H), 2.26 (m, 1 H), 2.32-2.43 (m, 1 H), 2.56 (m, 1 H), 2.96 (m, 1 H), 3.11 (m, br, 2 H), 3.56 (s, 3 H), 4.14 (m, 1 H), 4.21 (m, 1 H), 4.38 (m, 1 H), 4.47 (m, 1 H), 5.15 (m, 1 H), 5.31 (m, 1 H), 5.75 (m, 1 H), 5.94 (s, 1 H), 6.47 (d, J=7.02 Hz, 1 H), 7.29 (s, 4 H), 7.49 (m, 1 H), 7.56 (m, 1 H), 7.74 (d, J=8.24 Hz, 1 H), 7.88 (d, J=8.24 Hz, 1 H), 8.11 (d, J=7.02 Hz, 1 H). MS m/z 724 (MH+).

Intermediate 64 can be used to make compounds of Formula I.

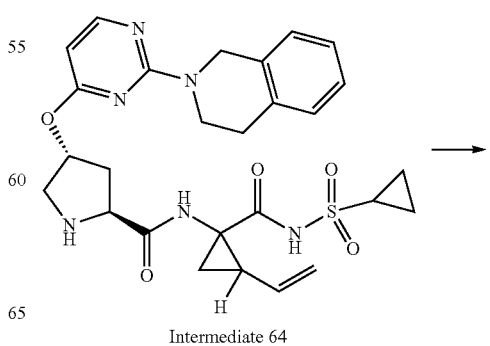

Intermediate 64

-continued

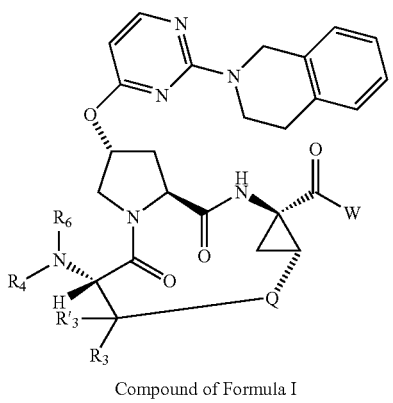

Compound of Formula I

Example 65

Preparation of Intermediate 65

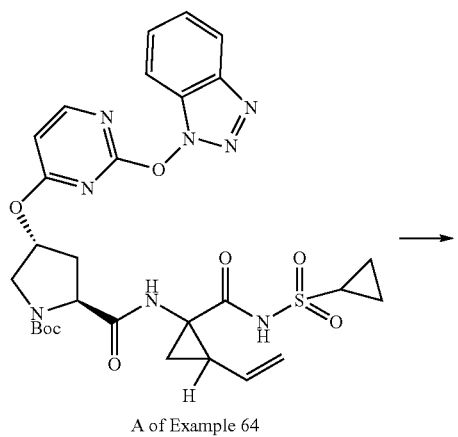

A of Example 64 dissolved in 4N HCl in dioxane (1 mL) and stirred for overnight. Evaporation of solvent gave crude product which was purified by Prep.HPLC again to afford yellowish solid as TFA salt. (8.5 mg, 14% yield). MS m/z 539 (MH+).

Intermediate 65 can be used to make compounds of Formula I.

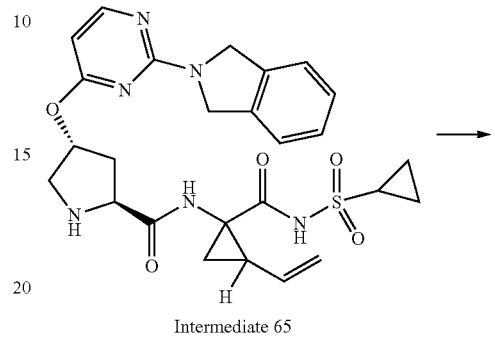

Intermediate 65

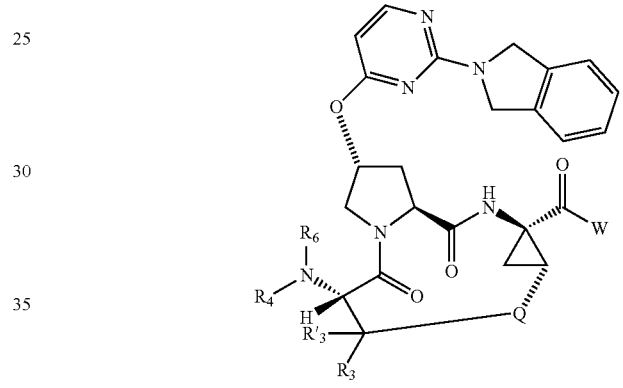

Compound of Formula I

Example 66

Preparation of Intermediate 66

Intermediate 65

To a solution of A (50 mg, 0.061 mmol) in CH$_2$Cl$_2$ (2.5 mL), isoindoline (0.013 mL, 0.115 mmol) and Et3N (0.026 mL, 0.19 mmol) were added. The reaction mixture was stirred at rt for 2 days. The solvent was stripped and the residue was purified by Prep. HPLC to give a colorless oil. It was then

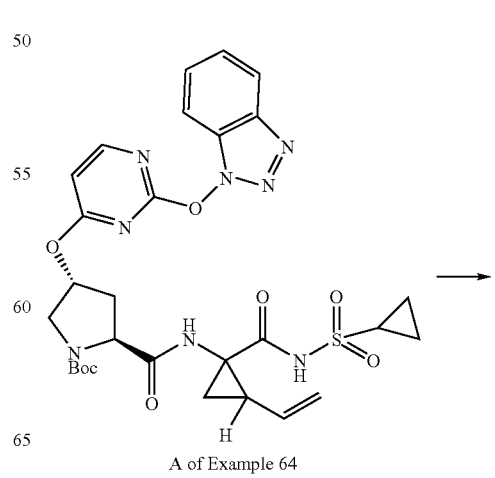

A of Example 64

-continued

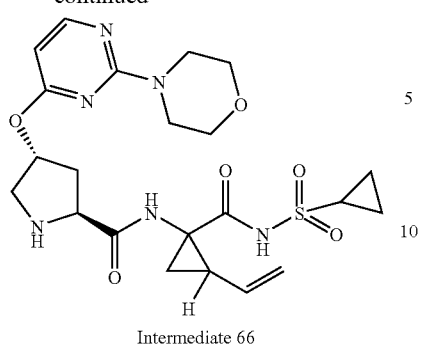

Intermediate 66

To a solution of A of Example 64 (50 mg, 0.061 mmol) in CH₂Cl₂ (2.5 mL), morpholine (0.008 mL, 0.0915 mmol) and Et3N (0.021 mL, 0.153 mmol) were added. The reaction mixture was stirred at rt for overnight and at 40° C. for 1 day. The solvent was stripped and the residue was purified by Prep. HPLC to give a colorless oil. It was then dissolved in 4N HCl in dioxane (1 mL) and stirred for overnight. Evaporation of solvent gave a colorless oil as hydrochloride salt. (12.6 mg, 36% yield); MS m/z 507 (MH+).

Intermediate 66 can be used to make compounds of Formula I.

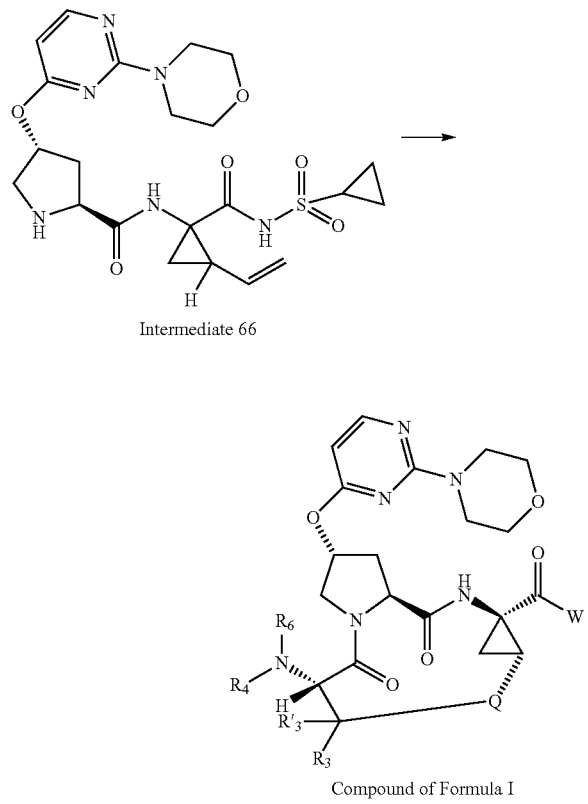

Example 67

Intermediate 67

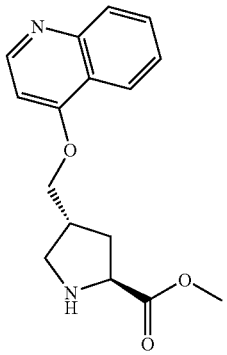

Intermediate 67

Preparation of Intermediate 67

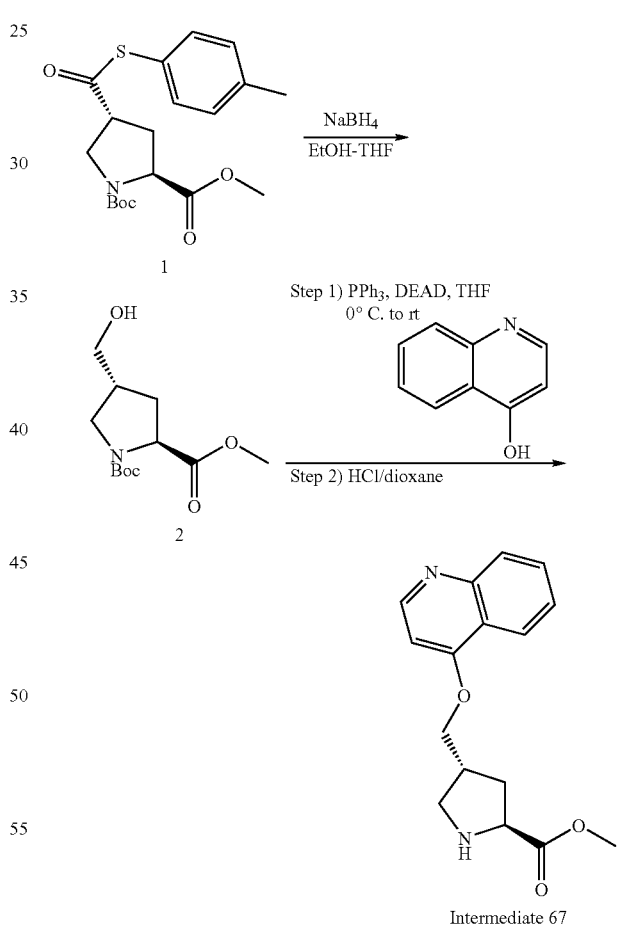

To a solution of 1,4-p-tolylsulfanylcarbonyl-pyrrolidine-1,2-dicarboxylic acid 1-tert-butyl ester 2-methyl ester (3.0 g, 7.91 mmol) in ethanol (15 mL) and THF (30 mL) mixture, sodium borohydride (0.6 g, 15.8 mmol) was added. The reaction mixture was stirred at rt. for overnight. Then it was concentrated, washed with 1 N HCl solution and extracted with EtOAc three times. The organic layers were combined, washed with saturated NaHCO3 solution and dried (MgSO4). Evaporation of solvent gave yellowish oil which was purified by flash column chromatography (silica gel, 3:1 EtOAc:Hexanes) to afford colorless oil as product (2). (1.77 g, 86% yield)

$^1$H NMR (CD$_3$OD, 500 MHz) δ 1.43 (m, 9 H), 2.00-2.13 (m, 2 H), 2.46 (m, 1 H), 3.19 (m, 1 H), 3.47-3.53 (m, 2 H), 3.61 (m, 1 H), 3.73 (m, 3 H), 4.31 (m, 1 H).MS m/z 282 (M+Na+).

To a solution of 2 (80 mg, 0.309 mmol) in THF (10 mL) at 0° C., triphenylphosphine (121.4 mg, 0.463 mmol) and 4-hydroxyquinoline (67.2 mg, 0.463 mmol) were added. Then DEAD (80.6 mg, 0.463 mmol) was added. The reaction mixture was warmed to rt. and stirred for 2 days. Then solvent was evaporated and the residue was purified by Prep. HPLC to give colorless oil. It was then dissolved in 4N HCl in dioxane (3 mL) and stirred for 2 hr. Evaporation of solvent gave thick colorless oil as bis HCl salt. (110 mg, 99% yield)

$^1$H NMR (500 MHz, CD$_3$OD) δ 2.52 (m, 1 H). 2.60 (m, 1 H), 3.19 (m, 1 H), 3.45 (m, 1 H), 3.66 (s, 3 H), 3.86 (m, 1 H), 4.61-4.75 (m, 3 H), 7.56 (d, J=6.7 Hz, 1 H), 7.94 (t, J=7.3 Hz, 1 H), 8.10-8.20 (m, 2 H), 8.55 (d, J=8.2 Hz, 1 H), 9.07 (d, J=6.7 Hz, 1 H).

MS m/z 287 (MH+).

Intermediate 67 can be used to make compounds of Formula I.

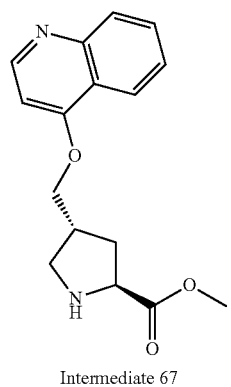

Intermediate 67

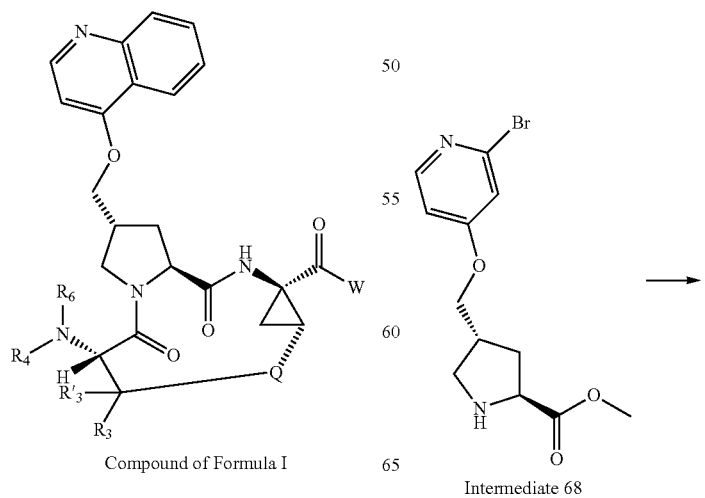

Compound of Formula I

Example 68

Preparation of Intermediate 68

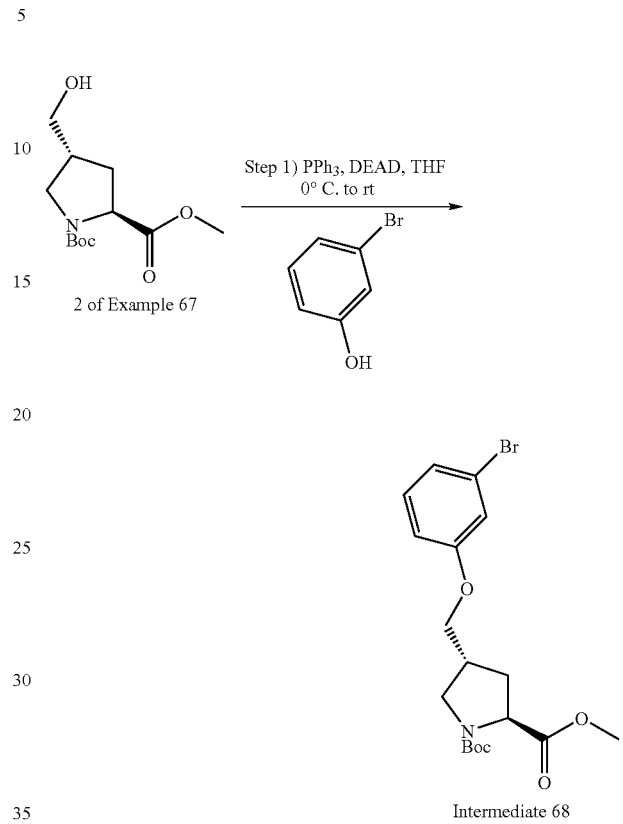

To a solution of 2 from Example 67 (150 mg, 0.578 mmol) in THF (15 mL) at 0° C., triphenylphosphine (228 mg, 0.868 mmol) and 3-bromophenol (150 mg, 0.868 mmol) were added. Then DEAD (0.14 mL, 0.868 mmol) was added. The reaction mixture was warmed to rt. and stirred for 2 days. Then solvent was evaporated and the residue was purified by Prep. HPLC to give colorless oil as product. (105 mg, 44% yield). MS m/z 436 (M+Na+).

Intermediate 68 can be used to make compounds of Formula I.

-continued

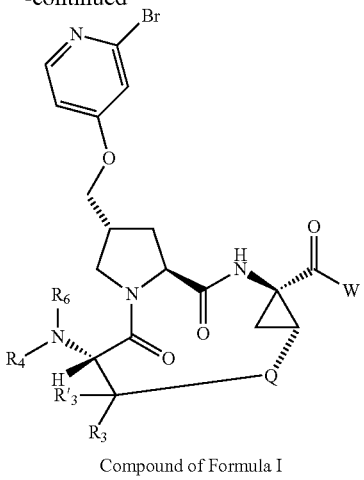

Compound of Formula I

Example 69

Preparation of Intermediate 69

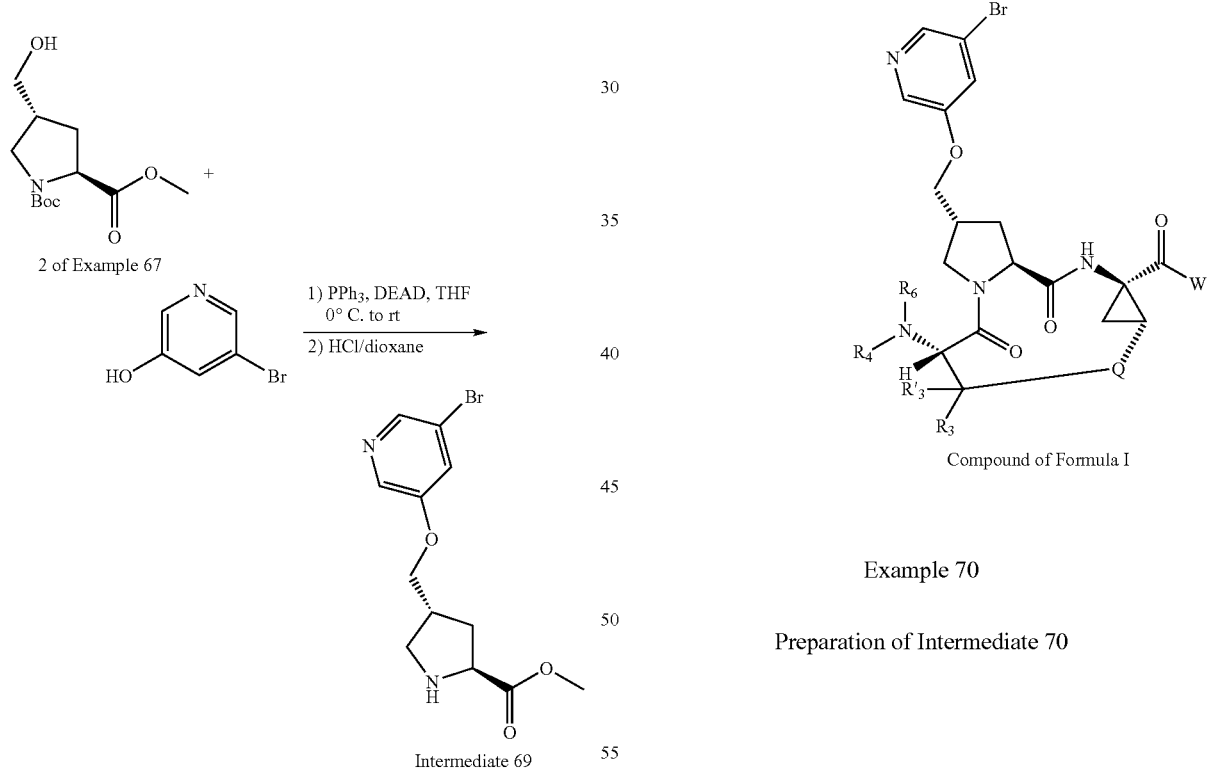

solution in dioxane (3.0 mL) and stirred for 4 hr. Evaporation of solvent gave crude product which was further purified by Prep. HPLC to afford a yellowish oil as TFA salt. (70 mg, 11% yield) MS m/z 315 (MH+).

Intermediate 69 can be used to make compounds of Formula I.

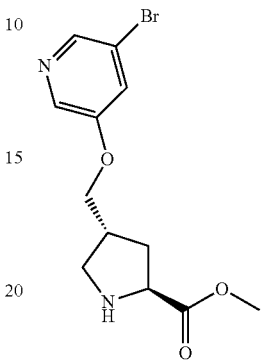

Intermediate 69

Example 70

Preparation of Intermediate 70

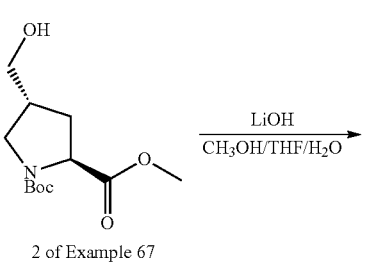

To a solution of 4-hydroxymethyl-pyrrolidine-1,2-dicarboxylic acid 1-tert-butyl ester 2-methyl ester (2 of Example 67, 300 mg, 1.157 mmol) in THF (15 mL) at 0° C., triphenylphosphine (455 mg, 1.735 mmol) and 5-bromo-pyridin-3-ol (prepared according to F. E. Ziegler et al., J. Am. Chem. Soc., (1973), 95, 7458) (302 mg, 1.735 mmol) were added. Then DEAD (0.273 mL, 1.735 mmol) was added. The reaction mixture was warmed to rt. and stirred for 2 days. Then solvent was evaporated and the residue was purified by Prep. HPLC to give a yellowish oil. Then it was dissolved in 4N HCl -continued

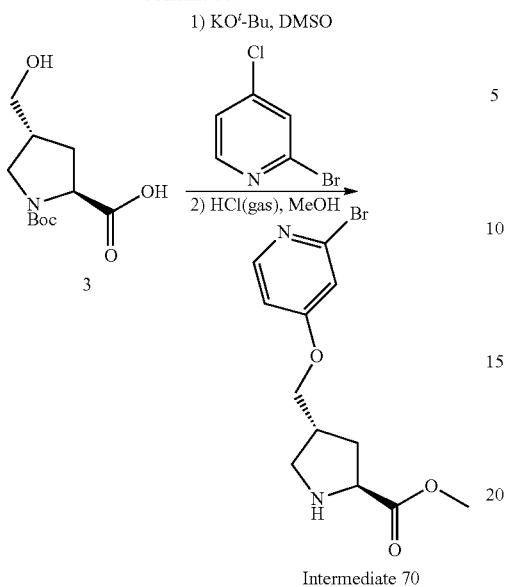

Intermediate 70

Step 1: To a solution of 2 from Example 67 (700 mg, 2.7 mmol) in THF (90 mL), methanol (50 mL) and water (12 mL) mixture, lithium hydroxide monohydrate (1700 mg, 2.0 mmol) was added. The reaction mixture was stirred at rt. for overnight. Then it was acidified with 1N HCl solution to pH=3 to 5. Extracted with ethyl acetate (2×20 mL) and the organic layers were combined and dried (MgSO4). Evaporation of solvent gave thick colorless oil as product (0.58, 88% yield).

$^1$H NMR (CD$_3$OD, 400 MHz) δ 1. 42 (m, 9 H), 2.00-2.09 (m, 2 H), 2.45 (m, 1 H), 3.17 (m, 1 H), 3.49 (m, 2 H), 3.59 (m, 1 H), 4.24 (m, 1 H). MS m/z 268 (M+Na+).

Step 2: To a solution of the proline carboxylic acid (270 mg, 1.1 mmol) in DMSO (10 mL), potassium t-butoxide (309 mg, 2.75 mmol) was added. The reaction mixture was stirred at rt for 1 hr. Then 2-Bromo-4-chloro-pyridine (254 mg, 1.32 mmol) was added. The reaction mixture was stirred at rt for overnight. Then it was quenched with water and washed with ethyl acetate. The aqueous layer was separated and acidified with 1N HCl solution to pH=3. Extracted with ethyl acetate twice and the organic layers were combined and dried (MgSO4). Evaporation of solvent gave an orange oil. It was then dissolved in methanol and HCl (gas) was bubbled through for 2 min at −78° C. Then the reaction mixture was warmed to rt and stirred for overnight. Evaporation of solvent gave an orange oil as crude to carry on. MS m/z 315 (MH+).

Intermediate 70 can be used to make compounds of Formula I.

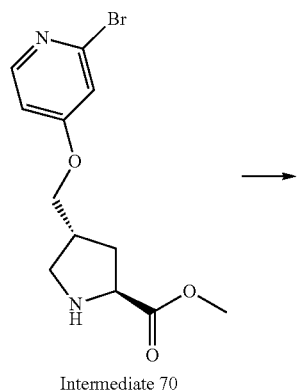

Intermediate 70

→

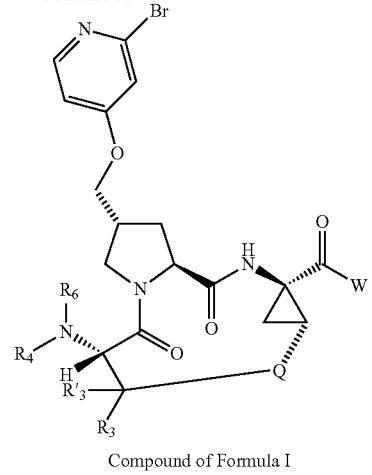

Compound of Formula I

Example 71

Preparation of Intermediate 71

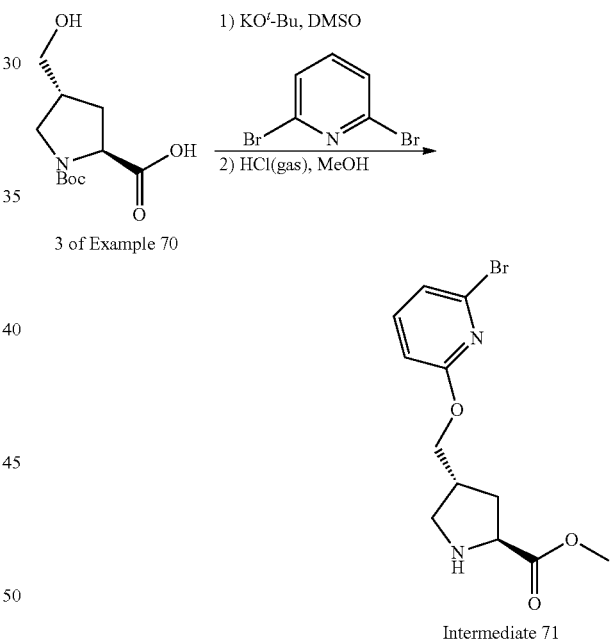

Intermediate 71

To a solution of intermediate 3 from Example 70 (270 mg, 1.1 mmol) in DMSO (10 mL), potassium t-butoxide (309 mg, 2.75 mmol) was added. The reaction mixture was stirred at rt for 1 hr. Then 2,6-dibromopyridine (313 mg, 1.32 mmol) was added. The reaction mixture was stirred at rt for overnight. Then it was quenched with water and washed with ethyl acetate. The aqueous layer was separated and acidified with 1N HCl solution to pH=3. Extracted with ethyl acetate twice and the organic layers were combined and dried (MgSO4). Evaporation of solvent gave an orange oil. It was then dissolved in methanol and HCl (gas) was bubbled through for 2 min at −78° C. Then the reaction mixture was warmed to rt and stirred for overnight. Evaporation of solvent gave an orange oil as crude to carry on. MS m/z 315 (MH+).

Intermediate 71 can be used to make compounds of Formula I.

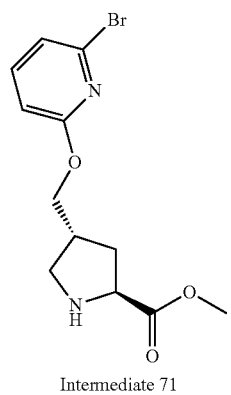

Intermediate 71

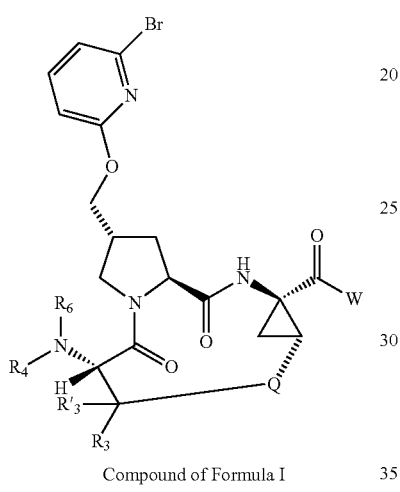

Compound of Formula I

Example 72

Preparation of Intermediate 72

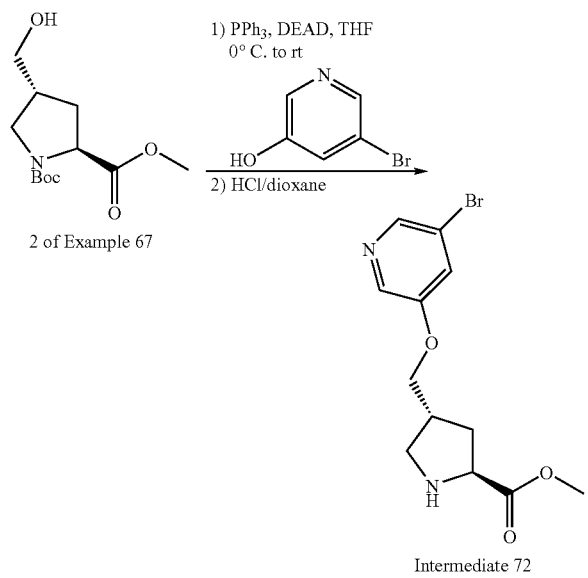

2 of Example 67

Intermediate 72

To a solution of 4-hydroxymethyl-pyrrolidine-1,2-dicarboxylic acid 1-tert-butyl ester 2-methyl ester (2 of Example 67, 300 mg, 1.157 mmol) in THF (15 mL) at 0° C., triphenylphosphine (455 mg, 1.735 mmol) and 5-bromo-pyridin-3-ol (prepared according to F. E. Ziegler et al., J. Am. Chem. Soc., (1973), 95, 7458) (302 mg, 1.735 mmol) were added. Then DEAD (0.273 mL, 1.735 mmol) was added. The reaction mixture was warmed to rt. and stirred for 2 days. Then solvent was evaporated and the residue was purified by Prep. HPLC to give a yellowish oil. Then it was dissolved in 4N HCl solution in dioxane (3.0 mL) and stirred for 4 hr. Evaporation of solvent gave crude product which was further purified by Prep. HPLC to afford a yellowish oil as TFA salt. (70 mg, 11% yield). MS m/z 315 (MH+).

Intermediate 72 can be used to make compounds of Formula I.

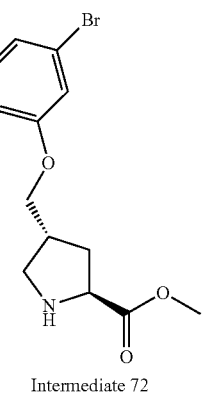

Intermediate 72

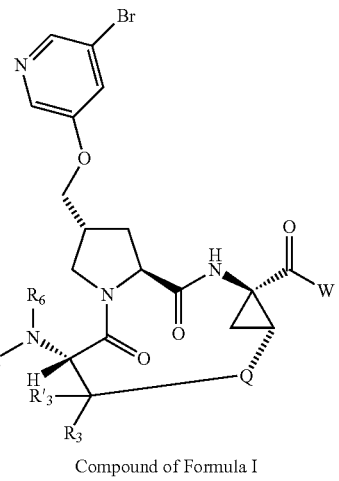

Compound of Formula I

In Examples 68-72, the intermediates described (68-72) and the proposed compounds of Formula J, each contain a halopyridine functionality. This functionality can be employed in coupling reactions wherein the halo group is replace with a ring system or alternate functionality. This reaction is well recognized in the art and the following reactions serve as examples of said coupling process.

Example 73

Coupling Reaction: Example A

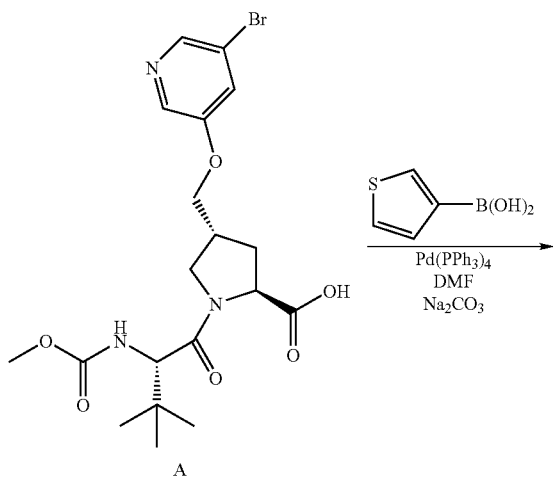

To a solution of A (16 mg, 0.0339 mmol) in DMF (1 mL), 3-thiopheneboronic acid (5.6 mg, 0.044 mmol), tetrakis(triphenylphosphine) palladium (2.0 mg, 0.0017 mmol) and 2M Na2CO3 solution (0.051 mL, 0.1017 mmol) were added. The reaction mixture was heated at 110° C. for 4 hr. Then it was filtered and washed with methanol. The filtrate was concentrated and purified by Prep.HPLC to give brownish oil as product. (6 mg, 37% yield)

$^1$H NMR (CD$_3$OD, 400 MHz) δ1.05 (s, 9 H), 2.21-2.30 (m, 2 H), 2.95 (m, 1 H), 3.42 (s, 3 H), 3.93 (m, 1 H), 4.01 (m, 1 H), 4.20-4.30 (m, 3 H), 4.60 (dd, J=8.56, 5.87 Hz, 1 H), 7.64 (m, 2 H), 8.12 (m, 1 H) 8.37 (m, 1 H), 8.45 (m, 1 H), 8.75 (s, 1H). MS m/z 476 (MH+).

Example 74

Coupling Reaction: Example B

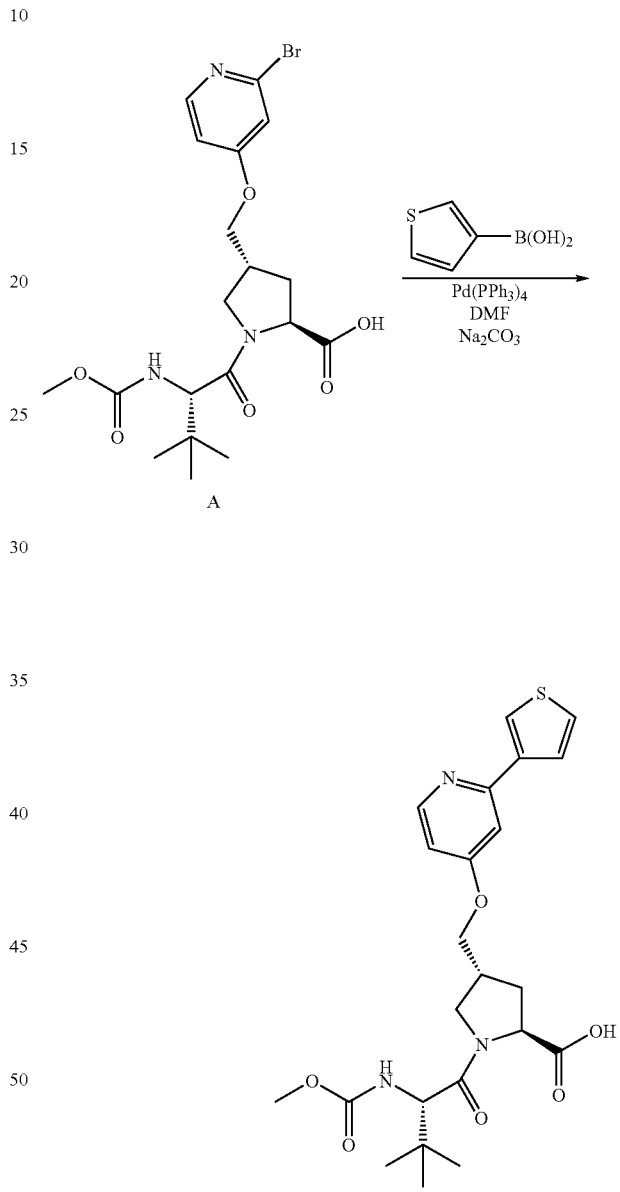

To a solution of A (20 mg, 0.0423 mmol) in DMF (1 mL), 3-thiopheneboronic acid (7.0 mg, 0.055 mmol), tetrakis(triphenylphosphine) palladium (2.4 mg, 0.00212 mmol) and 2M Na2CO3 solution (0.063 mL, 0.127 mmol) were added. The reaction mixture was heated at 110° C. for 30 hr. Then it was filtered and washed with methanol. The filtrate was concentrated and purified by Prep.HPLC to give brownish oil as product. (10.5 mg, 42% yield) MS m/z 476 (MH+).

Example 75

Coupling Reaction: Example C

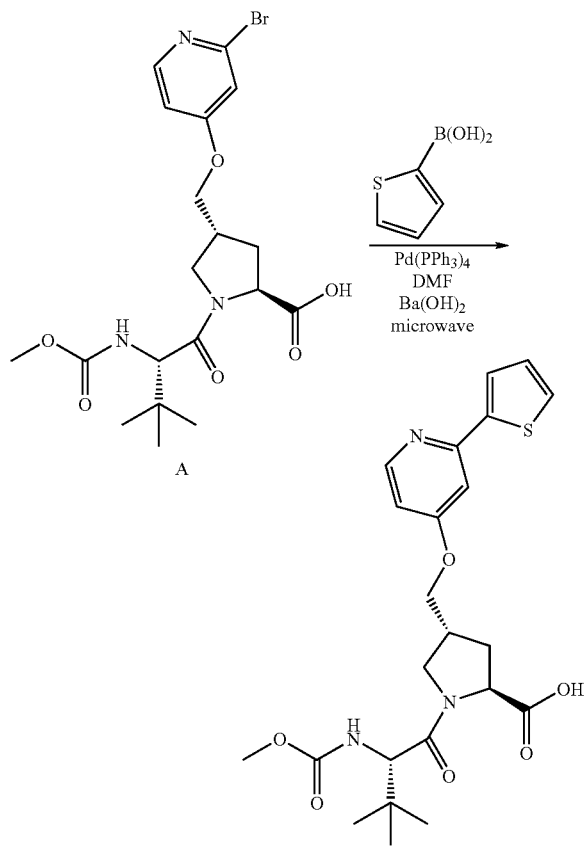

To a solution of A (20 mg, 0.0423 mmol) in DMF (2 mL), 2-thiopheneboronic acid (7.0 mg, 0.055 mmol), tetrakis (triphenylphosphine) palladium (2.4 mg, 0.00212 mmol) and barium hydroxide (40 mg, 0.127 mmol) were added. The reaction mixture was heated at 150° C. in Smith microwave reactor for 110 min. Then it was filtered and washed with methanol. The filtrate was concentrated and purified by Prep.HPLC to give yellowish oil as product. (5.0 mg, 20% yield). MS m/z 476 (MH+).

Example 76
Coupling Reaction: Example D

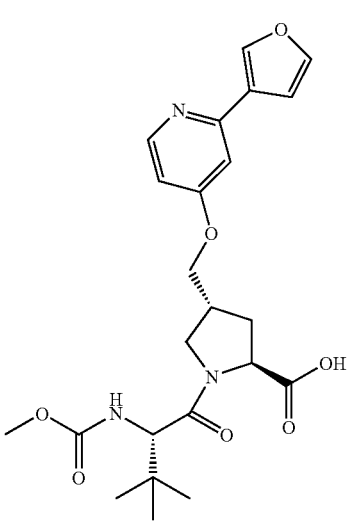

To a solution of A (20 mg, 0.0423 mmol) in DMF (2 mL), 3-furanboronic acid (6.2 mg, 0.055 mmol), tetrakis(triphenylphosphine) palladium (2.4 mg, 0.00212 mmol) and barium hydroxide (40 mg, 0.127 mmol) were added. The reaction mixture was heated at 150° C. in Smith microwave reactor for 30 min. Then it was filtered and washed with methanol. The filtrate was concentrated and purified by Prep.HPLC to give yellowish oil as product. (12 mg, 49% yield) MS m/z 460 (MH+).

Example 77

Coupling Reaction: Example E

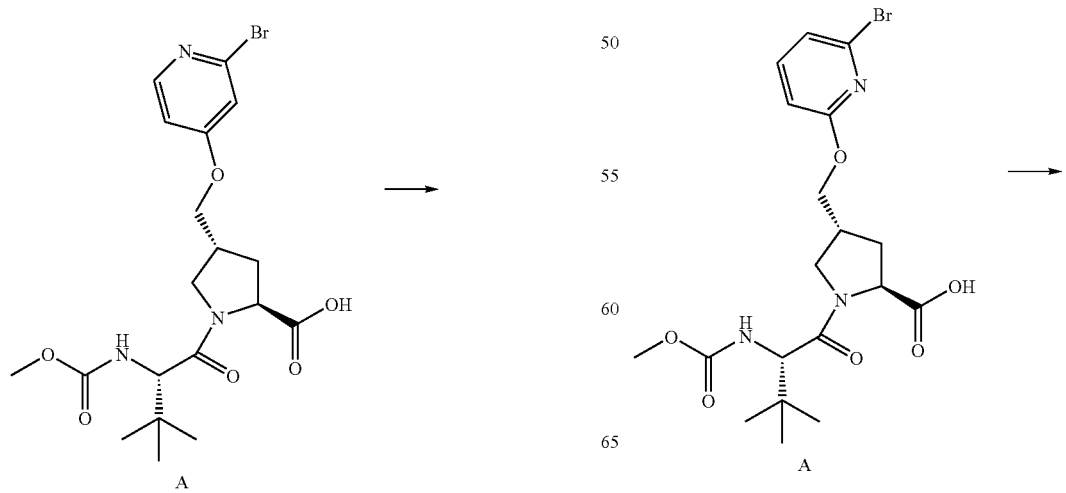

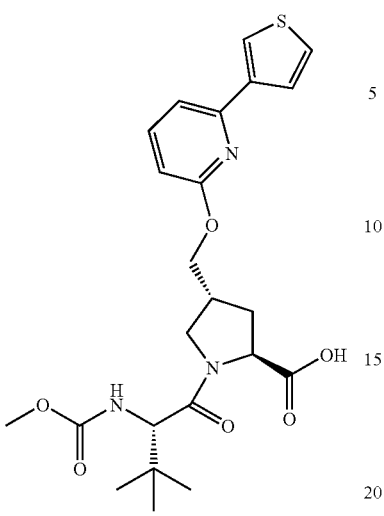

To a solution of A (25 mg, 0.053 mmol) in DMF (1 mL), 3-thiopheneboronic acid (8.8 mg, 0.0688 mmol), tetrakis(triphenylphosphine) palladium (3.1 mg, 0.00265 mmol) and 2M Na2CO3 solution (0.080 mL, 0.159 mmol) were added. The reaction mixture was heated at 110° C. for overnight. Then it was filtered and washed with methanol. The filtrate was concentrated and purified by Prep.HPLC to give brownish oil as product. (15 mg, 48% yield)

$^1$H NMR (CD$_3$OD, 500 MHz) δ 1.06 (s, 9H), 2.20-2.31 (m, 2H), 2.94 (m, 1H), 3.55 (s, 3H), 3.91 (m, 1H), 3.98 (m, 1H), 4.34 (s, 1H), 4.37-4.46 (m, 2H), 4.61 (dd, J=8.85, 5.19 Hz, 1H), 6.77 (d, J=8.24 Hz, 1H), 7.39 (d, J=7.32 Hz, 1H), 7.48 (dd, J=5.19, 3.05 Hz, 1H), 7.68 (dd, J=4.88, 1.22 Hz, 1H), 7.77 (t, J=7.93 Hz, 1H), 8.04 (m, 1H). MS m/z 476 (MH+).

Example 78

Coupling Reaction: Example F

To a solution of A (20 mg, 0.0423 mmol) in DMF (1 mL), phenyl boronic acid (6.7 mg, 0.0688 mmol), tetrakis(triphenylphosphine) palladium (2.4 mg, 0.00212 mmol) and Cs2CO3 (41 mg, 0.127 mmol) were added. The reaction mixture was heated at 110° C. for overnight. Then it was filtered and washed with methanol. The filtrate was concentrated and purified by Prep.HPLC to give yellowish oil as product. (12 mg, 49% yield). MS m/z 470 (MH+).

Example 79

Coupling Reaction: Example G

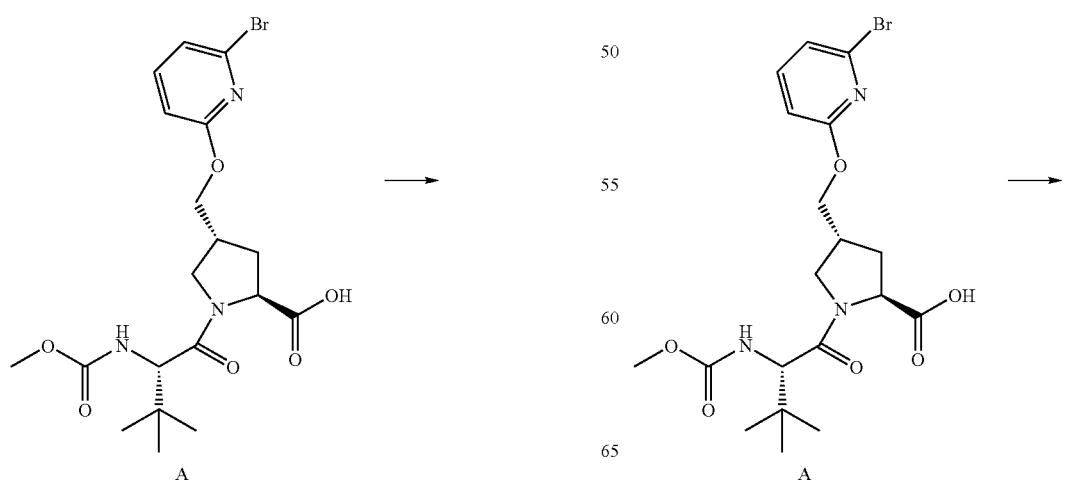

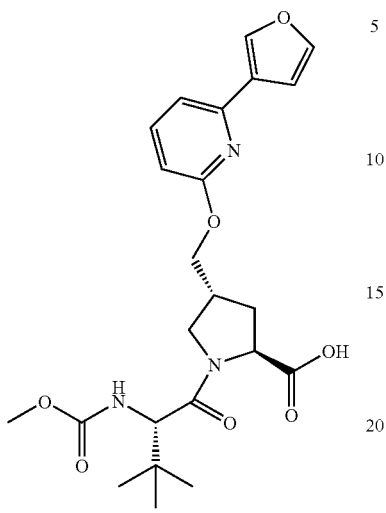

To a solution of A (20 mg, 0.0423 mmol) in DMF (1 mL), 3-furan boronic acid (6.2 mg, 0.055 mmol), tetrakis(triphenylphosphine) palladium (2.4 mg, 0.002115 mmol) and 2M Na2CO3 solution (0.064 mL, 0.127 mmol) were added. The reaction mixture was heated at 110° C. for 2 days. Then it was filtered and washed with methanol. The filtrate was concentrated and purified by Prep.HPLC to give yellowish oil as product. (7.0 mg, 29% yield)

Example 80

Coupling Reaction: Example H

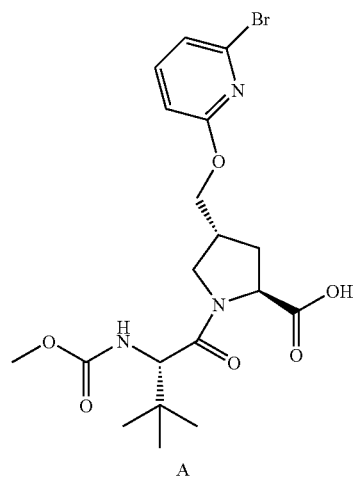

A

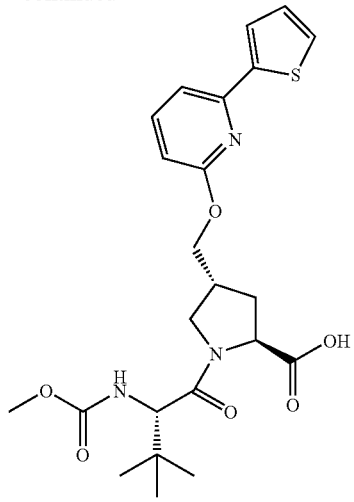

To a solution of A (20 mg, 0.0423 mmol) in DMF (2 mL), 2-thiopheneboronic acid (7.0 mg, 0.055 mmol), tetrakis(triphenylphosphine) palladium (2.4 mg, 0.00212 mmol) and barium hydroxide (40 mg, 0.127 mmol) were added. The reaction mixture was heated at 150° C. in Smith microwave reactor for 30 min. Then it was filtered and washed with methanol. The filtrate was concentrated and purified by Prep.HPLC to give brownish oil as product. (13.0 mg, 52% yield)

$^1$H NMR (CD$_3$OD, 400 MHz) δ 1.03 (s, 9 H), 2.18-2.25 (m, 2 H), 2.93 (m, 1 H), 3.55 (s, 3 H), 3.83 (m, 1 H), 3.98 (m, 1 H), 4.34 (s, 1 H), 4.38 (m, 2 H), 4.58 (dd, J=8.05, 5.14 Hz, 1 H), 6.63 (d, J=8.07 Hz, 1 H), 7.07 (dd, J=4.89, 3.67 Hz, 1 H), 7.33 (d, J=7.34 Hz, 1 H), 7.42 (d, J=5.14 Hz, 1 H), 7.60-7.66 (m, 2 H). MS m/z 476 (MH+).

Example 81

Using the above coupling examples (A-H) as a reference in the design of reaction conditions, the following intermediates could be prepared. Each of these proposed intermediates (Intermediates 73-80) could then be converted into Compounds of Formula I by employing the teachings described, and referenced, herein.

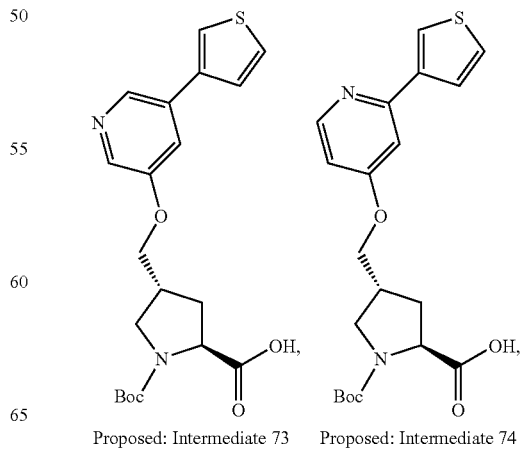

Proposed: Intermediate 73    Proposed: Intermediate 74

-continued

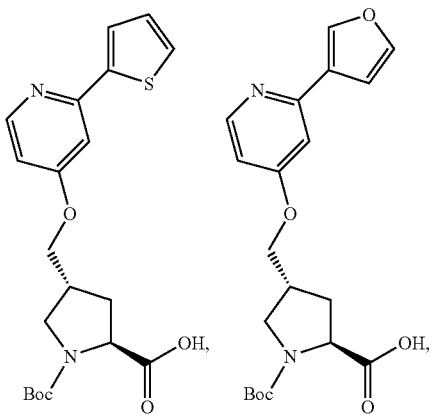

Proposed: Intermediate 75   Proposed: Intermediate 76

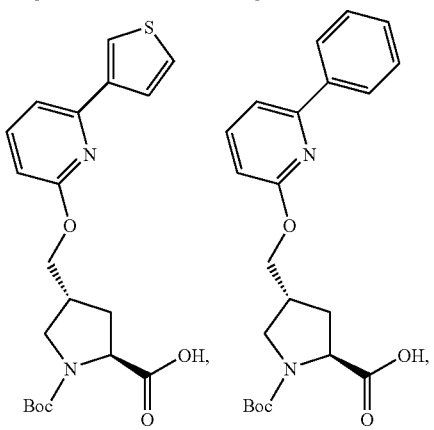

Proposed: Intermediate 77   Proposed: Intermediate 78

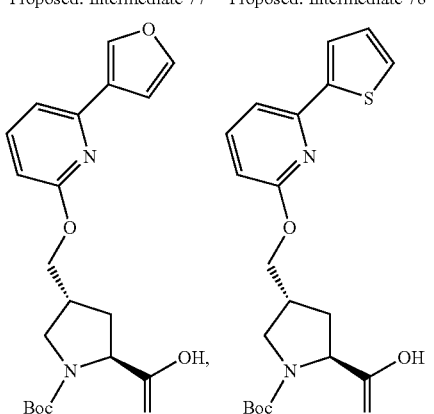

Proposed: Intermediate 79   Proposed: Intermediate 80

Example 82

Preparation of Intermediate 82

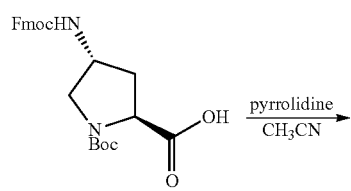

-continued

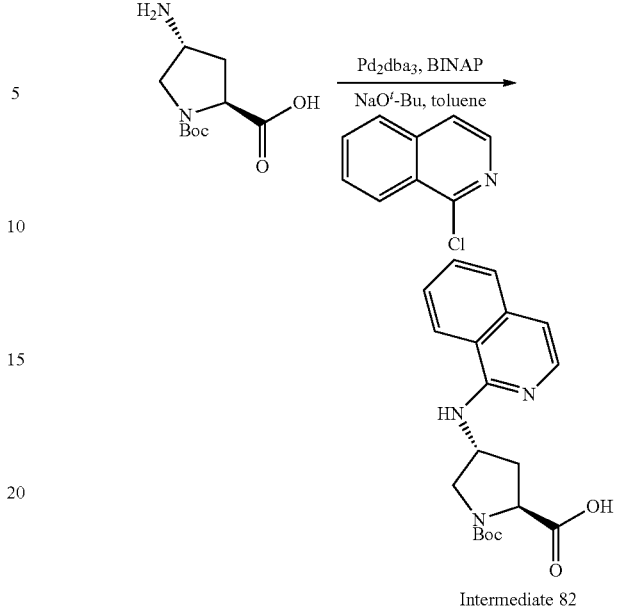

Intermediate 82

To a solution of (2S,4R) Fmoc-4-amino-1-boc-pyrrolidine-2-carboxylic acid (400 mg, 0.884 mmol) in acetonitrile (15 mL), five drops of pyrrolidine was added.

The reaction mixture was stirred at rt for 3 hr. Then it was concentrated and put on high vacuum to give crude 4-amino-1-boc-pyrrolidine-2-carboxylic acid. In another round-bottomed flask, a solution of Pd2 dba3 (40 mg, 5% mol) and racemic-BINAP (56 mg, 10% mol) was stirred under nitrogen in degassed toluene (8 mL) at rt for 1 h. Then 1-chloroisoquinoline (216 mg, 1.326 mmol) and sodium t-butoxide (340 mg, 3.536 mmol) were added and the reaction mixture was stirred for 30 min. Then 4-amino-1-boc-pyrrolidine-2-carboxylic acid was added and the reaction mixture was heated under reflux for 1 h. Water was added to quench the reaction and the aqueous layer was separated and filtered through filter paper. It was then concentrated and purified by Prep. HPLC to give coupled product as TFA salt. (165 mg, 40% yield)

$^1$H NMR (CD$_3$OD, 400 MHz) δ 1.44 (m, 9H), 2.51-2.74 (m, 2H), 3.64 (m, 1H), 4.01 (m, 1H), 4.49 (m, 1H), 4.64 (m, 1H), 7.30 (d, J=6.85 Hz, 1H), 7.58 (d, J=6.85 Hz, 1H), 7.79 (m, 1H), 7.91-7.99 (m, 2H), 8.56 (d, J=8.56 Hz, 1H). MS m/z 358 (MH+).

Intermediate 82 can be used to make compounds of Formula I.

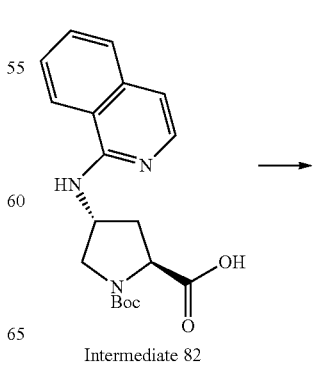

Intermediate 82

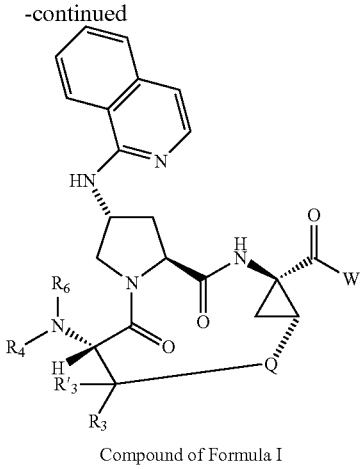

Compound of Formula I

Example 83

Preparation of Intermediate 83

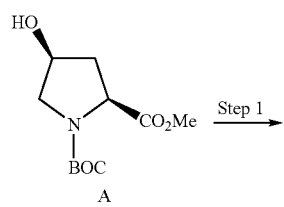

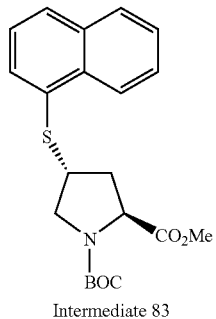

Intermediate 83

Step 1: The tosylate of the Boc proline intermediate (A) was prepared as described in the literature (Patchett, A. A.; Witkof, B. J. Am. Chem. Soc. 1957, 185-192) and was used without further purification.

To a slurry of NaH (76 mg, 1.90 mmol) in DMF (20 ml) was added 1-thionaphthol (0.29 mg, 1.80 mmol) and the mixture stirred for 30 minutes. A solution of the Boc proline tosylate (0.61 g, 1.80 mmol) was added and the mixture stirred for 12 h at 230C. The mixture was concentrated and the residue partitioned between EtOAc/H2O. The organic extracts are dried (MgSO4) and concentrated. The residue was purified by column chromatography (elution with 5% EtOAc/hexanes to 30% EtOAc/hexanes to give 261 mg (38%) of the product as a yellow oil.

$^1$H NMR (CDCl$_3$, 3:2 mixture of rotamers) δ 1.41 (s, 9H), 1.44 (s, 9H), 2.25-2.29 (m, 2H), 3.69 (s, 3H), 3.35-3.42 (m, 1H), 3.51-3.53 (m, 1H), 3.80-3.86 (m, 2H), 4.38-4.39 (m, 1H), 4.46-4.48 (m, 1H), 7.41-7.46 (m, 1H), 7.42-7-54 (m, 1H), 7.57-7.59 (m, 1H), 7.58 (d, J=4 Hz, 1H), 7.82-7.88 (m, 2H), 8.46 (d, J=5 Hz, 1H); MS m/z 388 (M++1).

Intermediate 83 can be used to make compounds of Formula I.

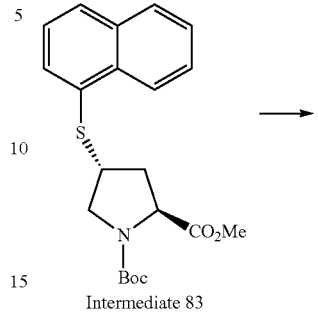

Intermediate 83

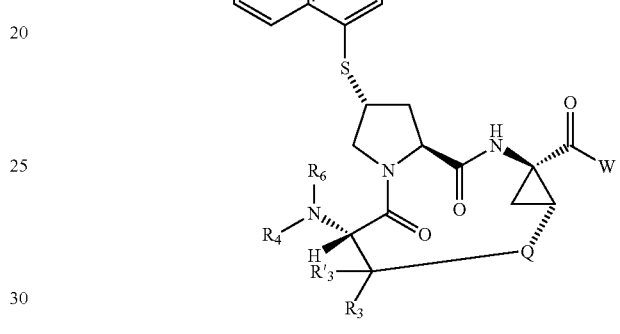

Compound of Formula I

Example 84

Preparation of Intermediate 84

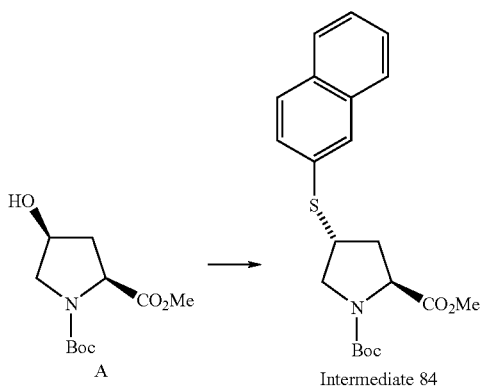 [SMILES: COC(=O)[C@@H]1C[C@H](O)CN1C(=O)OC(C)(C)C ; COC(=O)[C@@H]1C[C@@H](Sc2ccc3ccccc3c2)CN1C(=O)OC(C)(C)C]

Intermediate 84

To a slurry of NaH (76 mg, 1.90 mmol) in DMF (20 mL) was added 2-thionaphthol (0.29 g, 1.80 mmol) and the mixture was stirred for 30 minutes. A solution of the tosylate (Example 451, Step 1) (0.61 g, 1.79 mmol) in DMF (2 ml) was added and the mixture was stirred for 12 h at 230C. The mixture was concentrated, then partitioned between EtOAc/ H2O. The organic layer was washed with saturated NaHCO3, dried (MgSO4) and concentrated. The residue was chromatographed with 5% EtOAc/hexanes followed by 30% EtOAc/ hexanes to give 261 mg (38%) of the product as a clear oil.

¹H NMR (DMSO-d6) δ 1.32 (s, 9H), 2.29-2.35 (m, 2H), 3.33-3.47 (m, 2H), 3.66 (s, 3H), 3.71-3.81 (m, 1H), 4.29-4.32 (s, 1H), 7.49-7.55 (m, 3H), 7.70-7.80 (m, 1H), 7.81-7.97 (m, 3H); MS m/z 387 (M+1).

Intermediate 84 can be used to make compounds of Formula I.

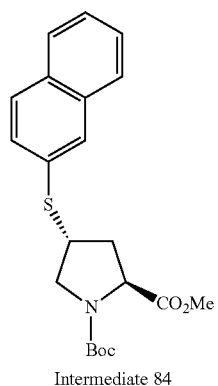

Intermediate 84

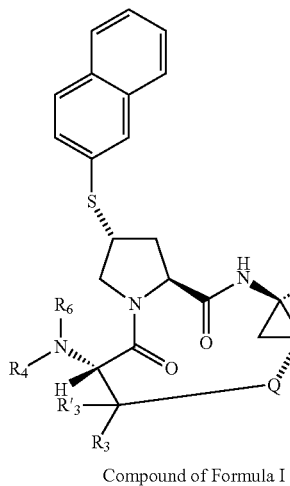

Compound of Formula I

Example 85

Preparation of Intermediate 85

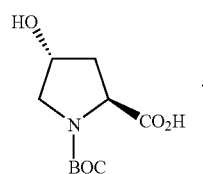

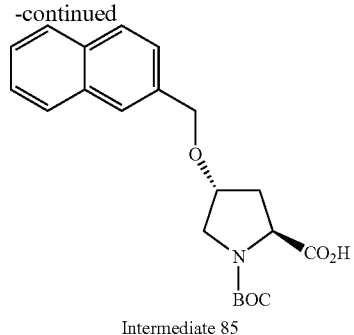

Intermediate 85

To slurry of the sodium hydride (0.91 g, 22.7 mmol) in THF (50 mL) was added N—BOC-trans-4(R)-hydroxy-L-proline (2.5 g, 10.8 mmol) and the mixture stirred at 23OC. for 1 h. 2-Chloromethylnapthalene (1.9 g, 10.8 mmol) was added and the mixture stirred for 12 h at room temperature. The solvent was removed and the residue poured into water and washed with hexanes. The aqueous layer was acidified (1 N HCl) and extracted with EtOAc. The EtOAc layer is separated, dried (MgSO4), and concentrated to give a light yellow residue. The oil was purified by flash chromatography with 1:1 EtOAc/hexanes with 1% acetic acid added to give 1.56 g (39%) of the desired product as a thick oil.

¹H NMR (DMSO-d6, 3:1 mixture of rotamers) δ 1.35, 1.37 (s, 9H, major and minor respectively), 1.92-2.02, 2.15-2.20 (m, 2H, major and minor respectively), 2.35-2.50 (m, 2H), 3.41-3.49 (m, 2H), 4.12-4.16, 4.20-4.21 (m, 2H), 4.65-4.68 (m, 2H), 7.46-7.52 (m, 3H), 7.74-7.91 (m, 4H), (Acid OH not observed); MS m/z 394 (M++1+Na).

Intermediate 85 can be used to make compounds of Formula I.

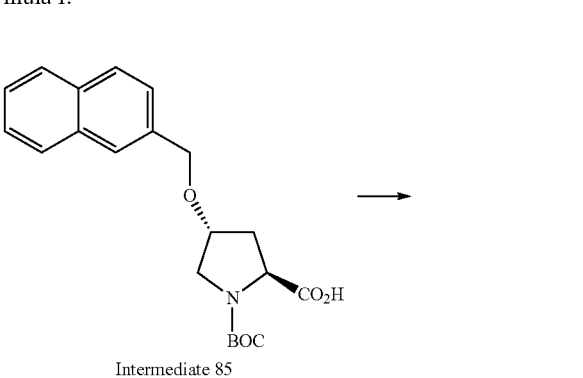

Intermediate 85

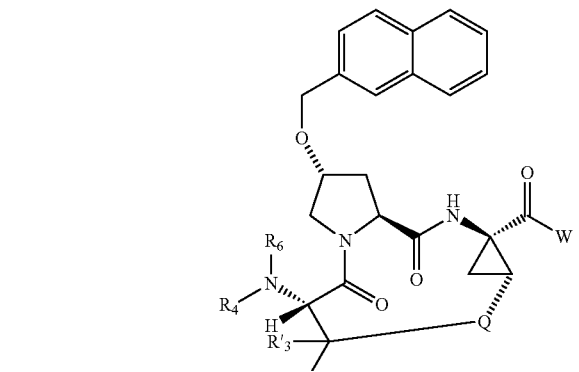

Compound of Formula I

Example 86

Preparation of Intermediate 86

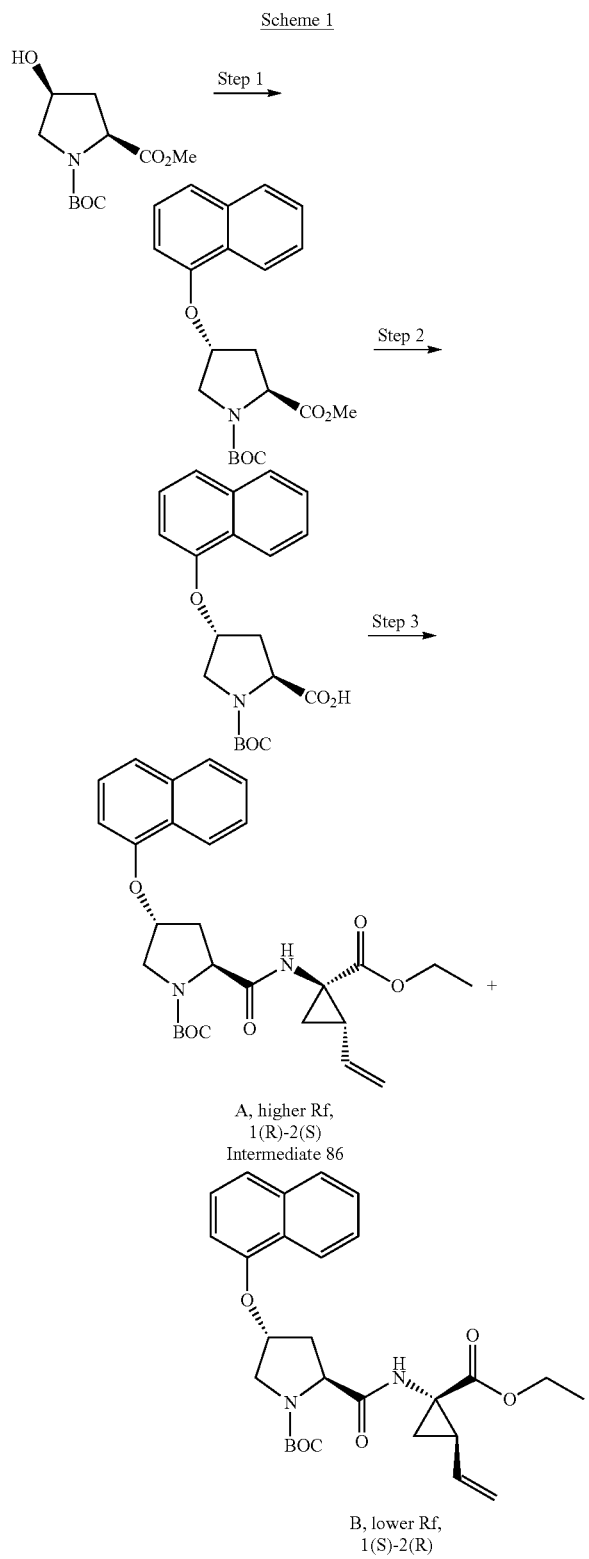

Step 1: To a solution of commercially available N-Boc-(4S)-(cis)-Hydroxyproline-OMe (200 mgs, 0.82 mmole), triphenylphosphine (320 mgs, 1.22 mmole) and 1-naphthol (176 mgs, 1.22 mmole) in 2.5 mL tetrahydrofuran was added dropwise a solution of diethyldiazodicarboxylate (190 μL, 1.22 mmole) in 1.0 mL THF over 10 minutes. After stirring for 5.5 days, the reaction was concentrated in vacuo. The crude yellow oil was chromatographed on a 20×40cM preparative TLC plate (Analtech SiO2) eluting with 6-1 hexanes-ethyl acetate to yield the desired product as a pale yellow oil (150 mgs, 33%).

$^1$H NMR (CDCl$_3$, 500 MHz) δ 1.44 (s, 9H) 2.33 (1H, m), 2.72 (1H, m), 3.77 and 3.38 (2s, 3H, rotamers), 3.88 (dd, 1H, J=4.3, 12.4 Hz), 3.97 (bd, 1H), 4.53 and 4.62 (2t, 1H, J=7.8 Hz, rotamers), 5.10 (bd, 1H), 6.76 (t, 1H, J=9.5 Hz), 7.37 (m, 1H), 7.46 (m, 3H), 7.80 (d, 1H, J=7.7 Hz), 8.18 (m, 1H); MS m/z 394 (M+Na)+

Step 2: To a stirred solution of Boc-(4R)-naphthal-1-oxo)-Pro-OEt (150 mgs, 0.40 mmole) in 1.5 mL THF and 0.5 mL water was added lithium hydroxide (10 mgs). The solution was stirred for 21 hours at room temperature and then diluted with 0.5N NaHCO3. The basic solution was extracted with ethyl acetate and then the aqueous layer was acidified to pH 2 with the dropwise addition of conc. HCl. This acidified layer was then extracted again with ethyl acetate. This second ethyl acetate layer was dried with magnesium sulfate, filtered and then concentrated in vacuo to yield Boc-(4R)-naphthal-1-oxo)-Pro-OH as pale-pink crystals (147 mgs, 100%).

$^1$H NMR (CDCl$_3$, 500 MHz) δ 1.47 and 1.48 (2s, 9H, rotamers), 2.40 and 2.52 (2m, 1H), 2.68 and 2.78 (2m, 1H), 3.78-4.07 (m, 2H), 4.57 and 4.69 (2t, 1H, J=7.6 and 8.0 Hz, rotamers), 5.12 (bd, 1H), 6.77 (dd, 1H, J=7.6, 21.2 Hz), 7.37 (m, 1H), 7.46 (m, 3H), 7.81 (t, 1H, J=5.8 Hz), 8.19 (m, 1H); MS m/z 358 (M+H)+

Step 3: To a solution of Boc-((4R)-naphthal-1-oxo)-Pro-OH (147 mgs, 0.41 mmole) and racemic (1R/2S)/(1S/2R)-1-amino-2-vinylcyclopropane carboxylic acid ethyl ester hydrochloride salt (79 mgs, 0.41 mmole) in 2.8 mL methylene chloride was added DIPEA (250 μL, 1.44 mmole) and TBTU (158 mgs, 0.49 mmole). The resulting solution was stirred under nitrogen for 20 hours and then diluted with 40 mL methylene chloride. The organic layer was washed with water, 1N NaHCO3, 1N HCl, water and brine. The solution was then dried with sodium sulfate and concentrated in vacuo. Purification by preparative TLC yielded two separate diastereomers, higher Rf diastereomer A (P2-[Boc(4R)-(naphthal-1-oxo)proline]-P1(1R,2S Vinyl Acca)-OEt, 78 mgs, 38%) and lower Rf diastereomer B (P2[Boc(4R)-(naphthal-1-oxo)proline]-P1(1S,2R Vinyl Acca)-OEt, 91 mgs, 45%) as off white solids:

Diastereomer A: P2-[Boc(4R)-(naphthal-1-oxo)proline]-P1(1R,2S Vinyl Acca)-OEt: $^1$H NMR (CDCl$_3$, 500 MHz) δ 1.24 (t, 3H), 1.43 (s, 9H), 1.52 (m, 1H), 1.84 (m, 1H), 2.02 (m, 1H), 2.14 (m, 1H), 2.81 (m, 1H), 3.88 (m, 2H), 4.11 (q, 1H, J=7.15), 4.19 (m, 1H), 4.54 (m, 1H), 5.15 (m, 1H), 5.31 (dd, 1H, J=17, 0.8 Hz), 5.77 (m, 1H), 6.83 (m, 1H), 7.36 (t, 1H, J=7.8 Hz), 7.46 (m, 3H), 7.78 (d, 1H, J=7.6 Hz), 8.14 (d, 1H, J=8.15 Hz);

MS m/z 495 (M+H)+

Diastereomer B, Example 10B: P2-[Boc(4R)-(naphthal-1-oxo)proline]-P 1(1S, 2R Vinyl Acca)-OEt: $^1$H NMR (dl-CHCl$_3$, 500 MHz) δ 1.24 (t, 3H), 1.42 (s, 9H), 1.85 (m, 1H), 2.15 (q, 1H, J=8.9 Hz), 2.40 (m, 1H), 2.78 (m, 1H), 3.78 (m, 1H), 4.12 (m, 2H), 4.52 (m, 1H), 5.15 (m, 1H), 5.31 (m, 1H), 5.79 (m, 1H), 6.80 (m, 1H), 7.35 (t, 1H, J=7.6 Hz), 7.46 (m, 3H), 7.78 (d, 1H, J=7.6 Hz), 8.14 (d, 1H, J=8.10 Hz).

MS m/z 495 (M+H)+

Intermediate 86 can be used to make compounds of Formula I.

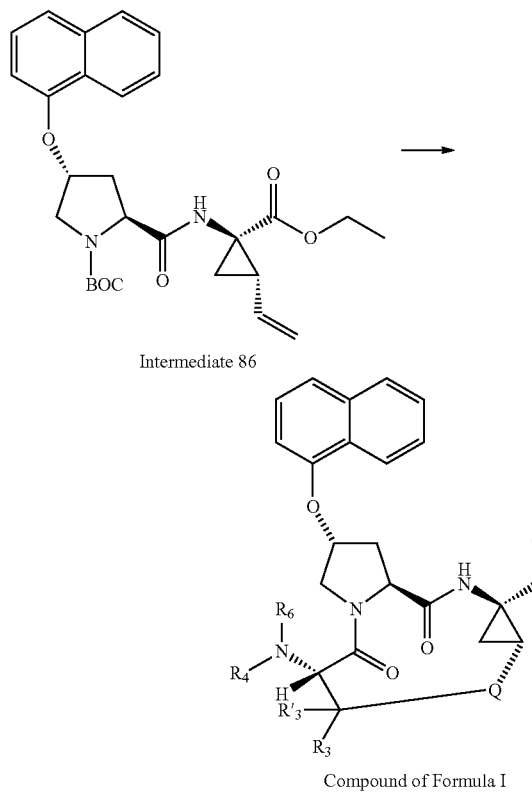

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR(RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16),8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride (MgCl2), 1 µg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 h at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS- PAGE and mass spectrometry analyses. The enzyme was stored at −80° C., thawed on ice and diluted prior to use in assay buffer.

FRET Peptide Assay to Monitor HCV NS3/4A Proteolytic Activty

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound was determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 µM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100 - [(\delta F_{inh}/\delta F_{con}) \times 100]$$

where δF is the change in fluorescence over the linear range of the curve. A non-linear curve fit was applied to the inhibition-concentration data, and the 50% effective concentration (IC$_{50}$) was calculated by the use of Excel XLfit software using the equation, $y = A + ((B-A)/(1+((C/x)^D)))$.

All of the compounds tested were found to inhibit the activity of the NS3/4A protease complex with IC$_{50}$'s of 18 µM or less. Further, compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases, a 96-well plate format protocol using colorimetric p-nitroaniline (pNA) substrate or fluorometric Amino-Methyl-Coumarin (AMC) substrate, specific for each enzyme was used as described previously (PCT Patent Application No. WO 00/09543) with some modifications. All enzymes were purchased from Sigma or EMDbiosciences while the substrates were from Bachem.

Each pNA assay included a 2 h enzyme-inhibitor pre-incubation at room temperature followed by addition of substrate and hydrolysis to ~15% conversion as measured on a Spectramax Pro microplate reader. The cathepsin B assay was initiated by adding substrate to a 10 min enzyme-inhibitor pre-incubation at room temperature, and the assay plate measured immediately using the Cytofluor Series 4000. Compound concentrations varied from 100 to 0.4 µM depending on their potency.

The final conditions for each assay were as follows:

50 mM Tris(hydroxymethyl)aminomethane hydrochloride (Tris-HCl) pH 8, 0.5 M Sodium Sulfate (Na2SO4), 50 mM NaCl, 0.1 mM EDTA, 3% DMSO, 0.01% Tween-20 with:

133 µM succ-AAA-pNA and 20 nM HNE or 8 nM PPE; 100 µM succ-AAPF-pNA and 250 µM Chymotrypsin.

100 mM NaHPO4 (Sodium Hydrogen Phosphate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 µM Z-FR-AMC diluted in H2O.

The percentage of inhibition was calculated using the formula:

$$[1 - ((UV_{inh} - UV_{blank})/(UV_{ctl} - UV_{blank}))] \times 100$$

A non-linear curve fit was applied to the inhibition-concentration data, and the 50% effective concentration (IC50) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424): 110-3 (1999). This system enabled us to evaluate the effects of our HCV Protease compounds on HCV RNA replication. Briefly, using the HCV strain 1b sequence described in the Lohmann paper (Assession number:AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before (1.5×104 cells/well) in 96-well tissue-culture sterile plates. Compound and no compound controls were prepared in DMEM containing 4% FCS, 1:100 Penicillin/Streptomycin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a CC50 reading. The toxicity of compound (CC50) was determined by adding 1/10th volume of alamar Blue to the media incubating the cells. After 4 hours, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 μl). The cells were lysed with 25 μl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 μM final from a 2 mM stock in 100% DMSO. The HCV protease substrate. The plate was then placed into the Cytofluor 4000 instrument which had been set to 340 nm excitation/490 nm emission, automatic mode for 21 cycles and the plate read in a kinetic mode. EC50 determinations were carried out as described for the IC50 determinations.

HCV Replicon Luciferase Reporter Assay

As a secondary assay, EC50 determinations from the replicon FRET assay were confirmed in a replicon luciferase reporter assay. Utilization of a replicon luciferase reporter assay was first described by Krieger et al (Krieger N, Lohmann V, and Bartenschlager R, J. Virol. 75(10):4614-4624 (2001)). The replicon construct described for our FRET assay was modified by inserting cDNA encoding a humanized form of the *Renilla* luciferase gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, Science 290(5498): 1972-1974). A stable cell line constitutively expressing this HCV replicon construct was generated as described above. The luciferase reporter assay was set up as described for the HCV replicon FRET assay with the following modifications. Following 4 days in a 37° C./5% CO2 incubator, cells were analyzed for *Renilla* Luciferase activity using the Promega Dual-Glo Luciferase Assay System. Media (100 μl) was removed from each well containing cells. To the remaining 50 μl of media, 50 μl of Dual-Glo Luciferase Reagent was added, and plates rocked for 10 minutes to 2 hours at room temperature. Dual-Glo Stop & Glo Reagent (50 μl) was then added to each well, and plates were rocked again for an additional 10 minutes to 2 h at room temperature. Plates were read on a Packard TopCount NXT using a luminescence program.

The percentage inhibition was calculated using the formula below:

% control=average luciferase signal in experimental wells(+compound)

average luciferase signal in DMSO control wells(−compound)

The values were graphed and analyzed using XLfit to obtain the EC50 value.

Representative compounds of the disclosure were assessed in the HCV enzyme assays, HCV replicon cell assay and/or in several of the outlined specificity assays. For example, Compound 1 was found to have an IC50 of 98 nanomolar (nM) against the NS3/4A BMS strain in the enzyme assay. Similar potency values were obtained with the published H77 (IC50 of 18 nM) and J4L6S (IC50 of 12 nM) strains. The EC50 value in the replicon FRET assay was 1087 nM, and 202 nM in the replicon Luciferase assay.

In the specificity assays, the same compound was found to have the following activity: HLE>100 μM; PPE>100 μM; Chymotrypsin>100 μM; Cathepsin B>100 μM. These results indicate this family of compounds are highly specific for the NS3 protease and many of these members inhibit HCV replicon replication.

The compounds of the current disclosure were tested and found to have activities in the ranges as follow:

$IC_{50}$ Activity Ranges (NS3/4A BMS Strain): A is >1 micromolar (μM); B is 0.1-1 μM; C is <0.1 μM $EC_{50}$ Activity Range (for compounds tested): A is >1 μM; B is 0.1-1 μM; C is <0.11M In accordance with one embodiment of the present disclosure, the compounds have a biological activity (EC50) of 100 μM or less, and in another embodiment, 1 μM or less, and most preferably 0.1 μM or less.

Table 2 is a list of compounds that could be synthesized using the teachings described or referenced herein.

TABLE 2

| Cmpd | R₂ | X | R' | R₃ | R₃' | NR₄R₆ | Q |
|---|---|---|---|---|---|---|---|
| 101 | cyclopropyl | O | quinazolin-4-yl | H | H | NHBoc | N-cyclopropyl-N-(pent-3-enyl) |
| 102 | 1-benzylcyclopropyl | O | 1,8-naphthyridin-4-yl | H | H | NHBoc | N-cyclopropyl-N-(pent-3-enyl) |
| 103 | 1-propylcyclopropyl | O | phthalazin-1-yl | H | H | NHBoc | N-cyclopropyl-N-(pent-3-enyl) |
| 104 | 1-propylcyclopropyl | O | 2-oxo-2H-chromen-4-yl | H | H | NHBoc | N-cyclopropyl-N-(pent-3-enyl) |
| 105 | 1-methylcyclopropyl | O | furo[3,2-c]pyridin-4-yl | H | H | NHBoc | N-cyclopropyl-N-(pent-3-enyl) |
| 106 | cyclobutyl | O | thieno[3,2-c]pyridin-4-yl | H | H | NHBoc | N-cyclopropyl-N-(pent-3-enyl) |

TABLE 2-continued

| Cmpd | R₂ | X | R' | R₃ | R₃' | NR₄R₆ | Q |
|---|---|---|---|---|---|---|---|
| 107 | cyclopropyl | O | isoxazolo[4,5-b]pyridine | H | H | NHC(O)O-tBu | N(cyclopropyl)(CH₂CH₂CH=CH-) |
| 108 | cyclopropyl | O | benzisoxazol-3-yl | H | H | NHC(O)OMe | N(cyclopropyl)(CH₂CH₂CH=CH-) |
| 109 | cyclopropyl | O | benzisothiazol-3-yl | H | H | NHC(O)O-neopentyl | N(cyclopropyl)(CH₂CH₂CH=CH-) |
| 110 | cyclopropyl | O | 1H-indazol-3-yl | H | H | NHC(O)O-(tetrahydropyran-4-yl) | N(cyclopropyl)(CH₂CH₂CH=CH-) |
| 111 | cyclopropyl | O | 1-Me-indazol-3-yl | H | H | NHC(O)O-(tetrahydrofuran-3-yl) | N(cyclopropyl)(CH₂CH₂CH=CH-) |
| 112 | cyclopropyl | O | 1-Ph-indazol-3-yl | H | H | NHC(O)O-iPr | N(cyclopropyl)(CH₂CH₂CH=CH-) |

TABLE 2-continued

| Cmpd | R₂ | X | R' | R₃ | R₃' | NR₄R₆ | Q |
|---|---|---|---|---|---|---|---|
| 113 | cyclopropyl | O | 1-benzyl-indazol-3-yl | H | H | NHC(O)OtBu | N(cyclopropyl)(cis-pent-3-enyl) |
| 114 | cyclopropyl | O | 2-phenylpyridin-4-yl | H | H | NHC(O)OtBu | N(cyclopropyl)(cis-pent-3-enyl) |
| 115 | cyclopropyl | O | 5-phenylpyridin-3-yl | H | H | NHC(O)OtBu | N(cyclopropyl)(cis-pent-3-enyl) |
| 116 | cyclopropyl | O | 6-phenylpyrimidin-4-yl | H | H | NHC(O)O-cyclopentyl | N(cyclopropyl)(cis-pent-3-enyl) |
| 117 | cyclopropyl | O | 4-phenylpyrimidin-2-yl | H | H | NHC(O)O-cyclopropyl | N(cyclopropyl)(cis-pent-3-enyl) |

TABLE 2-continued

| Cmpd | R₂ | X | R' | R₃ | R₃' | NR₄R₆ | Q |
|---|---|---|---|---|---|---|---|
| 118 | cyclopropyl | O | 2-phenylpyridin-6-yl | H | H | -NHC(O)NH-propyl | N-cyclopropyl-N-(pent-3-enyl) |
| 119 | cyclopropyl | S | naphthalen-1-yl | H | H | -NHC(O)CH₂OMe | N-cyclopropyl-N-(pent-3-enyl) |
| 120 | cyclopropyl | S | naphthalen-2-yl | H | H | -NHC(O)CH₃ | N-cyclopropyl-N-(pent-3-enyl) |
| 121 | cyclopropyl | SO₂ | naphthalen-2-yl | H | H | -NHC(O)O-tBu | N-cyclopropyl-N-(pent-3-enyl) |
| 122 | 1-ethylcyclopropyl | NH | 4-(pyridin-2-yl)thiazol-2-yl | H | H | -NHC(O)O-tBu | N-cyclopropyl-N-(pent-3-enyl) |
| 123 | cyclopropyl | OCH₂ | naphthalen-1-yl | H | H | -NHC(O)O-iPr | N-cyclopropyl-N-(pent-3-enyl) |

TABLE 2-continued

| Cmpd | R₂ | X | R' | R₃ | R₃' | NR₄R₆ | Q |
|---|---|---|---|---|---|---|---|
| 124 | cyclopropyl | CH₂O | naphthalen-2-yl | H | H | NHC(O)NH-cyclopentyl | N-cyclopropyl, N-(pent-3-enyl) |
| 125 | cyclopropyl | CH₂O | 6-phenylpyridin-2-yl | H | H | NHC(O)NH-tBu | N-cyclopropyl, N-(pent-3-enyl) |
| 126 | 1-methylcyclopropyl | CH₂O | 5-phenylpyridin-3-yl | H | H | NHC(O)O-iPr | N-cyclopropyl, N-(pent-3-enyl) |
| 127 | 1-methylcyclopropyl | CH₂O | 2-phenylpyridin-4-yl | H | H | NHC(O)NH-cyclopentyl | N-cyclopropyl, N-(pent-3-enyl) |
| 128 | 1-ethylcyclopropyl | O | quinazolin-4-yl | H | H | NHC(O)O-iPr | N-cyclopropyl, N-(pent-3-enyl) |

TABLE 2-continued

| Cmpd | R₂ | X | R' | R₃ | R₃' | NR₄R₆ | Q |
|---|---|---|---|---|---|---|---|
| 129 | cyclopropyl-Et | O | 1,8-naphthyridin-4-yl | H | H | NHC(O)O-tBu | N(cyclopropyl)(CH₂CH₂CH₂CH=CH-) |
| 130 | cyclopropyl-Et | O | phthalazin-1-yl | H | H | NHC(O)O-tBu | N(cyclopropyl)(CH₂CH₂CH₂CH=CH-) |
| 131 | cyclopropyl-Me | O | 2-oxo-2H-chromen-4-yl | H | H | NHC(O)O-tBu | N(cyclopropyl)(CH₂CH₂CH₂CH=CH-) |
| 132 | cyclopropyl | O | furo[3,2-c]pyridin-4-yl | H | H | NHC(O)O-(1-methylcyclopentyl) | N(cyclopropyl)(CH₂CH₂CH₂CH=CH-) |
| 133 | cyclopropyl-Me | O | thieno[3,2-c]pyridin-4-yl | H | H | NHC(O)O-tBu | N(cyclopropyl)(CH₂CH₂CH₂CH=CH-) |
| 134 | cyclopropyl-Et | O | isoxazolo[4,5-b]pyridin-7-yl | H | H | NHC(O)O-tBu | N(cyclopropyl)(CH₂CH₂CH₂CH=CH-) |

TABLE 2-continued

| Cmpd | R₂ | X | R' | R₃ | R₃' | NR₄R₆ | Q |
|---|---|---|---|---|---|---|---|
| 135 | cyclopropyl | O | benzisoxazol-3-yl | H | H | NHC(O)O-(1-methylcyclobutyl) | N(cyclopropyl)(pent-3-enyl) |
| 136 | cyclopropyl | O | benzisothiazol-3-yl | H | H | NHC(O)O-tBu | N(cyclopropyl)(pent-3-enyl) |
| 137 | cyclopropyl | O | 1H-indazol-3-yl | H | H | NHC(O)O-tBu | N(cyclopropyl)(pent-3-enyl) |
| 138 | cyclopropyl | O | 1-methyl-1H-indazol-3-yl | H | H | NHC(O)O-(1-methylcyclopropyl) | N(cyclopropyl)(pent-3-enyl) |
| 139 | cyclopropyl | O | 1-phenyl-1H-indazol-3-yl | H | H | NHC(O)-pyrrolidin-1-yl | N(cyclopropyl)(pent-3-enyl) |
| 140 | cyclopropyl | O | 1-benzyl-1H-indazol-3-yl | Me | H | NHC(O)O-tBu | N(cyclopropyl)(pent-3-enyl) |

TABLE 2-continued

| Cmpd | R₂ | X | R' | R₃ | R₃' | NR₄R₆ | Q |
|---|---|---|---|---|---|---|---|
| 141 | cyclopropyl | O | 2-phenylpyridin-4-yl | Me | H | neopentyl carbamate | N-cyclopropyl-N-(pent-3-enyl) |
| 142 | cyclopropyl | O | 5-phenylpyridin-3-yl | Me | H | isopropyl carbamate | N-cyclopropyl-N-(pent-3-enyl) |
| 143 | cyclopropyl | O | 6-phenylpyrimidin-4-yl | Me | H | cyclopentyl urea | N-cyclopropyl-N-(pent-3-enyl) |
| 144 | 1-methylcyclopropyl | O | 4-phenylpyrimidin-2-yl | Me | H | tert-butyl carbamate | N-cyclopropyl-N-(pent-3-enyl) |
| 145 | 1-methylcyclopropyl | O | 6-phenylpyridin-2-yl | Me | H | neopentyl carbamate | N-cyclopropyl-N-(pent-3-enyl) |

TABLE 2-continued

| Cmpd | R₂ | X | R' | R₃ | R₃' | NR₄R₆ | Q |
|---|---|---|---|---|---|---|---|
| 146 | 1-methylcyclopropyl | S | naphthalen-1-yl | Me | H | NH-C(O)O-iPr | N-cyclopropyl, N-(pent-3-enyl) |
| 147 | 1-methylcyclopropyl | S | naphthalen-2-yl | Me | H | NH-C(O)NH-cyclopentyl | N-cyclopropyl, N-(pent-3-enyl) |
| 148 | 1-(methyl)cyclopropylmethyl | SO₂ | naphthalen-2-yl | Me | H | NH-C(O)O-tBu | N-cyclopropyl, N-(pent-3-enyl) |
| 149 | 1-(methyl)cyclopropylmethyl | NH | 4-phenylthiazol-2-yl | Me | H | NH-C(O)O-iPr | N-cyclopropyl, N-(pent-3-enyl) |
| 150 | 1-(methyl)cyclopropylmethyl | OCH₂ | naphthalen-1-yl | Me | H | NH-C(O)NH-cyclopentyl | N-cyclopropyl, N-(pent-3-enyl) |
| 151 | cyclopropyl | CH₂O | naphthalen-2-yl | H | H | NH-C(O)O-neopentyl | N-cyclopropyl, N-(pent-3-enyl) |

TABLE 2-continued

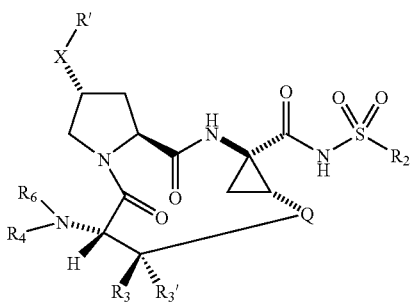

| Cmpd | R<sub>2</sub> | X | R' | R<sub>3</sub> | R<sub>3</sub>' | NR<sub>4</sub>R<sub>6</sub> | Q |
|---|---|---|---|---|---|---|---|
| 152 | cyclopropylmethyl | CH<sub>2</sub>O | 2-phenylpyridin-6-yl | H | H | NHBoc | N-cyclopropyl-N-(pent-3-enyl) |
| 153 | cyclopropylmethyl | CH<sub>2</sub>O | 5-phenylpyridin-3-yl | H | H | NHBoc | N-cyclopropyl-N-(pent-3-enyl) |
| 154 | cyclopropylmethyl | CH<sub>2</sub>O | 2-phenylpyridin-4-yl | H | H | NHBoc | N-cyclopropyl-N-(pent-3-enyl) |
| 155 | cyclopropylmethyl | O | quinazolin-4-yl | H | H | NH-C(O)O-neopentyl | N-cyclopropyl-N-(pent-3-enyl) |
| 156 | cyclopropylmethyl | O | 1,8-naphthyridin-4-yl | H | H | NH-C(O)O-iPr | N-cyclopropyl-N-(pent-3-enyl) |

TABLE 2-continued

| Cmpd | R₂ | X | R' | R₃ | R₃' | NR₄R₆ | Q |
|---|---|---|---|---|---|---|---|
| 156 | cyclopropyl | O | phthalazinyl | H | H | cyclopentyl carbamate | N-cyclopropyl, pentenyl |
| 158 | cyclopropyl | O | coumarin-4-yl | H | H | tert-butyl carbamate (Boc) | N-cyclopropyl, pentenyl |
| 159 | cyclopropyl | O | furo[3,2-c]pyridin-4-yl | H | H | tert-butyl urea | N-cyclopropyl, pentenyl |
| 160 | cyclopropyl | O | thieno[3,2-c]pyridin-4-yl | H | H | pyrrolidine-1-carboxamide | N-cyclopropyl, pentenyl |
| 161 | cyclopropyl | O | isoxazolo[5,4-b]pyridin-7-yl | H | H | cyclopentyl carbamate | N-cyclopropyl, pentenyl |
| 162 | cyclopropyl | O | benzisoxazol-3-yl | H | H | neopentyl carbamate | N-cyclopropyl, pentenyl |

TABLE 2-continued

| Cmpd | R₂ | X | R' | R₃ | R₃' | NR₄R₆ | Q |
|---|---|---|---|---|---|---|---|
| 163 | cyclopropyl | O | benzisothiazol-3-yl | H | H | -NH-C(O)-O-iPr | N-cyclopropyl, pentenyl |
| 164 | cyclopropyl | O | 1H-indazol-3-yl | H | H | -NH-C(O)-O-tBu | N-cyclopropyl, pentenyl |
| 165 | cyclopropyl | O | 1-Me-indazol-3-yl | H | H | -NH-C(O)-O-iPr | N-cyclopropyl, pentenyl |
| 166 | cyclopropyl | O | 1-Ph-indazol-3-yl | H | H | -NH-C(O)-O-cyclopentyl | N-cyclopropyl, pentenyl |
| 167 | cyclopropyl | O | 1-Bn-indazol-3-yl | H | H | -NH-C(O)-pyrrolidin-1-yl | N-cyclopropyl, pentenyl |
| 168 | cyclopropyl | O | 2-phenylpyridin-4-yl | H | H | -NH-C(O)-NH-cyclopentyl | N-cyclopropyl, pentenyl |

TABLE 2-continued

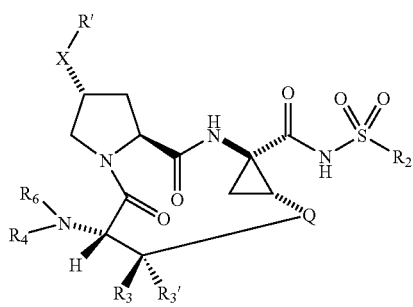

| Cmpd | R₂ | X | R' | R₃ | R₃' | NR₄R₆ | Q |
|------|----|----|----|----|----|-------|---|
| 169 | cyclopropyl | O | 3-phenylpyridin-5-yl | H | H | tBu-NH-C(O)-NH- | N(cyclopropyl)(pent-3-enyl) |
| 170 | cyclopropyl | O | 6-phenylpyrimidin-4-yl | H | H | neopentyl-O-C(O)-NH- | N(cyclopropyl)(pent-3-enyl) |
| 171 | cyclopropyl | O | 4-phenylpyrimidin-2-yl | H | H | tBuO-C(O)-NH- | N(cyclopropyl)(pent-3-enyl) |
| 172 | cyclopropyl | O | 6-phenylpyridin-2-yl | H | H | tBu-NH-C(O)-NH- | N(cyclopropyl)(pent-3-enyl) |
| 173 | cyclopropyl | S | naphthalen-1-yl | H | H | iPrO-C(O)-NH- | N(cyclopropyl)(pent-3-enyl) |

TABLE 2-continued

| Cmpd | R₂ | X | R' | R₃ | R₃' | NR₄R₆ | Q |
|---|---|---|---|---|---|---|---|
| 174 | cyclopropyl | S | 2-naphthyl | H | H | NHC(O)O-cyclopentyl | N(cyclopropyl)(CH₂CH₂CH=CHCH₃) |
| 175 | cyclopropyl | SO₂ | 2-naphthyl | H | H | NHC(O)-pyrrolidinyl | N(cyclopropyl)(CH₂CH₂CH=CHCH₃) |
| 176 | cyclopropyl | NH | 4-phenyl-thiazol-2-yl | H | H | NHC(O)O-tBu | N(cyclopropyl)(CH₂CH₂CH=CHCH₃) |
| 177 | cyclopropyl | OCH₂ | 1-naphthyl | H | H | NHC(O)O-tBu | N(cyclopropyl)(CH₂CH₂CH=CHCH₃) |
| 178 | 1-methyl-cyclopropyl | CH₂O | 2-naphthyl | H | H | NHC(O)O-tBu | N(cyclopropyl)(CH₂CH₂CH=CHCH₃) |
| 179 | 1-methyl-cyclopropyl | CH₂O | 6-phenyl-pyridin-2-yl | H | H | NHC(O)O-tBu | N(cyclopropyl)(CH₂CH₂CH=CHCH₃) |

TABLE 2-continued

TABLE 2-continued
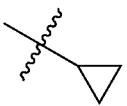
| Cmpd | R₂ | X | R' | R₃ | R₃' | NR₄R₆ | Q |
|---|---|---|---|---|---|---|---|
| 186 | 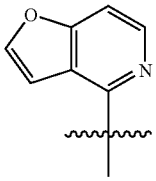 [SMILES: *c1nccc2occc12] | O | 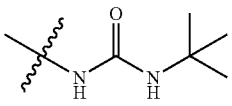 [SMILES: *NC(=O)NC(C)(C)C] | H | H | 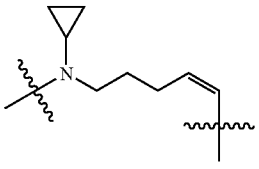 [SMILES: */C=C\CCCN(*)C1CC1] | 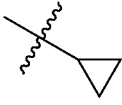 [SMILES: *C1CC1] |
| 187 | 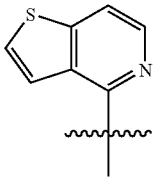 [SMILES: *c1nccc2sccc12] | O | 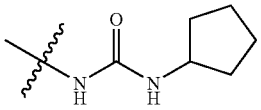 | H | H | 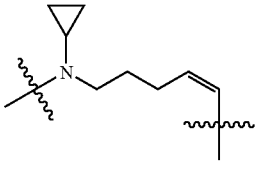 [SMILES: */C=C\CCCN(*)C1CC1] | 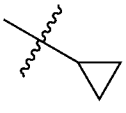 |
| 188 | 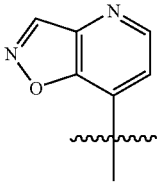 [SMILES: *c1ccnc2cnoc12] | O | 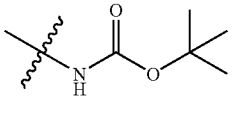 [SMILES: *NC(=O)OC(C)(C)C] | H | H | 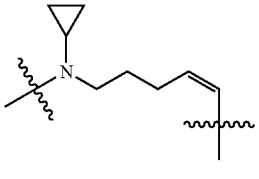 [SMILES: */C=C\CCCN(*)C1CC1] | 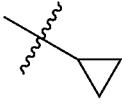 |
| 189 | 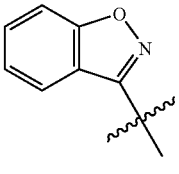 [SMILES: *c1noc2ccccc12] | O | 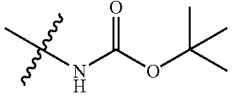 [SMILES: *NC(=O)OC(C)(C)C] | H | H | 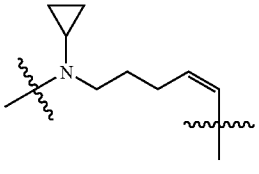 [SMILES: */C=C\CCCN(*)C1CC1] | 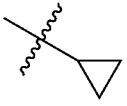 [SMILES: *C1CC1] |
| 190 | 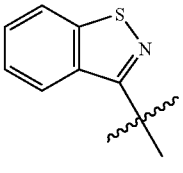 [SMILES: *c1nsc2ccccc12] | O | 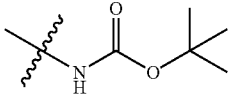 [SMILES: *NC(=O)OC(C)(C)C] | H | H | 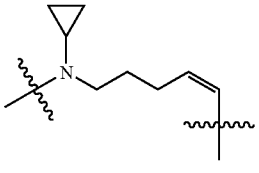 [SMILES: */C=C\CCCN(*)C1CC1] | 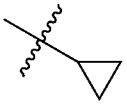 |
| 191 | 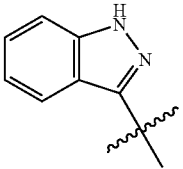 [SMILES: *c1n[nH]c2ccccc12] | O | 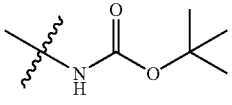 [SMILES: *NC(=O)OC(C)(C)C] | H | H | 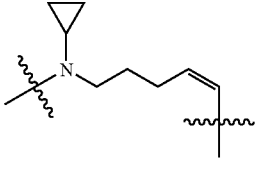 [SMILES: */C=C\CCCN(*)C1CC1] |  |

TABLE 2-continued

| Cmpd | R₂ | X | R' | R₃ | R₃' | NR₄R₆ | Q |
|---|---|---|---|---|---|---|---|
| 192 | 1-methylcyclopropyl | O | 1-methyl-1H-indazol-3-yl | H | H | NHBoc | N-cyclopropyl-N-(pent-3-enyl) |
| 193 | cyclopropyl | O | 1-phenyl-1H-indazol-3-yl | H | H | NHC(O)-pyrrolidin-1-yl | N-cyclopropyl-N-(pent-3-enyl) |
| 194 | cyclopropyl | O | 1-benzyl-1H-indazol-3-yl | H | H | NHBoc | N-cyclopropyl-N-(pent-3-enyl) |
| 195 | cyclopropyl | O | 6-phenylpyridin-3-yl | H | H | NHBoc | N-cyclopropyl-N-(pent-3-enyl) |
| 196 | cyclopropyl | O | 5-phenylpyridin-3-yl | H | H | NHBoc | N-cyclopropyl-N-(pent-3-enyl) |

TABLE 2-continued

| Cmpd | R₂ | X | R' | R₃ | R₃' | NR₄R₆ | Q |
|---|---|---|---|---|---|---|---|
| 197 | 1-methylcyclopropyl | O | 4-phenylpyrimidin-6-yl | H | H | NHBoc | N-cyclopropyl, N-(pent-3-enyl) |
| 198 | cyclopropyl | O | 4-phenylpyrimidin-2-yl | H | H | NHBoc | N-cyclopropyl, N-(pent-3-enyl) |
| 199 | cyclopropyl | O | 6-phenylpyridin-2-yl | H | H | NHBoc | N-cyclopropyl, N-(pent-3-enyl) |
| 200 | 1-ethylcyclopropyl | S | naphthalen-1-yl | H | Me | NHBoc | N-cyclopropyl, N-(pent-3-enyl) |
| 201 | cyclopropyl | S | naphthalen-2-yl | H | Me | NHBoc | N-cyclopropyl, N-(pent-3-enyl) |
| 202 | cyclopropyl | SO₂ | naphthalen-2-yl | H | Me | NH-C(O)O-cyclopentyl | N-cyclopropyl, N-(pent-3-enyl) |

TABLE 2-continued

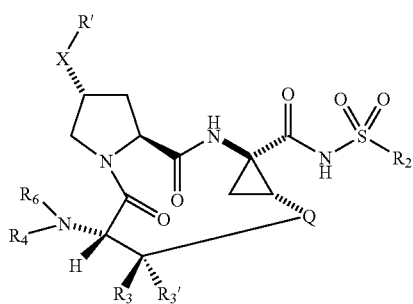

| Cmpd | R₂ | X | R' | R₃ | R₃' | NR₄R₆ | Q |
|---|---|---|---|---|---|---|---|
| 203 | ethylcyclopropyl | NH | 4-phenylthiazol-2-yl | H | H | NHC(O)O-iPr | N-cyclopropyl, N-(pent-3-enyl) |
| 204 | cyclopropyl | OCH₂ | naphthalen-1-yl | H | H | NHC(O)O-tBu | N-cyclopropyl, N-(pent-3-enyl) |
| 205 | cyclopropyl | CH₂O | naphthalen-2-yl | H | H | NHC(O)O-tBu | N-cyclopropyl, N-(pent-3-enyl) |
| 206 | cyclopropyl | CH₂O | 6-phenylpyridin-2-yl | H | H | NHC(O)O-tBu | N-cyclopropyl, N-(pent-3-enyl) |
| 207 | ethylcyclopropyl | CH₂O | 5-phenylpyridin-3-yl | H | H | NHC(O)O-tBu | N-cyclopropyl, N-(pent-3-enyl) |

TABLE 2-continued

| Cmpd | R₂ | X | R' | R₃ | R₃' | NR₄R₆ | Q |
|---|---|---|---|---|---|---|---|
| 208 | cyclopropyl | CH₂O | 2-phenylpyridin-4-yl | H | H | pyrrolidine-1-carboxamide | N-cyclopropyl-pentenyl |
| 209 | cyclopropyl | O | 6-phenylpyrimidin-2-yl | H | H | pyrrolidine-1-carboxamide | N-cyclopropyl-pentenyl |
| 210 | cyclopropyl | O | furo[3,2-c]pyridin-4-yl | H | H | tert-butyl carbamate | N-cyclopropyl-pentenyl |
| 211 | cyclopropyl | O | 1-phenyl-1H-indazol-3-yl | H | H | tert-butyl carbamate | N-cyclopropyl-pentenyl |

What is claimed is:
1. A compound of formula I,

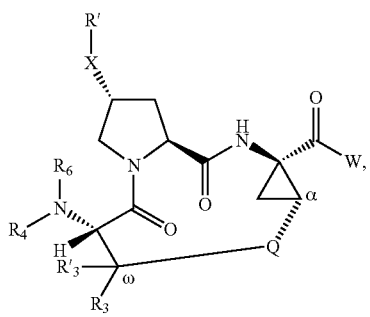

I or a pharmaceutically acceptable salt thereof, wherein:
(a) $R_4$ is hydrogen; $C_{1-6}$ alkyl; $C_{3-7}$ cycloalkyl; alkoxy; —C(O)—$R_5$; C(O)—N($R_5$)$_2$; C(O)—O$R_5$; $C_{7-14}$ alkylaryl; or $C_{3-7}$ cycloalkyl, wherein the alkyl and the cycloalkyl are optionally substituted with halo; and wherein each $R_5$ is independently selected from $C_{1-9}$ alkyl, wherein the alkyl is optionally substituted with $C_{1-6}$ alkoxy, $C_{3-7}$ cycloalkoxy, halo-$C_{1-6}$ alkoxy, cyano, halo, hydroxy, amino, $C_{1-6}$ alkylamino, di ($C_{1-6}$) alkylamino, di ($C_{1-6}$) alkylamide, carboxyl, or ($C_{1-6}$) carboxyester;
(b) $R_6$ is hydrogen, $C_{1-6}$ alkyl, or $C_{3-7}$ cycloalkyl;
(c) $R_3$ and $R'_3$ are each independently hydrogen or methyl;
(d) Q is

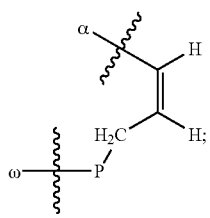

wherein P is a $C_3$ saturated chain containing one $NR_8$ group, wherein $R_8$ is hydrogen; $C_{1-6}$ alkyl; or $C_{1-6}$ cycloalkyl, wherein the alkyl and the cycloalkyl are optionally substituted with halo, $C_{1-6}$ alkoxy, cyano or $C_{1-6}$ haloalkoxy; —C(O)—$R_9$, C(O)—O$R_{10}$, C(O)—N$R_{11}R_{12}$ or —SO$_2R_{13}$; $R_9$, $R_{11}$, and $R_{12}$ are each independently hydrogen; $C_{1-6}$ alkyl or $C_{1-6}$ cycloalkyl, wherein the alkyl and the cycloalkyl are optionally substituted with halo, $C_{1-6}$ alkoxy, cyano or $C_{1-6}$ haloalkoxy; $R_{10}$ is $C_{1-6}$ alkyl or $C_{1-6}$ cycloalkyl, wherein the alkyl and the cycloalkyl are optionally substituted with halo, $C_{1-6}$ alkoxy, cyano or $C_{1-6}$ haloalkoxy; $R_{13}$ is aryl, $C_{1-6}$ alkyl or $C_{1-6}$ cycloalkyl, wherein the aryl, the alkyl, and the alkyl are optionally substituted with halo, $C_{1-6}$ alkoxy, cyano or $C_{1-6}$ haloalkoxy;
(e) W is OH, —O—$R_1$, or —NH—SO$_2$—$R_2$; wherein $R_1$ is $C_{1-6}$ alkyl, unsaturated $C_{3-7}$ cycloalkyl, $C_{6-14}$ aryl, or $C_{7-16}$ alkylaryl; and $R_2$ is $C_{1-8}$ alkyl, $C_{4-10}$ alkylcycloalkyl, or unsubstituted $C_{3-7}$ cycloalkyl; or $R_2$ is cyclopropyl or cyclobutyl optionally substituted with $C_{1-4}$ alkyl, $C_{2-5}$ alkenyl, $C_{7-16}$ alkylaryl, alkoxy, alkoxyalkyl, $C_{5-7}$ cycloalkyl, $C_{5-7}$ cycloalkenyl, $C_{6-10}$ alkylcycloalkyl, halo, haloalkyl, cyano, alkylcyano, haloalkoxy, or C(O)—X; wherein the $C_{5-7}$ cycloalkyl, the $C_{5-7}$ cycloalkenyl, and the $C_{6-10}$ alkylcycloalkyl are further optionally substituted with $C_{1-4}$ alkyl or hydroxy; and wherein X is selected from phenyl and —NHR$^X$; wherein R$^X$ is selected from $C_{1-6}$ alkyl, Het, and $C_{6-10}$ aryl;
(f) X is O, S, SO, SO$_2$, OCH$_2$, CH$_2$O or NH;
(g) R' is Het, $C_{6-10}$ aryl or $C_{7-14}$ alkylaryl, each optionally substituted with from one to five of the same or different R$^a$ groups; or $C_{3-9}$ cycloalkyl or $C_{1-7}$ alkyl, wherein the cycloalkyl and the alkyl are optionally substituted with from one to five of the same or different members of the group consisting of halo, cyano, alkoxy, and dialkylamino; provided Het is not substituted or unsubstituted isoquinolinyl; and
(h) R$^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, CF$_3$, mono-or di- halo-$C_{1-6}$ alkoxy, cyano, halo, thioalkyl, hydroxy, alkanoyl, NO$_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, di ($C_{1-6}$) alkyl(alkoxy)amine, $C_{6-10}$ aryl, $C_{7-14}$ alkylaryl, or a 5-7 membered monocyclic heterocycle.

2. A composition comprising the compound of claim 1, or a pharmaceutically acceptable salt thereof, and a pharmaceutically acceptable carrier.

3. The composition of claim 2 further comprising at least one additional compound having anti-HCV activity.

4. The composition of claim 3 wherein at least one of the additional compounds is an interferon or a ribavirin.

5. The composition of claim 4 wherein the interferon is selected from interferon alpha 2B, pegylated interferon alpha, consensus interferon, interferon alpha 2A, and lymphoblastiod interferon tau.

6. The composition of claim 3 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

7. The composition of claim 3 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

8. A method of relieving an HCV infection in a patient, comprising administering to the patient a therapeutically effective amount of a compound of claim 1, or a pharmaceutically acceptable salt thereof.

9. The method of claim 8 further comprising administering at least one additional compounds having anti-HCV activity prior to, after, or simultaneously with the compound of claim 1, or a pharmaceutically acceptable salt thereof 10. The method of claim 9 wherein at least one of the additional compounds is an interferon or a ribavirin.

11. The method of claim 10 wherein the interferon is selected from interferon alpha 2B, pegylated interferon alpha, consensus interferon, interferon alpha 2A, and lymphoblastiod interferon tau.

12. The method of claim 9 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

13. The method of claim 9 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 8,343,477 B2
APPLICATION NO. : 11/923918
DATED : January 1, 2013
INVENTOR(S) : Andrea D. Stanley et al.

Page 1 of 1

It is certified that error appears in the above-identified patent and that said Letters Patent is hereby corrected as shown below:

Title Page, Col. 1, line 1, item 56, (U.S. Patent Documents)
Above "2005/0153877 A1  7/2005  Miao el al." insert -- 5223432  06/1993  Wirz, et al. --; and Title Page, Col. 2, line 7, item 56, (Foreign Patent Documents), delete "6/2004" and insert
-- 8/2004 --, therefor.

<u>In the Claims</u>:

Claim 1, col. 203, line 66, , delete "aryl,or" and insert - - aryl, or - -,

Claim 1, col. 204, line 24, delete "mono-or" and insert - - mono- or - -,

Claim 5, col. 204, lines 42-43, delete "lymphoblastiod" and insert - - lymphoblastoid - -, Claim 6, col. 204, line 48, delete "Imiqimod," and insert - - imiquimod, - -, Claim 6, col. 204, lines 48-49, delete "5'-monophospate" and insert - - 5'-monophosphate - -, Claim 9, col. 204, line 65, delete "thereof" and insert - - thereof. - -, Claim 11, col. 205, lines 3-4, delete "lymphoblastiod" and insert - - lymphoblastoid - -, Claim 12, col. 205, line 9, delete "imiqimod," and insert - - imiquimod, - -, and Claim 12, col. 205, lines 9-10, delete "5'-monophospate" and insert - - 5'-monophosphate - -,
therefor.

Signed and Sealed this
Seventeenth Day of September, 2013

Teresa Stanek Rea
*Deputy Director of the United States Patent and Trademark Office*